(12) United States Patent
Luzzio et al.

(10) Patent No.: US 8,440,822 B2
(45) Date of Patent: May 14, 2013

(54) SULFONYL AMIDE DERIVATIVES FOR THE TREATMENT OF ABNORMAL CELL GROWTH

(76) Inventors: Michael Joseph Luzzio, Groton, CT (US); Kevin Daniel Freeman-Cook, Clinton, CT (US); Samit Kumar Bhattacharya, Niantic, CT (US); Matthew Merrill Hayward, Old Lyme, CT (US); Catherine Angela Hulford, North Stonington, CT (US); Christopher Lowell Autry, New London, CT (US); Xumiao Zhao, East Lyme, CT (US); Jun Xiao, Waterford, CT (US); Kendra Louise Nelson, Mystic, CT (US)

( * ) Notice: Subject to any disclaimer, the term of this patent is extended or adjusted under 35 U.S.C. 154(b) by 0 days.

(21) Appl. No.: 13/557,049

(22) Filed: Jul. 24, 2012

(65) Prior Publication Data
US 2013/0005964 A1  Jan. 3, 2013

Related U.S. Application Data

(63) Continuation of application No. 13/045,923, filed on Mar. 11, 2011, now Pat. No. 8,247,411, which is a continuation of application No. 12/105,151, filed on Apr. 17, 2008, now Pat. No. 7,928,109.

(60) Provisional application No. 60/912,597, filed on Apr. 18, 2007.

(51) Int. Cl.
*C07D 239/48* (2006.01)
*C07D 403/12* (2006.01)

(52) U.S. Cl.
USPC ........... 544/122; 544/295; 544/296; 544/323; 544/324

(58) Field of Classification Search .................. 544/122, 544/295, 296, 323, 324
See application file for complete search history.

(56) References Cited

U.S. PATENT DOCUMENTS

| | | | |
|---|---|---|---|
| 4,507,146 A | 3/1985 | Tobler et al. | |
| 5,863,924 A | 1/1999 | Berger et al. | |
| 7,107,335 B1 | 9/2006 | Arcieri et al. | |
| 7,109,335 B2 | 9/2006 | Kath et al. | |
| 7,928,109 B2 | 4/2011 | Luzzio et al. | |
| 2002/0032199 A1 | 3/2002 | Poss et al. | |
| 2002/0156087 A1 | 10/2002 | Nuss et al. | |
| 2003/0149064 A1 | 8/2003 | Pease et al. | |
| 2003/0162802 A1 | 8/2003 | Guo et al. | |
| 2003/0171359 A1 | 9/2003 | Dahmann et al. | |
| 2003/0181474 A1 | 9/2003 | Pease et al. | |
| 2004/0102630 A1 | 5/2004 | Brumby et al. | |
| 2004/0167141 A1 | 8/2004 | Bebbington et al. | |
| 2004/0198739 A1 | 10/2004 | Guillemont et al. | |
| 2004/0220177 A1 | 11/2004 | Kath et al. | |
| 2005/0014753 A1 | 1/2005 | Ding et al. | |
| 2005/0101620 A1 | 5/2005 | Kath et al. | |
| 2005/0256111 A1 | 11/2005 | Kath et al. | |
| 2005/0256125 A1 | 11/2005 | Kath et al. | |
| 2005/0256144 A1 | 11/2005 | Kath et al. | |
| 2005/0256145 A1 | 11/2005 | Kath et al. | |
| 2005/0261295 A1 | 11/2005 | Stadtmueller et al. | |
| 2005/0272753 A1 | 12/2005 | Nagashima et al. | |
| 2006/0079543 A1 | 4/2006 | Sum et al. | |
| 2006/0122156 A1 | 6/2006 | Sun et al. | |
| 2006/0122209 A1 | 6/2006 | Zhang et al. | |

FOREIGN PATENT DOCUMENTS

| | | |
|---|---|---|
| EP | 0566226 B1 | 11/1995 |
| EP | 0602851 B1 | 10/1996 |
| EP | 0520722 B1 | 12/1996 |
| EP | 0635507 B1 | 9/1999 |
| EP | 0635498 B1 | 4/2001 |
| WO | 9220642 A1 | 11/1992 |
| WO | 9510506 A1 | 4/1995 |
| WO | 9609294 A1 | 3/1996 |
| WO | 9616960 A1 | 6/1996 |
| WO | 9730034 A1 | 8/1997 |
| WO | 9802434 A1 | 1/1998 |
| WO | 9802437 A1 | 1/1998 |

(Continued)

OTHER PUBLICATIONS

Gura, "Systems for Identifying Drugs are Often Faulty, Cancer Models", Science, vol. 278, No. 5340, pp. 1041-1042 (Nov. 1997).

(Continued)

*Primary Examiner* — Deepak Rao
(74) *Attorney, Agent, or Firm* — Lando & Anastasi LLP

(57) ABSTRACT

The present invention relates to a compound of the formula I

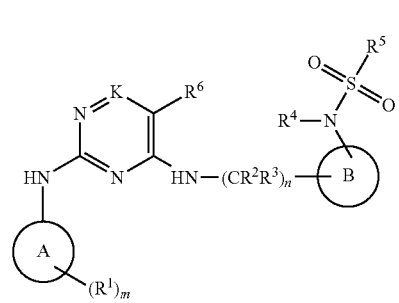

I wherein $R^1$ to $R^6$, A, B, n and m are as defined herein. Such novel sulfonyl amide derivatives are useful in the treatment of abnormal cell growth, such as cancer, in mammals. This invention also relates to a method of using such compounds in the treatment of abnormal cell growth in mammals, especially humans, and to pharmaceutical compositions containing such compounds.

38 Claims, No Drawings

FOREIGN PATENT DOCUMENTS

| | | | |
|---|---|---|---|
| WO | 9802438 | A1 | 1/1998 |
| WO | 9941253 | A1 | 8/1999 |
| WO | 0042003 | A1 | 7/2000 |
| WO | 0114375 | A1 | 3/2001 |
| WO | 0172744 | A1 | 10/2001 |
| WO | 0204429 | A1 | 1/2002 |
| WO | 0185699 | A3 | 2/2002 |
| WO | 0185700 | A3 | 2/2002 |
| WO | 0248133 | A3 | 11/2002 |
| WO | 02102783 | A1 | 12/2002 |
| WO | 0250066 | A3 | 1/2003 |
| WO | 02102313 | A3 | 4/2003 |
| WO | 03030909 | A1 | 4/2003 |
| WO | 03040141 | A1 | 5/2003 |
| WO | 03078404 | A1 | 9/2003 |
| WO | 03063794 | A3 | 12/2003 |
| WO | 2004014382 | A1 | 2/2004 |
| WO | 2004/046118 | A2 | 6/2004 |
| WO | 2004/048343 | A1 | 6/2004 |
| WO | 2004069812 | A1 | 8/2004 |
| WO | 2004080980 | A1 | 9/2004 |
| WO | 2004041164 | A3 | 10/2004 |
| WO | 2005009443 | A1 | 2/2005 |
| WO | 2005009980 | A1 | 2/2005 |
| WO | 2005016894 | A1 | 2/2005 |
| WO | 2005003103 | A3 | 11/2005 |
| WO | 2005121121 | A3 | 3/2006 |
| WO | 2006007532 | A3 | 8/2006 |
| WO | 2007/063384 | A2 | 6/2007 |
| WO | 2007/072158 | A2 | 6/2007 |
| WO | 2007014011 | A3 | 4/2009 |

OTHER PUBLICATIONS

Johnson, et al., "Relationships between drug activity in NCI preclinical in vitro and in vivo models and early clinical trials", British Journal of Cancer, 64(10) 1424-1431 (2001).

Simone, "Oncology: Introduction" Cecil Textbook of Medicine, 20th Edition, vol. 1, pp. 1004-1010 (1996).

International Search Report mailed Aug. 22, 2008 for International Patent Application No. PCT/IB2008/000845.

Written Opinion mailed Aug. 22, 2008, for International Patent Application No. PCT/IB2008/000845.

International Preliminary Report on Patentability mailed Apr. 29, 2010 for International Patent Application No. PCT/IB2008/000845.

Notice of Allowance mailed on Dec. 14, 2010 for U.S. Appl. No. 12/105,151.

SULFONYL AMIDE DERIVATIVES FOR THE TREATMENT OF ABNORMAL CELL GROWTH

CROSS-REFERENCE TO RELATED APPLICATION

This application is a continuation of U.S. patent application Ser. No. 13/045,923, which was filed on Mar. 11, 2011 now U.S. Pat. No. 8,247,411, which is a continuation of U.S. patent application Ser. No. 12/105,151, which was filed on Apr. 17, 2008 now U.S. Pat. No. 7,928,109, which claims the benefit of U.S. Provisional Application Ser. No. 60/912,597, filed on Apr. 18, 2007, each of which is incorporated herein by reference in its entirety.

BACKGROUND OF THE INVENTION

This invention relates to novel sulfonyl amide derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma that expresses epidermal growth factor receptor tyrosine kinase (EGFR) but is without effect on the growth of another carcinoma that does not express the EGF receptor. Thus, selective inhibitors of certain receptor tyrosine kinases, are useful in the treatment of abnormal cell growth, in particular cancer, in mammals. In addition to receptor tyrosine kinases, selective inhibitors of certain non-receptor tyrosine kinases, such as FAK (focal adhesion kinase), lck, src, abl or serine/threonine kinases (e.g., cyclin dependent kinases), are useful in the treatment of abnormal cell growth, in particular cancer, in mammals. FAK is also known as the Protein-Tyrosine Kinase 2, PTK2.

Convincing evidence suggests that FAK, a cytoplasmic, non-receptor tyrosine kinase, plays an essential role in cell-matrix signal transduction pathways (Clark and Brugge 1995, *Science* 268: 233-239) and its aberrant activation is associated with an increase in the metastatic potential of tumors (Owens et al. 1995, *Cancer Research* 55: 2752-2755). FAK was originally identified as a 125 kDa protein highly tyrosine-phosphorylated in cells transformed by v-Src. FAK was subsequently found to be a tyrosine kinase that localizes to focal adhesions, which are contact points between cultured cells and their underlying substratum and sites of intense tyrosine phosphorylation. FAK is phosphorylated and, thus, activated in response to extracellular matrix (ECM)-binding to integrins. Recently, studies have demonstrated that an increase in FAK mRNA levels accompanied invasive transformation of tumors and attenuation of the expression of FAK (through the use of antisense oligonucleotides) induces apoptosis in tumor cells (Xu et al. 1996, *Cell Growth and Diff.* 7: 413-418). In addition to being expressed in most tissue types, FAK is found at elevated levels in most human cancers, particularly in highly invasive metastases.

Various compounds, such as styrene derivatives, have also been shown to possess tyrosine kinase inhibitory properties. Five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties.

Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. In addition, the following list of publications relate to bis-mono and bicyclic aryl and heteroaryl compounds that may optionally be used as tyrosine kinase inhibitors: WO 03/030909, WO 03/032997, US Patent Application Publication No. 2003/0181474, US Patent Application Publication No. 2003/0162802, U.S. Pat. No. 5,863,924, WO 03/078404, U.S. Pat. No. 4,507,146, WO 99/41253, WO 01/72744, WO 02/48133, US Patent Application Publication No. 2002/156087, WO 02/102783, and WO 03/063794.

U.S. Patent Application Publication No. 20040220177 relates to a broad class of novel pyrimidine derivatives that are kinase inhibitors, and more specifically, inhibitors of FAK. Moreover, U.S. Pat. No. 7,107,335 relates more specifically to a subset of pyrimidine derivatives, i.e., those bearing a 5-aminooxindole, which are tyrosine kinase inhibitors, and more particularly, FAK inhibitors. Compounds such as these are useful in the treatment of abnormal cell growth.

Accordingly, a need exists for additional selective inhibitors of certain receptor and non-receptor tyrosine kinases, useful in the treatment of abnormal cell growth, such as cancer, in mammals. The present invention provides novel sulfonyl amide derivatives that are kinase inhibitors and inhibitors of the non-receptor tyrosine kinase, FAK, Aurora (e.g., Aurora-1 and Aurora-2), Pyk, HgK, and are useful in the treatment of abnormal cell growth.

SUMMARY OF THE INVENTION

The present invention provides a compound of formula I:

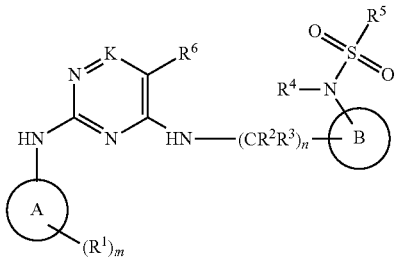

or a pharmaceutically acceptable salt thereof; wherein
A is a ring moiety selected from the group consisting of a:
(a) 4- to 7-membered carbocyclyl,
(b) 4- to 7-membered heterocyclyl,
(c) phenyl, and
(d) 5- to 6-membered heteroaryl ring, wherein each of said 4- to 7-membered carbocyclyl and 4- to 7-membered heterocyclyl of said A group may optionally contain one or two olefinic bonds; and wherein one or two carbon ring atoms in each of said 4- to 7-membered carbocyclyl and 4- to 7-membered heterocyclic of said A group may independently optionally be replaced with one or two moieties independently selected from the group consisting of —C(O)—, —C(S)— and —C(=NR$^4$)—;
B is phenyl or a 5- to 6-membered heteroaryl;
K is CH, C(NH$_2$) or N;
each R$^1$ is independently selected from the group consisting of —H, halo, —CF$_3$, —CN, —NO$_2$, —NR$^7$R$^8$, —NR$^7$C(NR$^7$R$^8$)(=CR$^9$), —CR$^7$(NR$^7$R$^8$)(=NR$^7$), —NR$^7$C(NR$^7$R$^8$)(=NR$^7$), —NR$^7$C(O)R$^9$, —C(O)NR$^7$R$^8$, —C(O)R$^9$, —C(O)C(O)R$^9$, —C(O)OR$^{10}$, —OC(O)R$^9$, —OR$^{10}$, —OC(O)OR$^{10}$, —S(O)$_j$R$^{11}$, —S(O)(=NR$^7$)R$^8$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_3$)heterocycloalkenyl, —(C$_6$-C$_{10}$)aryl and —(C$_1$-C$_9$)heteroaryl moieties of said R$^1$ is optionally independently substituted by one to three R$^{12}$ groups;
R$^2$ and R$^3$ are each independently selected from the group consisting of —H, -halo, —OR$^{10}$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^2$ and R$^3$ is optionally substituted by one to three R$^{12}$ groups;
R$^4$ and R$^5$ are each independently selected from the group consisting of —H, —NR$^7$R$^8$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl moieties of said R$^4$ and R$^5$ is optionally substituted by one to three R$^{12}$ groups;
R$^6$ is selected from the group consisting of -halo, —NR$^7$R$^8$, —OR$^{10}$, —C(O)R$^9$, —CO$_2$R$^{10}$, —CONR$^7$R$^8$, —S(O)$_j$R$^{11}$, —NR$^7$CONR$^7$R$^8$, and —NR$^8$SO$_2$R$^{11}$, —NO$_2$, —CN, —CF$_3$, —(C$_1$-C$_6$)alkyl, —(C$_2$-C$_6$)alkenyl, —(C$_2$-C$_6$)alkynyl, —(C$_2$-C$_6$)perfluorinated alkyl, —(C$_2$-C$_6$)perfluorinated alkenyl, —(C$_3$-C$_6$)perfluorinated alkynyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_1$-C$_9$)heterocyclyl, —(C$_1$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, —(C$_1$-C$_9$)heteroaryl, —(C$_6$-C$_{10}$)perfluorinated aryl, and —(C$_1$-C$_9$)perfluorinated heteroaryl; and wherein each of said —(C$_1$-C$_6$)alkyl, —(C$_2$-C$_6$)alkenyl, —(C$_2$-C$_6$)alkynyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_1$-C$_9$)heterocyclyl, —(C$_1$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl moieties of said R$^6$ is optionally substituted by one to three R$^{12}$ groups;
R$^7$ and R$^8$ are each independently selected from the group consisting of —H, —OR$^{10}$, —S(O)$_j$R$^{11}$, —NO$_2$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^7$ and R$^8$ is optionally substituted by one to three R$^{12}$ groups;
each R$^9$ is independently selected from the group consisting of —H, -halo, —NR$^{13}$R$^{14}$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^9$ is optionally substituted by one to three R$^{12}$ groups;
each R$^{10}$ is independently selected from the group consisting of —H, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{10}$ is optionally substituted by one to three R$^{12}$ groups;
each R$^{11}$ is independently selected from the group consisting of —H, —NR$^{13}$R$^{14}$, —C(O)R$^{13}$, —CF$_3$, —(C$_1$-C$_6$)alkyl, —(C$_2$-C$_6$)alkenyl, —(C$_2$-C$_6$)alkynyl, (C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)

heterocycloalkenyl, —($C_6$-$C_9$)heterobicycloalkyl, —($C_6$-$C_9$) heterobicycloalkenyl —($C_6$-$C_{10}$)aryl, and —($C_1$-$C_9$) heteroaryl; land wherein each of the foregoing —($C_1$-$C_6$) alkyl, —($C_2$-$C_6$)alkenyl, —($C_2$-$C_6$)alkynyl, —($C_3$-$C_{10}$) cycloalkyl, —($C_5$-$C_{10}$)cycloalkenyl, —($C_2$-$C_9$) heterocycloalkyl, ($C_4$-$C_9$)heterocycloalkenyl, —($C_6$-$C_{10}$) aryl and —($C_1$-$C_9$)heteroaryl moieties of said $R^{11}$ is optionally substituted by one to three $R^{12}$ groups;

each $R^{12}$ is independently selected from the group consisting of —H, —$OR^{13}$, —$C(O)R^{13}$, —$C(O)OR^{13}$, —OC(O) $R^{13}$, —$OC(O)OR^{13}$, —$C(O)NR^{13}R^{14}$, —$NR^{13}C(O)$ $NR^{13}R^{14}$, —$NR^{13}R^{14}$, —$NR^{13}C(NR^{13}R^{14})(=NR^{13})$, —$NR^{13}C(NR^{13}R^{14})(=N$—$C(O)R^{13})$, —$NR^{13}C(O)R^{14}$, —$NR^{13}S(O)_jR^{13}$, —$S(O)_jR^{13}$, —$CF_3$, —CN, —($C_1$-$C_6$) alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkenyl, —($C_6$-$C_9$)heterobicycloalkyl, —($C_6$-$C_9$) heterobicycloalkenyl, —($C_6$-$C_{10}$)aryl, and —($C_1$-$C_9$) heteroaryl of said $R^{12}$ is optionally independently substituted by one to three groups selected from the group consisting of -halo, —$CF_3$, —CN, —$NO_2$, —OH, —O(($C_1$-$C_6$)alkyl), —$C(O)R^{15}$, —$C(O)NR^{15}R^{16}$, —$S(O)_jR^{15}$, and —$S(O)_j$ $NR^{15}R^{16}$, —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$) alkyl) and —N(($C_1$-$C_6$)alkyl)$_2$;

$R^{13}$ and $R^{14}$ are each independently selected from the group consisting of —H, —$NR^{15}C(O)R^{16}$, —$CF_3$, —CN, —$S(O)_jR^{15}$, —($C_1$-$C_6$)alkyl, —($C_2$-$C_6$)alkenyl, —($C_2$-$C_6$) alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl of said $R^{13}$ and $R^{14}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

$R^{15}$ and $R^{16}$ are each independently selected from the group consisting of —H, —($C_1$-$C_6$)alkyl, —($C_2$-$C_6$)alkenyl, —($C_2$-$C_6$)alkynyl, —($C_3$-$C_{10}$)cycloalkyl, —($C_3$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$) heterobicycloalkenyl, —($C_6$-$C_{10}$)aryl, and —($C_1$-$C_9$) heteroaryl; and wherein each of the foregoing —($C_1$-$C_6$) alkyl, —($C_2$-$C_6$)alkenyl, —($C_2$-$C_6$)alkynyl, —($C_3$-$C_{10}$) cycloalkyl, —($C_6$-$C_{10}$)cycloalkenyl, —($C_6$-$C_{10}$) bicycloalkyl, —($C_6$-$C_{10}$)bicycloalkenyl, —($C_2$-$C_9$) heterocycloalkyl, —($C_4$-$C_9$)heterocycloalkenyl, —($C_6$-$C_9$) heterobicycloalkyl, —($C_6$-$C_9$)heterobicycloalkenyl, —($C_6$-$C_{10}$)aryl, and —($C_1$-$C_9$)heteroaryl of said $R^{15}$ and $R^{16}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

wherein one or two carbon ring atoms in each of the aforementioned —($C_1$-$C_6$)alkyl, —($C_2$-$C_6$)alkenyl, —($C_2$-$C_6$) alkynyl, —($C_3$-$C_{10}$)cycloalkyl, —($C_6$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl and —($C_6$-$C_9$)heterobicycloalkenyl in said $R^1$-$R^{14}$ groups may optionally and independently be replaced with —C(O)— or —C(S)—;

wherein two groups attached to the same tetravalent carbon atom in each of the aforementioned —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$) heterocycloalkenyl, —($C_6$-$C_9$)heterobicycloalkyl and —($C_6$-$C_9$)heterobicycloalkeny of said $R^1$ to $R^{14}$ groups may optionally join to form a ring system selected from the group consisting of a —($C_3$-$C_{10}$)cycloalkyl, —($C_5$-$C_{10}$)cycloalkenyl, —($C_2$-$C_9$)heterocycloalkyl, and —($C_4$-$C_9$)heterocycloalkenyl; and wherein j is an integer from 0 to 2;

n is an integer from 1 to 3; and m is an integer from 0 to 3.

In one embodiment, the invention relates to a compound of formula I wherein A is a 4- to 7-membered carbocyclyl; and wherein said carbocyclyl may additionally contain one or two olefinic bonds.

In another embodiment, the invention relates to a compound of formula I wherein A is a 4- to 7-membered carbocyclyl selected from the group consisting of cyclopropyl, cyclobutyl, cyclobutenyl, cyclopentyl, cyclopentenyl, cyclopentendienyl, cyclohexyl, cyclohexenyl, cyclohexadienyl, cycloheptyl, cycloheptenyl, and cycloheptadienyl.

In another embodiment, the invention relates to a compound of formula I wherein A is a 4- to 7-membered heterocyclyl, and wherein said 4- to 7-membered heterocyclyl may additionally contain one or two olefinic bonds.

In another embodiment, the invention relates to a compound of formula I wherein A is a 4- to 7-membered heterocyclyl selected from the group consisting of azetidinyl, oxetanyl, pyrrolidynyl, dihydropyrazolyl, tetrahydropyrazolyl, dihydrofuranyl, tetradydrofuranyl, dihydrothiophenyl, tetrahydrothiopenyl, dihydropyridinyl, tetrahydropyridinyl, piperidinyl, piperazinyl, pyranyl, dihydropyranyl, tetrahydropyranyl, thiopyrianyl, dihydrothiopyranyl, tetrahydrothiopyranyl, morpholinyl, dihydroazepinyl, tetrahydroazepinyl, dihyrooxepinyl, tetrahydrooxepinyl, oxepanyl, dihyrothiepinyl, tetrahydrothiepinyl and thiepanyl.

In another embodiment, the invention relates to a compound of formula I wherein A is a phenyl.

In another embodiment, the invention relates to a compound of formula I wherein A is a 5- to 6-membered heteroaryl.

In another embodiment, the invention relates to a compound of formula I wherein A is a 5- to 6-membered heteroaryl selected from the group consisting of furanyl, pyrrolyl, thiopenyl, thiazolyl, isothiazolyl, pyrazolyl, oxazoyl, isoxazolyl, pyridyl, pyrimidyl, pyrazinyl, pyridazinyl, oxadiazoyl, thiadiazoyl, and benzothiazole, benzooxazole.

In one embodiment, the invention relates to a compound of formula I wherein each $R^1$ is independently selected from the group consisting of —H, halo, —$CF_3$, —CN, —$NO_2$, —$NR^7R^8$, —$NR^7C(NR^7R^8)(=CR^9)$, —$CR^7(NR^7R^8)$ (=NR$^7$), —NR$^7$C(NR$^7$R$^8$)(=NR$^7$), —NR$^7$C(O)R$^9$, —C(O)NR$^7$R$^8$, —C(O)R$^9$, —C(O)C(O)R$^9$, —C(O)OR$^{10}$, —OC(O)R$^9$, —OR$^{10}$, —OC(O)OR$^{10}$, —S(O)$_j$R$^{11}$, and —S(O)(=NR$^7$)R$^8$.

In another embodiment, the invention relates to a compound of formula I wherein R$^1$ is —S(O)$_j$R$^{11}$.

In another embodiment, the invention relates to a compound of formula I wherein R$^1$ is —S(O)$_j$R$^{11}$, and R$^{11}$ is selected from the group consisting of —H, —NR$^{13}$R$^{14}$ and —(C$_1$-C$_6$)alkyl; and wherein said —(C$_1$-C$_6$)alkyl of said R$^{11}$ is optionally independently substituted by one to three R$^{12}$ groups.

In another embodiment, the invention relates to a compound of formula I wherein R$^1$ is —C(O)OR$^{10}$.

In another embodiment, the invention relates to a compound of formula I wherein R$^1$ is —C(O)OR$^{10}$ and R$^{10}$ is —(C$_1$-C$_6$)alkyl optionally substituted by one to three R$^{12}$ groups.

In another embodiment, the invention relates to a compound of formula I wherein R$^1$ is —C(O)R$^9$.

In another embodiment, the invention relates to a compound of formula I wherein R$^1$ is —C(O)R$^9$ and R$^9$ is selected from the group consisting of —NR$^{13}$R$^{14}$, —(C$_1$-C$_6$)alkyl and —(C$_3$-C$_{10}$)cycloalkyl; wherein each of said —(C$_1$-C$_6$)alkyl, and —(C$_3$-C$_{10}$)cycloalkyl of said R$^9$ group is optionally substituted by one to three R$^{12}$ groups; and wherein two groups attached to the same tetravalent carbon atom of said —(C$_1$-C$_6$)alkyl and —(C$_3$-C$_{10}$)cycloalkyl of said R$^9$ may optionally join to form a ring system selected from the group consisting of a —(C$_3$-C$_{10}$)cycloalkyl, —(C$_5$-C$_{10}$)cycloalkenyl, —(C$_2$-C$_9$)heterocycloalkyl, and —(C$_4$-C$_9$)heterocycloalkenyl.

In another embodiment, the invention relates to a compound of formula I wherein R$^1$ is —C(O)R$^9$, and R$^9$ is —(C$_1$-C$_6$)alkyl optionally substituted by a group selected from the group consisting of —NR$^{13}$R$^{14}$, —NR$^{15}$C(O)R$^{16}$ and —CF$_3$.

In another embodiment, the invention relates to a compound of formula I wherein R$^1$ is —C(O)R$^9$, and R$^9$ is —NR$^{13}$R$^{14}$.

In another embodiment, the invention relates to a compound of formula I wherein R$^1$ is —C(O)R$^9$, R$^9$ is —NR$^{13}$R$^{14}$, and R$^{13}$ and R$^{14}$ are each independently selected from the group consisting of —H and —(C$_1$-C$_6$)alkyl; and wherein said —(C$_1$-C$_6$)alkyl of said R$^{13}$ and R$^{14}$ groups is optionally independently substituted with one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$.

In another embodiment, the invention relates to a compound of formula I wherein R$^1$ is —C(O)R$^9$, R$^9$ is —NR$^{13}$R$^{14}$, and R$^{13}$ and R$^{14}$ are each independently selected from the group consisting —H and —(C$_1$-C$_6$)alkyl; wherein said —(C$_1$-C$_6$)alkyl of said R$^{13}$ and R$^{14}$ are each optionally independently substituted with one to three groups selected from the group consisting of —(C$_3$-C$_{10}$)cycloalkyl, —(C$_2$-C$_9$)heterocycloalkyl, —(C$_6$-C$_{10}$)aryl, and —(C$_1$-C$_9$)heteroaryl; and wherein each of said —(C$_3$-C$_{10}$)cycloalkyl, —(C$_2$-C$_9$)heterocycloalkyl, —(C$_6$-C$_{10}$)aryl, and —(C$_1$-C$_9$)heteroaryl optional substituents of said —(C$_1$-C$_6$)alkyl of said R$^{13}$ and R$^{14}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$.

In another embodiment, the invention relates to a compound of formula I wherein R$^1$ is —C(O)R$^9$, R$^9$ is —NR$^{13}$R$^{14}$, and R$^{13}$ and R$^{14}$ are each independently selected from the group consisting of —(C$_3$-C$_{10}$)cycloalkyl and —(C$_2$-C$_9$)heterocycloalkyl, —(C$_6$-C$_{10}$)aryl, and —(C$_1$-C$_9$)heteroaryl; and wherein each of said —(C$_3$-C$_{10}$)cycloalkyl, —(C$_2$-C$_9$)heterocycloalkyl, —(C$_6$-C$_{10}$)aryl, and —(C$_1$-C$_9$)heteroaryl of said R$^{13}$ and R$^{14}$ is optionally independently substituted by one to three groups independently selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$.

In another embodiment, the invention relates to a compound of formula I wherein R$^1$ is —C(O)R$^9$, and R$^9$ is selected from the group consisting of —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_8$)heterobicycloalkyl and —(C$_6$-C$_9$)heterobicycloalkenyl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl and (C$_4$-C$_9$)heterocycloalkenyl moieties of said R$^9$ is optionally independently substituted by one to three R$^{12}$ groups.

In another embodiment, the invention relates to a compound of formula I wherein R$^1$ is —C(O)R$^9$, and R$^9$ is selected from the group consisting of —(C$_6$-C$_{10}$)aryl, and —(C$_1$-C$_9$)heteroaryl; and wherein each of the foregoing —(C$_6$-C$_{10}$)aryl and —(C$_1$-C$_9$)heteroaryl moieties of said R$^9$ is optionally independently substituted by one to three R$^{12}$ groups.

In another embodiment, the invention relates to a compound of formula I wherein R$^1$ is —NR$^7$R$^8$.

In another embodiment, the invention relates to a compound of formula I wherein R$^1$ is —NR$^7$R$^8$, and R$^7$ and R$^8$ are each independently selected from the group consisting of —H, —CF$_3$ and —S(O)$_j$R$^{11}$.

In another embodiment, the invention relates to a compound of formula I wherein R$^1$ is —NR$^7$R$^8$, and R$^7$ and R$^8$ are each independently selected from the group consisting of —(C$_1$-C$_6$)alkyl, —(C$_2$-C$_6$)alkenyl and —(C$_2$-C$_6$)alkynyl; and wherein each of the foregoing —(C$_1$-C$_6$)alkyl, —(C$_2$-C$_6$)alkenyl and —(C$_2$-C$_6$)alkynyl moieties of said R$^7$ and R$^8$ is optionally independently substituted by one to three R$^{12}$ groups.

In another embodiment, the invention relates to a compound of formula I wherein R$^1$ is —NR$^7$C(O)R$^9$.

In another embodiment, the invention relates to a compound of formula I wherein R$^1$ is —NR$^7$C(O)R$^9$ and R$^7$ is selected from the group consisting of —H and —(C$_1$-C$_6$)alkyl; and wherein said —(C$_1$-C$_6$)alkyl of said R$^7$ is optionally independently substituted by one to three R$^{12}$ groups.

In another embodiment, the invention relates to a compound of formula I wherein R$^1$ is —NR$^7$C(O)R$^9$ and R$^7$ is selected from the group consisting of —H and —(C$_1$-C$_6$)alkyl; and wherein said —(C$_1$-C$_6$)alkyl of said R$^7$ is optionally independently substituted by one to three R$^{12}$ groups.

In another embodiment, the invention relates to a compound of formula I wherein R$^1$ is —NR$^7$C(O)R$^9$, and R$^9$ is selected from the group consisting of —H and —S(O)$_j$R$^{11}$.

In another embodiment, the invention relates to a compound of formula I wherein R$^1$ is —NR$^7$C(O)R$^9$, and R$^9$ is selected from the group consisting of —H, —(C$_1$-C$_6$)alkyl, —(C$_2$-C$_6$)alkenyl, —(C$_2$-C$_6$)alkynyl; and wherein said —(C$_1$-C$_6$)alkyl, —(C$_2$-C$_6$)alkenyl and —(C$_2$-C$_6$)alkynyl of said R$^9$ is optionally independently substituted by one to three R$^{12}$ groups.

In another embodiment, the invention relates to a compound of formula I wherein R$^1$ is —NR$^7$C(O)R$^9$ and R$^9$ is —(C$_1$-C$_6$)alkyl; wherein said —(C$_1$-C$_6$)alkyl of said R$^9$ is optionally independently substituted by one to three R$^{12}$ groups; and wherein two groups attached to the same tetravalent carbon atom of said —(C$_1$-C$_6$)alkyl of said R$^9$ may optionally join to form a ring system selected from the group consisting of a —(C$_3$-C$_{10}$)cycloalkyl, —(C$_5$-C$_{10}$)cycloalkenyl, —(C$_2$-C$_9$)heterocycloalkyl, and —(C$_4$-C$_9$)heterocycloalkenyl.

In another embodiment, the invention relates to a compound of formula I wherein R$^1$ is —NR$^7$C(O)R$^9$ and R$^9$ is —(C$_1$-C$_6$)alkyl; and wherein said —(C$_1$-C$_6$)alkyl of said R$^9$ is substituted by one to three R$^{12}$ groups independently selected from the group consisting of —OR$^{13}$, —C(O)R$^{13}$, —C(O)OR$^{13}$, —OC(O)R$^{13}$, —OC(O)OR$^{13}$, —C(O)NR$^{13}$R$^{14}$, —NR$^{13}$C(O)NR$^{13}$R$^{14}$, —NR$^{13}$R$^{14}$, —NR$^{13}$C(NR$^{13}$R$^{14}$)(=NR$^{13}$), —NR$^{13}$C(NR$^{13}$R$^{14}$)(=N—C(O)R$^{13}$), —NR$^{13}$C(O)R$^{14}$, —NR$^{13}$S(O)$_j$R$^{13}$, —S(O)$_j$R$^{13}$, —CF$_3$, and —CN.

In another embodiment, the invention relates to a compound of formula I wherein R$^1$ is —NR$^7$C(O)R$^9$ and R$^9$ is —(C$_1$-C$_8$)alkyl, wherein said —(C$_1$-C$_6$)alkyl of said R$^9$ is substituted by one to three R$^{12}$ groups independently selected from the group consisting of —(C$_1$-C$_6$)alkyl, —(C$_2$-C$_6$)alkenyl and —(C$_2$-C$_6$)alkynyl.

In another embodiment, the invention relates to a compound of formula I wherein R$^1$ is —NR$^7$C(O)R$^9$ and R$^9$ is —(C$_1$-C$_6$)alkyl; wherein said —(C$_1$-C$_6$)alkyl of said R$^9$ is substituted by one to three R$^{12}$ groups independently selected from the group consisting of —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl; and wherein each of the foregoing —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl of said R$^{12}$ is optionally independently substituted by one to three groups independently selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$.

In another embodiment, the invention relates to a compound of formula I wherein R$^1$ is —NR$^7$C(O)R$^9$ and R$^9$ is —(C$_1$-C$_6$)alkyl; wherein said —(C$_1$-C$_6$)alkyl of said R$^9$ is substituted by one to three R$^{12}$ groups independently selected from the group consisting of —(C$_6$-C$_{10}$)aryl, and —(C$_1$-C$_9$) heteroaryl; and wherein each of the foregoing —(C$_6$-C$_{10}$)aryl and —(C$_1$-C$_9$)heteroaryl of said R$^{12}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$.

In another embodiment, the invention relates to a compound of formula I wherein each R$^1$ is independently selected from the group consisting of —(C$_1$-C$_6$)alkyl, —(C$_2$-C$_6$)alkenyl, and —(C$_2$-C$_6$)alkynyl; and wherein each of the foregoing —(C$_1$-C$_6$)alkyl, —(C$_2$-C$_6$)alkenyl and —(C$_2$-C$_6$)alkynyl moieties of said R$^1$ is optionally independently substituted by one to three R$^{12}$ groups.

In another embodiment, the invention relates to a compound of formula I wherein R$^1$ is —(C$_1$-C$_6$)alkyl optionally independently substituted by one to three R$^{12}$ groups.

In another embodiment, the invention relates to a compound of formula I wherein each R$^1$ is —(C$_1$-C$_6$)alkyl is independently substituted with a group selected from the group consisting of R$^{13}$, —S(O)$_j$R$^{13}$, and —NR$^{13}$S(O)$_j$R$^{13}$.

In another embodiment, the invention relates to a compound of formula I wherein each R$^1$ is independently selected from the group consisting of —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl; and wherein each of the foregoing —(C$_3$-C$_{10}$)cycloalkyl, —(C$_6$-C$_{10}$)cycloalkenyl, —(C$_2$-C$_9$)heterocycloalkyl and —(C$_4$-C$_9$)heterocycloalkenyl moieties of said R$^1$ is optionally independently substituted by one to three R$^{12}$ groups.

In another embodiment, the invention relates to a compound of formula I wherein R$^1$ is selected from the group consisting of —(C$_2$-C$_9$)heterocycloalkyl; and wherein said (C$_2$-C$_9$)heterocycloalkyl of said R$^1$ is optionally independently substituted by one to three R$^{12}$ groups.

In another embodiment, the invention relates to a compound of formula I wherein each R$^1$ is independently selected from the group consisting of —(C$_6$-C$_{10}$)aryl and —(C$_1$-C$_9$) heteroaryl; and wherein each of the foregoing —(C$_6$-C$_{10}$)aryl and —(C$_1$-C$_9$)heteroaryl of said R$^1$ moieties is optionally independently substituted by one to three R$^{12}$ groups.

In another embodiment, the invention relates to a compound of formula I wherein R$^1$ is —S(O)$_2$NR$^{13}$R$^{14}$.

In one embodiment, the invention relates to a compound of formula I wherein R$^2$ and R$^3$ are each independently selected from the group consisting of —H, -halo, and —OR$^{10}$.

In another embodiment, the invention relates to a compound of formula I wherein R$^2$ and R$^3$ are each independently selected from the group consisting of —H, —(C$_1$-C$_6$)alkyl, —(C$_2$-C$_6$)alkenyl, and —(C$_2$-C$_6$)alkynyl; and wherein each of the foregoing —(C$_1$-C$_6$)alkyl, —(C$_2$-C$_6$)alkenyl, and —(C$_2$-C$_6$)alkynyl moieties of said R$^2$ and R$^3$ is optionally independently substituted by one to three R$^{12}$ groups.

In another embodiment, the invention relates to a compound of formula I wherein R$^2$ and R$^3$ are each independently selected from the group consisting of —H, —(C$_3$-C$_{10}$)cycloalkyl, —(C$_6$-C$_{10}$)cycloalkenyl, —(C$_2$-C$_9$)heterocycloalkyl, and —(C$_4$-C$_9$)heterocycloalkenyl; and wherein each of the foregoing —(C$_3$-C$_{10}$)cycloalkyl, —(C$_5$-C$_{10}$)cycloalkenyl, —(C$_2$-C$_9$)heterocycloalkyl, and —(C$_4$-C$_9$)heterocycloalkenyl moieties of said R$^2$ and R$^3$ is optionally independently substituted by one to three R$^{12}$ groups.

In another embodiment, the invention relates to a compound of formula I wherein R$^2$ and R$^3$ are each independently selected from the group consisting of —H, —(C$_6$-C$_{10}$)aryl and —(C$_1$-C$_9$)heteroaryl; and wherein each of the foregoing —(C$_6$-C$_{10}$)aryl and —(C$_1$-C$_9$)heteroaryl moieties of said R$^2$ and R$^3$ is optionally independently substituted by one to three R$^{12}$ groups.

In one embodiment, the invention relates to a compound of formula I wherein R$^4$ and R$^5$ are each independently selected from the group consisting of —H, —(C$_1$-C$_6$)alkyl, —(C$_2$-C$_6$)alkenyl, and —(C$_2$-C$_6$)alkynyl; and wherein each of the foregoing —(C$_1$-C$_6$)alkyl, —(C$_2$-C$_6$)alkenyl and —(C$_2$-C$_6$)alkynyl moieties of said R$^4$ and R$^5$ is optionally independently substituted by one to three R$^{12}$ groups.

In another embodiment, the invention relates to a compound of formula I wherein $R^4$ and $R^5$ are each independently selected from the group consisting of —H, —($C_1$-$C_6$)alkyl, —($C_3$-$C_{10}$)cycloalkyl, —($C_5$-$C_{10}$)cycloalkenyl, —($C_2$-$C_9$)heterocycloalkyl and —($C_4$-$C_9$)heterocycloalkenyl; and wherein each of the foregoing —($C_1$-$C_6$)alkyl, —($C_3$-$C_{10}$)cycloalkyl, —($C_5$-$C_{10}$)cycloalkenyl, —($C_2$-$C_9$)heterocycloalkyl, and —($C_4$-$C_9$)heterocycloalkenyl moieties of said $R^4$ and $R^5$ is optionally independently substituted by one to three $R^{12}$ groups.

In another embodiment, the invention relates to a compound of formula I wherein $R^4$ and $R^5$ are each independently selected from the group consisting of —H, —($C_1$-$C_6$)alkyl, —($C_6$-$C_{10}$)aryl and —($C_1$-$C_9$)heteroaryl; and wherein each of the foregoing —($C_1$-$C_6$)alkyl, —($C_6$-$C_{10}$)aryl and —($C_1$-$C_9$)heteroaryl moieties of said $R^4$ and $R^5$ is optionally independently substituted by one to three $R^{12}$ groups.

In one embodiment, the invention relates to a compound of formula I wherein the moiety

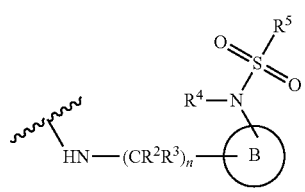

represents a moiety selected from the group consisting of:

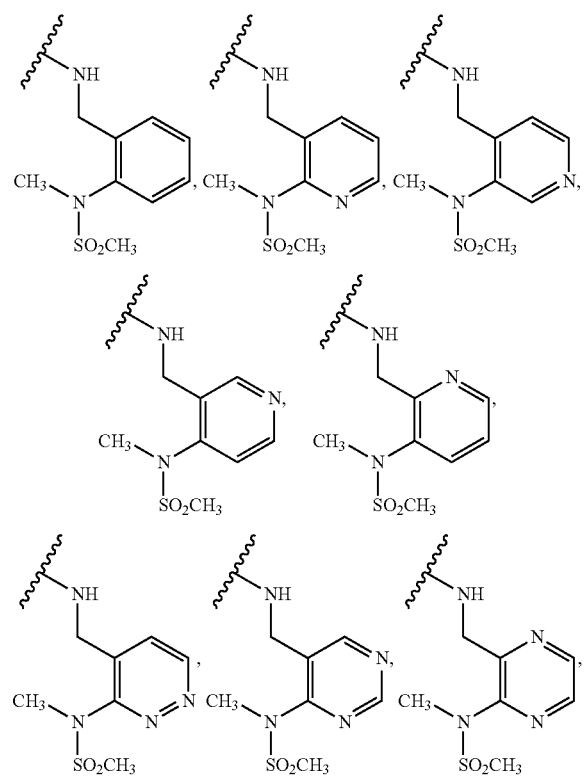

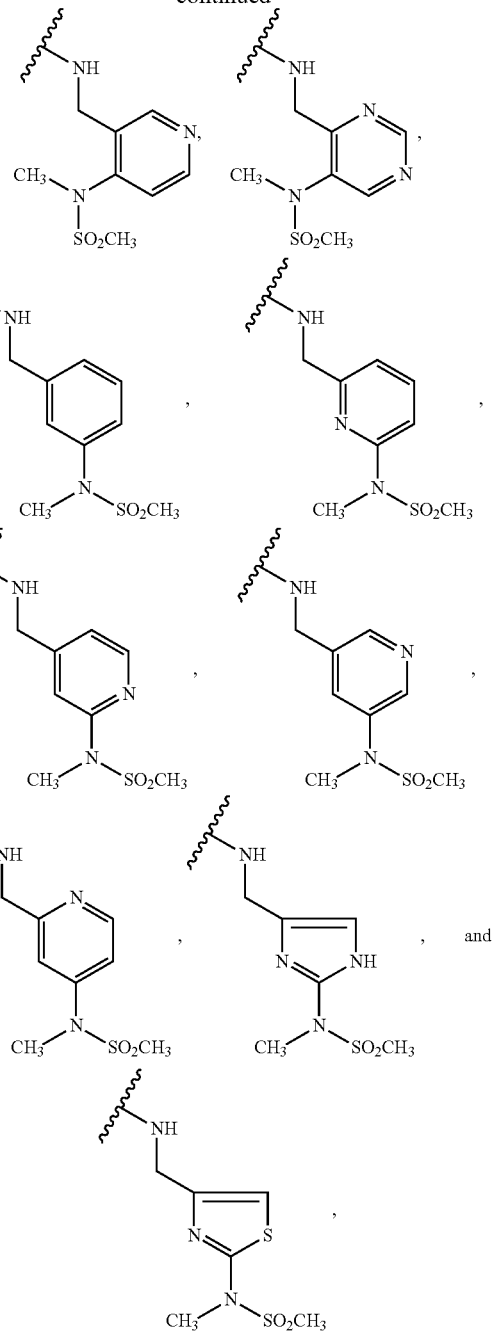

In one embodiment, the invention relates to a compound of formula I wherein $R^6$ is selected from the group consisting of —$NR^7R^8$, —$OR^{10}$, —$C(O)R^9$, —$CO_2R^{10}$, —$CONR^7R^8$, —$S(O)_jR^{11}$, —$NR^7CONR^7R^8$, —$NR^8SO_2R^{11}$ —$NO_2$, —CN and —$CF_3$.

In another embodiment, the invention relates to a compound of formula I wherein $R^6$ is selected from the group consisting of —$CF_3$, —($C_1$-$C_6$)alkyl, —($C_2$-$C_6$)alkenyl, —($C_2$-$C_6$)alkynyl, —($C_2$-$C_6$)perfluorinated alkyl, —($C_2$-$C_6$)perfluorinated alkenyl, and —($C_3$-$C_6$)perfluorinated alkynyl; and wherein each of said —($C_1$-$C_6$)alkyl, —($C_2$-$C_6$)alkenyl, —($C_2$-$C_6$)alkynyl moieties of said $R^6$ is optionally independently substituted by one to three $R^{12}$ groups.

In another embodiment, the invention relates to a compound of formula I wherein $R^6$ is —$CF_3$.

In another embodiment, the invention relates to a compound of formula I wherein $R^6$ is selected from the group consisting of —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, and —$(C_6-C_9)$heterobicycloalkenyl; and wherein each of said —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, and —$(C_6-C_9)$heterobicycloalkenyl moieties of said $R^6$ is optionally independently substituted by one to three $R^{12}$ groups.

In another embodiment, the invention relates to a compound of formula I wherein $R^6$ is selected from the group consisting of —$(C_6-C_{10})$aryl, —$(C_1-C_9)$heteroaryl, —$(C_6-C_{10})$perfluorinated aryl and —$(C_1-C_9)$perfluorinated heteroaryl; and wherein each of said —$(C_6-C_{10})$aryl and —$(C_1-C_9)$heteroaryl moieties of said $R^6$ is optionally independently substituted by one to three $R^{12}$ groups.

In one embodiment, the invention relates to a compound of formula I wherein K is CH.

In another embodiment, the invention relates to a compound of formula I wherein K is $C(NH_2)$.

In another embodiment, the invention relates to a compound of formula I wherein K is N.

In one embodiment, the invention relates to a compound of formula I wherein m is 1.

In another embodiment, the invention relates to a compound of formula I wherein m is 0.

In one embodiment, the invention relates to a compound of formula I wherein n is 1.

In another embodiment, the invention relates to a compound of formula I wherein n is 2.

In another embodiment, the invention relates to a compound of formula I wherein n is 3.

In one embodiment, the invention relates to a compound of formula I wherein K is CH, n is 1, and $R_6$ is —$CF_3$.

In one embodiment, the invention relates to a compound of formula I wherein K is CH, n is 2, and $R_6$ is —$CF_3$.

The present invention also provides a compound of formula Ia:

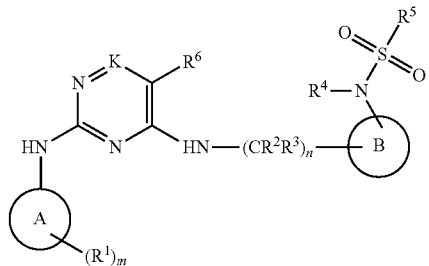

or a pharmaceutically acceptable salt thereof; wherein
A is phenyl;
B is phenyl or a 5- to 6-membered heteroaryl;
K is CH, $C(NH_2)$ or N;
each $R^1$ is independently selected from the group consisting of —H, halo, —$CF_3$, —CN, —$NO_2$, —$NR^7R^8$, —$NR^7C(NR^7R^8)(=CR^9)$, —$CR^7(NR^7R^8)(=NR^7)$, —$NR^7C(NR^7R^8)(=NR^7)$, —$NR^7C(O)R^9$, —$C(O)NR^7R^8$, —$C(O)R^9$, —$C(O)C(O)R^9$, —$C(O)OR^{10}$, —$OC(O)R^9$, —$OR^{10}$, —$OC(O)OR^{10}$, —$S(O)_jR^{11}$, —$S(O)(=NR^7)R^8$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, —$(C_4-C_9)$heterocycloalkenyl, —$(C_6-C_{10})$aryl and —$(C_1-C_9)$heteroaryl moieties of said $R^1$ is optionally independently substituted by one to three $R^{12}$ groups; $R^2$ and $R^3$ are each independently selected from the group consisting of —H, -halo, —$OR^{10}$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, —$(C_4-C_9)$heterocycloalkenyl, —$(C_6-C_{10})$aryl and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, $(C_4-C_9)$heterocycloalkyl, —$(C_6-C_{10})$aryl and —$(C_1-C_9)$heteroaryl moieties of said $R^2$ and $R^3$ is optionally substituted by one to three $R^{12}$ groups; $R^4$ and $R^5$ are each independently selected from the group consisting of —H, —$NR^7R^8$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, —$(C_4-C_9)$heterocycloalkenyl, —$(C_6-C_{10})$aryl and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, —$(C_4-C_9)$heterocycloalkenyl, —$(C_6-C_{10})$aryl and —$(C_1-C_9)$heteroaryl moieties of said $R^4$ and $R^5$ is optionally substituted by one to three $R^{12}$ groups; $R^6$ is selected from the group consisting of -halo, —$NR^7R^8$, —$OR^{10}$, —$C(O)R^9$, —$CO_2R^{10}$, —$CONR^7R^8$, —$S(O)_jR^{11}$, —$NR^7CONR^7R^8$, and —$NR^8SO_2R^{11}$, —$NO_2$, —CN, —$CF_3$, —$(C_1-C_6)$alkyl, —$(C_2-C_6)$alkenyl, —$(C_2-C_6)$alkynyl, —$(C_2-C_6)$perfluorinated alkyl, —$(C_2-C_6)$perfluorinated alkenyl, —$(C_3-C_6)$perfluorinated alkynyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, —$(C_6-C_9)$heterobicycloalkenyl, —$(C_6-C_{10})$aryl, —$(C_1-C_9)$heteroaryl, —$(C_6-C_{10})$perfluorinated aryl, and —$(C_1-C_9)$perfluorinated heteroaryl; and wherein each of said —$(C_1-C_6)$alkyl, —$(C_2-C_6)$alkenyl, —$(C_2-C_6)$alkynyl, —$(C_3-C_7)$cycloalkyl, —$(C_5-C_{10})$cycloalkenyl, —$(C_6-C_{10})$bicycloalkyl, —$(C_6-C_{10})$bicycloalkenyl, —$(C_1-C_9)$heterocyclyl, —$(C_1-C_{10})$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl moieties of said $R^6$ is optionally substituted by one to three $R^{12}$ groups;

$R^7$ and $R^8$ are each independently selected from the group consisting of —H, —$OR^{10}$, —$S(O)_jR^{11}$, —$NO_2$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl —$(C_6-C_{10})$aryl, and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, $(C_4-C_9)$heterocycloalkyl, —$(C_6-C_{10})$aryl and —$(C_1-C_9)$heteroaryl moieties of said $R^7$ and $R^8$ is optionally substituted by one to three $R^{12}$ groups;

each $R^9$ is independently selected from the group consisting of —H, -halo, —$NR^{13}R^{14}$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$ bicycloalkenyl, —($C_2$-$C_9$)heterocycloalkyl, —($C_4$-$C_9$) heterocycloalkenyl, —($C_6$-$C_9$)heterobicycloalkyl, —($C_6$-$C_9$) heterobicycloalkenyl —($C_6$-$C_{10}$)aryl, and —($C_1$-$C_9$) heteroaryl; and wherein each of the foregoing —($C_1$-$C_6$) alkyl, —($C_2$-$C_6$)alkenyl, —($C_2$-$C_6$)alkynyl, —($C_3$-$C_9$) cycloalkyl, —($C_5$-$C_{10}$)cycloalkenyl, —($C_2$-$C_9$) heterocycloalkyl, ($C_4$-$C_9$)heterocycloalkenyl, —($C_6$-$C_{10}$) aryl and —($C_1$-$C_9$)heteroaryl moieties of said $R^9$ is optionally substituted by one to three $R^{12}$ groups;

each $R^{10}$ is independently selected from the group consisting of —H, —($C_1$-$C_6$)alkyl, —($C_2$-$C_6$)alkenyl, —($C_2$-$C_6$) alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_2$-$C_9$)heterobicycloalkenyl —($C_4$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{10}$)aryl and —($C_1$-$C_9$)heteroaryl moieties of said $R^{10}$ is optionally substituted by one to three $R^{12}$ groups;

each $R^{11}$ is independently selected from the group consisting of —H, —$NR^{13}R^{14}$, —C(O)$R^{13}$, —$CF_3$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$) heterocycloalkenyl,—($C_6$-$C_9$)heterobicycloalkyl,—($C_6$-$C_9$) heterobicycloalkenyl —($C_6$-$C_{10}$)aryl, and —($C_1$-$C_9$) heteroaryl; land wherein each of the foregoing —($C_1$-$C_6$) alkyl, —($C_2$-$C_6$)alkenyl, —($C_2$-$C_6$)alkynyl, —($C_3$-$C_{10}$) cycloalkyl, —($C_5$-$C_{10}$)cycloalkenyl, —($C_2$-$C_9$) heterocycloalkyl, ($C_4$-$C_9$)heterocycloalkenyl, —($C_6$-$C_{10}$) aryl and —($C_1$-$C_9$)heteroaryl moieties of said $R^{11}$ is optionally substituted by one to three $R^{12}$ groups;

each $R^{12}$ is independently selected from the group consisting of —H, —$OR^{13}$, —C(O)$R^{13}$, —C(O)O$R^{13}$, —OC(O) $R^{13}$, —OC(O)O$R^{13}$, —C(O)$NR^{13}R^{14}$, —$NR^{13}$C(O) $NR^{13}R^{14}$, —$NR^{13}R^{14}$, —$NR^{13}$C($NR^{13}R^{14}$)(=$NR^{13}$), —$NR^{13}$C($NR^{13}R^{14}$)(=N—C(O)$R^{13}$), —$NR^{13}$C(O)$R^{14}$, —$NR^{13}$S(O)$_j$$R^{13}$, —S(O)$_j$$R^{13}$, —$CF_3$, —CN, —($C_1$-$C_6$) alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$) heterocycloalkenyl,—($C_6$-$C_9$)heterobicycloalkyl,—($C_6$-$C_9$) heterobicycloalkenyl, —($C_6$-$C_{10}$)aryl, and —($C_1$-$C_9$) heteroaryl of said $R^{12}$ is optionally independently substituted by one to three groups selected from the group consisting of -halo, —$CF_3$, —CN, —$NO_2$, —OH, —O(($C_1$-$C_6$)alkyl), —C(O)$R^{15}$, —C(O)$NR^{15}R^{16}$, —S(O)$_j$$R^{15}$, and —S(O)$_j$ $NR^{15}R^{16}$, —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$) alkyl) and —N(($C_1$-$C_6$)alkyl)$_2$;

$R^{13}$ and $R^{14}$ are each independently selected from the group consisting of —H, —$NR^{15}$C(O)$R^{16}$, —$CF_3$, —CN, —S(O)$_j$$R^{15}$, —($C_1$-$C_6$)alkyl, —($C_2$-$C_6$)alkenyl, —($C_2$-$C_6$) alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-

$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl of said $R^{13}$ and $R^{14}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

$R^{15}$ and $R^{16}$ are each independently selected from the group consisting of —H, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$) heterobicycloalkenyl, —($C_6$-$C_{10}$)aryl, and —($C_1$-$C_9$) heteroaryl; and wherein each of the foregoing —($C_1$-$C_6$) alkyl, —($C_2$-$C_6$)alkenyl, —($C_2$-$C_6$)alkynyl, —($C_3$-$C_{10}$) cycloalkyl, —($C_5$-$C_{10}$)cycloalkenyl, —($C_6$-$C_{10}$) bicycloalkyl, —($C_6$-$C_{10}$)bicycloalkenyl, —($C_6$-$C_9$) heterocycloalkyl, —($C_4$-$C_9$)heterocycloalkenyl, —($C_6$-$C_9$) heterobicycloalkyl, —($C_6$-$C_9$)heterobicycloalkenyl, —($C_6$-$C_{10}$)aryl, and —($C_1$-$C_9$)heteroaryl of said $R^{15}$ and $R^{16}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

wherein one or two carbon ring atoms in each of the aforementioned —($C_1$-$C_6$)alkyl, —($C_2$-$C_6$)alkenyl, —($C_2$-$C_6$) alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl and —($C_2$-$C_9$)heterobicycloalkenyl in said $R^1$-$R^{14}$ groups may optionally and independently be replaced with —C(O)— or —C(S)—;

wherein two groups attached to the same tetravalent carbon atom in each of the aforementioned —($C_1$-$C_6$)alkyl, —($C_2$-$C_6$)alkenyl, —($C_2$-$C_6$)alkynyl, —($C_3$-$C_{10}$cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$) heterocycloalkenyl, —($C_6$-$C_9$)heterobicycloalkyl and —($C_6$-$C_9$)heterobicycloalkeny of said $R^1$ to $R^{14}$ groups may optionally join to form a ring system selected from the group consisting of a —($C_3$-$C_{10}$)cycloalkyl, —($C_5$-$C_{10}$)cycloalkenyl, —($C_2$-$C_9$)heterocycloalkyl, and —($C_4$-$C_9$)heterocycloalkenyl; and wherein j is an integer from 0 to 2;
n is an integer from 1 to 3; and
m is an integer from 0 to 3.

In another embodiment, the invention relates to a compound of formula Ia wherein at least one $R^1$ is —C(O)O$R^{10}$.

In another embodiment, the invention relates to a compound of formula Ia wherein at least one $R^1$ is —C(O)O$R^{10}$ and $R^{10}$ is —($C_1$-$C_6$)alkyl optionally substituted by one to three $R^{12}$ groups.

In another embodiment, the invention relates to a compound of formula Ia wherein at least one $R^1$ is —C(O)$R^9$.

In another embodiment, the invention relates to a compound of formula Ia wherein at least one $R^1$ is —C(O)$R^9$ and $R^9$ is selected from the group consisting of —$NR^{13}R^{14}$, —($C_1$-$C_6$)alkyl and —($C_3$-$C_{10}$)cycloalkyl; wherein each of said —($C_1$-$C_6$)alkyl, and —($C_3$-$C_{10}$)cycloalkyl of said $R^9$ group is optionally substituted by one to three $R^{12}$ groups; and wherein two groups attached to the same tetravalent carbon atom of said —($C_1$-$C_6$)alkyl and —($C_3$-$C_{10}$)cycloalkyl of said $R^9$ may optionally join to form a ring system selected from the group consisting of a —($C_3$-$C_{10}$)cycloalkyl, —($C_5$-$C_{10}$)cycloalkenyl, —($C_2$-$C_9$)heterocycloalkyl, and —($C_4$-$C_9$)heterocycloalkenyl.

In another embodiment, the invention relates to a compound of formula Ia wherein at least one $R^1$ is —C(O)$R^9$ and $R^9$ is —($C_1$-$C_6$)alkyl optionally substituted by a group selected from the group consisting of —NR$^{13}$R$^{14}$, —NR$^{15}$C(O)R$^{16}$ and —CF$_3$.

In another embodiment, the invention relates to a compound of formula Ia wherein at least one $R^1$ is —C(O)$R^9$ and $R^9$ is —NR$^{13}$R$^{14}$.

In another embodiment, the invention relates to a compound of formula Ia wherein at least one $R^1$ is —C(O)$R^9$, $R^9$ is —NR$^{13}$R$^{14}$, and R$^{13}$ and R$^{14}$ are each independently selected from the group consisting of —H and —($C_1$-$C_6$)alkyl; and wherein said —($C_1$-$C_6$)alkyl of said R$^{13}$ and R$^{14}$ groups is optionally independently substituted with one to three groups selected from the group consisting of -halo, —CF$_3$, —CN, —NO$_2$, —OH, —O(($C_1$-$C_6$)alkyl), —C(O)(($C_1$-$C_6$)alkyl), —($C_3$-$C_{10}$cycloalkyl, —($C_2$-$C_9$)heterocycloalkyl, —SH, —S(($C_1$-$C_6$)alkyl), —NH$_2$, —NH(($C_1$-$C_6$)alkyl) and —N(($C_1$-$C_6$)alkyl)$_2$.

In another embodiment, the invention relates to a compound of formula Ia wherein at least one $R^1$ is —C(O)$R^9$, $R^9$ is —NR$^{13}$R$^{14}$, and R$^{13}$ and R$^{14}$ are each independently selected from the group consisting —H and —($C_1$-$C_6$)alkyl; wherein said —($C_1$-$C_6$)alkyl of said R$^{13}$ and R$^{14}$ are each optionally independently substituted with one to three groups selected from the group consisting of —($C_3$-$C_{10}$)cycloalkyl, —($C_2$-$C_9$)heterocycloalkyl, —($C_6$-$C_{10}$)aryl, and —($C_1$-$C_9$)heteroaryl; and wherein each of said —($C_3$-$C_{10}$)cycloalkyl, —($C_2$-$C_9$)heterocycloalkyl, —($C_6$-$C_{10}$)aryl, and —($C_1$-$C_9$)heteroaryl optional substituents of said —($C_1$-$C_6$)alkyl of said R$^{13}$ and R$^{14}$ is optionally independently substituted by one to three groups selected from the group consisting of -halo, —CF$_3$, —CN, —NO$_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —NH$_2$, —NH(($C_1$-$C_6$)alkyl) and —N(($C_1$-$C_6$)alkyl)$_2$.

In another embodiment, the invention relates to a compound of formula Ia wherein m is 1.

The present invention also provides a compound of formula Ib:

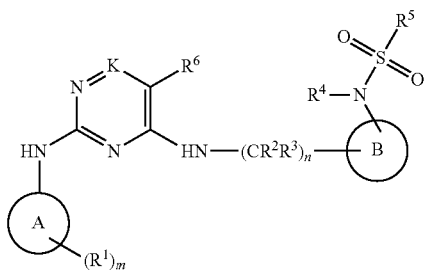

or a pharmaceutically acceptable salt thereof; wherein
A is phenyl;
B is phenyl or a 5- to 6-membered heteroaryl;
K is CH, C(NH$_2$) or N;
at least one $R^1$ is —($C_1$-$C_6$)alkyl optionally independently substituted by one to three R$^{12}$ groups; $R^2$ and $R^3$ are each independently selected from the group consisting of —H, -halo, —OR$^{10}$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{70}$)aryl and —($C_1$-$C_9$)heteroaryl moieties of said $R^2$ and $R^3$ is optionally substituted by one to three R$^{12}$ groups;

$R^4$ and $R^5$ are each independently selected from the group consisting of —H, —NR$^7$R$^8$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl moieties of said $R^4$ and $R^5$ is optionally substituted by one to three R$^{12}$ groups;

R$^6$ is selected from the group consisting of -halo, —NR$^7$R$^8$, —OR$^{10}$, —C(O)R$^9$, —CO$_2$R$^{10}$, —CONR$^7$R$^8$, —S(O)$_j$R$^{11}$, —NR$^7$CONR$^7$R$^8$, and —NR$^8$SO$_2$R$^{11}$, —NO$_2$, —CN, —CF$_3$, —($C_1$-$C_6$)alkyl, —($C_2$-$C_6$)alkenyl, —($C_2$-$C_6$)alkynyl, —($C_2$-$C_6$)perfluorinated alkyl, —($C_2$-$C_6$)perfluorinated alkenyl, —($C_3$-$C_6$)perfluorinated alkynyl, —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_1$-$C_9$)heterocyclyl, —($C_1$-$C_{10}$)heterocycloalkenyl, —($C_6$-$C_9$)heterobicycloalkyl, —($C_6$-$C_9$)heterobicycloalkenyl, —($C_6$-$C_{10}$)aryl, —($C_1$-$C_9$)heteroaryl, —($C_6$-$C_{10}$)perfluorinated aryl, and —($C_1$-$C_9$)perfluorinated heteroaryl; and wherein each of said —($C_1$-$C_6$)alkyl, —($C_2$-$C_6$)alkenyl, —($C_2$-$C_6$)alkynyl, —($C_3$-$C_7$)cycloalkyl, —($C_5$-$C_{10}$)cycloalkenyl, —($C_6$-$C_{10}$)bicycloalkyl, —($C_6$-$C_{10}$)bicycloalkenyl, —($C_1$-$C_9$)heterocyclyl, —($C_1$-$C_{10}$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl moieties of said R$^6$ is optionally substituted by one to three R$^{12}$ groups;

R$^7$ and R$^8$ are each independently selected from the group consisting of —H, —OR$^{10}$, —S(O)$_j$R$^{11}$, —NO$_2$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{10}$)aryl and —($C_1$-$C_9$)heteroaryl moieties of said R$^7$ and R$^8$ is optionally substituted by one to three R$^{12}$ groups;

each R$^9$ is independently selected from the group consisting of —H, -halo, —NR$^{13}$R$^{14}$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, ($C_4$-$C_9$)heterocycloalkenyl, —($C_6$-$C_3$)heterobicycloalkyl, —($C_6$-$C_3$)heterobicycloalkenyl —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_3$)heterocycloalkenyl, —($C_6$-$C_{10}$)aryl and —($C_1$-$C_9$)heteroaryl moieties of said R$^9$ is optionally substituted by one to three R$^{12}$ groups;

each $R^{10}$ is independently selected from the group consisting of —H, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl —$(C_6-C_{10})$aryl, and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, $(C_4-C_9)$heterocycloalkenyl, —$(C_6-C_{10})$aryl and —$(C_1-C_9)$heteroaryl moieties of said $R^{10}$ is optionally substituted by one to three $R^{12}$ groups;

each $R^{11}$ is independently selected from the group consisting of —H, —$NR^{13}R^{14}$, —$C(O)R^{13}$, —$CF_3$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl —$(C_6-C_{10})$aryl, and —$(C_1-C_9)$heteroaryl; land wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_2-C_9)$heterocycloalkyl, $(C_4-C_9)$heterocycloalkenyl, —$(C_6-C_{10})$aryl and —$(C_1-C_9)$heteroaryl moieties of said $R^{11}$ is optionally substituted by one to three $R^{12}$ groups;

each $R^{12}$ is independently selected from the group consisting of —H, —$OR^{13}$, —$C(O)R^{13}$, —$C(O)OR^{13}$, —$OC(O)R^{13}$, —$OC(O)OR^{13}$, —$C(O)NR^{13}R^{14}$, —$NR^{13}C(O)NR^{13}R^{14}$, —$NR^{13}R^{14}$, —$NR^{13}C(NR^{13}R^{14})(=NR^{13})$, —$NR^{13}C(NR^{13}R^{14})(=N-C(O)R^{13})$, —$NR^{13}C(O)R^{14}$, —$NR^{13}S(O)_jR^{13}$, —$S(O)_jR^{13}$, —$CF_3$, —CN, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl; wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_3)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_3)$heteroaryl of said $R^{12}$ is optionally independently substituted by one to three groups selected from the group consisting of -halo, —$CF_3$, —CN, —$NO_2$, —OH, —$O((C_1-C_6)$alkyl), —$C(O)R^{15}$, —$C(O)NR^{15}R^{16}$, —$S(O)_jR^{15}$, and —$S(O)_jNR^{15}R^{16}$, —$(C_3-C_{10})$cycloalkyl, —$(C_2-C_9)$heterocycloalkyl, —SH, —$S((C_1-C_6)$alkyl), —$NH_2$, —$NH((C_1-C_6)$alkyl) and —$N((C_1-C_6)$alkyl)$_2$;

$R^{13}$ and $R^{14}$ are each independently selected from the group consisting of —H, —$NR^{15}C(O)R^{16}$, —$CF_3$, —CN, —$S(O)_jR^{15}$, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl of said $R^{13}$ and $R^{14}$ is optionally independently substituted by one to three groups selected from the group consisting of -halo, —$CF_3$, —CN, —$NO_2$, —OH, —$O((C_1-C_6)$alkyl), —$C(O)((C_1-C_6)$alkyl), —$(C_3-C_{10})$cycloalkyl, —$(C_2-C_9)$heterocycloalkyl, —SH, —$S((C_1-C_6)$alkyl), —$NH_2$, —$NH((C_1-C_6)$alkyl) and —$N((C_1-C_6)$alkyl)$_2$;

$R^{15}$ and $R^{16}$ are each independently selected from the group consisting of —H, —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl; and wherein each of the foregoing —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl, —$(C_6-C_9)$heterobicycloalkenyl, —$(C_6-C_{10})$aryl, and —$(C_1-C_9)$heteroaryl of said $R^{15}$ and $R^{16}$ is optionally independently substituted by one to three groups selected from the group consisting of -halo, —$CF_3$, —CN, —$NO_2$, —OH, —$O((C_1-C_6)$alkyl), —$C(O)((C_1-C_6)$alkyl), —$(C_3-C_{10})$cycloalkyl, —$(C_2-C_9)$heterocycloalkyl, —SH, —$S((C_1-C_6)$alkyl), —$NH_2$, —$NH((C_1-C_6)$alkyl) and —$N((C_1-C_6)$alkyl)$_2$;

wherein one or two carbon ring atoms in each of the aforementioned —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl and —$(C_6-C_9)$heterobicycloalkenyl in said $R^1$-$R^{14}$ groups may optionally and independently be replaced with —C(O)— or —C(S)—;

wherein two groups attached to the same tetravalent carbon atom in each of the aforementioned —$(C_1-C_6)$alkyl, —$(C_2-C_6)$alkenyl, —$(C_2-C_6)$alkynyl, —$(C_3-C_{10})$cycloalkyl, —$(C_5-C_{10})$cycloalkenyl, —$(C_6-C_{10})$bicycloalkyl, —$(C_6-C_{10})$bicycloalkenyl, —$(C_2-C_9)$heterocycloalkyl, —$(C_4-C_9)$heterocycloalkenyl, —$(C_6-C_9)$heterobicycloalkyl and —$(C_6-C_9)$heterobicycloalkeny of said $R^1$ to $R^{14}$ groups may optionally join to form a ring system selected from the group consisting of a —$(C_3-C_{10})$cycloalkyl, —$(C_5-C_{10})$cycloalkenyl, —$(C_2-C_9)$heterocycloalkyl, and —$(C_4-C_9)$heterocycloalkenyl; and wherein j is an integer from 0 to 2;

n is an integer from 1 to 3; and m is an integer from 0 to 3.

In another embodiment, the invention relates to a compound of formula Ia or 1b wherein $R^2$ and $R^3$ are each independently selected from the group consisting of —H, -halo, and —$OR^{10}$.

In another embodiment, the invention relates to a compound of formula Ia or 1b wherein $R^4$ and $R^5$ are each independently selected from the group consisting of —H, —$(C_1-C_6)$alkyl, —$(C_2-C_6)$alkenyl, and —$(C_2-C_6)$alkynyl; and wherein each of the foregoing —$(C_1-C_6)$alkyl, —$(C_2-C_6)$alkenyl and —$(C_2-C_6)$alkynyl moieties of said $R^4$ and $R^5$ is optionally independently substituted by one to three $R^{12}$ groups.

In another embodiment, the invention relates to a compound of formula Ia or 1b wherein $R^6$ is —$CF_3$.

In another embodiment, the invention relates to a compound of formula Ia or 1b wherein K is CH.

In another embodiment, the invention relates to a compound of formula Ia or 1b wherein m is 1.

In another embodiment, the invention relates to a compound of formula Ia or 1b wherein n is 1.

The present invention provides a compound of formula Ic:

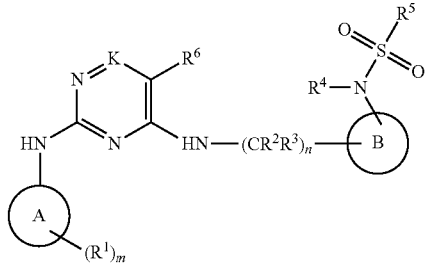

or a pharmaceutically acceptable salt thereof; wherein the moiety

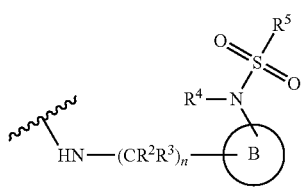

represents a moiety selected from the group consisting of:

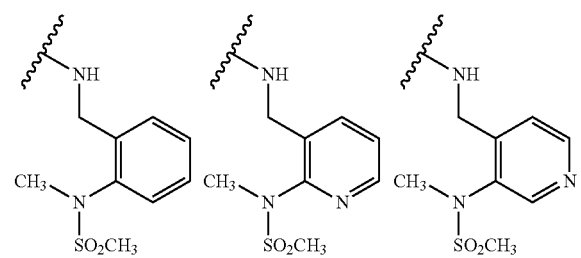

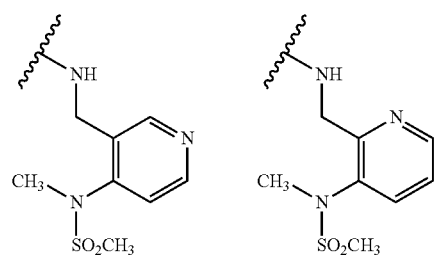

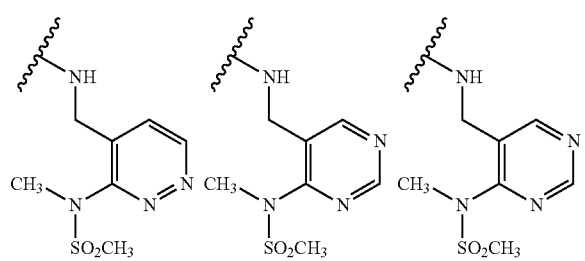

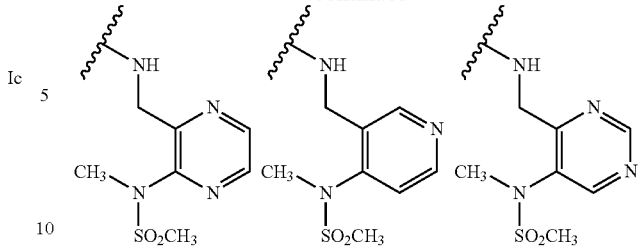

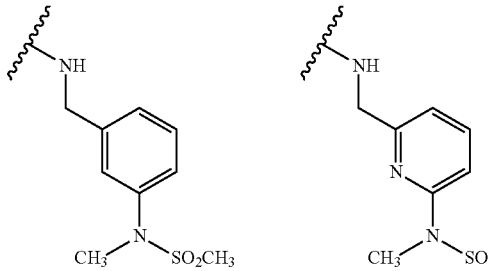

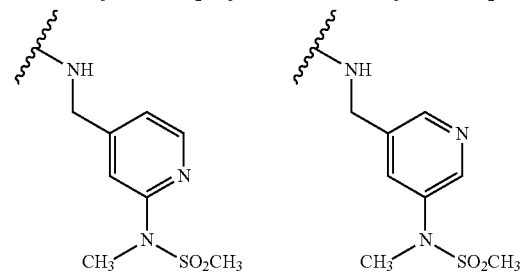

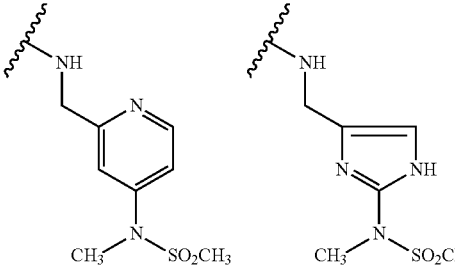

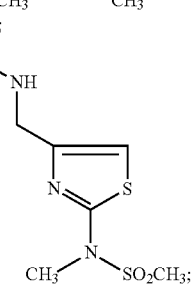

A is a ring moiety selected from the group consisting of a:
(a) 4- to 7-membered carbocyclyl,
(b) 4- to 7-membered heterocyclyl,
(c) phenyl, and
(d) 5- to 6-membered heteroaryl ring,
wherein each of said 4- to 7-membered carbocyclyl and 4- to 7-membered heterocyclyl of said A group may optionally contain one or two olefinic bonds; and wherein one or two carbon ring atoms in each of said 4- to 7-membered carbocyclyl and 4- to 7-membered heterocyclic of said A group may independently optionally be replaced with one or two moieties independently selected from the group consisting of —C(O)—, —C(S)— and —C(=NR$^4$)—;
K is CH, C(NH$_2$) or N;

each $R^1$ is independently selected from the group consisting of —H, halo, —CN, —NO$_2$, —NR$^7$R$^8$, —NR$^7$C(NR$^7$R$^8$)(=CR$^9$), —CR$^7$(NR$^7$R$^8$)(=NR$^7$), —NR$^7$C(NR$^7$R$^8$)(=NR$^7$), —NR$^7$C(O)R$^9$, —C(O)NR$^7$R$^8$, —C(O)R$^9$, —C(O)C(O)R$^9$, —C(O)OR$^{10}$, —OC(O)R$^9$, —OR$^{10}$, —OC(O)OR$^{10}$, —S(O)$_j$R$^{11}$, —S(O)(=NR$^7$)R$^8$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl moieties of said R$^1$ is optionally independently substituted by one to three R$^{12}$ groups; R$^6$ is selected from the group consisting of -halo, —NR$^7$R$^8$, —OR$^{10}$, —C(O)R$^9$, —CO$_2$R$^{10}$, —CONR$^7$R$^8$, —S(O)$_j$R$^{11}$, —NR$^7$CONR$^7$R$^8$, and —NR$^8$SO$_2$R$^{11}$, —NO$_2$, —CN, —CF$_3$, —(C$_1$-C$_6$)alkyl, —(C$_2$-C$_6$)alkenyl, —(C$_2$-C$_6$)alkynyl, —(C$_2$-C$_6$)perfluorinated alkyl, —(C$_2$-C$_6$)perfluorinated alkenyl, —(C$_3$-C$_6$)perfluorinated alkynyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_1$-C$_9$)heterocyclyl, —(C$_1$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, —(C$_1$-C$_9$)heteroaryl, —(C$_6$-C$_{10}$)perfluorinated aryl, and —(C$_1$-C$_9$)perfluorinated heteroaryl; and wherein each of said —(C$_1$-C$_6$)alkyl, —(C$_2$-C$_6$)alkenyl, —(C$_2$-C$_6$)alkynyl, —(C$_3$-C$_7$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_1$-C$_9$)heterocyclyl, —(C$_1$-C$_{10}$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl moieties of said R$^6$ is optionally substituted by one to three R$^{12}$ groups;

R$^7$ and R$^8$ are each independently selected from the group consisting of —H, —OR$^{10}$, —S(O)$_j$R$^{11}$, —NO$_2$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl moieties of said R$^7$ and R$^8$ is optionally substituted by one to three R$^{12}$ groups;

each R$^9$ is independently selected from the group consisting of —H, -halo, —NR$^{13}$R$^{14}$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, (C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^9$ is optionally substituted by one to three R$^{12}$ groups;

each R$^{10}$ is independently selected from the group consisting of —H, —(C$_1$-C$_6$)alkyl, —(C$_2$-C$_6$)alkenyl, —(C$_2$-C$_6$)alkynyl, —(C$_3$-C$_{10}$)cycloalkyl, —(C$_3$-C$_{10}$)cycloalkenyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{10}$ is optionally substituted by one to three R$^{12}$ groups;

each R$^{11}$ is independently selected from the group consisting of —H, —NR$^{13}$R$^{14}$, —C(O)R$^{13}$, —CF$_3$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; land wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{11}$ is optionally substituted by one to three R$^{12}$ groups;

each R$^{12}$ is independently selected from the group consisting of —H, —OR$^{13}$, —C(O)R$^{13}$, —C(O)OR$^{13}$, —OC(O)R$^{13}$, —OC(O)OR$^{13}$, —C(O)NR$^{13}$R$^{14}$, —NR$^{13}$C(O)NR$^{13}$R$^{14}$, —NR$^{13}$R$^{14}$, —NR$^{13}$C(NR$^{13}$R$^{14}$)(=NR$^{13}$), —NR$^{13}$C(NR$^{13}$R$^{14}$)(=N—C(O)R$^{13}$), —NR$^{13}$C(O)R$^{14}$, —NR$^{13}$S(O)$_j$R$^{13}$, —S(O)$_j$R$^{13}$, —CF$_3$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{12}$ is optionally independently substituted by one to three groups selected from the group consisting of -halo, —CF$_3$, —CN, —NO$_2$, —OH, —O((C$_1$-C$_6$)alkyl), —C(O)R$^{15}$, —C(O)NR$^{15}$R$^{16}$, —S(O)$_j$R$^{15}$, and —S(O)$_j$NR$^{15}$R$^{16}$, —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

R$^{13}$ and R$^{14}$ are each independently selected from the group consisting of —H, —NR$^{15}$C(O)R$^{16}$, —CF$_3$, —CN, —S(O)$_j$R$^{16}$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{13}$ and R$^{14}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

R$^{15}$ and R$^{16}$ are each independently selected from the group consisting of —H, —(C$_1$-C$_6$)alkyl, —(C$_2$-C$_6$)alkenyl, —(C$_2$-C$_6$)alkynyl, —(C$_3$-C$_{10}$)cycloalkyl, —(C$_6$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{15}$ and R$^{16}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

wherein one or two carbon ring atoms in each of the aforementioned —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl in said R$^1$ and R$^6$-R$^{14}$ groups may optionally and independently be replaced with —C(O)— or —C(S)—;

wherein two groups attached to the same tetravalent carbon atom in each of the aforementioned —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl of said R$^1$ and R$^6$-R$^{14}$ groups may optionally join to form a ring system selected from the group consisting of a —(C$_3$-C$_{10}$)cycloalkyl, —(C$_5$-C$_{10}$)cycloalkenyl, —(C$_2$-C$_9$)heterocycloalkyl, and —(C$_4$-C$_9$)heterocycloalkenyl; and wherein j is an integer from 0 to 2; and
m is an integer from 0 to 3.

The present invention also provides a compound of formula Id:

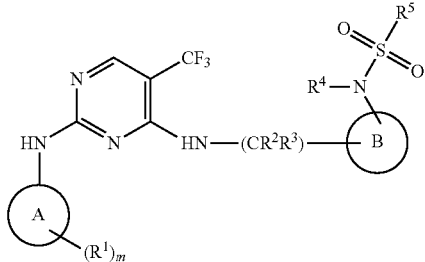

or a pharmaceutically acceptable salt thereof; wherein

A is phenyl or a 5- to 6-membered heteroaryl;

B is selected from the group consisting of phenyl, pyridyl, pyrimidinyl and pyrazinyl;

each R$^1$ is independently selected from the group consisting of —H, halo, —CF$_3$, —CN, —C(O)NR$^7$R$^8$, —C(O)R$^9$, —OR$^{10}$, and —(C$_1$-C$_6$)alkyl; and wherein the —(C$_1$-C$_6$)alkyl moiety of said R$^1$ is optionally independently substituted by one to three R$^{12}$ groups;

R$^2$ and R$^3$ are each independently selected from the group consisting of —H and —(C$_1$-C$_6$)alkyl;

R$^4$ and R$^5$ are each independently selected from the group consisting of —H and —(C$_1$-C$_6$)alkyl;

R$^7$ and R$^8$ are each independently selected from the group consisting of —H, —OR$^{10}$, —S(O)$_j$R$^{11}$, —NO$_2$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^7$ and R$^8$ is optionally substituted by one to three R$^{12}$ groups;

each R$^9$ is independently selected from the group consisting of —H, -halo, —NR$^{13}$NR$^{14}$, (C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_6$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^9$ is optionally substituted by one to three R$^{12}$ groups;

each R$^{10}$ is independently selected from the group consisting of —H, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{10}$ is optionally substituted by one to three R$^{12}$ groups;

each R$^{11}$ is independently selected from the group consisting of —H, —NR$^{13}$R$^{14}$, —C(O)R$^{13}$, —CF$_3$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; land wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{11}$ is optionally substituted by one to three R$^{12}$ groups;

each R$^{12}$ is independently selected from the group consisting of —H, —OR$^{13}$, —C(O)R$^{13}$, —C(O)OR$^{13}$, —OC(O)R$^{13}$, —OC(O)OR$^{13}$, —C(O)NR$^{13}$R$^{14}$, —NR$^{13}$C(O)NR$^{13}$R$^{14}$, —NR$^{13}$R$^{14}$, —NR$^{13}$C(NR$^{13}$R$^{14}$)(=NR$^{13}$), —NR$^{13}$C(NR$^{13}$R$^{14}$)(=N—C(O)R$^{13}$), —NR$^{13}$C(O)R$^{14}$, —NR$^{13}$S(O)$_j$R$^{13}$, —S(O)$_j$R$^{13}$, —CF$_3$, —CN, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-

$C_{10}$)bicycloalkenyl, —($C_2$-$C_9$)heterocycloalkyl, —($C_4$-$C_9$) heterocycloalkenyl, —($C_6$-$C_9$)heterobicycloalkyl, —($C_6$-$C_9$) heterobicycloalkenyl, —($C_6$-$C_{10}$)aryl, and —($C_1$-$C_9$) heteroaryl of said $R^{12}$ is optionally independently substituted by one to three groups selected from the group consisting of -halo, —$CF_3$, —CN, —$NO_2$, —OH, —O(($C_1$-$C_6$)alkyl), —C(O)$R^{15}$, —C(O)N$R^{15}R^{16}$, —S(O)$_j R^{16}$, and —S(O)$_j$ N$R^{15}R^{16}$, —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$) alkyl) and —N(($C_1$-$C_6$)alkyl)$_2$;

$R^{13}$ and $R^{14}$ are each independently selected from the group consisting of —H, —N$R^{15}$C(O)$R^{16}$, —$CF_3$, —CN, —S(O)$_j R^{15}$, —($C_1$-$C_6$)alkyl, —($C_2$-$C_6$)alkenyl, —($C_2$-$C_6$) alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl of said $R^{13}$ and $R^{14}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

$R^{15}$ and $R^{16}$ are each independently selected from the group consisting of —H, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$) heterobicycloalkenyl, —($C_6$-$C_{10}$)aryl, and —($C_1$-$C_9$) heteroaryl; and wherein each of the foregoing —($C_1$-$C_6$) alkyl, —($C_2$-$C_6$)alkenyl, —($C_2$-$C_6$)alkynyl, —($C_3$-$C_{10}$) cycloalkyl, —($C_5$-$C_{10}$)cycloalkenyl, —($C_6$-$C_{10}$) bicycloalkyl, —($C_6$-$C_{10}$)bicycloalkenyl, —($C_2$-$C_9$) heterocycloalkyl, —($C_4$-$C_9$)heterocycloalkenyl, —($C_6$-$C_9$) heterobicycloalkyl, —($C_6$-$C_9$)heterobicycloalkenyl, —($C_6$-$C_{10}$)aryl, and —($C_1$-$C_9$)heteroaryl of said $R^{15}$ and $R^{16}$ is optionally independently substituted by one to three groups selected from the group consisting of -halo, —$CF_3$, —CN, —$NO_2$, —OH, —O(($C_1$-$C_6$)alkyl), —C(O)(($C_1$-$C_6$)alkyl), —($C_3$-$C_{10}$)cycloalkyl, —($C_2$-$C_9$)heterocycloalkyl, —SH, —S(($C_1$-$C_6$)alkyl), —$NH_2$, —NH(($C_1$-$C_6$)alkyl) and —N(($C_1$-$C_6$)alkyl)$_2$;

j is an integer from 0 to 2; and
m is an integer from 1 to 3.

In another embodiment, the invention relates to a compound of formula Id wherein A is a phenyl.

In another embodiment, the invention relates to a compound of formula Id wherein the moiety

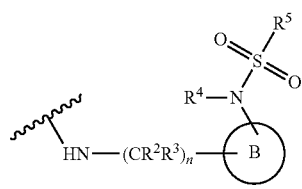

represents a moiety selected from the group consisting of:

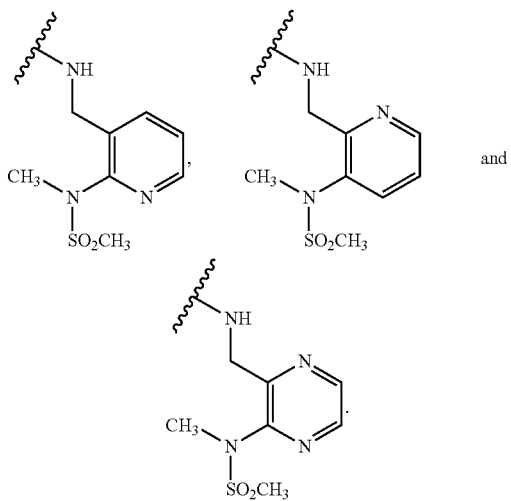

In another embodiment, the invention relates to a compound of formula Id wherein $R^1$ is —C(O)N$R^7R^8$ and $R^7$ and $R^8$ are each independently selected from the group consisting —H and —($C_1$-$C_6$)alkyl.

In another embodiment, the invention relates to a compound of formula Id wherein $R^1$ is —O$R^{10}$ and $R^{10}$ is —($C_1$-$C_6$)alkyl.

In another embodiment, the invention relates to a compound of formula Id wherein each $R^1$ is independently selected from the group consisting of —H, fluoro, chloro, —$CF_3$, —CN, methyl, —C(O)$NH_2$, —C(O)$NHCH_3$, —C(O)$NHCH_2CH_3$, —C(O)N($CH_3$)$_2$, and —$OCH_3$.

In another embodiment, the invention relates to a compound of formula Id wherein the moiety

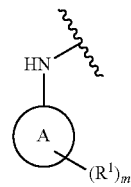

represents a moiety selected from the group consisting of:

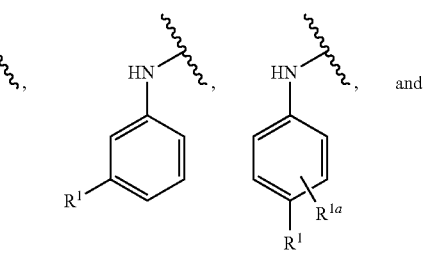

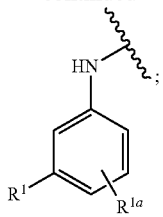

$R^1$ is —C(O)NH$_2$ or —C(O)NHCH$_3$; and $R^{1a}$ is selected from the group consisting of fluoro, chloro, methyl and —OCH$_3$.

In another embodiment, the invention relates to a compound of formula Id wherein $R^2$ and $R^3$ are —H.

In another embodiment, the invention relates to a compound of formula Id wherein $R^4$ and $R^5$ are methyl.

In another embodiment, the invention relates to a compound of formula Id wherein m is 1 or 2.

In another embodiment, the invention relates to a compound of formula I wherein each $R^1$ is independently selected from the group consisting of —H, fluoro, chloro, —CF$_3$, —CN, —(C$_1$-C$_6$)alkyl, —C(O)NR$^7$R$^8$, and —OR$^{10}$.

In another embodiment, the invention relates to a compound of formula I wherein $R^1$ is —C(O)NR$^7$R$^8$ and $R^7$ and $R^8$ are each independently selected from the group consisting —H and —(C$_1$-C$_6$)alkyl.

In another embodiment, the invention relates to a compound of formula I wherein $R^2$, $R^3$, $R^4$ and $R^5$ are each independently selected from the group consisting of —H and —(C$_1$-C$_6$)alkyl.

In another embodiment, the invention relates to a compound of formula I wherein $R^2$ and $R^3$ are —H.

In another embodiment, the invention relates to a compound of formula I wherein $R^4$ and $R^5$ are methyl.

In another embodiment, the invention relates to a compound of formula I wherein $R^6$ is —CF$_3$, K is CH, m is 1 or 2, and n is 1.

In another embodiment, the invention relates to a compound of formula I wherein the moiety

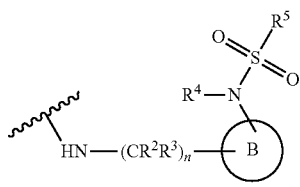

represents a moiety selected from the group consisting of:

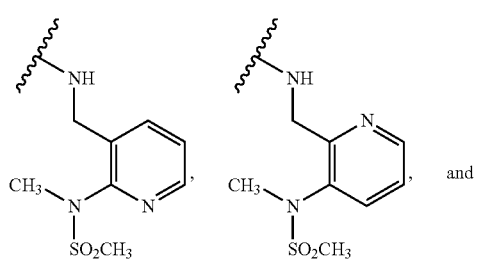

and

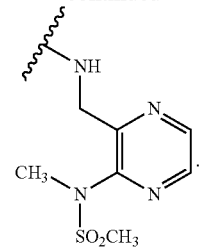

In another embodiment, the invention relates to a compound of formula I, Ia, Ib, Ic or Id wherein $R^{12}$ further includes halo.

In another embodiment, the invention relates to a compound of formula I, Ia or Ib wherein $R^4$ is selected from the group consisting of —H, —NR$^7$R$^8$, —OR$^{10}$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl; wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl moieties of said $R^4$ is optionally substituted by one to three $R^{12}$ groups; and wherein $R^4$ is not —H when B is a 5- to 6-membered heteroaryl; and $R^5$ is selected from the group consisting of —NR$^7$R$^8$, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, —(C$_4$-C$_9$)heterocycloalkenyl, —(C$_6$-C$_{10}$)aryl and —(C$_1$-C$_9$)heteroaryl moieties of said $R^5$ is optionally substituted by one to three $R^{12}$ groups;

In one embodiment, the invention also relates to the compounds described as Compounds 1-415 in Examples 1-415 in the Examples section of the subject application, and pharmaceutically acceptable salts thereof.

Non-limiting examples of compounds representing the scope of this invention include:

4-({4-[({2-[methyl(methylsulfonyl)amino]pyridin-3-yl}methyl)amino]-5-(trifluoromethyl)pyrimidin-2-yl}amino)benzamide;

4-({4-[({3-[methyl(methylsulfonyl)amino]pyridin-2-yl}methyl)amino]-5-(trifluoromethyl)pyrimidin-2-yl}amino)benzamide;

4-{[4-({3-[methyl(methylsulfonyl)amino]benzyl}amino)-5-(trifluormethyl)pyrimidin-2-yl]amino}benzamide;

3-({4-[({3-[methyl(methylsulfonyl)amino]pyrazin-2-yl}methyl)amino]-5-(trifluoromethyl)pyrimidin-2-yl}amino)benzamide;

4-methoxy-3-({4-[({3-[methyl(methylsulfonyl)amino]pyrazin-2-yl}methyl)amino]-5-(trifluoromethyl)pyrimidin-2-yl}amino)benzamide;

N-methyl-4-({4-[({3-[methyl(methylsulfonyl)amino]pyridin-2-yl}methyl)amino]-5-(trifluoromethyl)pyrimidin-2-yl}amino)benzamide;

N-methyl-4-({4-[({3-[methyl(methylsulfonyl)amino]pyrazin-2-yl}methyl)amino]-5-(trifluoromethyl)pyrimidin-2-yl}amino)benzamide;

3-fluoro-4-({4-[({2-[methyl(methylsulfonyl)amino]pyridin-3-yl}methyl)amino]-5-(trifluoromethyl)pyrimidin-2-yl}amino)benzamide;

2-fluoro-4-({4-[({3-[methyl(methylsulfonyl)amino]pyridin-2-yl}methyl)amino]-5-(trifluoromethyl)pyrimidin-2-yl}amino)benzamide;

2-fluoro-4-{[4-({3-[methyl(methylsulfonyl)amino]benzyl}amino)-5-(trifluoromethyl)pyrimidin-2-yl]amino}benzamide;

2-methyl-4-({4-[({2-[methyl(methylsulfonyl)amino]pyridin-3-yl}methyl)amino]-5-(trifluoromethyl)pyrimidin-2-yl}amino)benzamide;

2-methyl-4-({4-[({3-[methyl(methylsulfonyl)amino]pyridin-2-yl}methyl)amino]-5-(trifluoromethyl)pyrimidin-2-yl}amino)benzamide;

2-methyl-4-({4[({3-[methyl(methylsulfonyl)amino]pyrazin-2-yl}methyl)amino]-5-(trifluoromethyl)pyrimidin-2-yl}amino)benzamide;

3-methyl-4-({4-[({2-[methyl(methylsulfonyl)amino]pyridin-3-yl}methyl)amino]-5-(trifluoromethyl)pyrimidin-2-yl}amino)benzamide;

3-methyl-4-({4-[({3-[methyl(methylsulfonyl)amino]pyridin-2-yl}methyl)amino]-5-(trifluoromethyl)pyrimidin-2-yl}amino)benzamide;

3-methyl-4-({-4-[({3-[methyl(methylsulfonyl)amino]pyrazin-2-yl}methyl)amino]-5-(trifluoromethyl)pyrimidin-2-yl}amino)benzamide;

2-chloro-4-({4-[({2-[methyl(methylsulfonyl)amino]pyridin-3-yl}methyl)amino]-5-(trifluoromethyl)pyrimidin-2-yl}amino)benzamide;

2-chloro-4-({-4-[({3-[methyl(methylsulfonyl)amino]pyridin-2-yl}methyl)amino]-5-(trifluoromethyl)pyrimidin-2-yl}amino)benzamide;

2-chloro-4-({-4-[({3-[methyl(methylsulfonyl)amino]pyrazin-2-yl}methyl)amino]-5-(trifluoromethyl)pyrimidin-2-yl}amino)benzamide;

3-fluoro-N-methyl-4-({4-[({3-[methyl(methylsulfonyl)amino]pyrazin-2-yl}methyl)amino]-5-(trifluoromethyl)pyrimidin-2-yl}amino)benzamide;

2-fluoro-N-methyl-4-({4-[({3-[methyl(methylsulfonyl)amino]pyrazin-2-yl}methyl)amino]-5-(trifluoromethyl)pyrimidin-2-yl}amino)benzamide;

N,2-dimethyl-4-({4-[({3-[methyl(methylsulfonyl)amino]pyrazin-2-yl}methyl)amino]-5-(trifluoromethyl)pyrimidin-2-yl}amino)benzamide;

N,3-dimethyl-4-({4-[({3-[methyl(methylsulfonyl)amino]pyrazin-2-yl}methyl)amino]-5-(trifluoromethyl)pyrimidin-2-yl}amino)benzamide; and N,3-dimethyl-4-({-4-[({2-[methyl(methylsulfonyl)amino]pyridin-3-yl}methyl)amino]-5-(trifluoromethyl)pyrimidin-2-yl}amino)benzamide; or a pharmaceutically acceptable salt thereof.

Non-limiting examples of compounds representing the scope of this invention also include:

(R)—N-(3-((2-(4-(1-aminoethyl)phenylamino)-5-(trifluoromethyl)pyrimidin-4-ylamino)methyl)pyridin-2-yl)-N-methylmethane-sulfonamide;

N-(3-((2-(4-(aminomethyl)phenylamino)-5-(trifluoromethyl)pyrimidin-4-ylamino)methyl)pyridin-2-yl)-N-methylmethane-sulfonamide;

N-[4-({4-[({2-[methyl(methylsulfonyl)amino]pyridin-3-yl}methyl)amino]-5-(trifluoromethyl)pyrimidin-2-yl}amino)benzyl]acetamide;

N-(3-((2-(4-(hydroxymethyl)phenylamino)-5-(trifluoromethyl)pyrimidin-4-ylamino)methyl)pyridin-2-yl)-N-methylmethane-sulfonamide;

N-(3-((2-(4-(chloromethyl)phenylamino)-5-(trifluoromethyl)pyrimidin-4-ylamino)methyl)pyridin-2-yl)-N-methylmethane-sulfonamide;

N-(3-((2-(4-((1,3-dihydroxypropan-2-ylamino)methyl)phenylamino)-5-(trifluoromethyl)pyrimidin-4-ylamino)methyl)pyridin-2-yl)-N-methylmethane-sulfonamide;

tert-butyl 3-({4-[({2-[methyl(methylsulfonyl)amino]pyridin-3-yl}methyl)amino]-5-(trifluoromethyl)pyrimidin-2-yl}amino)benzoate;

3-({4-[({2-[methyl(methylsulfonyl)amino]pyridin-3-yl}methyl)amino]-5-(trifluoromethyl)pyrimidin-2-yl}amino)benzoic acid;

N-cyclopropyl-3-({4-[({2-[methyl(methylsulfonyl)amino]pyridin-3-yl}methyl)amino]-5-(trifluoromethyl)pyrimidin-2-yl}amino)benzamide;

N-(3-((2-(4-(1-hydroxyethyl)phenylamino)-5-(trifluoromethyl)pyrimidin-4-ylamino)methyl)pyridin-2-yl)-N-methylmethanesulfonamide;

2-fluoro-4-({-4-[({2-[methyl(methylsulfonyl)amino]pyridin-3-yl}methyl)amino]-5-(trifluoromethyl)pyrimidin-2-yl}amino)benzamide;

3-fluoro-4-({4[({2-[methyl(methylsulfonyl)amino]pyridin-3-yl}methyl)amino]-5-(trifluoromethyl)pyrimidin-2-yl}amino)benzamide; and N-methyl-4-({4-[({3-[methyl(methylsulfonyl)amino]pyrazin-2-yl}methyl)amino]-5-(trifluoromethyl)pyrimidin-2-yl}amino)benzamide; or a pharmaceutically acceptable salt thereof.

Non-limiting examples of compounds representing the scope of this invention also include:

2-fluoro-4-({-4-[({2-[methyl(methylsulfonyl)amino]pyridin-3-yl}methyl)amino]-5-(trifluoromethyl)pyrimidin-2-yl}amino)benzamide;

3-fluoro-4-({-4-[({2-[methyl(methylsulfonyl)amino]pyridin-3-yl}methyl)amino]-5-(trifluoromethyl)pyrimidin-2-yl}amino)benzamide; and N-methyl-4-({4-[([3-[methyl(methylsulfonyl)amino]pyrazin-2-yl]methyl)amino]-5-(trifluoromethyl)pyrimidin-2-yl}amino)benzamide; or a pharmaceutically acceptable salt thereof.

Non-limiting examples of compounds representing the scope of this invention also include:

2-fluoro-4-({4-[({2-[methyl(methylsulfonyl)amino]pyridin-3-yl}methyl)amino]-5-(trifluoromethyl)pyrimidin-2-yl}amino)benzamide formate;

3-fluoro-4-({4-[({2-[methyl(methylsulfonyl)amino]pyridin-3-yl}methyl)amino]-5-(trifluoromethyl)pyrimidin-2-yl}amino)benzamide formate; and N-methyl-4-({4-[({3-[methyl(methylsulfonyl)amino]pyrazin-2-yl}methyl)amino]-5-(trifluoromethyl)pyrimidin-2-yl}amino)benzamide hydrochloride.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, —($C_1$-$C_6$) alkoxy, —($C_6$-$C_{10}$)aryloxy, trifluoromethoxy, difluoromethoxy or —($C_1$-$C_6$)alkyl. The phrase "each of said alkyl" as used herein refers to any of the preceding alkyl moieties within a group such alkoxy, alkenyl or alkylamino. Preferred alkyls include ($C_1$-$C_6$)alkyl, more preferred are ($C_1$-$C_4$)alkyl, and most preferred are methyl and ethyl.

As used herein, the term "halogen" or "halo' includes fluoro, chloro, bromo or iodo or fluoride, chloride, bromide or iodide.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term "alkynyl" means straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term "carbonyl" or "C(O)" (as used in phrases such as alkylcarbonyl, alkyl-C(O)— or alkoxycarbonyl) refers to the joinder of the >C=O moiety to a second moiety such as an alkyl or amino group (i.e. an amido group). Alkoxycarbonylamino (i.e. alkoxy-C(O)—NH—) refers to an alkyl carbamate group. The carbonyl group is also equivalently defined herein as C(O). Alkylcarbonylamino refers to groups such as acetamide.

As used herein, the term "cycloalkyl" refers to a mono-carbocyclic ring (e.g., cyclopropyl, cyclobutyl, cyclopentyl, cyclohexyl, cycloheptyl, cyclooctyl, cyclononyl); optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl. Cycloalkyls include —($C_3$-$C_{10}$)cycloalkyl.

As used herein, the term "cycloalkenyl" refers to a cycloalkyl as defined above and further containing 1 or 2 double bonds (e.g., cyclopentenyl, cyclohexenyl). Cycloalkenyls include —($C_5$-$C_{10}$)cycloalkenyl.

The term "4- to 7-membered carbocyclyl" refers to a non-aromatic ring containing 4 to 7 carbon ring atoms, optionally containing 1 or 2 double bonds, and optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl. Non-limiting examples of 4- to 7-membered carbocyclyls include cyclopropyl, cyclobutyl, cyclobutenyl, cyclopentyl, cyclopentenyl, cyclopentendienyl, cyclohexyl, cyclohexenyl, cyclohexadienyl, cycloheptyl, cycloheptenyl, and cycloheptadienyl.

As used herein, the term "bicycloalkyl" refers to a cycloalkyl as defined above which is bridged to a second carbocyclic ring (e.g., bicyclo[2.2.1]heptanyl, bicyclo[3.2.1]octanyl and bicyclo[5.2.0]nonanyl, etc.). Bicycloalkyls include —($C_6$-$C_{10}$)bicycloalkyl.

As used herein, the term "bicycloalkenyl" refers to a bicycloalkyl as defined above and further containing 1 or 2 double bonds. Bicycloalkenyls include —($C_6$-$C_{10}$)bicycloalkenyl.

As used herein, the term "($C_6$-$C_{10}$)aryl" means aromatic radicals such as phenyl, naphthyl, tetrahydronaphthyl, indanyl and the like; optionally substituted by 1 to 3 suitable substituents as defined above.

As used herein, the term "($C_1$-$C_9$)heteroaryl" refers to an aromatic heterocyclic group having from 1 to 9 carbon atoms and containing from 1 to 4 heteroatoms in the ring selected from the group consisting of O, S and N. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

The term "5- to 6-membered heteroaryl ring" refers to an aromatic ring containing from 1 to 5 carbon atoms ring atoms and from 1 to 4 hetero ring atoms, and optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl. Non-limiting examples of 5- to 6-membered heteroaryl rings include furanyl, pyrrolyl, thiopenyl, thiazolyl, isothiazolyl, pyrazolyl, oxazoyl, isoxazolyl, pyridyl, pyrimidyl, pyrazinyl, pyridazinyl, oxadiazoyl, thiadiazoyl, benzothiazolyl, and benzooxazolyl.

As used herein, the term heteroatom refers to an atom or group selected from N, O, S(O)$_q$ or NR, where q is an integer from 0 to 2 and R is a substituent group. The term "($C_1$-$C_9$) heterocycloalkyl" as used herein refers to a cyclic group containing 1 to 9 carbon atoms and 1 to 4 hetero atoms. Non-limiting examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidinyl, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl.

As used herein, the term "heterocycloalkenyl" refers to a heterocycloalkyl as defined above and further containing 1 or 2 double bonds. Heterocycloalkenyls include —($C_4$-$C_9$)heterocycloalkenyl.

The term "4- to 7-membered heterocyclyl" refers to a non-aromatic ring containing from 1 to 6 carbon atoms ring atoms and from 1 to 4 hetero ring atoms, optionally containing 1 or 2 double bonds, and optionally substituted by 1 to 3 suitable substituents as defined above such as fluoro, chloro, trifluoromethyl, —($C_1$-$C_6$)alkoxy, —($C_6$-$C_{10}$)aryloxy, trifluoromethoxy, difluoromethoxy or —($C_1$-$C_6$)alkyl. Non-limiting examples of 4- to 7-membered heterocyclyls include azetidinyl, oxetanyl, pyrrolidinyl, dihydropyrazolyl, tetrahydropyrazolyl, dihydrofuranyl, tetrahydrofuranyl, dihydrothiophenyl, tetrahydrothiophenyl, dihydropyridinyl, tetrahydropyridinyl, piperidinyl, piperazinyl, pyranyl, dihydropyranyl, tetrahydropyranyl, thiopyrianyl, dihydrothiopyranyl, tetrahydrothiopyranyl, morpholinyl, dihydroazepinyl, tetrahydroazepinyl, dihydrooxepinyl, tetrahydrooxepinyl, oxepanyl, dihyrothiepinyl, tetrahydrothiepinyl and thiepanyl.

As used herein, the term "heterobicycloalkyl" refers to a bicycloalkyl as defined above, wherein at least one of the carbon ring atoms has been replaced by at least one heteroatom (e.g. tropane). Heterobicycloalkyls include —($C_6$-$C_9$) heterobicycloalkyl.

As used herein, the term "heterobicycloalkenyl" refers to a heterobicycloalkyl as defined above and further containing 1 or 2 double bonds. Heterobicycloalkenyls include —($C_6$-$C_9$) heterobicycloalkenyl.

Nitrogen heteroatoms as used herein refers to N=, >N and —NH; wherein —N= refers to a nitrogen double bond; >N refers to a nitrogen containing two bond connections and —N refers to a nitrogen containing one bond.

The term "perfluorinated" or "perfluoro" refer to a compound having 4 or more fluorine groups.

The term "replaced by" refers to compounds in which an element selected from the group consisting of —C(O)— and —C(S)— replaces a methylene moiety in a non-aromatic cyclic ring system. For example, if a substituent is a heterocycloalkyl group, such as an azetidine group:

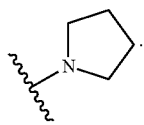 [SMILES: *N1CCCC1]

a methylene ring moiety may be replaced by, e.g., a —C(O)— to form a pyrrolidinone group:

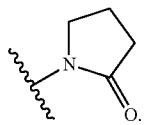

Compounds of the invention can accommodate up to three such replacements.

The present invention also includes isotopically-labeled compounds, which are identical to those recited in formulae I, Ia, Ib, Ic, Id and II, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples and Preparations below, by substituting a readily available isotopically-labeled reagent for a non-isotopically-labeled reagent.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare pharmaceutically acceptable base salts of those compounds of the compounds of the invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical-Salts: Properties, Selection, and Use* by Stahl and Wermuth (Wiley-VCH, 2002). Methods for making pharmaceutically acceptable salts of compounds of the invention are known to one of skill in the art.

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the invention (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of the invention that can be separated into rotationally restricted isomers.

The compounds of this invention may contain olefin-like double bonds. When such bonds are present, the compounds of the invention exist as cis and trans configurations and as mixtures thereof.

The compounds of the invention may also exist in unsolvated and solvated forms. Accordingly, the invention also relates to the hydrates and solvates of the compounds of the invention. Thus, it will be understood that the compounds of formula I, and pharmaceutically acceptable salts thereof also include hydrates and solvates of said compounds of formula I, and pharmaceutically acceptable salts thereof, as discussed below.

The term "solvate" is used herein to describe a noncovelent or easily reversible combination between solvent and solute, or dispersion means and disperse phase. It will be understood that the solvate can be in the form of a solid, slurry (e.g., a suspension or dispersoid), or solution. Non-limiting examples of solvents include ethanol, methanol, propanol, acetonitrile, dimethyl ether, diethyl ether, tetrahydrofuan, methylene chloride, and water. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

Some non-limiting examples of prodrugs in accordance with the invention include (i) where the compound of the invention contains a carboxylic acid functionality (—COOH), an ester thereof, for example, a compound wherein the hydrogen of the carboxylic acid functionality of the compound of formula (I) is replaced by $(C_1-C_6)$alkyl;

(ii) where the compound of the invention contains an alcohol functionality (—OH), an ether thereof, for example, a compound wherein the hydrogen of the alcohol functionality of the compound of the invention is replaced by $(C_1-C_6)$ alkanoyloxymethyl; and (iii) where the compound of the invention contains a primary or secondary amino functionality (—NH$_2$ or —NHR where R≠H), an amide thereof, for example, a compound wherein, as the case may be, one or both hydrogen atoms of the amino functionality of the compound of the invention is/are replaced by $(C_1-C_6)$alkanoyl.

Further examples of replacement groups in accordance with the foregoing examples and examples of other prodrug types may be found in the aforementioned references.

Moreover, certain compounds of the invention may themselves act as prodrugs of other compounds of the invention.

Also included within the scope of the invention are metabolites of compounds of the invention, that is, compounds formed in vivo upon administration of the drug. Some examples of metabolites in accordance with the invention include:

(i) where the compound of the invention contains a methyl group, an hydroxymethyl derivative thereof (e.g., —CH$_3$→—CH$_2$OH):

(ii) where the compound of the invention contains an alkoxy group, an hydroxy derivative thereof (e.g., —OR$^7$→—OH);

(iii) where the compound of the invention contains a tertiary amino group, a secondary amino derivative thereof (e.g., —NR$^3$R$^4$→—NHR$^3$ or —NHR$^4$);

(iv) where the compound of the invention contains a secondary amino group, a primary derivative thereof (e.g., —NHR$^3$→—NH$_2$);

(v) where the compound of the invention contains a phenyl moiety, a phenol derivative thereof (e.g., -Ph→-PhOH); and (vi) where the compound of the invention contains an amide group, a carboxylic acid derivative thereof (e.g., —CONH$_2$→COOH).

Compounds of the invention containing one or more asymmetric carbon atoms can exist as two or more stereoisomers. Where a compound of the invention contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, d-lactate or 1-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of an alcoholic solvent such as isopropanol, typically from 2% to 20%, and from 0 to 5% by volume of an alkylamine, typically 0.1% diethylamine. Concentration of the eluate affords the enriched mixture.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

In one embodiment, the invention relates to compositions comprising a compound of the invention and at least one additional ingredient (hereinafter "the compositions of the invention"). It will be understood that the compositions of the invention will encompass any combination of the compound of the invention and the at least one additional ingredient. Non-limiting examples of the at least one additional ingredient include impurities (e.g., intermediates present in the unrefined compounds of the invention), active ingredients as discussed herein (e.g., an additional anti-tumor agent), pharmaceutically acceptable excipients, or one or more solvents (e.g., a pharmaceutically acceptable carrier as discussed herein).

The term "solvent" as it relates to the compositions of the invention includes organic solvents (e.g., methanol, ethanol, isopropanol, ethyl acetate, methylene chloride, and tetrahydrofuran) and water. The one or more solvents may be present in a non-stoichiometric amount, e.g., as a trace impurity, or in sufficient excess to dissolve the compound of the invention. Alternatively, the one or more solvents may be present in a stoichiometric amount, e.g., 0.5:1, 1:1, or 2:1 molar ratio, based on the amount of compound of the invention.

In one embodiment, the at least one additional ingredient that is present in the composition of the invention is an organic solvent.

In another embodiment, the at least one additional ingredient that is present in the composition of the invention is water.

In one embodiment, the at least one additional ingredient that is present in the composition of the invention is a pharmaceutically acceptable carrier.

In another embodiment, the at least one additional ingredient that is present in the composition of the invention is a pharmaceutically acceptable excipient.

In one embodiment, the composition of the invention is a solution.

In another embodiment, the composition of the invention is a suspension.

In another embodiment, the composition of the invention is a solid.

In another embodiment, the composition of the invention comprises an amount of the compound of the invention effective for treating abnormal cell growth.

In yet another embodiment, the invention relates to a composition comprising an effective amount of the compound of the invention, and a pharmaceutically acceptable carrier.

In another embodiment, the invention relates to a composition comprising a therapeutically effective amount of the compound the invention as defined above, a pharmaceutically acceptable carrier and, optionally, at least one additional medicinal or pharmaceutical agents (hereinafter "the pharmaceutical compositions of the invention"). In a preferred embodiment, the at least one additional medicinal or pharmaceutical agent is an anti-cancer agent.

In another embodiment, the invention relates to a composition useful for treating abnormal cell growth in a mammal comprising an effective amount of the compound of the invention, and a pharmaceutically acceptable carrier.

The invention also relates to methods of making the compounds of the invention.

In one embodiment, the invention relates to a method for making a compound of formula I comprising allowing a compound of formula

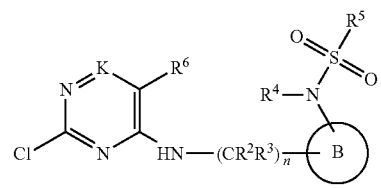

to react with a compound of formula

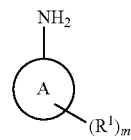

to provide the compound of formula I.

In another embodiment, the invention relates to a method for making the compounds of the invention comprising allowing a compound of formula

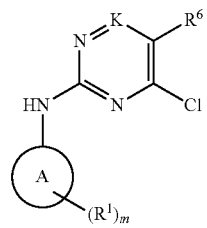

to react with a compound of formula

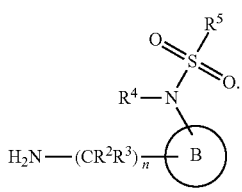

When preparing compounds of the invention in accordance with the invention, it is open to a person skilled in the art to routinely select the form of the intermediate compound which provides the best combination of features for this purpose. Such features include the melting point, solubility, processability and yield of the intermediate form and the resulting ease with which the product may be purified on isolation.

The invention also relates to intermediate compounds that are useful for making the compounds of the invention.

In one embodiment, the invention relates to intermediate compounds having the formula II:

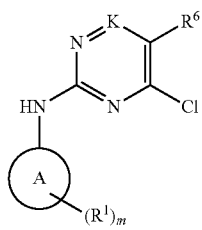

wherein A, K, $R^1$, $R^6$ and m are as defined above for the compound of formula I.

The invention also relates to methods for the treatment of abnormal cell growth in a mammal. In one embodiment, the invention relates to a method for the treatment of abnormal cell growth in a mammal comprising administering to said mammal an amount of a compound of the invention that is effective in treating abnormal cell growth.

In another embodiment, the abnormal cell growth is cancer.

In another embodiment, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

The invention also relates to methods for the treatment of cancer solid tumors in a mammal. In one embodiment, the invention relates to the treatment of cancer solid tumor in a mammal comprising administering to said mammal an amount of a compound of the invention that is effective in treating said cancer solid tumor.

In another embodiment, the cancer solid tumor is breast, lung, colon, brain, prostate, stomach, pancreatic, ovarian, skin (melanoma), endocrine, uterine, testicular, or bladder.

In another embodiment, the invention relates to a method for the treatment of abnormal cell growth in a mammal which comprises administering to said mammal an amount of a compound of the invention that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

A particular aspect of this invention is directed to methods for treating or preventing a condition that presents with low bone mass in a mammal (including a human being) which comprise administering to a mammal in need of such treatment a condition that presents with low bone mass treating amount of a compound of the invention or a pharmaceutically acceptable salt of said compound of the invention. This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a compound of the invention or a pharmaceutically acceptable salt of said compound.

Another aspect of this invention is directed to methods for treating a bone fracture or an osteoporotic fracture in a mammal which comprise administering to a mammal in need of such treatment a bone fracture treating or an osteoporotic fracture treating amount of a compound of the invention or a pharmaceutically acceptable salt of said compound.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophospatasemia.

DETAILED DESCRIPTION OF THE INVENTION

Synthesis of 2,4-Diamino Pyrimidines

The compounds of the invention can be prepared by the following general methods and by methods described in detail in the Experimental Section.

Non-limiting methods for making the sulfonyl amides of the invention are depicted in Schemes 1-6 below. For sake of clarity, only the pyrimidine derivatives of the compounds of formula I are depicted in the Schemes (i.e., where K of the compound of formula I is CH). However, the same methods can be used for making the 1,2,4-triazine derivatives compounds of formula I (i.e., where K is N).

Scheme 1 shows one method for preparing 2,4-diamino pyrimidines.

Scheme 1

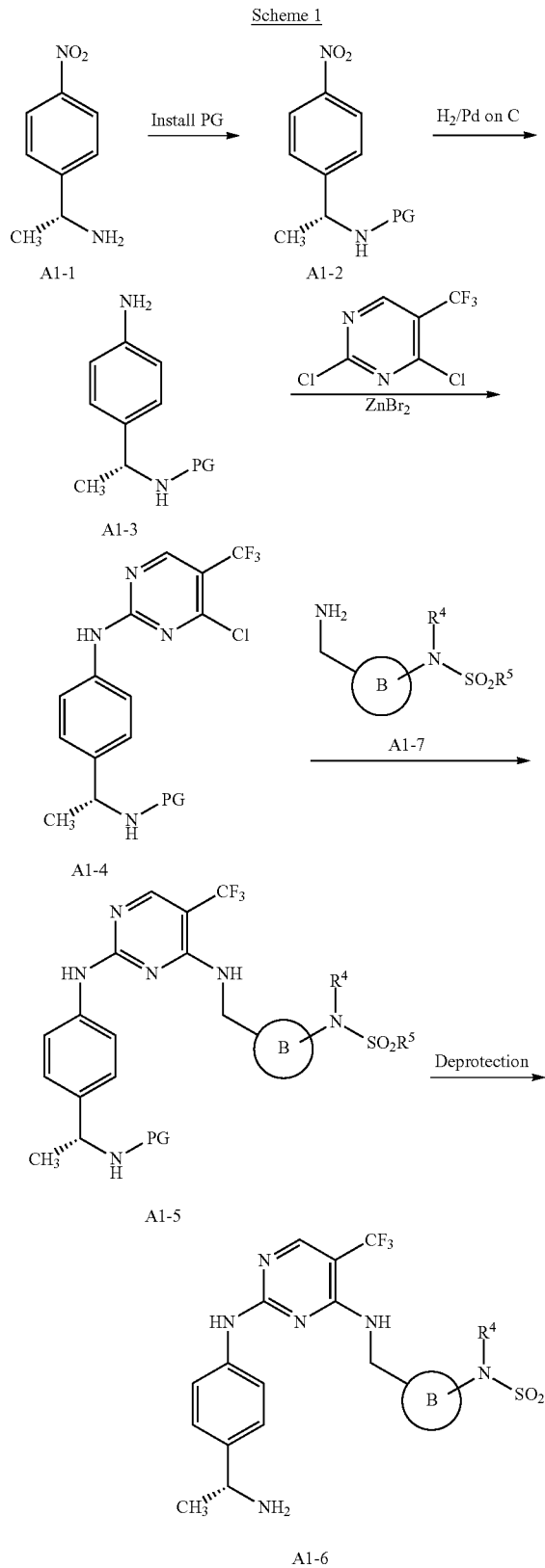

In Scheme 1, the amino group of an amino-nitroaryl compound of structure A1-1 is protected (PG=protecting group such as BOC) to form the protected compound A1-2. The nitro group of A1-2 can then be selectively reduced to the corresponding aniline A1-3, using, e.g., hydrogen in the presence of a palladium-supported catalyst. Reaction of aniline A1-3 with 2,4-dichloro-5-(trifluoromethyl)pyrimidine in the presence of an appropriate zinc salt (e.g., $ZnBr_2$) provides the corresponding C-2 addition product A1-4. Reaction of compounds of formula A1-4 with amines of formula A1-7 under basic conditions provides compound of formula I having the structure A1-5. Other compounds of formula I can be prepared by selectively deprotecting A1-5 to provide the aminoalkyl compound of formula I having the structure A1-6.

Scheme 2 depicts a non-limiting method for making amide derivatives of the compound of formula I.

Scheme 2

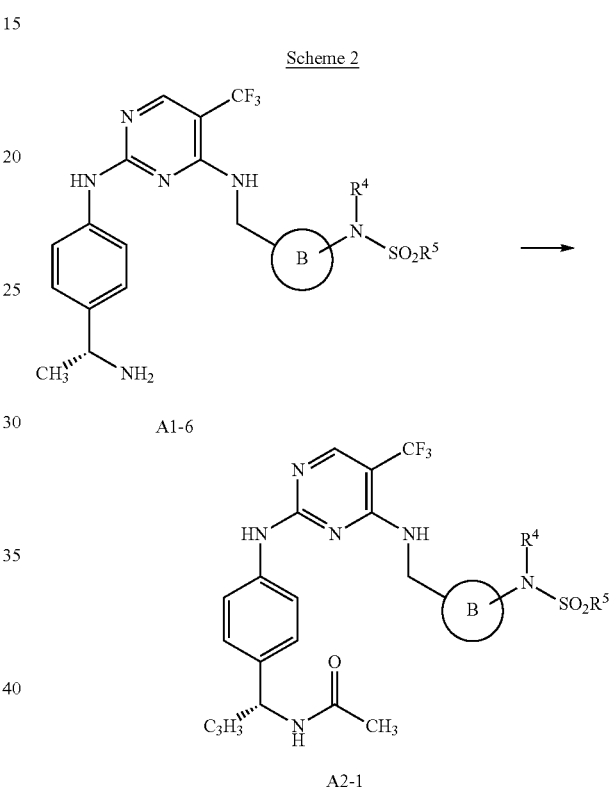

In Scheme 2, an aminoalkyl such as the compound of formula I having the structure A1-6 can be reacted with an acid halide (e.g., acetyl chloride) under basic conditions to provide the amide derivative of the compound of formula I having the structure A2-1.

Scheme 3 represents another general non-limiting method of making compounds of formula I.

Scheme 3

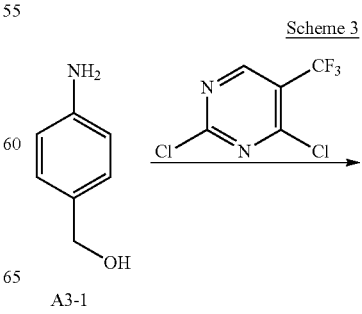

-continued

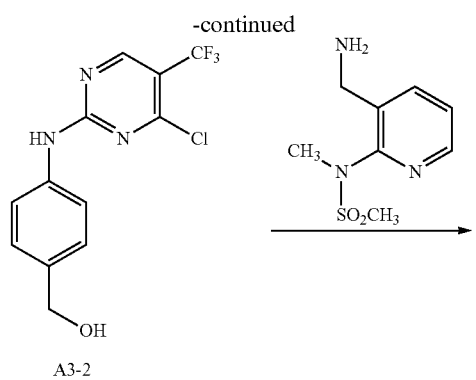

A3-2

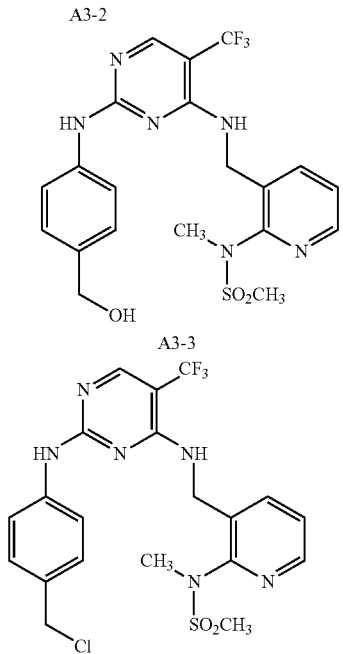

A3-3

A3-4

A3-5

In Scheme 3, an hydroxyalkyl-aniline of formula A3-1 is reacted with 2,4-dichloro-5-(trifluoromethyl)pyrimidine in the presence of a zinc salt (e.g., ZnBr$_2$) to provide the corresponding C-2 addition product A3-2. Treatment of the A3-2 with an amine of formula A3-6 provides hydroxyalkyl derivatives of the compound of formula I having the structure A3-3.

Compound A3-3 may further be selectively converted to a compound of formula I where the hydroxyl group is replaced for another reactive functional group (e.g., alkyl halide or alkyl sulfonate). For example, in Scheme 3, the hydroxylalkyl compound of formula A3-3 is reacted with thionyl chloride to provide the chloroalkyl compound of formula I having the structure A3-4. Compound A3-4 may further be reacted with amines (e.g., HNR$^7$R$^8$) to provide aminoalkyl derivatives of the compounds of formula I having the structure A3-5. If desired, the compounds of structure A3-5 can be used as a starting material to prepare other compounds of formula I.

Scheme 4 represents yet another general non-limiting method for making compounds of formula I.

Scheme 4

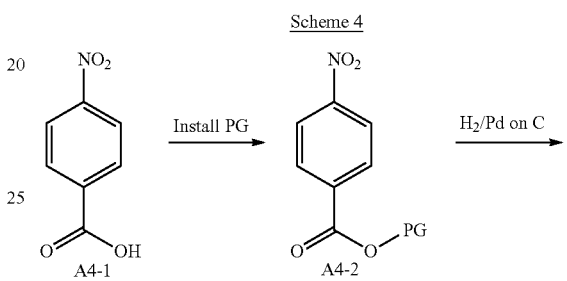

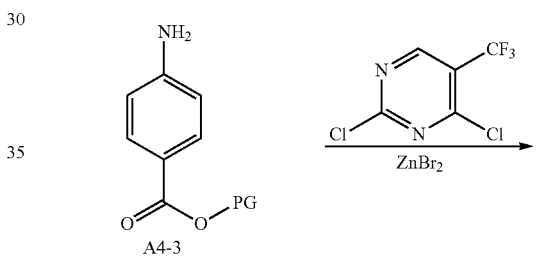

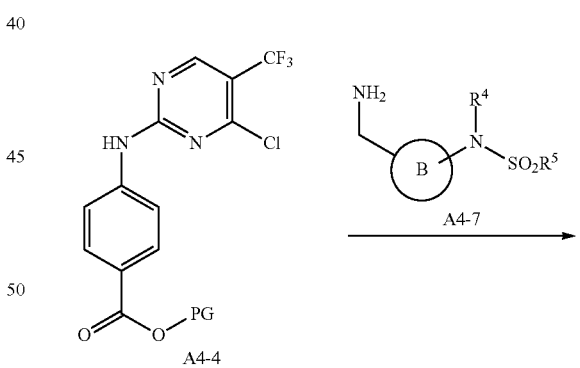

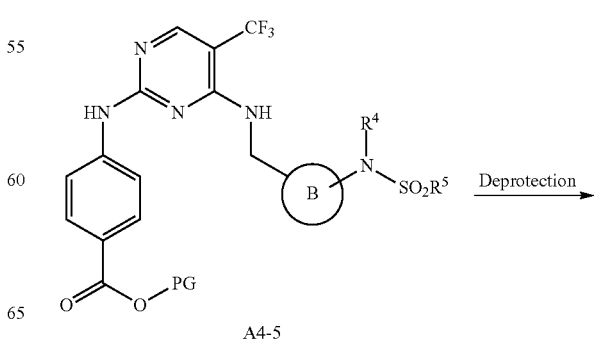

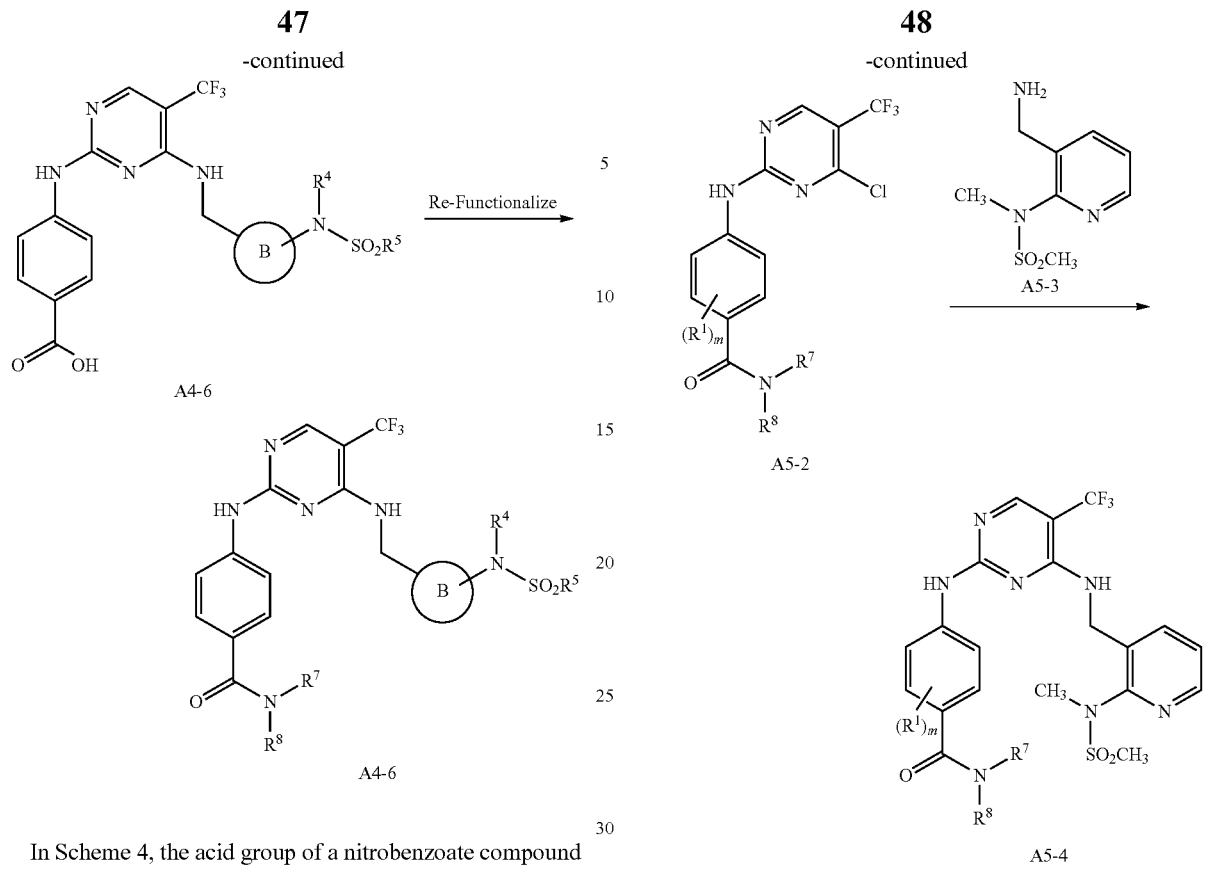

In Scheme 4, the acid group of a nitrobenzoate compound of structure A4-1 is protected to form the protected compound A4-2. The nitro group of A4-2 can then be selectively reduced to the corresponding aniline A4-3, using, e.g., hydrogen in the presence of a palladium-supported catalyst. Reaction of aniline A4-3 with 2,4-dichloro-5-(trifluoromethyl)pyrimidine in the presence of an appropriate zinc salt (e.g., $ZnBr_2$) provides the corresponding C-2 addition product A4-4. Treatment of the chloro-pyrimidine compounds of formula A4-4 with amines of formula A4-7 provides benzoate-protected compounds of formula I having the structure A4-5. Selective deprotection of compound A4-5 can provide benzoic acid derivatives of the compound of formula I having the structure A4-6. The benzoic acid derivatives of formula A4-6 may be further reacted with an amine to provide the amide derivatives of the compound of formula I having the structure A4-6.

Scheme 5 depicts yet another general non-limiting method for making compounds of formula I.

In Scheme 5, an aniline amide compound of structure A5-1 is be reacted with 2,4-dichloro-5-(trifluoromethyl)pyrimidine in the presence of a zinc salt (e.g., $ZnBr_2$) to provide the corresponding C-2 addition product A5-2. Treatment of the chloro pyrimidine compounds of formula A5-2 with an amine of formula A5-3 provides amide derivatives of the compounds of formula I having the structure A5-4. The amide derivatives of formula A5-4 may be used as a starting material to provide other compounds of formula I.

In Schemes 1 and 3-5, the 2,4-dichloro-5-(trifluoromethyl) pyrimidine first formed a C-2 addition product ("the C4-chloro intermediate"). The C-4 group was then added by allowing the C4-chloro intermediate to react with an aralkylamino reagent. Scheme 6 depicts another non-limiting method for making the compounds of the invention where the first formed intermediate is the C-4 addition intermediate ("the C2-chloro intermediate").

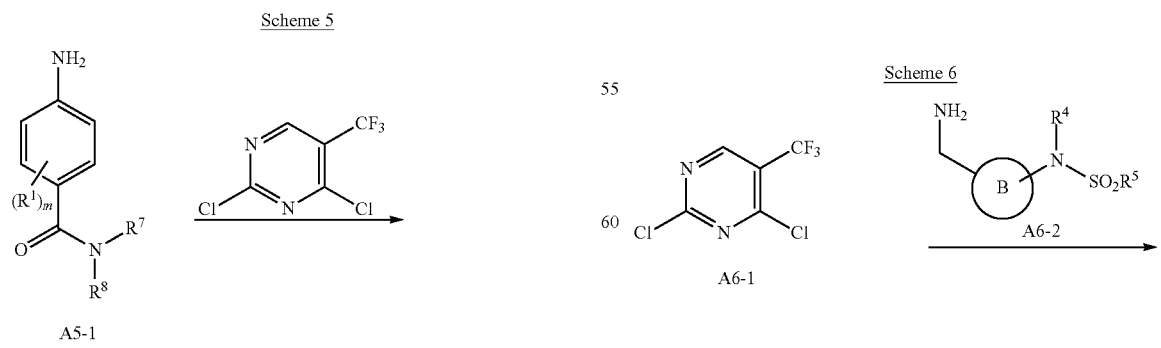

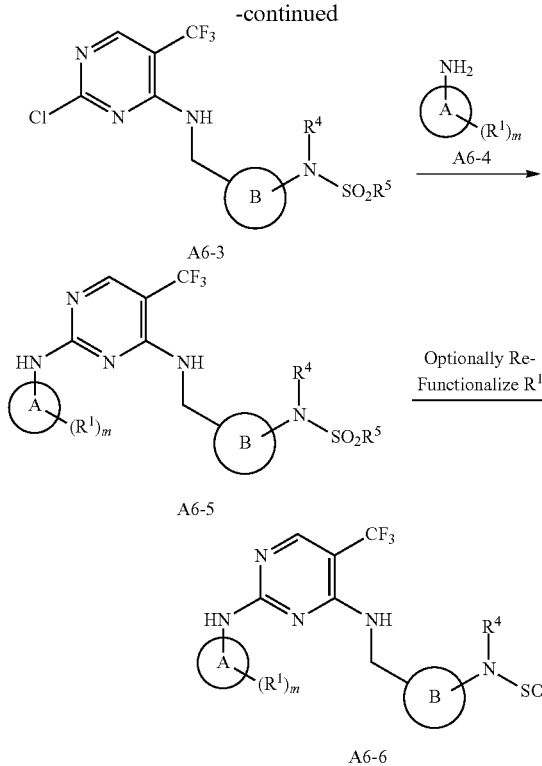

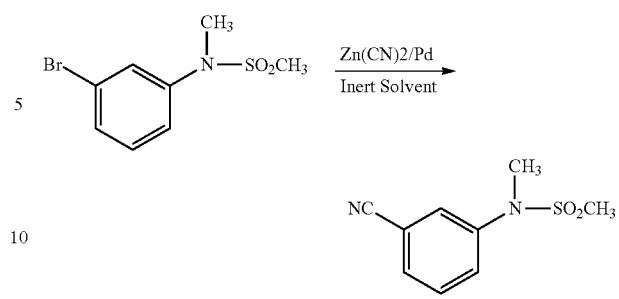

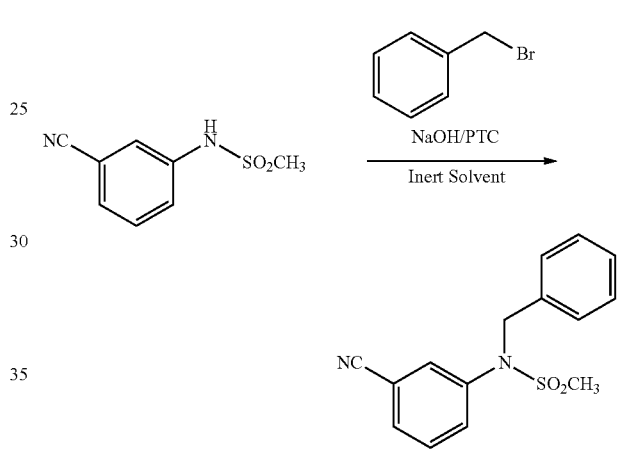

In Scheme 6, 2,4-dichloro-5-(trifluoromethyl)pyrimidine is reacted with an aralkylamino reagent of formula A6-2 to provide the 2-chloro-pyrimidine addition product A6-3. Reaction of A6-3 with an amino reagent of formula A6-4 provides the compound of formula I having the structure A6-5. Depending on the substituent groups $R^1$, the compounds of formula A6-5 can be further reacted as described above in Schemes 1-5 to provide additional compounds of formula I.

Arylalkylamines or heteroarylalkylamines (e.g., A1-7 in Scheme 1) that are attached to the 4 position of the pyrimidine core (or the 5 position of the 1,2,4-triazine core) may be prepared from the corresponding nitrile by catalytic hydrogenation using catalysts such as Pd/C or Raney Nickel or by lithium aluminum hydride reduction, (see Rylander, Catalytic Hydrogenation in Organic Synthesis, Academic Press, 1979); or by methods described herein in the Examples section.

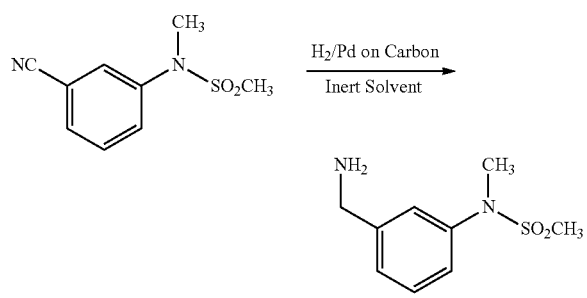

The nitrile starting materials can be either purchased or prepared from the corresponding aryl/heteroaryl bromide, iodide or triflate and $Zn(CN)_2$ using Pd coupling conditions found in Tschaen, D. M., et. at Synthetic Communications (1994), 24, 6, pp 887-890.

Appropriately protected amines may be converted to different amines of formula A1-7 (see Scheme 1) according to methods familiar to those skilled in the art as, for example, N-alkylation of a sulfanilide under phase transfer using conditions as described by Brehme, R. "Synthesis", (1976), pp 113-114.

As understood by those skilled in the art, the chemical transformation to convert an aryl halide or triflate or heteroaryl halide or triflate to an aromatic or heteroaromatic amine may be carried out using conditions currently outlined in the literature, see Hartwig, J. F.: "Angew. Chem. Int. Ed." (1998), 37, pp. 2046-2067, Wolfe, J. P.; Wagaw, S.; Marcoux, J. F.; Buchwald, S. L.; "Acc. Chem. Res.", (1998), 31, pp 805-818, Wolfe, J. P.; Buchwald, S. L.; "J. Org. Chem.", (2000), 65, pp 1144-1157, Muci, A. R.; Buchwald, S. L.; "Topics in Current Chemistry" (2002), pp 131-209 and references cited therein. Further, as understood by those skilled in the art, these same aryl or heteroaryl amination chemical transformations may alternatively be carried out on nitrile (or primary amide) precursors which provide amines after nitrile (or amide) reduction.

Other methods for making the intermediate compounds (e.g. A1-7 in Scheme 1) can be found in U.S. Patent Appl. Publ. No. 20040220177, U.S. Pat. No. 7,109,335, U.S. Pat. No. 7,109,337, and PCT/IB2006/003349, the entire contents of each of the foregoing references being expressly incorporated herein by reference.

As noted above, amines comprising the ring moiety A (e.g., A6-4 in Scheme 6) are attached to the 2 position of the pyrimidine core (or the 3 position of the 1,2,4-triazine core). Such amino-ring groups are commercially available or can be made by methods known to those skill in the art. For example, amines comprising alkyl-, hydroxyl-, carboxyl-, and halo-substituted ring moieties are commercially available. In addition, certain of these commercially available amines such as, e.g., the halo- and hydroxyl-substituted ring compounds, can be reacted to form other compounds of the invention using the methods described above, in the Examples section, or known to those skilled in the art. Such reactions can be carried out prior to the reaction with pyrimidine core. Alternatively, such reactions can be carried out after the cyclic amine is attached to the C2 position of the pyrimidine core.

This invention also relates to a method for the treatment of abnormal cell growth in a mammal, including a human, comprising administering to said mammal an amount of a compound of the invention, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound of the invention that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the invention, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the invention, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also contemplates a pharmaceutical composition for treating abnormal cell growth wherein the composition includes a compound of the invention, as defined above, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a method for the treatment of a disorder associated with angiogenesis in a mammal, including a human, comprising administering to said mammal an amount of a compound of the invention, as defined above, or a pharmaceutically acceptable salt, solvate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a composition for) treating abnormal cell growth in a mammal which comprise an amount of a compound of the invention, or a pharmaceutically acceptable salt, solvate or prodrug thereof, in combination with an amount of one or more substances selected from anti-angiogenesis agents, signal transduction inhibitors, and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the invention in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Publication No. EP0818442, European Patent Publication No. EP1004578, WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Publication No. WO99/007675, European Patent Application No. 99302232.1 (filed Mar. 25, 1999), Great Britain patent application number 9912961.1 (filed Jun. 3, 1999), U.S. Pat. No. 7,030,242, U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

VEGF inhibitors, for example, SU-11248, SU-5416 and SU-6668 (Sugen Inc. of South San Francisco, Calif., USA), can also be combined with a compound of the invention. VEGF inhibitors are described in, for example in WO 99/24440 (published May 20, 1999), PCT International Application PCT/1899/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of the invention. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Pat. No. 6,465,449, and in U.S. Pat. No. 6,284,764, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of the invention may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the famesyl protein transferase inhibitors described in the references cited in the "Background" section, supra. Specific CTLA4 antibodies that can be used in the present invention include those described in U.S. Provisional Application 60/113,647 (filed Dec. 23, 1998) which is herein incorporated by reference in its entirety.

A compound of formula I may be applied as a sole therapy or may involve one or more other anti-tumor substances, for example those selected from, for example, mitotic inhibitors, for example vinblastine; alkylating agents, for example cisplatin, oxaliplatin, carboplatin and cyclophosphamide; antimetabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and antihormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds of the present invention may be used alone or in combination with one or more of a variety of anti-cancer agents or supportive care agents. For example, the compounds of the present invention may be used with cytotoxic agents; e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. The invention also contemplates the use of the compounds of the present invention together with hormonal therapy, e.g., exemestane (Aromasin), Lupron, anastrozole (Arimidex), tamoxifen citrate (Nolvadex), Trelstar, and combinations thereof. Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, tria pine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals include interferons and numerous other immune enhancing agents. Interferons include interferon alpha, interferon alpha-2a, interferon, alpha-2b, interferon beta, interferon gamma-1a or interferon gamma-n1. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, and Provenge;

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, or ubenimex;

Other anticancer agents include alitretinoin, ampligen, atrasentan, bexarotene, bortezomib, Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TLK-286, Velcade, Tarceva, or tretinoin;

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors are Iressa or SU5416;

Antibodies include Herceptin, Erbitux, Avastin, or Rituximab; and

Interferons include interferon alpha, interferon alpha-2a, interferon, alpha-2b, interferon beta, interferon gamma-1a or interferon gamma-n1.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The compounds of the present invention are potent inhibitors of the FAK protein tyrosine kinases, and thus are all adapted to therapeutic use as antiproliferative agents (e.g., anticancer), antitumor (e.g., effective against solid tumors), antiangiogenesis (e.g., stop or prevent proliferationation of blood vessels) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

In one preferred embodiment of the present invention cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In a more preferred embodiment cancer is selected a solid tumor, such as, but not limited to, breast, lung, colon, brain, prostate, stomach, pancreatic, ovarian, skin (melanoma), endocrine, uterine, testicular, and bladder.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

A particular aspect of this invention is directed to methods for treating or preventing a condition that presents with low bone mass in a mammal (including a human being) which comprise administering to a mammal in need of such treatment a condition that presents with low bone mass treating amount of a Formula I compound or a pharmaceutically acceptable salt of said compound.

This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a Formula I compound or a pharmaceutically acceptable salt of said compound.

Another aspect of this invention is directed to methods for treating a bone fracture or an osteoporotic fracture in a mammal which comprise administering to a mammal in need of such treatment a bone fracture treating or an osteoporotic fracture treating amount of a Formula I compound or a pharmaceutically acceptable salt of said compound.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophospatasemia.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

As noted above, the compounds of the invention are useful for treating abnormal cell growth such, e.g., cancer. Without being limited by theory, Applicants believe that the compounds of the invention are useful for treating or preventing abnormal cell growth by inhibiting the FAK kinases.

In Vitro and In Vivo Assays

As noted above, the compounds of the invention are useful as inhibitors of receptor tyrosine kinases such as, e.g., FAK, Aurora-1, Aurora-2, HgK and Pyk. Methods for determining the in vitro and in vivo activity of these compounds inhibitors of receptor tyrosine kinases are described below:

A. In-Vitro Activity of FAK:

The in vitro activity of the compounds of the compounds of the invention may be determined by the following procedure. More particularly, the following assay provides a method to determine whether compounds of the compounds of the invention inhibit the tyrosine kinase activity of the catalytic construct FAK(410-689). The assay is an ELISA-based format, measuring the inhibition of poly-glu-tyr phosphorylation by FAK(410-689). The assay protocol has three parts:

I. Purification and cleavage of His-FAK(410-689)
II. FAK410-689 (a.k.a. FAKcd) Activation
III. FAKcd Kinase ELISA Materials:
  Ni-NTA agarose (Qiagen)
  XK-16 column (Amersham-Pharmacia)
  300 mM Imidizole
  Superdex 200 HiLoad 16/60 prep grade column (Amersham Biotech.)
  Antibody: Anti-Phosphotyrosine HRP-Conjugated Py20 (Transduction labs)
  FAKcd: Purified and activated in house
  TMB Microwell Peroxidase Substrate (Oncogene Research Products #CL07)
  BSA: Sigma #A3294
  Tween-20: Sigma #P1379
  DMSO: Sigma #D-5879
  D-PBS: Gibco #14190-037
Reagents for Purification:
  Buffer A: 50 mM HEPES pH 7.0
  500 mM NaCl
  0.1 mM TCEP
  Complete™ protease inhibitor cocktail tablets (Roche)
  Buffer B: 25 mM HEPES pH 7.0
  400 mM NaCl
  0.1 mM TCEP
  Buffer C: 10 mM HEPES pH 7.5
  200 mM Ammonium Sulfate
  0.1 mM TCEP
Reagents for Activation:
  FAK(410-689): 3 tubes of frozen aliquots at 150 µl/tube for a total of 450 µl at 1.48 mg/ml (660 µg)
  His-Src(249-524): ~0.74 mg/ml stock in 10 mM HEPES, 200 mM (NH4)2SO4
  Src reaction buffer (Upstate Biotech):
  100 mM Tris-HCl pH7.2
  125 mM MgCl2
  25 mM MnCl2
  2 mM EDTA
  250 µM Na3VO4
  2 mM DTT
  Mn2+/ATP cocktail (Upstate Biotech)
  75 mM MnCl2
  500 µM ATP
  20 mM MOPS pH 7.2
  1 mM Na3VO4
  25 mM -glycerol phosphate
  5 mM EGTA
  1 mM DTT
  ATP: 150 mM stock
  MgCl2: 1 M Stock
  DTT: 1M stock
Reagents for FAKcd Kinase ELISA:
  Phosphorylation Buffer:
  50 mM HEPES, pH 7.5
  125 mM NaCl
  48 mM MgCl2
  Wash Buffer: TBS+0.1% Tween-20.
  Blocking Buffer:
  Tris Buffer Saline
  3% BSA
  0.05% Tween-20, filtered
  Plate Coating Buffer:
  50 mg/ml Poly-Glu-Tyr (Sigma #P0275) in Phosphate buffer Saline (DPBS).
  ATP: 0.1M ATP in H2O or HEPES, pH7
  Note: ATP Assay Buffer:
  Make up as 75 uM ATP in PBS, so that 80 µl in 120 µl reaction volume=50 µM final ATP concentration.

I. Purification of His-FAKcd(410-689):
1. Resuspend 130 g baculovirus cell paste containing the over expressed His-FAKcd410-689 recombinant protein in 3 volumes (400 ml) of Buffer A.
2. Lyse cells with one pass on a microfluidizer.
3. Remove cell debris by centrifugation at 4° C. for 35 minutes at 14,000 rpm in a Sorval SLA-1500 rotor.
4. Transfer the supernatant to a clean tube and add 6.0 ml of Ni-NTA agarose (Qiagen).
5. Incubate the suspension with gentle, rocking at 4° C. for 1 hour.
6. Centrifuge suspension at 700×g in a swinging bucket rotor.
7. Discard the supernatant and resuspend the agarose beads in 20.0 ml of Buffer A.
8. Transfer the beads to an XK-16 column (Amersham-Pharmacia) connected to a FPLC™.
9. Wash the agarose-beads with 5 column volumes of Buffer A and elute off the column with a step gradient of Buffer A containing 300 mM Imidizole.
10. Perform a buffer exchange of the eluted fractions into Buffer B.

11. Following buffer exchange, pool the fractions and add thrombin at a 1:300 (w/w) ratio and incubated overnight at 13° C. to remove the N-terminal His-tag (His-FAK410-698 a FAK410-689 (a.k.a. FAKcd)).

12. Add the reaction mixture back onto the Ni-NTA column equilibrated with Buffer A and collect the flow-through.

13. Concentrate the flow-through down to 1.7 ml and load directly onto a Superdex 200 HiLoad 16/60 prep grade column equilibrated with Buffer C. The desired protein elutes between 85-95 ml.

14. Aliquot the FAKcd protein and store frozen at −80° C.

II. FAK Activation

1. To 450 ul of FAK(410-689) at 1.48 mg/ml (660 µg) add the following:
30 µl 0.037 mg/ml (1 µM) His-Src(249-524)
30 µl 7.5 mM ATP
12 µl of 20 mM MgCl2
10 µl Mn2+/ATP cocktail (UpState Biotech.)
4 µl 6.7 mM DTT
60 µl Src Reaction Buffer (UpState Biotech.)

2. Incubate Reaction for at least 3 hours at room temperature At time t0, almost all of the FAK(410-689) is singly phosphorylated. The second phosphorylation is slow. At t120 (t=120 minutes), add 10 µl of 150 mM ATP.
T0=(Start) 90% singly phosphorylated FAK(410-689) (1 PO4)
T43=(43 min) 65% singly phosphorylated (1 PO4), 35% doubly phosphorylated (2 PO4)
T90=(90 min) 45% 1 PO4, 55% 2 PO4
T150=15% 1 PO4, 85% 2 PO4
T210=<10% 1 PO4, >90% 2 PO4 desalted sample 3. Add 180 µl aliquots of the desalted material to NiNTA spin column and incubate on spin column 4. Spin at 10 k rpm (microfuge), for 5 minutes to isolate and collect flow through (Activated FAK(410-689)) and remove His-Src (captured on column)

III. FAKcd Kinase ELISA

1. Coat 96-well Nunc MaxiSorp plates with poly-glu-tyr (pGT) at 10 µg/well: Prepare 10 µg/ml of pGT in PBS and aliquot 100 µl/well. Incubate the plates at 37° C. overnight, aspirate the supernatant, wash the plates 3 times with Wash Buffer, and flick to dry before storing at 4° C.

2. Prepare compound stock solutions of 2.5 mM in 100% DMSO. The stocks are subsequently diluted to 60× of the final concentration in 100% DMSO, and diluted 1:5 in Kinase Phosphorylation Buffer.

3. Prepare a 75 µM working ATP solution in Kinase phosphorylation buffer. Add 80 µl to each well for a final ATP concentration of 50 µM.

4. Transfer 10 µl of the diluted compounds (0.5 log serial dilutions) to each well of the pGT assay plate, running each compound in triplicates on the same plate.

5. Dilute on ice, FAKcd protein to 1:1000 in Kinase Phosphorylation Buffer. Dispense 30 µl per well.

6. Note: Linearity and the appropriate dilution must be predetermined for each batch of protein. The enzyme concentration selected should be such that quantitation of the assay signal will be approximately 0.8-1.0 at OD450, and in the linear range of the reaction rate.

7. Prepare both a No ATP control (noise) and a No Compound Control (Signal):

8. (Noise) One blank row of wells receives 10 µl of 1:5 diluted compounds in DMSO, 80 µl of Phosphorylation buffer (minus ATP), and 30 µl FAKcd solution.

9. (Signal) Control wells receive 10 µl of 1:5 diluted DMSO (minus Compound) in Kinase phosphorylation buffer, 80 µl of 75 uM ATP, and 30 µl of 1:1000 FAKcd enzyme.

10. Incubate reaction at room temperature for 15 minutes with gentle shaking on a plate shaker.

11. Terminate the reaction by aspirating off the reaction mixture and washing 3 times with wash buffer.

12. Dilute phospho-tyrosine HRP-conjugated (pY20HRP) antibody to 0.250 µg/ml (1:1000 of Stock) in blocking buffer. Dispense 100 µl per well, and incubate with shaking for 30 minutes at 25°.

13. Aspirate the supernatant and wash the plate 3 times with wash buffer.

14. Add 100 µl per well of room temperature TMB solution to initiate color development. Color development is terminated after approximately 15-30 sec. by the addition of 100 µl of 0.09M H2SO4 per well.

15. The signal is quantitated by measurement of absorbance at 450 nm on the BioRad microplate reader or a microplate reader capable of reading at OD450.

16. Inhibition of tyrosine kinase activity would result in a reduced absorbance signal. The signal is typically 0.8-1.0 OD units. The values are reported as IC50s, µM concentration.

FAK Inducible Cell-Based ELISA: Final Protocol

Materials:
Reacti-Bind Goat Anti-Rabbit Plates 96-well (Pierce Product#15135ZZ @115.00 USD)
FAKpY397 rabbit polyclonal antibody (Biosource #44624 @315.00 USD)
ChromePure Rabbit IgG, whole molecule (Jackson Laboratories #001-000-003 @60/25 mg USD)
UBI aFAK clone 2A7 mouse monoclonal antibody (Upstate#05-182 @ 289.00 USD)
Peroxidase-conjugated AffiniPure Goat Anti-Mouse IgG (Jackson Labs #1.15-035-146 @95/1.5 ml USD)
SuperBlock TBS (Pierce Product#37535ZZ @99 USD)
Bovine Serum Albumin (Sigma #A-9647 @117.95/100 g USD)
TMB Peroxidase substrate (Oncogene Research Products #CL07-100 ml @40.00 USD)
Na3VO4 Sodium Orthovanadate (Sigma #S6508 @43.95/50 g USD)
MTT substrate (Sigma # M-2128 @25.95/500 mg USD)
Growth Media: DMEM+10% FBS, P/S, Glu, 750 µg/ml Zeocin and 50 µg/ml Hygromycin (Zeocin InVitrogen #R250-05 @ 725 USD and Hygromycon InVitrogen #R220-05 @ 150 USD)
Mifepristone InVitrogen # H110-01 @ 125 USD
Complete™ EDTA-free Protease Inhibitor pellet Boehringer Mannheim #1873580

FAK cell-based Protocol for selectivity of kinase-dependent phosphoFAKY397

Procedure:

An inducible FAK cell-based assay in ELISA format for the screening of chemical matter to identify tyrosine kinase specific inhibitors was developed. The cell-based assay exploits the mechanism of the GeneSwitch™ system (InVitrogen) to exogenously control the expression and phosphorylation of FAK and the kinase-dependent autophosphorylation site at residue Y397.

Inhibition of the kinase-dependent autophosphorylation at Y397 results in a reduced absorbance signal at OD450. The signal is typically 0.9 to 1.5 OD450 units with the noise falling in the range of 0.08 to 0.1 OD450 units. The values are reported as IC50s, µM concentration.

On day 1, grow A431•FAKwt in T175 flasks. On the day prior to running the FAK cell-assay, seed A431•FAKwt cells in growth media on 96-well U-bottom plates. Allow cells to sit at 37° C., 5% CO2 for 6 to 8 hours prior to FAK induction. Prepare Mifepristone stock solution of 10 µM in 100% Ethanol. The stock solution is subsequently diluted to 10× of the final concentration in Growth Media. Transfer 10 µl of this dilution (final concentration of 0.1 nM Mifepristone) into each well. Allow cells to sit at 37° C., 5% CO2 overnight (12 to 16 hours). Also, prepare control wells without Mifepristone induction of FAK expression and phosphorylation.

On day 2, coat Goat Anti-Rabbit plate(s) with 3.5 µg/ml of phosphospecific FAKpY397 polyclonal antibody prepared in SuperBlock TBS buffer, and allow plate(s) to shake on a plate shaker at room temperature for 2 hours. Optionally, control wells may be coated with 3.5 µg/ml of control Capture antibody (Whole Rabbit IgG molecules). prepared in SuperBlock TBS. Wash off excess FAKpY397 antibody 3 times using buffer. Block Anti-FAKpY397 coated plate(s) with 200 µl per well of 3% BSA/0.5% Tween Blocking buffer for 1 hour at room temperature on the plate shaker. While the plate(s) are blocking, prepare compound stock solutions of 5 mM in 100% DMSO. The stock solutions are subsequently serially diluted to 100× of the final concentration in 100% DMSO. Make a 1:10 dilution using the 100× solution into growth media and transfer 10 µl of the appropriate compound dilutions to each well containing either the FAK induced or uninduced control A431 cells for 30 minutes at 37° C., 5% CO$_2$. Prepare RIPA lysis buffer (50 mM Tris-HCl, pH7.4, 1% NP-40, 0.25% Na-deoxycholate, 150 mM NaCl, 1 mM EDTA, 1 mM Na3VO4, 1 mM NaF, and one Complete™ EDTA-free protease inhibitor pellet per 50 ml solution). At the end of 30 minutes compound treatment, wash off compound 3 times using TBS-T wash buffer. Lyse cells with 100 µl/well of RIPA buffer.

To the coated plate, remove blocking buffer and wash 3 times using TBS-T wash buffer. Using a 96-well automated microdispenser, transfer 100 µl of whole cell-lysate (from step 6) to the Goat Anti-Rabbit FAKpY397 coated plate(s) to capture phosphoFAKY397 proteins. Shake at room temperature for 2 hours. Wash off unbound proteins 3 times using TBS-T wash buffer. Prepare 0.5 µg/ml (1:2000 dilution) of UBI aFAK detection antibody in 3% BSA/0.5% Tween blocking buffer. Dispense 100 µl of UBI aFAK solution per well and shake for 30 minutes at room temperature. Wash off excess UBI aFAK antibody 3 times using TBS-T wash buffer. Prepare 0.08 µg/ml (1:5000 dilution) of secondary Anti-Mouse Peroxidase (Anti-2 MHRP) conjugated antibody. Dispense 100 µl per well of the Anti-2 MHRP solution and shake for 30 minutes at room temperature. Wash off excess Anti-2 MHRP antibody 3 times using TBS-T wash buffer. Add 100 µl per well of room temperature TMB substrate solution to allow for color development. Terminate the TMB reaction with 100 µl per well of TMB stop solution (0.09M H2SO4) and quantitate the signal by measurement of absorbance at 450 nm on the BioRad microplate reader.

Additional FAK cell assays are hereby incorporated by reference from WO2004/027018.

In a preferred embodiment, the compounds of the present invention have an in vitro activity as determined by a kinase assay, e.g., such as that described herein, of less than 500 nM. Preferably, the compounds have an IC50 of less than 25 nM in the kinase assay, and more preferably less than 10 nM. In a further preferred embodiment, the compounds exhibit an IC50 in a FAK cell based assay, e.g., such as that described herein, of less than 1 µM, more preferably less than 100 nM, and most preferably less than 25 nM.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

All patents, applications, publications, test methods, literature, and other materials cited herein are hereby incorporated herein by reference in their entireties.

EXAMPLES

General Methods

HPLC:
Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.
Preparation of Intermediates:

The groups attached to the 4 position of the pyridine core were prepared by the methods described below for compounds B1-B19.

Preparation of
N-(3-aminomethyl-phenyl)-N-methanesulfonamide
acetate (B1)

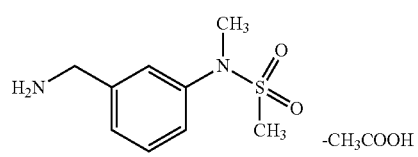

Step 1. Preparation of N-(3-cyano-phenyl)-methanesulfonamide (B1-1): A solution of 3-amino benzonitrile (10 g, 84.64 mmol) in pyridine (160 mL) was cooled to 0° C. and methane sulphonyl chloride (8.6 mL, 74.8 mmol) was added. The reaction mixture was allowed to warm to 25° C. and stirred for about 20 hours. The reaction mixture was then concentrated, and the resultant residue was dissolved in ethyl acetate (EtOAc) (250 mL), washed with 2N HCl (50 mL), brine (25 mL), and dried over anhydrous $Na_2SO_4$. The solution was then concentrated to provide (B1-1) as a brown solid. Yield: 17.1 g. $^1$HNMR ($d_6$-DMSO) δ: 10.25 (s, 1H), 7.45-7.65 (m, 4H) and 3.1 (s, 3H). Mass: (M−1) 195 calculated for $C_8H_8N_2O_2S$.

Step. 2. Preparation of N-(3-cyano-phenyl)-N-methyl-methanesulfonamide (B1-2): A mixture of benzyltriethylammonium chloride (BTEAC) (2.44 g, 10.7 mmol) and B1-1 (21 g, 107.1 mmol) in tetrahydrofuran (THF) (250 mL) and 40% NaOH solution (250 mL) was cooled to 10° C., treated with methyl iodide (8.6 mL, 139.0 mmol), and allowed to warm to 25° C. After about 20 hours the THF was removed by distillation, and the concentrated mixture was extracted with dichloromethane (DCM) (3×200 mL). The combined organic layers were washed with water (100 mL), brine (50 mL), dried over anhydrous sodium sulfate, and concentrated. The resultant residue was then purified by column chromatography (60-120 mesh silica gel; 20% EtOAc in hexane as eluting solvent) to provide B1-2 as a white solid. Yield: 20 g, 89.3%. $^1$HNMR ($d_6$-DMSO) δ: 7.9 (s, 1H), 7.7-7.84 (m, 2H), 7.52-7.65 (m, 2H), 3.3 (s, 3H) and 3.02 (s, 3H). Mass: (M+1) 211 calculated for $C_9H_{10}N_2O_2S$.

Step 3. A solution of B1-2 (20 g, 95.12 mmol) in THF (100 mL) and acetic acid (400 mL) was charged to a Parr reactor. The contents of the reactor were then treated with 10% Pd/C (10.12 g) and hydrogenated at 50 Psi hydrogen pressure and 25° C. for 4 hours. The contents of the reactor were filtered through a bed of Celite® and washed with ethanol (50 mL). The combined filtrates were then concentrated under reduced pressure, and the resultant residue was azeotroped with EtOAc (3×50 mL). The resultant oily mass was dissolved in EtOAc and allowed stand at 25° C. for about 20 hours. The resultant white solids were collected by filtration and dried to provide B1 as the acetate salt. Yield: 15.2 g, 60%. $^1$HNMR ($d_6$-DMSO) δ: 7.2-7.45 (m, 4H), 4.6-5.65 (broad, 4H), 3.75 (s, 2H), 3.2 (s, 3H), 2.95 (s, 3H) and 1.9 (s, 3H). Mass: (M+1) 215 calculated for $C_9H_{14}N_2O_2S$. HPLC Purity: 99.1%.

Preparation of N-(3-aminomethyl-pyrazin-2-yl)-N-methyl-methane sulfonamide acetate (B2)

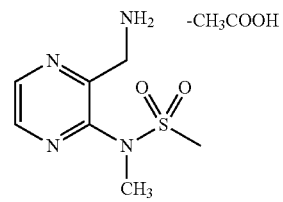

Step 1. Preparation of N-(3-cyano-pyrazin-2-yl)-N-methyl-methane sulfonamide (B2-1): A solution of chloropyrazine-2-carbonitrile (4.2 g, 30.21 mmol) in acetonitrile (200 mL) at 25° C. was treated sequentially with $Cs_2CO_3$ (13.7831 g, 42.293 mmol) and N-methyl-methane sulfonamide (3.957 g, 36.25 mmol). The mixture was then heated to 80° C. After about 20 hours the mixture was cooled to 25° and filtered. The solids were washed with EtOAc (3×25 mL) and the combined filtrates were concentrated. The resultant residue was treated with water (50 mL) and extracted with EtOAc (3×75 mL). The combined organic layers were washed with water (50 mL), brine, dried over anhydrous sodium sulfate and concentrated. The resultant residue was purified by column chromatography (100-200 mesh silica gel; 40% EtOAc in petroleum ether as eluting solvent) to provide 62-1 as a pale brown liquid. Yield: 4.7 g, 73.43%). $^1$HNMR (CDCl$_3$) δ: 8.92 (d, 2H), 3.4 (s, 3H) and 3.25 (s, 3H). Mass: (M+1) 213 calculated for C$_7$H$_8$N$_4$O$_2$S. (Note: The product contained unreacted N-methanesulfonamide as an impurity. The product was used without further purification to prepare B2 in the step described below.

Step 2. A suspension of B2-1 (5.345 g, 23.21 mmol) in 2N methanolic NH$_3$ (566.7 mL) in a Parr reactor was treated with 10% Pd/C (395 mg, 3.78 mmol), and the contents of the reactor were hydrogenated at 45 Psi hydrogen pressure and 25° C. for 3 hours. The contents of the reactor were then filtered through a bed of Celite®, washed with methanol (MeOH), and concentrated. The resultant residue was treated with EtOAc (25 mL) and acetic acid (1.5 g), stirred at 25° C., and concentrated. The resultant residue was treated with EtOAc (100 mL) and allowed to stand at 25° C. for about 20 hours. The resultant solids were collected, washed with EtOAc, and dried to provide B2. Yield: 3.5 g, 64.3%. IR (cm$^{-1}$): 3453, 3222, 2937, 3859, 1641, 1560, 1405, 1340 and 1155. $^1$HNMR (d$_6$-DMSO) δ: 8.7 (s, 1H), 8.5 (s, 1H), 5.3-5.8 (broad, 2H), 4.0 (s, 2H), 3.2 (s, 3H), 3.12 (s, 3H) and 1.84 (s, 3H). Mass: (M+1) 217 calculated for C$_7$H$_{12}$N$_4$O$_2$S.

Preparation of N-(2-aminomethyl-phenyl)-N-methyl-methanesulfonamide acetate (B3)

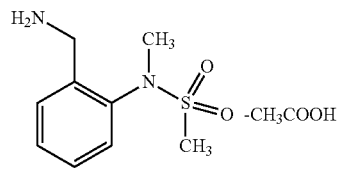

Step 1. Preparation of N-(2-cyano-phenyl)-N-dimethane-sulfonamide (B3-1): A solution of 2-amino benzonitrile (10 g, 8.46 mmol) in pyridine (250 mL) at 25° C. was treated drop-wise over 30 minutes with methane sulphonyl chloride (21.33 g, 18.62 mmol). The reaction mixture was then stirred at 25° C. for about 20 hours and concentrated The resultant residue was dissolved in EtOAc (200 mL), washed with 2 N HCl (200 mL) and brine (30 mL), and dried over anhydrous sodium sulfate. The solution was then concentrated to provide B3-1 as a yellow solid. Yield: 20.7 g, 89%. $^1$HNMR (d$_6$-DMSO) δ: 8.06 (d, 1H), 7.82-7.85 (m, 2H), 7.7-7.75 (m, 1H), 3.62 (s, 6H).

Step 2. Preparation of N-(2-cyano-phenyl)-N-methyl-methanesulfonamide (B3-2): A solution of B3-1 (4 g, 1.45 mmol) in THF (30 mL) at 25° C. was treated with 40% NaOH solution (30 mL) and BTEAC (0.331 g, 0.145 mmol) and stirred vigorously for 30 minutes. The mixture was then treated with methyl iodide (2.48 g, 1.7 mmol) and stirred at 25° C. for about 20 hours. The THF was removed under reduced pressure and the mixture extracted with DCM (3×50 mL). The combined organic layers were washed with brine, dried over anhydrous sodium sulfate, and concentrated to provide B3-2 as a pale yellow solid. Yield: 3 g, 96%. $^1$HNMR (CDCl$_3$) δ: 7.62-7.8 (m, 2H), 7.55-7.56 (m, 1H), 7.4-7.52 (m, 1H), 3.4 (s, 3H) and 3.15 (s, 3H). Mass: (M−1) 209 calculated for C$_9$H$_{10}$N$_2$O$_2$S. The product was used without further purification to prepare B3 in the step described below.

Step 3. A solution of B3-2 (2 g, 9.5 mmol) in a mixture of acetic acid (100 mL) and THF (25 mL) was charged to a Parr shaker. The contents of the reactor were treated with 10% Pd/C (1.01 g) and hydrogenated at 60 Psi hydrogen pressure and 25° C. for 3.5 hours. The contents of the reactor were then filtered through a bed of Celite® and washed with MeOH (20 mL). The combined filtrates were then concentrated. The resultant residue was azeotroped with toluene (2×20 mL) and EtOAc (20 mL) and dried under vacuum to provide B3 as a white solid. Yield: 1.9 g, 95%. $^1$HNMR (d$_6$-DMSO) δ: 7.5-7.62 (m, 1H), 7.25-7.5 (m, 3H), 3.92-5.6 (broad, 3H), 3.8 (s, 2H), 3.16 (s, 3H), 3.04 (s, 3H) and 1.9 (s, 2H). Mass: (M+1) 215 calculated for C$_9$H$_{14}$N$_2$O$_2$S. HPLC Purity: 98.8%.

Preparation of N-(2-aminomethyl-pyridin-3-yl)-N-methyl-methanesulfonamide acetate salt (B4)

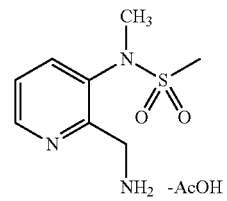

Step 1. Preparation of 6-chloro-pyridin-3-ylamine (B4-1): A solution of 2-chloro-5-nitro pyridine (30 g, 189 mmol) in MeOH (600 mL) was charged to a Parr reactor. The contents of the reactor were treated with Raney nickel (2 g) and hydrogenated at 60 Psi hydrogen pressure and 25° C. for 16 hours. The contents of the reactor were then filtered through a Celite® bed and washed with MeOH (100 mL). The combined filtrates were concentrated, and the resultant residue was purified by column chromatography (60-120 mesh silica gel column; 10% MeOH in CHCl$_3$ as eluting solvent) to provide B4-1 as a pale yellow solid. Yield: 19 g, 78%. $^1$HNMR (CDCl$_3$) δ: 7.85 (d, 1H), 7.1 (d, 1H), 6.95 (dd, 1H) and 3.52-3.98 (broad s, 2H).

Step 2. Preparation of N-(6-chloro-pyridin-3-yl)-methane-sulfonamide (B4-2): A solution of B4-1 (38 g, 295.7 mmol) and pyridine (28 g, 354 mm) in DCM (874 mL) at 10° C. was treated drop-wise over 30 minutes with methane sulphonyl chloride (37.2 g, 325 mmol). The reaction mixture was allowed to warm to 25° C., and stirred at 25° C. for 20 hours. The mixture was then treated with DCM (300 mL) and washed with water (1500 mL) and brine. The organic layer was dried over anhydrous sodium sulfate and concentrated. The resultant residue was washed with petroleum ether (80 mL), filtered, and dried to provide B4-2 as an off-white solid. Yield: 36 g, 60%. $^1$HNMR (d$_6$-DMSO) δ: 10.12 (s, 1H), 8.22 (d, 1H), 7.65 (dd, 1H), 7.46 (d, 1H) and 3.08 (s, 3H).

Step 3. Preparation of N-(6-chloro-pyridin-3-yl)-N-methyl-methanesulfonamide (B4-3): A solution of B4-2 (13 g, 62.8 mmol), BTEAC (1.42 g, 6.2 mmol) and 40% aq. NaOH (117 mL) in THF (117 mL) at 0° C. was treated drop-wise over 30 minutes with methyl iodide (10.6 g, 75.3 mmol). The reaction mixture was allowed to warm to 25° C. and stirred for an additional 3 hours. The mixture was then treated with THF (100 mL), and the resultant organic layer was collected. The aqueous layer was extracted with EtOAc (2×100 mL), and the combined organic layers were washed with 1N NaOH and brine. The organic layer was dried over anhydrous sodium sulfate and concentrated. The resultant residue was then triturated with petroleum ether to provide B4-3 as a pale yellow solid. Yield: 12 g, 86%. $^1$HNMR (CDCl$_3$) δ: 8.4 (d, 1H), 7.72 (dd, 1H), 7.35 (d, 1H), 3.38 (s, 3H) and 2.88 (s, 3H). Mass: (M+1) 221 calculated for $C_7H_9ClN_2O_2S$.

Step 4. Preparation of N-(6-chloro-1-hydroxy-pyridin-3-yl)-N-methyl-methanesulfonamide (B4-4): A solution of B4-3 (15 g, 68.1 mmol) in DCM (172 mL) was cooled to 0° C. and treated slowly over 10 minutes with a solution of 77% m-chloroperoxybenzoic acid (MCPBA) (27.9 g, 124 mm) in DCM (200 mL). The rate of addition was controlled so that the temperature of the reaction mixture did not exceed 3 to 5° C. The reaction mixture was allowed to warm to 25° C. and stirred at 25° C. for 20 hours. The mixture was then cooled to 0° C. and treated with 1N NaOH (300 mL). The resultant organic layer was collected and washed with 1N NaOH (100 mL) and 10% sodium sulfite (100 mL). The organic layer was then dried over anhydrous Na$_2$SO$_4$ and concentrated to provide B4-4 as a white crystalline solid. Yield: 8 g, 49%. $^1$HNMR (d$_6$-DMSO) δ: 8.55 (s, 1H), 7.85 (d, 1H), 7.46 (dd, 1H), 3.26 (s, 3H) and 3.1 (s, 3H). Mass: (M+1) 237 calculated for $C_7H_{11}ClN_2O_3S$.

Step 5. Preparation of N-(6-chloro-2-cyano-pyridin-3-yl)-N-methyl-methanesulfonamide (B4-5): Dimethylsulfate (3.2 mL) was cooled to 0° C. and treated portion-wise with B4-4 (8 g, 33.6 mmol) over 3 hours. The resultant suspension was allowed to warm to 25° and maintained at 25° C. for 16 hours. The resulted gummy mass was then washed with diethyl ether. The resultant white residue was dissolved in water (37.6 mL) and added drop-wise over 30 minutes to an aqueous solution of sodium cyanide (6.5 g, 134.4 mm) at 10° C. The reaction mixture was allowed to warm to 25° C., and it was maintained at 25° C. for 16 hours. The resultant brown solids were collected and dissolved in EtOAc (200 mL). The organic solution was then washed with water (500 mL) and brine, and dried over anhydrous sodium sulfate. The organic solution was concentrated, and the resultant residue was purified by column chromatography (silica gel; 10% MeOH in CHCl$_3$ as eluting solvent) to provide B4-5 as a white solid. Yield: 2.5 g, 30%. $^1$HNMR (d$_6$-DMSO) δ: 8.38 (d, 1H), 8.02 (d, 1H), 3.3 (s, 3H) and 3.28 (s, 3H).

Step 6. A solution of B4-5 (2.5 g, 10.2 mmol) in a mixture of THF (80 mL) and acetic acid (200 mL) was charged to a Parr reactor. The contents of the Parr reactor were then treated with 10% Pd/C (2.4 g, 22.4 mmol) and hydrogenated at 60 Psi hydrogen pressure and 25° C. for 16 hours. The contents of the reactor were filtered through a Celite® bed and washed with MeOH (100 mL). The combined organic filtrates were concentrated, and the resultant residue was azeotroped with EtOAc (2×50 mL). The resultant solids were collected and dried to provide B4 as an off-white solid. Yield: 2.0 g, 95%. IR (cm$^{-1}$): 3438, 3245, 2994, 2601, 1590, 1467, 1328, 1151 and 1047. $^1$HNMR (d$_6$-DMSO) δ: 8.65 (d, 1H), 8.25-8.55 (broad s, 2H), 8.15 (d, 1H), 7.5-7.7 (m, 1H), 4.0-4.42 (s, 2H), 3.25 (s, 3H) and 3.14 (s, 3H). Mass: (M+1) 216 calculated for $C_8H_{13}N_3O_2S$.

Preparation of N-(3-Aminomethyl-pyridin-2-yl)-N-methyl-methanesulfonamide acetate (B5)

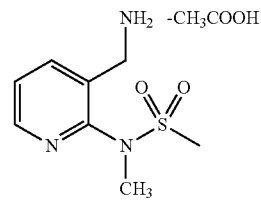

Step 1. Preparation of N-(3-cyano-pyridin-2-yl)-N-methyl-methanesulfonamide (B5-1): A solution of 2-chloro-3-cyano-pyridine (10 g, 72.4 mmol) in acetonitrile (200 mL) at 25° C. was treated with N-methyl-methanesulfonamide (14 g, 128.2 mmol) and Cs$_2$CO$_3$ (33 g, 101.2 mmol). The reaction mixture was slowly heated to 80° C. and maintained at 80° C. for 8 hours. The reaction mixture was then cooled to 25 C, filtered through a Celite® bed, and concentrated. The resultant residue was treated with water (300 mL) and extracted with EtOAc (3×200 mL). The combined organic layers were washed with brine, dried over sodium sulfate, treated with carbon, and filtered. The filtrate was then concentrated, and the resultant residue was triturated with ether (100 mL). The resultant solids were collected and dried to provide B5-1 as an off-white solid. Yield: 7 g, 46%. $^1$HNMR (CDCl$_3$) δ: 8.6-8.72 (m, 1H), 8.02-8.12 (d, 1H), 7.3-7.45 (m, 1H), 3.4 (s, 3H) and 3.2 (s, 3H). Mass: (M+1) 212 calculated for $C_8H_9N_3O_2S$. HPLC purity: 99.9%.

Step 2. A solution of B5-1 (10 g, 47.3 mmol) in ethanol was charged to a Parr reactor, and the contents of the reactor were treated with 300 mL of a 2M ammonia solution in ethanol and 5% Pd/C (1.2 g). The contents of the reactor were then hydrogenated at 60 Psi hydrogen pressure and 37° C. for 3 hours and then at 30° C. for 20 hours. The contents of the reactor were filtered through a Celite® bed and concentrated. The resultant residue was treated with EtOAc, cooled to 20° C., and treated with acetic acid (10 mL). The mixture was then stirred for 10 minutes and concentrated. The resultant residue was dissolved in EtOAc (150 mL) in a glass flask. The walls of the flask were then scratched, and white solids began to form. The solids were collected and washed with EtOAc followed by petroleum ether. The solids were then dried to provide B5. Yield: 11 g, 85%. $^1$HNMR (CDCl$_3$) δ: 8.3-8.5 (m, 1H), 8.04 (d, 1H), 7.4-7.55 (m, 1H), 6.02-7.15 (broad, 3H), 3.85 (s, 2H), 3.14 (d, 6H), 1.9 (s, 3H). Mass: (M+1) 216 calculated for $C_8H_{13}N_3O_2S$.

Preparation of N-(2-Aminomethyl-phenyl)-N-methyl-methanesulfonamide acetate (B6)

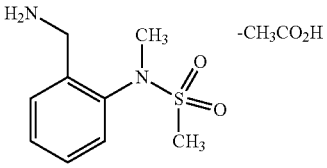

Step 1. Preparation of N-(2-Cyano-phenyl)-N-dimethanesulfonamide (B6-1): A solution of 2-amino benzonitrile (10 g, 8.46 mmol) in pyridine (250 mL) was treated drop-wise at 25° C. over 30 minutes with methane sulphonyl chloride (21.33 g, 18.62 mmol). The reaction mixture was then stirred at 25° C. for 20 hours and concentrated. The resultant residue was dissolved in EtOAc (200 mL) and washed with 2 N HCl (200 mL) and brine (30 mL). The solution was dried over anhydrous sodium sulfate and concentrated to provide B6-1 as a yellow solid. Yield: 20.7 g, 89%. $^1$HNMR ($d_6$-DMSO): δ 8.06 (d, 1H), 7.82-7.85 (m, 2H), 7.7-7.75 (m, 1H), 3.62 (s, 6H). The product was used without further purification to prepare B6-2 in the step described below.

Step 2. Preparation of N-(2-Cyano-phenyl)-N-methyl-methanesulfonamide (B6-2): A solution of B6-1 (4 g, 1.45 mmol) in THF (30 mL) was treated with 40% NaOH (30 mL) and BTEAC (0.331 g, 0.145 mmol) at 25° C. and stirred vigorously for 30 minutes. The mixture was then treated with methyl iodide (2.48 g, 1.7 mmol) and stirred at 25° C. for 20 hours. The THF was removed under reduced pressure, and the concentrated mixture was extracted with DCM (3×50 mL). The combined organic layers were washed with brine, dried over anhydrous sodium sulfate, and concentrated to provide B6-2 as pale yellow solid. Yield: 3 g, 96%. $^1$H NMR (CDCl$_3$): δ 7.62-7.8 (m, 2H), 7.55-7.56 (m, 1H), 7.4-7.52 (m, 1H), 3.4 (s, 3H) and 3.15 (s, 3H). Mass: (M−1) 209 calculated for $C_3H_{10}N_2O_2S$. The product was used without further purification to prepare B6 in the step described below.

Step 3. A solution at B6-2 (2 g, 9.5 mmol) in a mixture of acetic acid (100 mL) and THF (25 mL) was charged to a Parr reactor. The contents of the reactor were treated with Pd/C (1.01 g) and hydrogenated at 60 Psi hydrogen pressure and 25° C. for 3.5 hours. The mixture was then filtered through a bed of Celite® and washed with methanol (20 mL). The combined filtrates were concentrated, and the resultant residue was azeotroped with toluene (2×20 mL) followed by EtOAc (20 mL). The residue was then dried under reduced pressure to provide B6 as a white solid. Yield: 1.9 g, 95%. $^1$HNMR ($d_6$-DMSO): δ 7.5-7.62 (m, 1H), 7.25-7.5 (m, 3H), 3.92-5.6 (broad, 3H), 3.8 (s, 2H), 3.16 (s, 3H), 3.04 (s, 3H) and 1.9 (s, 2H). Mass: (M+1) 215 calculated for $C_9H_{14}N_2O_2S$. HPLC Purity: 98.8%.

Preparation of N-(2-Aminomethyl-phenyl)-methanesulfonamide acetate (B7)

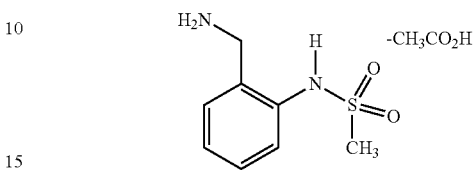

Step 1. Preparation of N-(2-cyano-phenyl)-methanesulfonamide (B7-1): A solution of B6-1 (4 g, 14.8 mmol) in THF (29.26 mL) was treated with 40% aqueous NaOH (29.26 mL) and BTEAC (0.331 g, 1.45 mmol) and stirred at 25° C. for 20 hours. The reaction mixture was then concentrated, and the resultant residue was diluted with water (100 mL) and neutralized with 6N HCl (30 mL). The mixture was extracted with DCM (200 mL), and the organic layer was washed with water (150 mL) and brine. The organic solution was then dried over anhydrous sodium sulfate and concentrated to provide B7-1 as a white solid. Yield: 2.8 g, 92%. $^1$HNMR (CDCl$_3$): δ 7.7-7.76 (m, 1H), 7.6-7.65 (m, 1H), 6.8-6.98 (broad, 1H) and 3.14 (s, 3H). Mass: (M−1) 195 calculated for $C_8H_8N_2O_2S$.

Step 2. A solution of B7-1 (2 g, 10.19 mmol) in a mixture of THF (133 mL) and acetic acid (250 mL) was charged to a Parr reactor. The contents of the reactor were then treated with 10% Pd/C (2 g) and hydrogenated at 60 Psi hydrogen pressure and 25° C. for 4 hours. The reaction mixture was filtered through Celite® bed and concentrated. The resultant residue was diluted with toluene (20 mL) and concentrated. The resultant residue was then diluted with EtOAc (20 mL) and concentrated to provide B7 as white solid. Yield: 2 g, 98%. $^1$HNMR ($d_6$-DMSO): δ 7.32-8.6 (broad, 4H), 7.25-7.32 (m, 1H), 7.1-7.32 (m, 2H), 6.82 (t, 1H), 3.9 (s, 2H), 2.85 (s, 3H) and 1.9 (s, 3H). Mass: (M+1) 201 calculated for $C_8H_{12}N_2O_2S$. HPLC Purity: 98.9%.

Preparation of N-(2-Aminomethyl-3-methyl-phenyl)-methanesulfonamide acetate (B8)

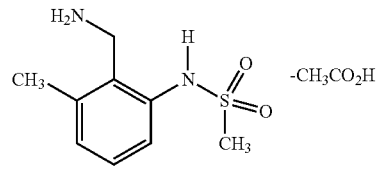

Step 1. Preparation of N-(2-cyano-3-methyl-phenyl)-N-dimethanesulfonamide (B8-1): A suspension of 2-amino-6-methyl benzonitrile (35 g, 265.5 mmol) in pyridine (600 mL) was cooled to about 0° C. to −5° C. and slowly treated with mesyl chloride (30 mL, 397.71 mmol) over 10 minutes. The reaction mixture was allowed to warm to 26° C. and stirred at 25° C. for 20 hours. The reaction mixture was concentrated and the resultant residue was diluted with EtOAc (600 mL). The organic solution was then washed with water (100 mL), 2N HCl (100 mL), and saturated brine (100 mL). The organic solution was then dried over anhydrous sodium sulfate and concentrated to provide B8-1 as a mixture of di- and monomesylated products. Yield: 49 g. The product was used without further purification to prepare B8-2 in the step described below.

Step 2. Preparation of N-(2-cyano-3-methyl-phenyl)-methanesulfonamide (B8-2): A solution of B8-1 (35 g, 166.6 mmol) in THF (300 mL) was treated with 40% aq. NaOH solution (300 mL) and BTEAC (1.84 g, 8.09 mmol) at 25° C. and stirred for 1 hour. The THF was removed under reduced pressure, and the concentrated mixture was extracted with DCM (500 mL). The aqueous layer was acidified with 2N HCl and extracted with DCM (250 mL). The combined organic layers were washed with water (100 mL) and brine (50 mL). The organic solution was then dried over anhydrous sodium sulfate and concentrated. The resultant residue was purified by column chromatography (60-120 mesh silica gel; 3% MeOH in CHCl$_3$ as eluting solvent) to provide B8-2 as a brown solid. Yield: 24 g. $^1$HNMR (d$_6$-DMSO): δ 9.98 (s, 1H), 7.6 (t, 1H), 7.26-7.4 (m, 2H), 3.1 (s, 3H), 2.5 (s, 3H). Mass: (M−1) 209 calculated for $C_9H_{10}N_2O_2S$.

Step 3. A solution of B8-2 (10 g, 47.6 mmol) in acetic acid (75 mL) and THF (250 mL) was charged to a Parr reactor and treated with 10% Pd/C (6 g). The reaction mixture was then hydrogenated at 50 Psi hydrogen pressure and 25° C. for 16 hours. The reaction mixture was filtered through a Celite® bed and washed with ethanol (3×20 mL). The combined filtrates were concentrated, and the resultant residue was co-distilled with EtOAc (100 mL). The resultant brown oil was dissolved in EtOAc (100 mL) and allowed to stand at 25° C. for 20 hours. The resultant white solids were collected and dried to provide B8. Yield: 11 g. $^1$HNMR (d$_6$-DMSO): δ 7.65-8.65 (broad, 3H), 7.15 (d, 1H), 7.05 (t, 1H), 6.68 (d, 1H), 3.9 (s, 2H), 2.8 (s, 3H), 2.26 (s, 3H) and 1.9 (s, 3H). Mass: (M+1) 215 calculated for $C_9H_{14}N_2O_2S$. HPLC Purity: 98.6%.

Preparation of N-(2-Aminomethyl-3-methyl-phenyl)-N-methyl-methanesulfonamide acetate (B9)

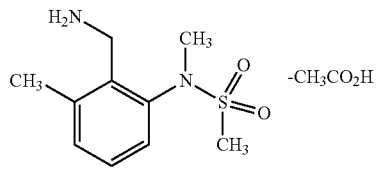

Step 1. Preparation of N-(2-cyano-3-methyl-phenyl)-N-methyl-methanesulfonamide (B9-1): A solution of B8-1 (15 g, 71.42 mmol) in THF (150 mL) was treated with 40% aq. NaOH (150 mL) and BTEAC (1.6 g, 7.14 mmol) at 25° C. and stirred for 10 minutes. The reaction mixture was then cooled to 10° C. and treated with methyl iodide (5.78 mL, 85.7 mmol). The reaction mixture was allowed to warm to 25° C. and stirred at 25° C. for 20 hours. The reaction mass was concentrated, and the resultant residue was diluted with DCM (600 mL). The organic solution was then washed with water (100 mL) and brine (50 mL). The organic solution was dried over anhydrous sodium sulfate and concentrated. The resultant residue was purified by column chromatography (60-120 mesh silica gel; 2% MeOH in CHCl$_3$ as eluting solvent) to provide B9-1 as pale brown solid. Yield: 20 g, 98%. $^1$HNMR (d$_6$-DMSO): δ 7.65 (d, 1H), 7.56 (d, 1H), 7.45 (d, 1H), 3.25 (s, 3H), 3.14 (s, 3H) and 2.5 (s, 3H). Mass: (M+1) 225 calculated for $C_{10}H_{12}N_2O_2S$.

Step 2. A solution of B9-1 (10 g, 47.6 mmol) in a mixture of THF (100 mL) and acetic acid (300 mL) was charged to a Parr reactor and treated with Pd/C (6 g). The contents of the reactor were then, hydrogenated at 50 Psi hydrogen pressure and 25° C. for 6 hours. The reaction mixture was filtered through a bed of Celite® and washed with ethanol (3×30 mL). The combined filtrates were concentrated, and the resultant residue was co-distilled with EtOAc (100 mL). The resultant brown oil was taken into EtOAc (100 mL) and stirred at 25° C. for 16 hours. The resultant white solids were collected, washed with EtOAc (2×25 mL), and dried to provide B9. Yield: 11.6 g, 89%. $^1$HNMR (d$_6$-DMSO): δ 7.15-7.36 (m, 3H), 4.64-5.45 (broad, 3H), 3.76 (d, 2H), 3.15 (s, 3H), 3.05 (s, 3H), 2.42 (s, 3H) and 1.9 (s, 3H). Mass: (M+1) 229 calculated for $C_{10}H_{16}N_2O_2S$. HPLC Purity: 97.4%.

Preparation of N-(2-Aminomethyl-5-methyl-phenyl)-methanesulfonamide acetate (B10)

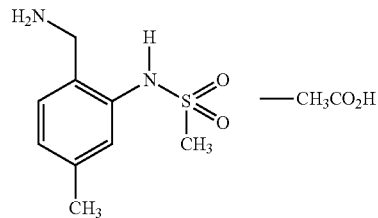

Step 1. Preparation of 2-amino-4-methyl-benzonitrile (B10-1): A solution of 4-methyl-2-nitrobenzonitrile (10 g, 61.72 mmol) in ethanol (200 mL) was charged to a Parr reactor and treated with 10% Pd/C (1 g). The contents of the reactor were then hydrogenated at 50 Psi hydrogen pressure 25° C. for 90 minutes. The reaction mixture was filtered through a Celite® bed and washed with ethanol. The combined filtrates were the concentrated to provide B10-1. Yield: 8.5 g. $^1$HNMR (CDCl$_3$): δ 7.28 (s, 1H), 6.5-6.62 (m, 2H), 4.2-4.42 (broad, 2H) and 2.3 (s, 3H). Mass: (M−1) 132 calculated for $C_8H_8N_2$. The product was used without further purification to prepare B10-2 in the step described below.

Step 2. Preparation of N-(2-cyano-5-methyl-phenyl)-methanesulfonamide and N-(2-cyano-5-methyl-phenyl)-N-(methylsulfonyl)methanesulfonamide (B10-2): A solution of B10-1 (8.5 g, 64.39 mmol) in pyridine (50 mL) was cooled to 0° C. and treated drop-wise with mesyl chloride (8.85 g, 77.22 mmol) over 15 minutes. The reaction mixture was allowed to warm to 25° C., and it was stirred at 25° C. for 20 hours. The reaction mixture was then concentrated, and the resultant residue acidified with 2N HCl (50 mL) and extracted with EtOAc (200 mL). The resultant organic layer was washed with water (50 mL) and brine (50 mL), and dried over anhydrous sodium sulfate. The organic solution was then concentrated to provide B10-2 as a mixture of both mono and di mesylated product. Yield: 9.2 g. The product was used without further purification to prepare B10-3 in the step described below.

Step 3. Preparation of N-(2-cyano-5-methyl-phenyl)-methanesulfonamide (610-3): A solution of B10-2 (17 g, 80.95 mmol) in a mixture of THF (70 mL) and 40% NaOH solution (70 mL) was treated with BTEAC (1.84 g, 8.09 mm) at 25° C. and stirred at 25° C. for 20 hours. The THF was removed under reduced pressure, and the concentrated mixture was extracted with DCM (300 mL). The aqueous layer was acidified with 2N HCl and extracted with DCM (200 mL). The combined organic layers were washed with water (100 mL) and brine (100 mL), and dried over anhydrous sodium sulfate. The organic solution was then concentrated, and the resultant residue was purified by column chromatography (60-120 mesh silica gel; 30% EtOAc in DCM as eluting solvent) to provide B10-3 as a pale brown solid. Yield: 16 g, 97%. $^1$HNMR (d$_6$-DMSO): δ 7.9 (d, 1H), 7.7 (s, 1H), 7.55 (d, 1H), 3.62 (s, 6H) and 2.45 (s, 3H). Mass: (M−1) 209 calculated for $C_8H_{10}N_2O_2S$.

Step 4. A solution of B10-3 (17 g, 80.95 mmol) in a mixture of THF (250 mL) and acetic acid (250 mL) was charged to a Parr reactor and treated with 10% Pd/C (8 g) at 25° C. The reaction mixture was then hydrogenated at 50 Psi hydrogen pressure and 25° C. for 4 hours. The mixture was filtered through a Celite® bed and washed with ethanol (3×20 mL). The combined filtrates were concentrated and the resultant residue was azeotroped with EtOAc (2×20 mL). The resultant brown-colored oil was taken into EtOAc (50 mL) and allowed to stand at 25° C. for 20 hours. The resultant white solids were collected and dried to provide B10. Yield: 15.1 g, 71.2%. $^1$HNMR (d$_6$-DMSO): δ 7.62-8.2 (broad, 3H), 7.02-7.18 (m, 2H), 6.7 (d, 1H), 3.85 (s, 2H), 2.88 (s, 3H), 2.25 (s, 3H) and 1.9 (s, 3H). Mass: (M+1) 215 calculated for $C_9H_{14}N_2O_2S$. HPLC Purity: 99.7%.

Preparation of N-(2-Aminomethyl)-5-methyl-phenyl)-N-methyl-methanesulfonamide acetate (B11)

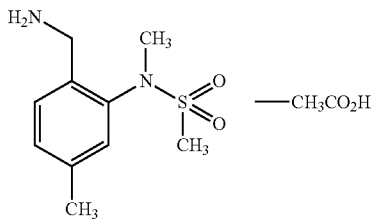

Step 1. Preparation of N-(2-cyano-5-methyl-phenyl)-N-methyl-methanesulfonamide (B11-1): A solution of B10-2 (10 g, 47.61 mmol) in a mixture of THF (100 mL) and 40% aq. NaOH solution (100 mL) at 25° C. was treated with BTEAC (1.1 g, 4.7 mmol) and methyl iodide (8.78 g, 61.89 mmol). The reaction mixture was then stirred at 25° C. for 20 hours. The THF was removed under reduced pressure, and the concentrated mixture was extracted with DCM (300 mL). The organic layer was washed with water (100 mL) and brine (50 mL), and dried over anhydrous sodium sulfate. The organic solution was then concentrated, and the resultant residue was purified by column chromatography (60-120 mesh silica gel; 10% EtOAc in CHCl$_3$ as eluting solvent) to provide B11-1 as a brown solid. Yield: 10.3 g, 96%. $^1$HNMR (CDCl$_3$): δ 7.62 (d, 1H), 7.38 (s, 1H), 3.38 (s, 3H), 3.1 (s, 3H) and 2.45 (s, 3H). Mass: (M−1) 223 calculated for $C_{10}H_{12}N_2O_2S$.

Step 2. A solution of B11-1 (4 g, 17.85 mmol) in acetic acid (150 mL) was charged to a Parr reactor and treated with Pd/C (2 g). The contents of the reactor were then hydrogenated at 50 Psi hydrogen pressure and 25° C. for 6 hours. The reaction mixture was filtered through a Celite® bed and washed with ethanol (2×20 mL). The combined filtrates were concentrated, and the resultant brown solid was azeotroped with EtOAc (3×25 mL). The resultant solid was taken into EtOAc (25 mL) at stirred at 25° C. for 20 hours. The resultant solids were collected and dried under reduced pressure to provide B11. Yield: 2.7 g, 53%. $^1$HNMR (d$_6$-DMSO): δ 7.45 (d, 1H), 7.3 (s, 1H), 7.2 (d, 1H), 5.04-5.7 (broad, 2H), 3.75-3.92 (broad, 2H), 3.15 (s, 3H), 3.05 (s, 3H), 2.3 (s, 3H) and 1.9 (s, 2H). Mass: (M+1) 229 calculated for $C_{10}H_{16}N_2O_2S$. HPLC Purity: 97.7%.

Preparation of N-(2-Aminomethyl-6-methyl-phenyl)-N-methyl-methanesulfonamide trifluoroacetate (B12)

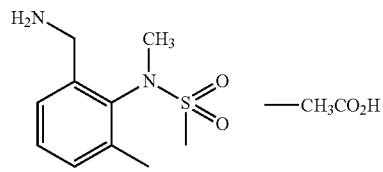

Step 1. Preparation of potassium di-tert-butyl iminodicarboxylate (B12-1): A solution of di-tert-butyl iminodicarboxylate (56 g, 258 mmol) in ethanol (200 mL) was cooled to 15° C. and treated over 30 minutes with a solution of KOH (17 g) in ethanol (150 mL). The reaction mixture was allowed to warm to 25° C., and it was stirred at 25° C. for 4 hours. The reaction mixture was then concentrated, and the resultant residue was diluted with diethyl ether (300 mL) and stirred for 3 hours. The resultant solids were collected and immediately dried under reduced pressure to provide B12-1 as a white crystalline solid. Yield: 57 g, 82%. $^1$HNMR (d$_6$-DMSO): δ 1.35 (s, 18H). Mass: (M−1) 216 calculated for $C_{10}H_{19}NO_4$.

Step 2. Preparation of 1-chloromethyl-3-methyl-2-nitrobenzene (B12-2): A solution of 3-(methyl-2-nitro-phenyl)-methanol (12 g, 71.78 mmol) in DCM (500 mL) was cooled to −5° C. and treated with dimethylaminopyridine (DMAP) (11.4 g, 93.3 mm) followed by treatment with a solution of tosyl chloride (17.79 g, 93.3 mmol) in DCM. The reaction mixture was stirred at −5° C. for 30 minutes. The reaction mixture was then allowed to warm to 25° C., and it was stirred at 25° C. for 20 hours. The reaction mixture was diluted with DCM (100 mL) and washed with 1N HCl (2×50 mL), saturated NaHCO$_3$ (2×25 mL), and brine. The organic solution was then dried over anhydrous MgSO$_4$ and concentrated. The resultant residue was purified by column chromatography (silica gel column; 15% EtOAc in hexane as eluting solvent) to provide B12-2 as a pale greenish-yellow oil. Yield: 14 g, 89%. $^1$HNMR (CDCl$_3$): δ 7.35-7.46 (m, 2H), 7.26-7.35 (m, 1H), 4.6 (s, 2H) and 2.36 (s, 3H).

Step 3. Preparation of 3-methyl-2-nitro-benzyl di-tert-butyl iminodicarboxylate (B12-3): A solution of B12-2 (14 g, 75.6 mmol) in N-methylpyrrolidinone (NMP) (135 mL) was cooled to −5° C. and treated with B12-1 (29.7 g, 116.4 mmol) over 20 minutes. The mixture was then heated at 50° C. for 4 hour. The reaction mixture was diluted with water (150 mL) and extracted with EtOAc (4×250 mL). The combined organic layers were washed with water (300 mL) and brine. The organic solution was then dried over anhydrous MgSO₄ and concentrated. The resultant residue was purified by column chromatography (silica gel; 20% EtOAc in hexane as eluting solvent) to provide B12-3 as an-off white solid. Yield: 21 g, 76%. ¹HNMR (CDCl₃): δ 7.35 (t, 1H), 7.1-7.25 (m, 2H), 4.76 (s, 2H), 2.3 (s, 3H) and 1.42 (s, 18H).

Step 4. Preparation of 2-amino-3-methyl benzyl di-tert-butyl iminodicarboxylate (B12-4): A solution of B12-3 (20 g, 54.64 mmol) in ethanol (500 mL) was charged to a Parr reactor and treated with 10% Pd/C (7 g). The contents of the reactor were then hydrogenated at 55 Psi hydrogen pressure and 25° C. for 5 hours. The reaction mixture was filtered through a Celite® bed and concentrated to provide B12-4 as a pale greenish-yellow oil (19 g). ¹HNMR (CDCl₃): δ 7.1 (d, 1H), 6.96 (d, 1H), 6.6 (t, 1H), 4.7 (s, 2H), 4.3-4.5 (broad, 2H), 2.15 (s, 3H) and 1.45 (s, 18H).

Step 5'. Preparation of di-BOC 3-methyl-2-(methylsulfonamido)benzylamine (B12-5): A solution of B12-4 (20 g, 59.6 mmol) in pyridine (150 mL) was cooled to 0° C. and treated over 25 minutes with mesyl chloride (6.15 mL, 79.4 mmol). The mixture was allowed to warm to 25° C., and it was stirred at 25° C. for 20 hours. The reaction mixture was diluted with EtOAc (300 mL) and washed with 1N HCl solution. The aqueous layer was collected and extracted with EtOAc (100 mL). The combined organic layers were washed with brine and dried over anhydrous MgSO₄. The organic solution was then concentrated, and the resultant residue was taken into petroleum ether and stirred for 1 hour. The resultant solids were collected and dried under reduced pressure to provide B12-5 as an off white solid. Yield: 22 g, 89%. ¹HNMR (CDCl₃): δ 7.9 (s, 1H), 7.35 (d, 1H), 7.05-7.25 (m, 2H), 4.9 (s, 2H), 3.1 (s, 3H), 2.45 (s, 3H) and 1.45 (s, 18H). Mass: (M−1) 413 calculated for C₁₉H₃₀N₂O₆S.

Step 6. Preparation of di-BOC 3-methyl-2-(N-methyl-methan-2-ylsulfonamido)benzylamine (B12-6): A solution of B12-5 (22 g, 53.14 mmol) in THF (58.6 mL) was cooled to 15° C. and treated with 40% aq NaOH solution (58.6 mL) followed by BTEAC (1.25 g, 5.5 mm). The mixture was stirred for 15 minutes and the treated over 20 minutes with methyl iodide (4.2 mL, 67.4 mmol). The reaction mixture was allowed to warm to 25° C., and it was stirred at 25° C. for 20 hours. The reaction mixture was then diluted with water (300 mL) and extracted with DCM (3×200 mL). The combined organic layers were washed with water (3×400 mL) and brine, dried over anhydrous MgSO₄, and concentrated. The resultant residue was dissolved in petroleum ether in a glass flask, and the wall of the flask was scratched to induce solids formation. The resultant solids were collected and dried to provide B12-6 as a pale yellow solid. Yield: 20 g, 88%. ¹HNMR (CDCl₃): δ 7.1-7.25 (m, 2H), 7.04 (d, 1H), 5.05 (d, 1H), 4.8 (d, 1H), 3.25 (s, 3H), 3.1 (s, 3H), 2.36 (s, 3H) and 1.45 (s, 18H).

Step 7. A solution of B12-6 (13 g, 30.3 mmol) in DCM (35 mL) was cooled to 0° C. and treated with trifluoroacetic acid (TFA) (70 mL). The reaction mixture was allowed to warm to 25° C., and it was stirred at 25° C. for 2 hours. The reaction mixture was concentrated, and the resultant residue was azeotroped with EtOAc (2×100 mL). The resultant residue was diluted with a mixture of DCM and pentane (1:1) in a glass flask, and the wall of the flask was scratched. The contents of the flask were stirred for 1 hour, and the resultant precipitate was collected and dried to provide B12 as an off white solid. Yield: 9 g, 87%. ¹HNMR (d₆-DMSO): δ 8.3-8.45 (broad, 2H), 7.38-7.5 (m, 3H), 4.2 (s, 2H), 3.14 (s, 6H), and 2.44 (s, 3H). Mass: (M+1) 229 calculated for C₁₀H₁₆N₂O₂S. HPLC Purity: 97.5%.

Preparation of N-(2-Aminomethyl-4-methyl-phenyl-N-methyl-methanesulfonamide trifluoroacetate (B13)

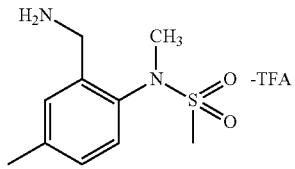

Step 1. Preparation of di-BOC-5-methyl-2-nitrobenzylamine (B13-1): A solution of 2-chloromethyl-4-methyl-1-nitro-benzene (20 g, 107.5 mmol) in NMP (140 mL) was cooled to 0° C. and treated over 30 minutes with potassium di-tert-butyl iminodicarboxylate (40 g, 156 mmol). The reaction mixture was allowed to warm to 25° C., and it was stirred at 25° C. for 20 hours. The reaction mixture was then diluted with water (150 mL) and extracted with EtOAc (2×500 mL). The resultant organic layer was washed with water (250 mL) and brine, and dried over anhydrous MgSO₄. The organic solution was then concentrated, and the resultant residue was purified by column chromatography (silica gel; 20% EtOAc in hexane as eluting solvent) to provide B13-1 as a pale yellow solid. Yield: 29 g, 73%. ¹HNMR (CDCl₃): δ 7.98 (d, 1H), 7.2 (d, 1H), 7.1 (s, 1H), 5.15 (s, 2H), 2.4 (s, 3H) and 1.44 (s, 18H).

Step 2. Preparation of di-BOC 2-amino-5-methylbenzylamine (B13-2): A solution of B13-1 (29 g, 79.23 mmol) in ethanol (500 mL) was charged to a Parr reactor and treated with Pd/C (9 g). The contents of the reactor were then hydrogenated 55 Psi hydrogen pressure and 25° C. for 2 hours. The reaction mixture was filtered through a Celite® bed and concentrated to provide B13-2 as an oil. Yield: 26 g. ¹HNMR (CDCl₃): δ 7.02 (s, 1H), 6.85 (d, 1H), 6.55 (d, 1H) 4.7 (s, 2H), 4.02-4.38 (broad, 2H), 2.22 (s, 3H) and 1.46 (s, 18H).

Step 3. Preparation of di-BOC 5-methyl-2-(methylsulfonamido)benzylamine (B13-3): A solution of B13-2 (26 g, 77.38 mmol) in pyridine (165 mL) was cooled to 0° C. and treated over 20 minutes with mesyl chloride (12.18 g, 106.4 mmol) was added over a period of 20 min. The mixture was allowed to warm to 25° C., and it was stirred at 25° C. for 20 hours. The reaction mixture was then diluted with EtOAc (350 mL) and washed with 1N HCl solution (2×250 mL). The resultant organic layer was washed with brine, dried over anhydrous MgSO₄, and concentrated. The resultant residue was treated with petroleum ether and stirred at 25° C. for 1 hour. The resultant solids were then collected and dried under reduced pressure to provide B13-3 as a pale yellow solid. Yield: 23 g, 71%. ¹HNMR (CDCl₃): δ 8.7 (s, 1H), 7.45 (d, 1H), 7.1 (d, 1H), 4.72 (s, 2H), 2.96 (s, 3H), 2.3 (s, 3H) and 1.46 (s, 18H). Mass: (M−1) 413 calculated for C₁₉H₃₀N₂O₆S.

Step 4. Preparation of di-BOC 5-methyl-2-(N-methyl-methan-2-ylsulfonamido)benzylamine (B13-4): A solution of B13-3 (22 g, 53.14 mmol) in THF (70 mL) was cooled to 0° C. and treated with 40% aq. NaOH solution (70 mL) followed by BTEAC (1.5 g, 6.6 mmol). After 15 minutes the mixture was treated with methyl iodide (9.51 g, 67.4 mmol) over a period of 20 minutes. The reaction mixture was allowed to warm to 25° C., and it was stirred at 25° C. for 20 hours. The reaction mixture was then diluted with DCM (800 mL). The organic layer was collected and washed with water (2×200 mL) and brine, and dried over anhydrous $MgSO_4$. The organic solution was concentrated, and the resultant residue was triturated with petroleum ether to provide B13-4 as a pale yellow solid. Yield: 20 g, 88%. $^1$HNMR ($CDCl_3$): δ 7.0-7.4 (m, 3H), 4.85-5.1 (d, 2H), 3.25 (s, 3H), 2.92 (s, 3H), 2.35 (s, 3H) and 1.45 (s, 18H).

Step 5. A solution of B13-4 (15 g, 35.04 mmol) in DCM (45 mL) was cooled to 0° C. and treated over 30 minutes with TFA (90 mL). The mixture was then allowed to warm to 25° C. After 3 hours the mixture was concentrated, and the resultant residue was azeotroped with EtOAc (2×200 mL). The resultant residue was diluted with a mixture of DCM and ether (8:2) and stirred for 1 hour. The resultant precipitate was collected and dried under reduced pressure to provide B13 as an off-white solid. Yield: 12 g, 98%. $^1$HNMR ($d_6$-DMSO): δ 7.98-8.2 (broad, 2H), 7.5 (d, 1H), 7.4 (s, 1H), 7.3 (d, 1H), 3.96-4.28 (broad, 2H), 3.2 (s, 3H), 3.05 (s, 3H) and 2.35 (s, 3H). Mass: (M+1) 229 calculated for $C_{10}H_{16}N_2O_2S$.

Preparation of N-(3-Aminomethyl-6-methyl-pyridin-2-yl-N-methyl-methanesulfonamide acetate (B14)

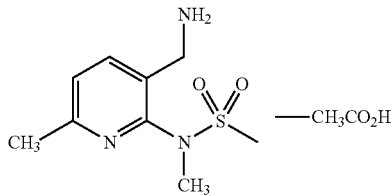

Step 1. Preparation of N-(3-cyano-6-methyl-pyridin-2-yl)-N-methyl-methanesulfonamide (B14-1): A solution of 2-chloro-6-methyl-nicotinonitrile (20 g, 131.5 mmol) in acetonitrile (300 mL) at 25° C. was treated with $HN(CH_3)SO_2Me$ (13.1 mL, 124.1 mmol) and $Cs_2CO_3$ (60 g, 184.0 mm). The reaction mixture was then stirred at 80° C. for 15 hours. The reaction mixture was allowed to cool to 25° C. and filtered. The resultant filtrate was concentrated and diluted with EtOAc (600 mL). The organic solution was then washed with water (2×250 mL) and brine, and dried over anhydrous sodium sulfate. The organic solution was then concentrated, and the resultant residue was recrystallized with ether to provide B14-1 as an off white solid. Yield: 18.5 g, 62.5%. $^1$HNMR ($CDCl_3$): δ 7.9 (d, 1H), 7.16-7.26 (m, 1H), 3.28 (s, 3H), 3.24 (s, 3H) and 2.22 (s, 3H). Mass: (M+1) 226 calculated for $C_9H_{11}N_3O_2S$.

Step 2. A solution B14-1 (10 g, 44.4 mmol) in a mixture of THF (100 mL) and acetic acid (900 mL) was charged to a Parr reactor and treated with 10% Pd/C (9 g, 84.9 mmol). The contents of the reactor were then hydrogenated at 55 Psi hydrogen pressure and 40° C. for 4 hours. The reaction mixture was then filtered through a Celite® bed and concentrated. The resultant residue was diluted with EtOAc (100 mL) and stirred for 3 hours. The resultant solids were collected and dried under reduced pressure to provide B14 as an off-white solid. Yield: 10 g, 98%. $^1$HNMR ($d_6$-DMSO): δ 7.9 (d, 1H), 7.3 (d, 1H), 7.0-7.25 (broad, 2H), 3.82 (s, 2H), 3.06-3.18 (d, 5H), 2.45 (s, 3H) and 1.82-1.96 (m, 5H). Mass: (M+1) 230 calculated for $C_9H_{15}N_3O_2S$. HPLC Purity: 98.1%.

Preparation of N-(3-Aminomethyl-5-methyl-pyridin-2-yl)-N-methyl-methanesulfonamide acetate (B15)

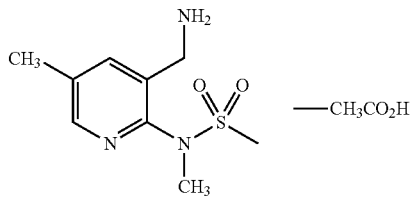

Step 1. Preparation of 5-methyl-nicotinic acid (B15-1): A solution of 3,5 lutidine (100 g, 934.57 mmol) in water at 25° C. was treated portion-wise over 5 hours with $KMnO_4$ (221.1 g, 1401.86 mmol). The reaction mixture was then heated at 45° C. for about 20 hours. The reaction mixture was filtered and washed with water. The resultant filtrates were concentrated, and the resultant residue was diluted with ethanol (3×500 mL), boiled, and filtered. The filtrate was then concentrated under reduced pressure to provide B15-1 as a white solid. Yield: 76 g, 59.4%. $^1$HNMR ($D_2O$): δ 8.6-8.7 (s, 1H), 8.3-8.4 (m, 1H), 7.92 (s, 1H) and 2.3 (s, 3H). Mass: (M+1) 138 calculated for $C_7H_7NO_2$.

Step 2. Preparation of 5-methyl-nicotinamide (B15-2): A suspension of B15-1 (70 g, 510 mmol) in thionyl chloride (350 mL) was heated at 80° C. for 20 hours. The resultant clear solution obtained was allowed to cool to 25° C. and concentrated. The resultant residue was diluted with 1,2 dichloroethane (1.5 L), cooled to −5° C., and treated with $NH_3$ gas via bubbler until the mixture was saturated. The mixture was allowed to warm to 25° C., stirred for 3 hours, and concentrated. The resultant brown solid was taken in EtOAc (3×800 mL), refluxed for 20 min, and filtered. The resultant filtrate was then concentrated to provide B15-2 as a brown solid. Yield: 52 g, 75%. $^1$HNMR ($d_6$-DMSO): δ 8.85-8.9 (s, 1H), 8.55 (s, 1H), 8.05-8.18 (m, 1H), 8.02 (s, 1H), 7.48-7.65 (s, 1H) and 2.35 (s, 3H). Mass: (M+1) 137 calculated for $C_7H_8N_2O$.

Step 3. Preparation of 1-Hydroxy-5-methyl-nicotinamide (B15-3): A solution of B15-2 (35 g) in acetic acid (200 mL) was cooled to 10° C. and treated over 10 minutes with $H_2O_2$ (40% solution in water, 200 mL). The reaction mixture was allowed to warm to 25° C. and then heated at 80° C. for 20 hours. The reaction mixture was cooled to 0° C., treated with 20% sodium sulfite solution (200 mL) and basified with 35% $NH_4OH$ (200 mL). The mixture was then allowed to warm to 25° C. and stirred for an additional 2 hours. The resultant solids were collected and dried under reduced pressure to provide B15-3 as a white solid. Yield: 30.1 g. $^1$HNMR ($d_6$-DMSO): δ 8.45 (s, 1H), 8.3 (s, 1H), 7.6 (s, 1H), 4.42-4.7 (broad m, 2H), 2.3 (s, 3H). Mass: (M−1) 153 calculated for $C_7H_{10}N_2O_2$.

Step 4. Preparation of 2-chloro-5-methyl-nicotinonitrile (B15-4): Neat $POCl_3$ (120 mL) was cooled to about 10° C. and treated portion-wise over 10 minutes with B15-3. The reaction mixture was then heated at 60° C. for 2 hours. The reaction mixture was concentrated, cooled to about 10° C., basified with saturated $Na_2CO_3$, and extracted with EtOAc (3×100 mL). The combined organic layers were washed with water (50 mL), and brine (50 mL), and dried over anhydrous sodium sulfate. The organic solution was then concentrated, and the resultant residue was purified by column chromatography (silica gel; 35% EtOAc in hexane as eluting solvent) to provide to B15-4 as a white solid. Yield: 3.5 g, 68%. $^1$HNMR ($d_6$-DMSO): δ 8.42 (s, 1H), 7.82 (s, 1H) and 2.4 (s, 3H). Mass: (M+1) 153 calculated for $C_7H_5ClN_2$.

Step 5. Preparation of N-(3-cyano-5-methyl-pyridin-2-yl)-N-methyl-methanesulfonamide (B15-5): A suspension of B15-4 (16 g, 0.1049 mmol) in acetonitrile (150 mL) at 25° C. was treated with $Cs_2CO_3$ (51.3 g, 0.157 mmol) and N-methyl methane sulphonamide (12.5 g, 0.115 mmol). The reaction mixture was then heated at 80° C. for 20 hours. The reaction mixture was filtered through a Celite® bed and washed with acetonitrile (3×50 mL). The combined filtrates were concentrated, and the resultant residue was diluted with EtOAc (500 mL) and washed with water (3×100 mL). The resultant organic layer was washed with brine (100 mL), dried over anhydrous sodium sulfate, and concentrated. The resultant residue was purified by column chromatography (silica gel; 40% EtOAc in hexane as eluting solvent) to provide B15-5 as pale yellow solid. Yield: 15.1 g, 62.8%. $^1$HNMR ($d_6$-DMSO): δ 8.65 (s, 1H), 8.3 (s, 1H), 3 3.22-3.26 (s, 3H), 0.15-3.22 (s, 3H) and 2.36 (s, 3H). Mass: (M+1) 226 calculated for $C_9H_{11}N_3O_2S$.

Step 6. A solution of B15-5 (15 g) in a mixture of acetic acid (200 mL) and THF (200 mL) was charged to a Parr reactor and treated with Pd/C (4 g). The contents of the reactor were then hydrogenated at 50 Psi hydrogen pressure and 25° C. for 5 hours. The mixture was filtered through a Celite® bed and washed with ethanol (50 mL). The filtrate was concentrated under reduced pressure, and the resultant residue was purified by column chromatography (silica gel; 5% MeOH in $CHCl_3$ as eluting solvent) to provide B15 as a reddish brown solid. Yield: 12.3 g, 98%. IR ($cm^{-1}$): 3450, 3264, 2937, 2161, 1706, 1633, 1548, 1413, 1321 and 1151. $^1$HNMR ($d_6$-DMSO): δ 8.3 (s, 1H), 7.9 (s, 1H), 7.02-7.25 (broad s, 2H), 3.92 (s, 2H), 3.15 (d, 6H), 2.4 (s, 3H), 1.92 (s, 3H). Mass: (M+1) $C_9H_{15}N_3O_2S$. (Note: Few drops of triethylamine was added to the mobile phase during the process of silica gel column purification.)

Preparation of N-(3-Aminomethyl-4-methyl-pyridin-2-yl)N-methyl-methanesulfonamide (B16)

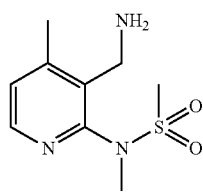

Step 1. Preparation of N-(3-cyano-4-methyl-Pyridin-2-yl)-N-methyl-methanesulfonamide (B16-1): A suspension of 2-chloro-4-methyl-nicotinonitrile (4 g, 26.2 mmol) (see WO 02/30901), N-methyl methane sulphonamide (3.43 g, 31.4 mmol) and $CsCO_3$ (12 g, 36.7 mmol) in acetonitrile (40 mL) was heated at 60° C. for 20 hours. The reaction mixture was filtered through a Celite® bed and washed with acetonitrile (40 mL). The combined filtrates were concentrated, and the resultant residue was diluted with EtOAc (100 mL). The organic solution was washed with water (100 mL) and brine (50 mL), and dried over anhydrous sodium sulfate. The organic solution was then concentrated, and the resultant residue was stirred in methanol. The resultant solids were collected and dried under reduced pressure to provide B16-1 as a white solid. Yield: 1.6 g, 26%. $^1$HNMR ($CDCl_3$): δ 8.46 (d, 1H), 7.25 (m, 1H), 3.26 (s, 3H), 3.18 (s, 3H) and 2.6 (s, 3H). Mass: (M+1) 226 calculated for $C_9H_{11}N_3O_2S$.

Step 2. A solution of B16-1 (5 g, 22.1 mmol) in 2N ethanolic ammonia (250 mL) was charged to a Parr reactor and treated with 10% Pd/C (5 g, 47 mm). The contents of the reactor were then hydrogenated at 60 Psi hydrogen pressure and 25° C. for 6 hours. The reaction mixture was filtered through a Celite® bed and washed with ethanol (50 mL). The combined filtrates were concentrated, and the resultant oily residue was triturated with diethyl ether (20 mL). The resultant white solids were collected and dried to provide B16 as a white solid. Yield: 5 g, 90%. $^1$HNMR ($d_6$-DMSO): δ 8.46 (d, 1H), 8.2-8.38 (broad s, 2H), 7.42 (d, 1H), 4.55-4.9 (broad s, 4H), 4.15-4.3 (broad s, 2H), 325 (s, 3H), 3.1 (s, 3H) and 2.5 (s, 3H). Mass: (M+1) 230 calculated for $C_9H_{15}N_3O_2S$. HPLC Purity: 95.03%.

Preparation of N-(5-aminomethyl-2-methyl-pyfridin-4-yl)-N-methyl-methansulfonamide acetate (B17)

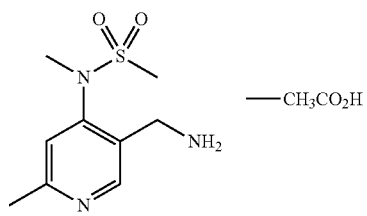

Step 1. Preparation of 2,4-dihydroxy-6-methyl-nicotinic acid ethyl ester (B17-1): Sodium metal pieces (33 g, 1434 mmol) were slowly added to dry ethanol (800 mL) at 25° C. and stirred until all the sodium pieces had reacted. The resultant suspension was then treated over 15 minutes with malonic acid diethyl ester (140 g, 875 mmol) followed by treatment over 15 minutes with ethyl-3-aminocrotonate (110 g, 850 mmol). The reaction mixture was then heated at 110° C. for 20 hours and concentrated. The resultant residue was cooled to 15° C., dissolved in water (800 mL), and stirred for 15 minutes. The mixture was neutralized with a mixture of $AcOH:H_2O$ (1:1) until a pH of 6-7 was achieved. The mixture was then stirred an addition 20 minutes. The resultant solids were collected, washed with petroleum ether (300 mL), and dried under reduced pressure to provide B17-1 as an off-white solid. Yield: 60.3 g, 35%. $^1$HNMR ($d_6$-DMSO): δ 12.6 (s, 1H), 11.38 (s, 1H), 5.8 (s, 1H), 4.25 (q, 2H), 2.14 (s, 3H) and 1.25 (t, 3H). Mass: (M+1) 198 calculated for $C_9H_{11}NO_4$.

Step 2. Preparation of 2,4-dichloro-6-methyl-nicotinic acid ethyl ester (B17-2): A suspension of B17-1 (36 g, 182.2 mmol) in N,N-bis(2-hydroxyethyl) 2-propanolamine (DEIPA) (36 mL) was cooled to 0° C. and slowly treated with $POCl_3$ (250 mL). The resultant clear solution was allowed to warm to 25° C. and then heated at 15° C. for 20 hours. The reaction mixture was concentrated, and the resultant residue was poured into crushed ice. The chilled mixture was then basified with saturated Na$_2$CO$_3$ until a pH of 8 was achieved. The organic layer was collected, and the aqueous layer was extracted with EtOAc (3×500 mL). The combined organic layers were washed with brine, dried over anhydrous sodium sulfate, and concentrated. The resultant residue was purified by chromatography (silica gel; 2% EtOAc in petroleum ether as eluting solvent) to provide B17-2 as a pale yellow solid. Yield: 24 g, 55%. $^1$HNMR (d$_6$-DMSO): δ 7.2 (s, 1H), 4.45 (q, 2H), 2.52 (s, 3H) and 1.42 (t, 3H). Mass: (M+1) 236 calculated for C$_9$H$_9$C$_{12}$NO$_2$.

Step 3. Preparation of 2-chloro-4-methoxy-6-methyl-nicotinic acid ethyl ester (B17-3): A solution of B17-2 (30 g, 128.2 mmol) in methanol (102 mL) was cooled to 0° C. and treated portion-wise over 30 minutes with NaOMe (8.5 g, 157.4 mmol). The reaction mixture was then heated at 60° C. for 5 hours. The reaction mixture was cooled to 25° C., filtered, and concentrated. The resultant residue was diluted with DCM (350 mL), filtered through a Celite® bed, and washed with DCM. The combined filtrates were concentrated, and the resultant residue was purified by chromatography (silica gel; 6% EtOAc in petroleum ether as eluting solvent) to provide B17-3 as a pale yellow solid. Yield: 20.62 g, 70%. $^1$HNMR (CDCl$_3$): δ 6.66 (s, 1H), 4.4 (q, 2H), 3.95 (s, 1H), 3.92 (s, 3H), 2.52 (s, 3H) and 1.38 (t, 3H). Mass: (M+1) 230 calculated C$_{10}$H$_{12}$ClNO$_3$.

Step 4. Preparation of 4-methoxy-6-methyl-nicotinic acid ethyl ester (B17-4): A mixture of B17-3 (27 g, 117.3 mmol) and potassium acetate (11.0 g, 112 mmol) in isopropanol (IPA) (500 mL) was charged to a Parr reactor and treated with Pd/C (9.5 g, 70.15 mmol). The contents of the reactor were then hydrogenated at 55 Psi hydrogen pressure and 25° C. for 4 hours. The mixture was filtered through a Celite® bed and concentrated. The resultant residue was purified by chromatography (silica gel; 8% EtOAc in petroleum ether as eluting solvent) to provide B17-4 as a green viscous liquid. Yield: 23 g, 90%. $^1$HNMR (CDCl$_3$): δ 8.84 (s, 1H), 6.75 (s, 1H), 4.35 (q, 2H), 3.98 (s, 3H), 2.6 (s, 3H) and 1.4 (t, 3H). Mass: (M+1) 196 calculated for C$_{10}$H$_{13}$NO$_3$.

Step 5. Preparation of 6-methyl-4-oxo-1,4-dihydro-pyridine-3-carboxylic acid hydrochloride (B17-5): A suspension of B17-4 (50 g, 256 mmol) in concentrated HCl (600 mL) was heated at 110° C. for 20 hours. The reaction mixture was then concentrated, and the resultant residue was washed in this order with ethanol (150 mL), DCM (2×300 mL), and a mixture of DCM:Et$_2$O (1:1). The resultant solids were collected and dried to provide B17-5 as an off-white solid. Yield: 40 g. IR (cm$^{-1}$): 3449, 3095, 2890, 1674, 1647, 1565, 1470, 1428, 1345, 1257, 1186 and 1028. $^1$HNMR (d$_6$-DMSO): δ 11.4-12.7 (b, 2H), 8.45 (s, 1H), 6.64 (s, 1H) and 2.4 (s, 3H). Mass: (M+1) 154 calculated for C$_7$H$_7$NO$_3$.

Step 6. Preparation of 6-methyl-4-oxo-1,4-dihydro-pyridine-3-carboxylic acid methyl ester (B17-6): A solution of B17-5 (40 g, 261.4 mmol) in methanol (600 mL) was cooled to 0° C. and treated drop-wise over 20 minutes with SOCl$_2$ (100 mL). The reaction mixture was allowed to warm to 25° C., heated at 70° C. for 20 hours, and concentrated. The resultant residue was washed with ethanol (100 mL), filtered and dried to provide B17-6 as a gummy solid. Yield: 40 g. $^1$HNMR (CDCl$_3$): δ 8.8 (s, 1H), 6.7 (s, 1H), 3.9 (s, 3H) and 2.45 (s, 3H). Mass: (M+1) 168 calculated for C$_8$H$_9$NO$_3$. The product was used in the preparation of B17-7 below without further purification.

Step 7. Preparation of 6-methyl-4-oxo-1,4-dihydro-pyridine-3-carboxylic acid amide (B17-7): A suspension of B17-6 (40 g, 239.5 mmol) in aqueous NH$_3$ (800 mL) was heated at 50° C. for 20 hours. The reaction mass was then concentrated, and the resultant residue was washed with a mixture of diethyl ether:DCM (8:2) (300 mL). The resultant solids were collected and dried under reduced pressure to provide B17-7 as an off-white solid. Yield. 40 g. $^1$HNMR (d$_6$-DMSO): δ 12.1 (b, 1H), 9.4 (s, 1H), 8.3 (s, 1H), 7.4 (s, 1H), 6.25 (s, 1H) and 2.25 (s, 3H). Mass: (M+1) 153 calculated for C$_7$H$_8$N$_2$O$_2$.

Step 8. Preparation of 4-Chloro-6-methyl-nicotinonitrile (B17-8): A suspension of B17-7 (20 g, 131.5 mmol) in POCl$_3$ (62 mL, 580 mmol) was heated at 110° C. for 15 minutes. The mixture was allowed to cool to 25° C. and treated portion-wise over 20 minutes with PCl$_5$ (38.12 g, 183.4 mmol). The mixture was then heated at 110° C. for 1 hour and concentrated. The resultant residue was diluted with EtOAc (100 mL), cooled to 10° C., and quenched with aqueous Na$_2$CO$_3$ (200 mL). The mixture was then extracted with EtOAc (3×250 mL), and the combined organic layers were washed with brine, dried over anhydrous sodium sulfate, and concentrated. The resultant residue was purified by chromatography (silica gel; 4-5% EtOAc in petroleum ether as eluting solvent) to provide B17-8 as an off-white puffy solid. Yield: 7.5 g, 37%. $^1$HNMR (CDCl$_3$): δ 8.75 (s, 1H), 7.38 (s, 1H), 2.65 (s, 3H). Mass: (M+1) 153 calculated for C$_7$H$_5$ClN$_2$.

Step 9. Preparation of N-(5-Cyano-2-methyl-pyridin-4-yl)-N-methyl-methanesulfonamide (B17-9): A solution of B17-8 (7 g, 46.8 mmol) in acetonitrile (165 mL) at 25° C. was treated sequentially with Cs$_2$CO$_3$ (19 g, 58.2 mmol) and HN(Me)SO$_2$Me (8.9 mL, 95 mmol). The mixture was heated at 60° C. for 20 hours and concentrated. The resultant residue was diluted with EtOAc (300 mL) and water (100 mL), and stirred for 10 minutes. The organic layer was collected, and the aqueous layer was extracted with EtOAc (2×100 mL). The combined organic layers were washed with brine, dried over MgSO$_4$, and concentrated. The resultant residue was purified by chromatography (silica gel; DCM as eluting solvent) to provide B17-9 as a solid. Yield: 9 g, 87%. $^1$HNMR (CDCl$_3$): δ 8.8 (s, 1H), 7.3 (d, 1H), 3.4 (s, 3H), 3.18 (s, 3H) and 2.65 (s, 3H). Mass: (M+1) 226 calculated for C$_9$H$_{11}$N$_3$O$_2$S.

Step 10. A solution of B17-9 (7.5 g, 33.3 mmol) in EtOH—NH$_3$ (300 mL) was charged to a Parr reactor and treated with Pd/C (5 g). The contents of the reactor were hydrogenated at 60 Psi hydrogen pressure and 25° C. for 4 hours. The mixture was filtered through a Celite® bed and concentrated. The resultant residue was diluted with EtOAc:acetic acid (1.1 eq.) and concentrated. The resultant gummy orange-colored liquid was then diluted with a mixture of ether and EtOAc in a glass flask, and the wall of the flaks was scratched. The resultant solids were collected to provide B17 as an off-white solid. Yield: 4.4 g, 42%. IR (cm$^{-1}$): 3484, 3343, 3166, 2975, 1644, 1601, 1560, 1505, 1412, 1313, 1136 and 1058. $^1$HNMR (d$_6$-DMSO): δ 8.62 (s, 1H), 7.4 (s, 1H), 4.7-5.3 (broad, 3H), 3.82 (s, 2H), 3.14 (d, 2H), 2.45 (s, 3H) and 1.9 (s, 3H). Mass: (M+1) 230 calculated 230 for C$_9$H$_{15}$N$_3$O$_2$S.

Preparation of N-(3-Aminomethyl-4-methyl-phenyl)-N-methyl-methanesulfonamide acetate (B18)

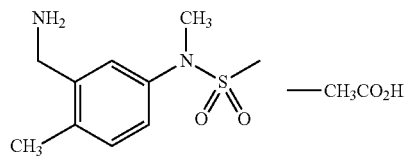

Step 1. Preparation of 5-amino-2-methyl-benzonitrile (B18-1): A stirred suspension of 2-methyl-5-nitro benzonitrile (20 g, 123.45 mmol) in a mixture of dioxane (640 mL), ethanol (480 mL) and water (160 mL) at 25° C. was treated with NH$_4$Cl (26.4 g, 493.8 mmol) followed by treatment with iron powder (34.4 g, 617.2 mmol). The mixture was then heated at 80° C. for 16 hours. The mixture was filtered through a Celite® bed and concentrated. The resultant residue was diluted with EtOAc (600 mL), washed with water (150 mL) and brine (100 mL), and dried over anhydrous sodium sulfate. The organic solution was then concentrated to provide B18-1 as an orange solid. Yield: 18.2 g. $^1$HNMR (CDCl$_3$): δ 7.08 (d, 1H), 6.84-6.9 (m, 1H), 6.75-6.82 (m, 1H), 3.65-3.82 (m, 2H) and 2.4 (s, 3H). Mass: (M+1) 133 calculated for C$_8$H$_8$N$_2$. The product was used below to prepare B18-2 without further purification.

Step 2. Preparation of N-(3-cyano-4-methyl-phenyl)-methanesulfonamide (B18-2): A solution of B18-1 (18 g, 136.36 mmol) in pyridine (150 mL) was cooled to 0° C. and treated with mesyl chloride (12.6 mL, 163.63 mmol). The mixture was allowed to warm to 25° C., stirred for 20 hours, and concentrated. The resultant residue was diluted with EtOAc (500 mL), and washed with 2N HCl (50 mL), water (100 mL), and brine (50 mL). The organic solution was then dried over anhydrous sodium sulfate and concentrated to provide B18-2 as a yellow solid. Yield: 25.1 g, 87.3%. $^1$HNMR (CDCl$_3$): δ 7.5 (s, 1H), 7.3-7.45 (m, 2H), 7.1-7.25 (m, 1H), 3.05 (s, 3H) and 2.5 (s, 3H). Mass: (M+1) 209 calculated for C$_9$H$_{10}$N$_2$O$_2$S.

Step 3. Preparation of N-(3-cyano-4-methyl-phenyl)-N-methyl-methanesulfonamide (B18-3): A solution of B18-2 (25 g, 119.04 mmol) in a mixture of THF (200 mL) and 40% NaOH solution (200 mL) at 25° C. was treated with BTEAC (2.7 g, 11.9 mmol) and stirred vigorously for 20 minutes. The mixture was then treated with methyl iodide (8.89 mL, 142.8 mmol), stirred for 20 hours, and concentrated. The resultant residue was extracted with DCM (500 mL) and washed with water (100 mL) and brine (50 mL). The organic solution was dried over anhydrous sodium sulfate and concentrated. The resultant residue was purified by column chromatography (60-120 mesh silica gel; 40% EtOAc in hexane as eluting solvent) to provide B18-2 as a white solid. Yield: 26.2 g, 97%. $^1$HNMR (CDCl$_3$): δ 7.55-7.65 (m, 1H), 7.5-7.54 (m, 1H), 7.3-7.4 (m, 1H), 3.34 (s, 3H), 2.85 (s, 3H) and 2.55 (s, 3H). Mass: (M+1) 225 calculated for C$_{10}$H$_{12}$N$_2$O$_2$S.

Step 4. A solution of B18-3 (28 g, 124.4 mmol) in acetic acid (500 mL) and THF (200 mL) was charged to a Parr reactor and treated with 10% Pd/C (8 g). The contents of the reactor were then hydrogenated at 50 PSi hydrogen pressure and 25° C. for 4 hours. The mixture was filtered through a Celite® bed and washed with ethanol (50 mL). The combined filtrates were concentrated, and the resultant residue was azeotroped with EtOAc (3×50 mL). The resultant oily residue was dissolved in EtOAc (200 mL) and maintained at 25° C. for 20 hours. The resultant solids were collected and dried to provide B18 as a white solid. Yield: 2.9 g, 81%. $^1$HNMR (d$_6$-DMSO): δ 7.42 (s, 1H), 7.15 (s, 2H), 5.7-5.98 (broad, 3H), 3.72 (s, 2H), 3.2 (s, 3H), 2.95 (s, 3H), 2.25 (s, 3H) and 1.86 (s, 3H). Mass: (M+1) 229 calculated for C$_{10}$H$_{16}$N$_2$O$_2$S. HPLC Purity: 99.9%.

Preparation of N-(5-Aminomethyl-2-methyl-pyrimidin-4-yl)-N-methyl-methansulfonamide acetate (B19)

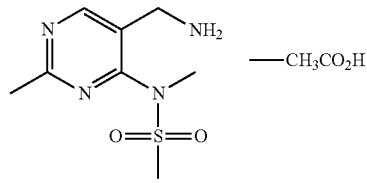

Step 1. Preparation of 4-hydroxy-2-methylsulfanyl-pyrimidine-5-carboxylic acid ethyl ester (B19-1): A mixture of water (410 mL) and a 50% NaOH solution (115.98 g, 2899 mmol) was cooled to 0° C. and treated with 2-methyl 2-thio pseudo urea sulfate (100 g, 359 mmol). The resultant clear solution was treated with a solution of ethoxy methylene malonate (155.38 g, 719 mmol) in ethanol (251 mL) and stirred until the reaction mixture was turbid. The mixture was then allowed to warm to 25° 5, and it was allowed to stand at 25° C. for 20 hours. The resultant solids were collected, washed with ethanol (2×50 mL), and dried under reduced pressure to provide B19-1 as a pale yellow solid. Yield: 58 g, 75%. $^1$HNMR (d$_6$-DMSO): δ 8.25 (s, 1H), 4.12 (q, 2H), 2.32 (s, 3H) and 1.24 (t, 3H).

Step 2. Preparation of 4-chloro-2-methylsulfanyl-pyrimidine-5-carboxylic acid ethyl ester (B19-2): Neat POCl$_3$ (120 mL) was cooled to 10° C. and treated portion-wise over 4 hours with B19-1 (50 g, 232 mmol) without exceeding a temperature of 25° C. The mixture was then heated at 65° C. After 3 hours the mixture was cooled to 10° C., poured into crushed ice (350 g), treated drop-wise with water (676 mL) under vigorous stirring. The resultant solids were collected and dried under reduced pressure to provide B19-2 as a pale yellow solid. Yield: 22 g, 40%. $^1$HNMR (CDCl$_3$): δ 8.95 (s, 1H), 4.44 (q, 2H), 2.62 (s, 3H) and 1.42 (t, 3H).

Step 3. Preparation of 4-chloro-2-methanesulfonyl-pyrimidine-5-carboxylic acid ethyl ester (B19-3): A solution of B19-2 (40 g, 172 mmol) in methanol (720 mL) was cooled to 0° C. and treated with a slurry of oxone (317.9 g, 517 mmol) in distilled water (720 mL). The mixture was allowed to warm to 25° C. and stirred at 5 hours. The mixture was filtered, and the solids were washed with DCM (500 mL). The resultant organic layer was collected, and the aqueous layer was extracted with DCM (3×200 mL). The combined organic layers were then washed with brine, dried over anhydrous sodium sulfate, and concentrated to provide B19-2 as a white solid. Yield: 31 g, 68%. IR (cm$^{-1}$): 3015, 2932, 1734, 1550, 1445, 1391, 1325, 1258, 1222, 1142 and 1067. $^1$HNMR (CDCl$_3$): δ 9.28 (s, 1H), 4.5 (q, 2H), 3.4 (s, 3H) and 1.45 (t, 3H). Mass: (M+1) 265 calculated for C$_8$H$_9$ClN$_2$O$_4$S.

Step 3. Preparation of 4-chloro-2-methyl-pyrimidine-5-carboxylic acid ethyl ester (B19-3): A solution of B19-2 (40 g, 151 mmol) in THF (700 mL) was cooled to 0° C. and treated drop-wise over 2 hours with a 3 molar solution of methyl magnesium chloride in THF (54 mL, 166 mmol). The mixture was allowed to warm to 25° C. and maintained for at 25° C. for 4 hours. The mixture was added to water (500 mL) and extracted with EtOAc (3×300 mL). The combined organic layers were washed with brine (250 mL), dried over anhydrous sodium sulfate, and concentrated to provide B19-2 as a brown liquid. Yield: 30 g, 98%. IR (cm$^{-1}$): 2983, 2934, 2868, 1736, 1574, 1523, 1434, 1373, 1269, 1181 and 1070. $^1$HNMR (CDCl$_3$): δ 9.1 (s, 1H), 4.5 (q, 2H), 2.74 (s, 3H) and 1.5 (t, 3H).

Step 3. Preparation of 4-(methanesulfonyl-methyl-amino)-2-methyl-pyrimidine-5-carboxylic acid ethyl ester (B19-3): A solution of N-methyl methane sulphonamide (18.2 g, 180 mmol) in acetonitrile (420 mL) was cooled to 0° C. and treated with cesium carbonate (68 g, 225 mmol). The mixture was then treated over 2 hours with B19-2 (30 g, 150 mmol). The mixture was allowed to warm to 25° C., and it was maintained at 25° C. for 20 hours. The mixture was then filtered, and the solids were washed with washed with EtOAc (200 mL). The combined filtrates were further diluted with EtOAc (500 mL), washed with water (2×500 mL) and brine, and dried over anhydrous sodium sulfate. The organic solution was then concentrated to provide B19-3 as an orange solid. Yield: 18 g, 44%. $^1$HNMR (d$_6$-DMSO): δ 8.94 (s, 1H), 4.3 (q, 2H), 3.25-3.3 (m, 6H), 2.65 (s, 3H) and 1.3 (t, 3H). Mass: (M+1) 274 calculated for C$_{10}$H$_{15}$N$_3$O$_4$S.

Step 4. Preparation of 4-(methanesulfonyl-methyl-amino)-2-methyl-pyrimidine-5-carboxylic acid amide (B19-4): A suspension of B19-3 (10 g, 36 mmol) in 25% NH$_4$OH (100 mL) was heated at 32° C. for 20 hours. The mixture was concentrated under reduced pressure, and the resultant residue was triturated with EtOAc. The mixture was then filtered and concentrated. The resultant residue was purified by column chromatography (60-120 mesh silica gel; 10% MeOH in CHCl$_3$ as eluting solvent) to provide B19-4 as a white solid. Yield: 3 g, 33%. $^1$HNMR (d$_6$-DMSO): δ 8.75 (s, 1H), 7.95 (s, 1H), 7.7 (s, 1H), 3.3-3.42 (m, 3H), 3.25 (s, 3H) and 2.65 (s, 3H). Mass: (M+1) 245 calculated for C$_8$H$_{12}$N$_4$O$_3$S.

Step 5. Preparation of N-(5-cyano-2-methyl-pyrimidin-4-yl)-N-methyl-methanesulfonamide (B19-5): A solution of B19-4 (5.2 g, 22.3 mmol) and pyridine (3.36 g, 42.6 mmol) in 1,4 dioxane (78 mL) was cooled to 0° C. and treated drop-wise over 10 minutes with TFA (5.8 g, 27.7 mmol). The mixture was allowed to warm to 25° C. After 4 hours the mixture was diluted with EtOAc (100 mL) and washed with water (2×200 mL). The aqueous layer was collected and washed with EtOAc (2×100 mL). The combined organic layers were then washed with brine (100 mL), dried over anhydrous sodium sulfate, and concentrated. The resultant residue was then washed with petroleum ether and dried to provide B19-5 as a pale yellow solid. Yield: 3.5 g, 76%. $^1$HNMR (CDCl$_3$): δ 8.84 (s, 1H), 3.54 (s, 3H), 3.4 (s, 3H) and 2.75 (s, 3H). Mass: (M−1) 225 calculated for C$_8$H$_{10}$N$_4$O$_2$S.

Step 6. A solution of B19-5 (5 g, 22 mmol) in 2N methanolic ammonia (350 mL) was charged to a Parr reactor and treated with 10% Pd/C (3.75 g, 35 mmol). The contents of the reactor were then hydrogenated at 48 Psi hydrogen pressure and 25° C. for 1 hour. The mixture was filtered through a Celite® bed and washed with methanol (200 mL). The combined filtrates were concentrated, and the resultant residue was diluted with EtOAc (25 mL) and acetic acid (1.3 g, 21 mmol). The mixture was stirred for 30 minutes, and the resultant solids were collected to provide B19 as a white solid. Yield: 4.2 g, 80%. IR (cm$^{-1}$): 3433, 3381, 3017, 2930, 1720, 1591, 1555, 1446, 1331, 1148 and 1058. $^1$HNMR (d$_6$-DMSO): δ 9.05 (s, 1H), 8.5-8.7 (broad s, 2H), 4.14 (s, 2H), 3.24 (s, 3H), 3.15 (s, 3H) and 2.66 (s, 3H). HPLC Purity: 99.9%.

4-Chloro-pyrimidine intermediates were prepared by methods similar to that described below for compound B20.

Preparation of 4-(4-chloro-5-(trifluoromethyl)pyrimidin-2-ylamino)-N-methylbenzamide (B20)

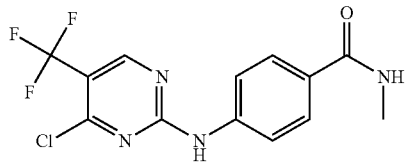 [SMILES: CNC(=O)c1ccc(Nc2ncc(C(F)(F)F)c(Cl)n2)cc1]

A solution of 2,4-dichloro-5-trifluoromethyl-pyrimidine (8.63 mmol) in 1:1 t-BuOH/DCE (10 mL) was cooled to 5° C., treated with solid ZnBr$_2$ (22.5 mmol), and stirred at 5° C. for 30 minutes. The resultant solution was maintained at 5° C. and treated first with solid 4-amino-N-methyl-benzamide (7.5 mmol) followed by TEA (16.5 mmol). The resultant white mixture was allowed to warm 25° C., and it was mixed at 25° C. for 20 hours. The mixture was adsorbed onto silica gel, and the fraction eluting 0-10% methanol/DCM was collected and concentrated. The resultant residue was triturated with water and filtered to provide B20. Yield: 3.0 mmol, 40%. LCMS 2.3 min, MZ+=331.1 $^1$H NMR (500 MHz, d$_6$-DMSO) δ ppm 10.89 (s, 1H), 8.87 (s, 1H), 8.34 (d, J=4.67 Hz, 1H), 7.73-7.89 (m, 3H), 2.78 (d, J=4.67 Hz, 3H).

Example 1

(R)-tert-butyl 1-(4-(4-((2-(N-methylmethan-5-ylsulfonamido)pyridin-3-yl)methylamino)-5-(trifluoromethyl)pyrimidin-2-ylamino)phenyl)ethylcarbamate (1)

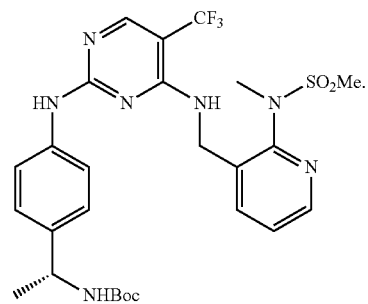 [SMILES: C[C@@H](NC(=O)OC(C)(C)C)c1ccc(Nc2ncc(C(F)(F)F)c(NCc3cccnc3N(C)S(C)(=O)=O)n2)cc1]

Step 1: Preparation of (R)-tert-butyl 1-(4-nitrophenyl)ethylcarbamate (C₁)

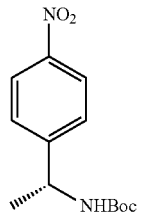 [SMILES: C[C@@H](NC(=O)OC(C)(C)C)c1ccc([N+](=O)[O-])cc1]

(R)-1-(4-nitrophenyl)ethanamine hydrochloride salt (1.0 g, 4.9 mmol), tert-butoxycarbonyl (BOC) anhydride (1.18 g, 5.43 mmol), and 10.0 mL of 1M sodium bicarbonate solution were dissolved in DCM (15 mL) and allowed to stir at 25° C. for 24 h. The organic layer was collected, and the aqueous layer was washed with DCM. The combined organic layers were then washed with water and 0.1 N HCl, dried over MgSO₄, filtered, and concentrated to provide C1 as a white solid. Yield: 1.2 g, 92%. GC-MS=266. $^1$H NMR (500 MHz, d₆-DMSO) δ: 8.15 (d, 2H), 7.56 (d, 1H), 7.52 (d, 2H), 4.68 (m, 1H), 1.32 (s, 9H), 1.27 (d, 3H).

Step 2: Preparation of (R)-tert-butyl 1-(4-aminophenyl)ethylcarbamate (C₂)

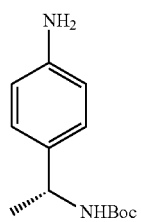 [SMILES: C[C@@H](NC(=O)OC(C)(C)C)c1ccc(N)cc1]

A solution of C1 (1.0 g, 3.8 mmol) in MeOH (20 mL) was charged to a Parr reactor, and the contents of the reactor were treated with 10% Pd/C (800 mg, 0.376 mmol). The contents of the reactor were then hydrogenated at 45 Psi hydrogen pressure and 25° C. for 4 hours. The contents of the reactor were filtered through Celite® and washed with DCM. The combined filtrates were concentrated to provide C2 as a sticky orange residue. Yield: 690 mg, 78% yield. GC MS=236. $^1$H NMR (500 MHz, d₆-DMSO) δ: 7.07 (d, 1H), 6.88 (d, 2H), 6.43 (d, 2H), 4.85 (s, 2H), 4.40 (m; 1H), 1.31 (s, 9H), 1.18 (d, 3H).

Step 3. Preparation of (R)-tert-butyl 1-(4-(4-chloro-5-(trifluoromethyl)pyrimidin-2-ylamino)phenyl)ethylcarbamate (C₃)

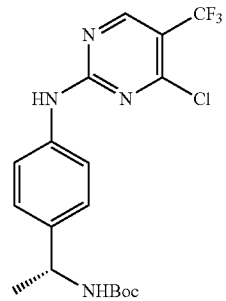 [SMILES: C[C@@H](NC(=O)OC(C)(C)C)c1ccc(Nc2ncc(C(F)(F)F)c(Cl)n2)cc1]

C2 (690 mg, 2.92 mmol) was dissolved in 10 mL DCE:t-BuOH (1:1 vol:vol), and the resultant solution was treated with ZnBr₂ (1.97 g, 8.76 mmol) and 2,4-dichloro-5-(trifluoromethyl)pyrimidine (748 mg, 3.45 mmol). The resultant mixture was then treated drop-wise with TEA (406 ml, 2.92 mmol), and the mixture was allowed to stir at 25° C. for about 20 hours. The reaction mixture was concentrated, and the resultant residue was treated with EtOAc. The resultant solution was washed with water and brine, and dried over MgSO₄. The mixture was then filtered, concentrated, and purified by column chromatography eluting with 22% EtOAc/Heptane. The product-containing eluents were combined and concentrated to provide C3 as a white solid. Yield: 680 mg, 56%. MS-415.2. $^1$H NMR (500 MHz, DMSO) δ: 10.59 (s, 1H), 8.74 (s, 1H), 7.53 (d, 2H), 7.31 (d, 1H), 7.23 (d, 2H), 4.54 (m, 1H), 1.33 (s, 9H), 1.25 (d, 3H).

Step 4. Compound C3 (100 mg, 0.24 mmol), B5 (88.5 mg, 0.264 mmol), and diethylamine (DIEA) (0.127 ml, 0.960 mmol) were dissolved in 1,2-dichloroethane (DCE):t-BuOH (1:1 vol:vol) (1.2 mL). The resultant solution was heated at 80° C. for about 20 hours, cooled to 25° C., treated with EtOAc, and washed with water. The organic phase was collected, and the aqueous phase was washed with EtOAc. The combined organic layers were dried over MgSO₄, filtered, and concentrated to provide 1 as a sticky residue. MS⁺ 596.8. $^1$H NMR (500 MHz, d₆-DMSO) δ: 9.50 (s, 1H), 8.41 (m, 1H), 8.22 (s, 1H), 7.61 (m, 2H), 7.35 (m, 3H), 6.99 (d, 2H), 4.76 (d, 2H), 4.47 (m, 1H), 3.14 (s, 3H), 3.11 (s, 3H), 1.33 (s, 9H), 1.21 (d, 3H). The product was used in the preparation of compound 2 in Example 2 below without further purification.

Example 2

Preparation of (R)—N-(3-((2-(4-(1-aminoethyl)phenylamino)-5-(trifluoromethyl)pyrimidin-4-ylamino)methyl)pyridin-2-yl)-N-methylmethanesulfonamide hydrochloride (2)

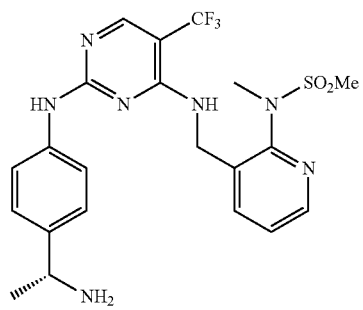 [SMILES: C[C@@H](N)c1ccc(Nc2ncc(C(F)(F)F)c(NCc3cccnc3N(C)S(C)(=O)=O)n2)cc1]

A solution of 1 (143 mg, 0.24 mmol) in THF (0.3 mL) was treated with 4N HCl in dioxane (0.240 ml, 0.96 mmol), and stirred at 25° C. for about 20 hours. The reaction mixture was then triterated with EtOAc and filtered, and the filtrate was concentrated to provide the HCl salt form of 2 as a white solid. Yield: 128 mg, 94% yield. MS⁻ 494.0. ¹H NMR (500 MHz, d₆-DMSO): δ 10.2 (s, 1H), 8.40 (m, 4H), 8.12 (s, 1H), 7.67 (d, 1H), 7.45 (m, 3H), 7.27 (d, 2H), 4.84 (d, 2H), 4.28 (m, 1H), 3.16 (s, 3H), 3.14 (s, 3H), 1.45 (d, 3H). FAK IC$_{50}$: <0.000595 μM (Table 1, Example 354)

Example 3

Preparation of tert-butyl 4-(4-((2-(N-methylmethan-5-ylsulfonamido)pyridin-3-yl)methylamino)-5-(trifluoromethyl)pyrimidin-2-ylamino)benzylcarbamate (3)

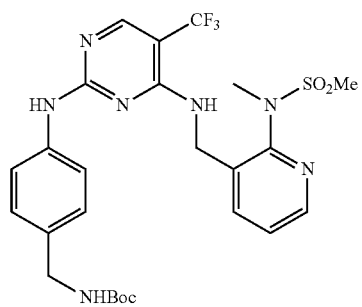 [SMILES: CN(c1ncccc1CNc1nc(Nc2ccc(CNC(=O)OC(C)(C)C)cc2)ncc1C(F)(F)F)S(C)(=O)=O]

Step 1: Preparation of tert-butyl 4-nitrobenzylcarbamate (C₄)

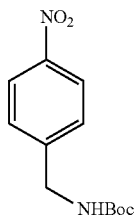 [SMILES: CC(C)(C)OC(=O)NCc1ccc([N+](=O)[O-])cc1]

A stirred solution of (4-nitrophenyl)methanamine hydrochloride (10 g, 53.0 mmol) in THF (150 mL) and water (13 mL) was cooled to 0° C. and treated with BOC anhydride (11.6 g, 53.0 mmol) and DIEA (27.7 mL, 159 mmol). The reaction mixture was stirred for about 20 hours as it was allowed to warm to 25° C. The mixture was then concentrated, and the resultant residue was dissolved in EtOAc. The resultant solution was washed with 1N HCl, saturated sodium bicarbonate, and brine. The organic phase was then dried over MgSO₄, filtered, and concentrated to provide C4 as an off white solid. Yield: 14.0 g, 99%. ¹H NMR (400 MHz, d₆-DMSO) δ: 8.16 (d, 2H), 7.55 (t, 1H), 7.46 (d, 2H), 4.21 (d, 2H), 1.36 (s, 9H).

Step 2. Preparation of tert-butyl 4-aminobenzylcarbamate (C5)

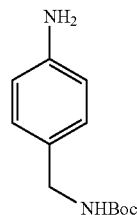 [SMILES: CC(C)(C)OC(=O)NCc1ccc(N)cc1]

C4 (7.0 g, 27.7 mmol) was dissolved in dioxane (325 mL), ethanol (240 mL), and water (160 mL). The resultant solution was then treated with Fe(0) powder (7.12 g, 127.4 mmol) and ammonium chloride (5.33 g, 99.7 mmol), and the resultant mixture was stirred at 70° C. for 4 hours. The reaction mixture was cooled to 25° C., filtered through Celite®, and washed with EtOAc. The organic solvents were evaporated, and the resultant aqueous residue was extracted with EtOAc. The combined organic layers were dried over MgSO₄, filtered, and concentrated to provide C5 as a yellow solid. Yield: 6.52 g, 99% yield. ¹H NMR (400 MHz, d₆-DMSO) δ: 7.146 (t, 1H), 6.87 (d, 2H), 6.48 (d, 2H), 4.95 (s, 2H), 3.92 (d, 2H), 1.38 (s, 9H).

Step 3. Tert-butyl 4-(4-chloro-5-(trifluoromethyl)pyrimidin-2-ylamino)benzylcarbamate (C₆)

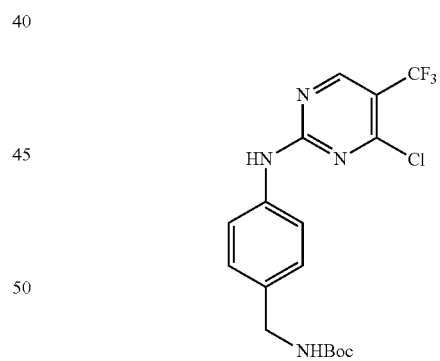

Compound C6 was prepared as a white solid in a manner similar to that described in Step 3 of Example 1 except that C5 (1.30 g, 5.86 mmol) was used instead of C2. Yield: 1.37 g, 49%. MS⁻ 401.1. ¹H NMR (400 MHz, d₆-DMSO) δ: 10.6 (s, 1H), 8.75 (s, 1H), 7.56 (d, 2H), 7.34 (t. 1H), 7.18 (d, 2H), 4.05 (d, 2H), 1.36 (s, 9H).

Step 4. Compound 3 was prepared as a white solid in a manner similar to that described in Step 4 of Example 1 except that C6 (1.2 g, 2.98 mmol) was used instead of C3, and the resultant crude product was purified by column chromatography, eluting with 45-55% EtOAc/Heptane. Yield: 1.17 g, 68%. MS⁺ 582.3. ¹H NMR (500 MHz, d₆-DMSO) δ: 9.57 (s, 1H), 8.42 (s, 1H), 8.58 (s, 1H), 7.64 (m, 2H), 7.35 (m, 4H), 6.94 (d, 2H), 4.80 (d, 2H), 3.98 (d, 2H), 3.16 (s, 3H), 3.14 (s, 3H), 1.39 (s, 9H).

Example 4

Preparation of N-(3-((2-(4-(aminomethyl)phenylamino)-5-(trifluoromethyl)pyrimidin-4-ylamino)methyl)pyridin-2-yl)-N-methylmethanesulfonamide (4)

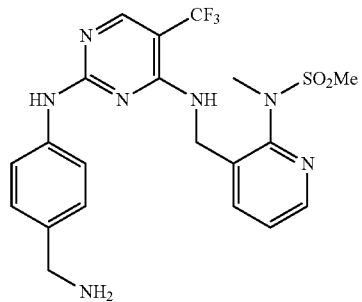 [SMILES: CN(c1ncccc1CNc1nc(Nc2ccc(CN)cc2)ncc1C(F)(F)F)S(C)(=O)=O]

The HCl salt form of 4 was prepared as a white solid in a manner similar to that described for preparing 2 in Example 2 except that 3 (1.0 g, 1.72 mmol) was used instead of 1.

The salt form of 4 was dissolved in DCM, and was washed with saturated sodium bicarbonate. The organic phase was then dried over $Na_2SO_4$, filtered, and concentrated to provide the free-base form of 4 as a foamy white solid. Yield: 904 mg, 99%. MS$^+$ 482. $^1$H NMR (500 MHz, d$_6$-DMSO) δ: 9.50 (s, 1H), 8.44 (d, 1H), 8.25 (s, 1H), 7.66 (d, 1H), 7.57 (t, 1H), 7.38 (m, 3H), 7.04 (d, 2H), 4.80 (d, 2H), 3.58 (d, 2H), 3.17 (s, 3H), 3.13 (s, 3H). FAK IC$_{50}$: 0.00059 µM (Table 1, Example 104)

Example 5

Preparation of N-(4-(4-((2-(N-methylmethan-5-ylsulfonamido)pyridin-3-yl)methylamino)-5-(trifluoromethyl)pyrimidin-2-ylamino)benzyl)acetamide (5)

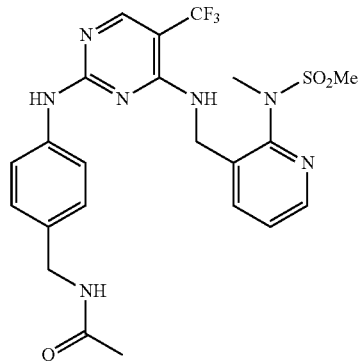 [SMILES: CC(=O)NCc1ccc(Nc2ncc(C(F)(F)F)c(NCc3cccnc3N(C)S(C)(=O)=O)n2)cc1]

The free-base form of 4 (80 mg, 0.166 mmol), acetic anhydride (0.019 ml, 0.199 mmol), and DIEA (0.043 ml, 0.249 mmol) were dissolved in THF (0.5 ml) and stirred at 25° C. for 24 hours. The reaction mixture was then treated with EtOAc and washed with 1N NaOH. The resultant organic layer was dried over MgSO$_4$, filtered, and concentrated to provide 5 as a white solid. Yield: 63 mg, 73%. MS$^+$ 524.5. $^1$H NMR (500 MHz, d$_6$-DMSO) δ: 9.55 (s, 1H), 8.44 (d, 1H), 8.25 (s, 1H), 8.22 (t, 1H), 7.60 (m, 2H), 7.38 (m, 3H), 6.96 (d, 2H), 4.80 (d, 2H), 4.11 (d, 2H), 3.16 (s, 3H), 3.13 (s, 3H), 1.85 (s, 3H). FAK IC$_{50}$: 0.0006 µM Example 6

Preparation of N-(3-((2-(4-(hydroxymethyl)phenylamino)-5-(trifluoromethyl)pyrimidin-4-ylamino)methyl)pyridin-2-yl)-N-methylmethanesulfonamide (6)

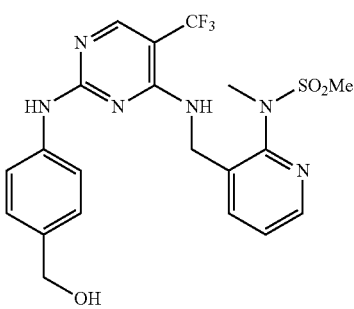 [SMILES: CN(c1ncccc1CNc1nc(Nc2ccc(CO)cc2)ncc1C(F)(F)F)S(C)(=O)=O]

Step 1. Preparation of (4-(4-chloro-5-(trifluoromethyl)pyrimidin-2-ylamino)phenyl)methanol (C$_7$)

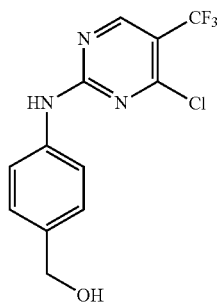 [SMILES: OCc1ccc(Nc2ncc(C(F)(F)F)c(Cl)n2)cc1]

Step 1. C7 was prepared in a manner similar to that described in for making C3 in Step 3 of Example 1 except that 4-aminobenzyl alcohol (2.4 g, 19 mmol) was used instead of C2. When the reaction was complete the reaction mixture was concentrated and dissolved in EtOA. The resultant solution was washed with water, brine, dried over MgSO$_4$, and concentrated. The resultant tan solid was triterated with ether and a small amount of EtOAc, filtered and concentrated to provide C7 as a tan solid. Yield: 2.98 g, 50%. MS$^+$ 304.1. $^1$H NMR (500 MHz, d$_6$-DMSO) δ: 10.61 (s, 1H), 8.76 (s, 1H), 7.59 (d, 2H), 7.26 (d, 2H), 5.10 (bs, 1H), 4.43 (s, 2H).

Step 2. Compound 6 was prepared in a manner similar to that described for making compound 1 in Step 4 of Example 1, except that C7 (2.5 g, 8.2 mmol) was used instead C3. When the reaction was complete the reaction mixture was concentrated and dissolved in EtOA. The resultant solution was washed with water, brine, and dried over MgSO$_4$, and concentrated. The resultant solid was triterated with hot EtOAc, and the mixture was cooled to 0° C. and filtered to provide 6 as a white solid. Yield: 2.94 g, 74%. MS$^+$ 483.4. $^1$H NMR (500 MHz, d$_6$-DMSO) δ: 9.50 (s, 1H), 8.41 (d, 1H), 8.22 (s, 1H), 7.62 (d, 1H), 7.55 (t, 1H), 7.36 (m, 3H), 6.99 (d, 2H), 4.98 (t, 1H), 4.76 (d, 2H), 4.32 (d, 2H), 3.13 (s, 3H); 3.11 (s, 3H). FAK $IC_{50}$: <0.000595 µM (Table 1, Example 319)

Example 7

Preparation of N-(3-((2-(4-(chloromethyl)phenylamino)-5-(trifluoromethyl)pyrimidin-4-ylamino)methyl)pyridin-2-yl)-N-methylmethanesulfonamide (7)

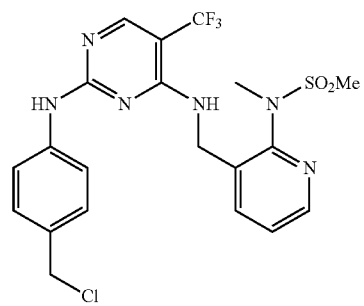 [SMILES: CN(c1ncccc1CNc1nc(Nc2ccc(CCl)cc2)ncc1C(F)(F)F)S(C)(=O)=O]

A suspension of 6 (800 mg, 1.66 mmol) in DCM (5 mL) was cooled to 0° C. and treated with a solution of thionyl chloride (0.266 ml, 3.65 mmol) in DCM (2.0 mL). The reaction mixture was allowed to warm to 25° C. and stirred at 25° C. for 20 hours. The reaction mixture was then treated with DCM and washed with water (2×). The aqueous layer was collected and washed with DCM. The combined organic layers were then dried over $MgSO_4$, filtered and concentrated to provide 7 as a white solid. Yield: 668 mg, 80%. $^1$H NMR (500 MHz, $d_6$-DMSO) δ: 6.68 (s, 1H), 8.45 (d, 1H), 8.28 (s, 1H), 7.64 (m, 2H), 7.42 (m, 3H), 7.14 (d, 2H), 4.82 (d, 2H), 4.66 (s, 2H), 3.17 (s, 3H), 3.15 (s, 3H). FAK $IC_{50}$: 0.00155 µM (Table 1, Example 348)

Example 8

Preparation of N-(3-((2-(4-((1,3-dihydroxypropan-2-ylamino)methyl)phenylamino)-5-(trifluoromethyl)pyrimidin-4-ylamino)methyl)pyridin-2-yl)-N-methylmethanesulfonamide (8)

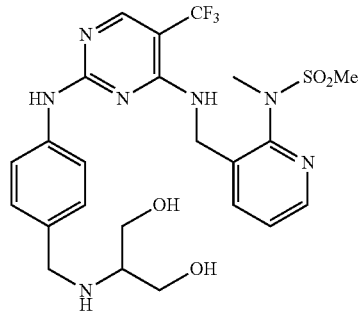 [SMILES: CN(c1ncccc1CNc1nc(Nc2ccc(CNC(CO)CO)cc2)ncc1C(F)(F)F)S(C)(=O)=O]

A mixture of 7 (100 mg, 0.200 mmol), 2-amino-1,3-propanediol (90.9 mg, 0.998 mmol), sodium hydroxide (7.98 mg, 0.200 mmol) and 2-propanol (0.5 mL) was heated to reflux. After 30 minutes the mixture was cooled, treated with DCM, and washed with water. The organic phase was dried over $MgSO_4$, filtered and concentrated. The resultant residue was then purified by column chromatography (silica gel; eluting with 6% MeOH/DCM with $NH_4OH$), and the eluents containing the product were combined and concentrated to provide 8 as a white solid. Yield: 60.9 mg, 55%. $MS^+$ 556.2. $^1$H NMR (500 MHz, $d_6$-DMSO) δ: 9.48 (s, 1H), 8.41 (s, 1H), 8.21 (s, 1H), 7.59 (m, 2H), 7.34 (m, 3H), 6.99 (d, 2H), 4.75 (d, 2H), 4.35 (t, 2H), 3.58 (s, 2H), 3.34 (m, 4H), 3.12 (s, 3H), 3.09 (s, 3H), 2.45 (m, 1H). FAK $IC_{50}$: <0.000595 µM (Table 1, Example 389)

Example 9

Preparation of tert-butyl 3-({4-[({2-[methyl(methylsulfonyl)amino]pyridin-3-yl}methyl)amino]-5-(trifluoromethyl)pyrimidin-2-yl}amino)benzoate (9)

Step 1. Preparation of tert-butyl 3-({4-chloro-5-(trifluoromethyl)pyrimidin-2-yl}amino)benzoate (C8)

A solution of pyrimidine (24.8 g, 115 mmol) in tert-butanol (150 mL) and DCE (150 mL) was treated with $ZnBr_2$ (25.8 g, 115 mmol), and the resultant mixture was stirred at 25° C. until all the $ZnBr_2$ dissolved. The resultant solution was cooled to 0° C. and treated drop-wise with aniline (22.13 g, 115 mmol). The resultant brown mixture was then treated drop-wise with DIEA (40.1 mL, 230 mmol). The mixture was allowed to warm to 25° C. and stirred for 16 hours under N₂ atmosphere. The mixture was concentrated, and the resultant residue was suspended in MeOH. The resultant white solids were collected to provide C8 as a white solid. Yield: 22.7 grams, 53%. APCI m/z 371.8/373.8 (M⁻); ¹H NMR (d₆-DMSO) δ: 10.84 (bs, 1H), 8.85 (s, 1 h), 8.37 (bs, 1H), 7.92 (d, J=7.8 Hz., 1 h), 7.62 (d, J=7.8 Hz., 1H), 7.48 (t, J=7.8 Hz., 1H), 1.56 (s, 9 H) ppm.

Step 2. A solution of tert-butanol (20.0 mL), DCE (20.0 mL) and DIEA (3.13 mL, 18.0 mmol) was treated with C8 (5.60 g, 15.0 mmol) and B5 (5.02 g, 15.0 mmol), and the resulting mixture was stirred at 80° C. under an atmosphere of nitrogen for 16 hours. The mixture was cooled to 25° C. and concentrated. The resultant residue was partitioned between EtOAc and 1 N sodium hydroxide, and the organic phase was collected. The aqueous layer was extracted with EtOAc, and the combined organic phases were dried over MgSO₄ and filtered. The resultant filtrate was concentrated under reduced pressure, and the resultant residue was triturated with hot EtOAc to provide 9 as a white solid. Yield: 7.83 grams, 95%. LC/MS (standard) 25°=3.0 min., m/z 553.6 (MH⁺). HPLC (FAK1) 25°=8.14 min. ¹H NMR (d₆-DMSO) δ: 9.75 (bs, 1H), 8.44 (d, J=5.2 Hz., 1H), 8.29 (s, 1H), 8.05 (bs, 1H), 7.82 (d, J=7.8 Hz., 1H), 7.60 (t, J=5.7 Hz., 1H), 7.44-7.40 (m, 2H), 7.17 (t, J=5.7 Hz, 1H), 4.82 (d, J=5.7 Hz., 2 H), 3.16 (s, 3H), 3.13 (s, 3H), 1.51 (s, 9H) ppm. FAK IC₅₀: 0.0006 μM Example 10

Preparation of 3-({4-[({2-[methyl(methylsulfonyl)amino]pyridin-3-yl}methyl)amino]-5-(trifluoromethyl)pyrimidin-2-yl}amino)benzoic acid trifluoroacetic acid salt (10)

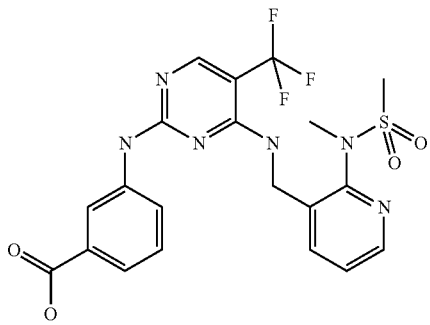 [SMILES: CN(c1ncccc1CNc1nc(Nc2cccc(C(=O)O)c2)ncc1C(F)(F)F)S(C)(=O)=O]

A solution of 9 (7.83 g, 14.1 mmol) in DCE (30.0 mL) was cooled to 0° C. and treated slowly with TFA (45.0 mL). The resultant orange-brown solution was allowed to slowly warm to 25° C. under an N2 atmosphere and stirred for 4 hours. The mixture was then concentrated, and the resultant residue was treated with EtOAc. The resultant white solids were collected by filtration and washed with EtOAc to provide the trifluoroacetate salt form of 10. Yield: 7.24 grams, 84%. APCI m/z 496.8 (MH⁺), HPLC (FAK1) 25°=5.29 min., ¹H NMR (d₆-DMSO) δ: 9.82 (bs, 1H), 8.44 (d, J=5.2 Hz., 1H), 8.29 (s, 1H), 8.08 (bs, 1H), 7.79 (d, J=7.8 Hz., 1H), 7.60-7.38 (m, 4H), 7.17 (t, J=5.7 Hz, 1H), 4.82 (d, J=5.7 Hz., 2H), 3.16 (s, 3H), 3.13 (s, 3H) ppm. FAK IC₅₀: 0.0006 μM Example 11

Preparation of N-cyclopropyl-3-({4-[({2-[methyl(methylsulfonyl)amino]pyridin-3-yl}methyl)amino]-5-(trifluoromethyl)pyrimidin-2-yl}amino)benzamide (11)

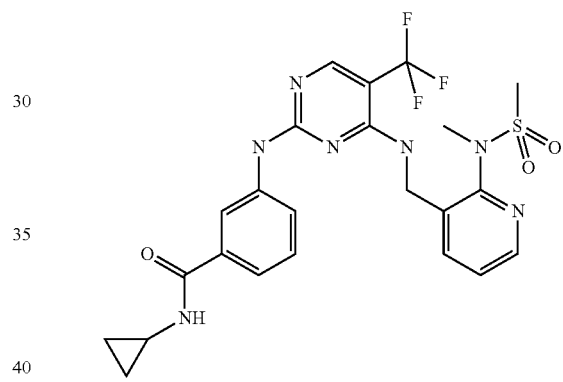

A polymer supported carbodiimide (PS-CDI) (0.326 mmol) was allowed to swell in acetonitrile (volume of 500 μL). The resultant suspension was treated with 10 (100 mg, 0.164 mmol) and DIEA (29 μL, 0.164 mmol). The resultant solution was then treated with cyclopropylamine (19 μL, 0.164 mmol). The resultant suspension was then mixed on a shaker plate for 16 hours. The mixture was then filtered, and the solids washed with 10% MeOH in chloroform. The combined filtrates were concentrated under reduced pressure, and the resultant residue was purified over silica (99:1:0.1 CHCl₃: CH₃OH:NH₄OH) to provide 11 as a white foam. Yield: 14.3 mg, 16%. LC Ret. Time (standard)=2.1 min., m/z 536.2 (MH⁺); ¹H NMR (CD₃OD) δ: 8.42 (d, J=7.8 Hz., 1 H), 8.20 (s, 1 h), 7.97 (t, J=7.8 Hz., 1H), 7.81 (d, J=7.8 Hz., 1H), 1.68 (d, J=7.8 Hz., 1H), 7.39-7.34 (m, 2H), 7.26 (t, J=7.8 Hz., 1H), 4.94 (s, 2H), 3.23 (s, 3H), 3.14 (s, 3H), 2.82 (m, 1H), 0.79 (m, 2 h), 0.60 (m, 2H) ppm. FAK IC₅₀: 0.00186 μM

Example 12

Preparation of N-(3-((2-(4-(1-hydroxyethyl)phenylamino)-5-(trifluoromethyl)pyrimidin-4-ylamino)methyl)pyridin-2-yl)-N-methylmethanesulfonamide (12)

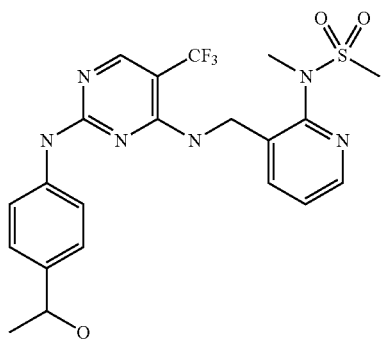 [SMILES: CC(O)c1ccc(Nc2ncc(C(F)(F)F)c(NCc3cccnc3N(C)S(C)(=O)=O)n2)cc1]

Step 1. N-(3-((2-chloro-5-(trifluoromethyl)pyrimidin-4-ylamino)methyl)pyridin-2-yl)-N-methyl-methanesulfonamide (C9)

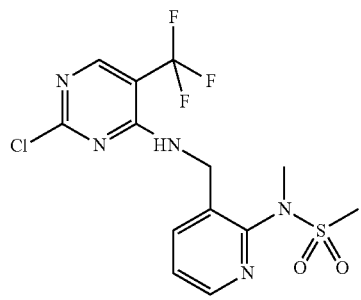 [SMILES: CN(c1ncccc1CNc1nc(Cl)ncc1C(F)(F)F)S(C)(=O)=O]

A solution of B5 and trifluoroethanol (120 mL) was treated with triethylamine (TEA) (16.6 mL) and stirred at 25° C. for 1 hour. In a separate reaction flask, a solution of 2,4-dichloro-5-trifluoromethylpyrimidine (13.2 g, 60.8 mmol) and trifluoroethanol (120 mL) was cooled to −45° C. The cold 2,4-dichloro-5-trifluoromethylpyrimidine solution was then treated drop-wise with the solution containing B5 and stirred at −45° C. for 2 hours. The mixture was allowed to warm to 25° C., and it was stirred at 25° C. for about 20 hours. The reaction mixture was then concentrated and cooled to 0° C. The resultant white mixture was diluted with EtOAc (15 ml), and the solids collected by filtration. The white solids were then washed with water and EtOAc to provide C9. Yield: 0.7 g, 45%. $^1$H NMR (400 MHz, $d_6$-DMSO) δ: 3.07 (s, 3H), 3.29 (s, 3H), 4.68 (d, 2H), 7.39 (m, 1H), 7.72 (d, 1H), 8.40 (s, 1H), 8.50 (t, 1H); ESI-MS: 396.0 (MH$^+$).

Step 2. A solution of C9 (0.253 mmol) and anhydrous DMSO (0.5 ml) was treated with 1-(4-aminophenyl)ethanol (0.277 mmol) followed by potassium phosphate dibasic (0.746 mmol). The mixture was stirred at 100° C. for 1.5 days, and treated with additional 1-(4-aminophenyl)ethanol (0.583 mmol). The mixture was stirred at 100° C. for 15 hours and concentrated. The resultant residue was purified first by column chromatography (silica gel; 10% (NH$_4$OH/MeOH)/CH$_2$Cl$_2$) followed by preparatory thin layer chromatography developed in 5% MeOH/CH$_2$Cl2 to provide 12. Yield: 13.6 mg, 10.8%. $^1$H NMR (CD$_3$OD) δ: 8.39 (d, 1H), 8.13 (s, 1H), 7.73 (d, 1H), 7.33 (m, 3H), 7.14 (d, 2H), 4.87 (s, 2H), 4.72 (q, 1H), 3.17 (s, 3H), 3.10 (s, 3H), 1.37 (d, 3H). MS: m/z 497 (MH$^+$).

Example 13

Preparation of 2-fluoro-4-({-4-[({2-[methyl(methylsulfonyl)amino]pyridin-3-yl}methyl)amino]-5-(trifluoromethyl)pyrimidin-2-yl}amino)benzamide formic acid salt (13)

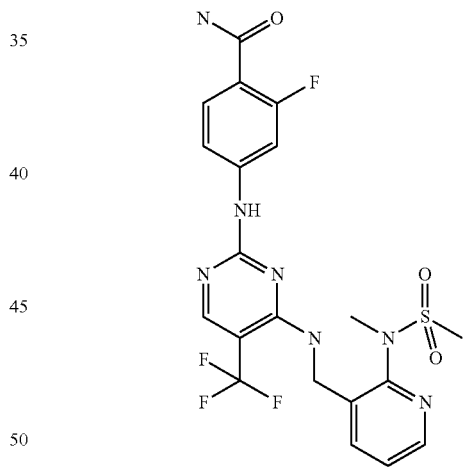

A mixture of 4-amino-2-fluorobenzamide (1.5 eq., 189 µM) in 2-propanol (1.0, mL) was treated with C9 (1 equiv., 130 uM) followed by trifluoroacetic acid (2.7 equiv., 341 µM) and stirred in a sealed vial at 100° C. for about 20 hours. The mixture was then cooled to 25° C., treated with DMSO, filtered, and purified on a Shimadzu using a reverse phase Symmetry C-8 column and eluting with 20-80% B for 10 min at 40 ml/min (A: 0.1% formic acid in water, B: 0.1% formic acid in acetonitrile to provide the formic acid salt of 13 as a cream colored solid. Yield: 17.5 mg, 27%. LC-MS M+1=514. NMR ($d_6$-DMSO) δ: 3.13 (6H, s), 4.81 (2H, s), 7.30-7.40

(6H, m), 7.41-7.73 (2H, m), 8.3 (1H, s), 8.41 (1H, s), 9.96 (1H, s). FAK $IC_{50}$: <0.000595 μM (Table 1, Example 320)

Example 14

Preparation of 3-fluoro-4-({4-[({2-[methyl(methylsulfonyl)amino]pyridin-3-yl}methyl)amino]-5-(trifluoromethyl)pyrimidin-2-yl}amino)benzamide formic acid salt (14)

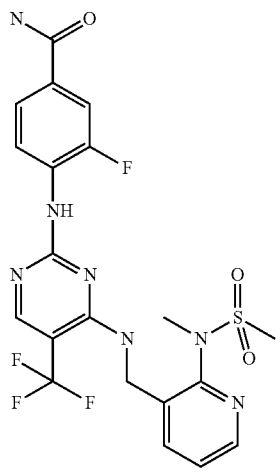 [SMILES: CN(c1ncccc1CNc1nc(Nc2ccc(C(N)=O)cc2F)ncc1C(F)(F)F)S(C)(=O)=O]

Compound 14 was prepared in a manner similar to that described Example 13 for the preparation of 13 except that 4-amino-3-fluorobenzamide (1.5 equ/189 μM) was used instead of 4-amino-2-fluorobenzamide to provide the formic acid salt of 14 as a cream colored solid. Yield: 26 mg, 37%. LC-MS M+1=514. NMR ($d_6$-DMSO) δ: 2.98 (3H, s), 3.09 (3H, s), 4.65 (2H, s), 7.35-7.66 (7H, m), 7.87 (1H, s), 8.23 (1H, s), 8.38 (1H, s), 9.19 (1H, s). FAK $IC_{50}$: <0.000595 μM (Table 1, Example 322)

Example 15

Preparation of 4-(4-{[(3-methanesulfonyl-methyl-amino)-pyrazin-2-ylmethyl]-amino}-5-(trifluoromethyl)-pyrimidin-2-ylamino)-N-methyl-benzamide (15)

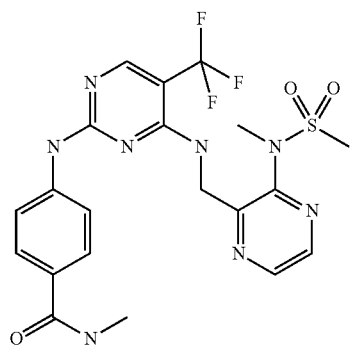 [SMILES: CNC(=O)c1ccc(Nc2ncc(C(F)(F)F)c(NCc3nccnc3N(C)S(C)(=O)=O)n2)cc1]

Step 1. A suspension of B20 (0.3 mmol), B2 (0.3 mmol), and diisopropylethyl amine (0.9 mmol) in 1:1 (v:v) DCE/tBuOH was mixed at 80° C. for 9 hours. The mixture was allowed to cool to 25° C., and it was mixed at 25° C. for 20 hours. The mixture was then treated with 9:1 (v:v) ether/ethanol. The solids were collected and washed with water to provide 15. Yield: 0.23 mmol, 78%. HPLC (KDC 10_90) 3.526 min. $^1$H NMR (500 MHz, $d_6$-DMSO) δ ppm 9.83 (s, 1H), 8.69 (d, J=2.59 Hz, 1H), 8.58 (d, J=2.59 Hz, 1H), 8.31 (s, 1H), 8.20 (d, J=4.67 Hz, 1H), 7.58-7.70 (m, 3H), 7.41 (t, J=5.18 Hz, 1 H), 5.00 (d, J=5.18 Hz, 2H), 3.23 (s, 3H), 3.20 (s, 3H), 2.75 (d, J=4.15 Hz, 3H). FAK $IC_{50}$: <0.000595 μM (Table 1, Example 317)

Example 15A

Preparation of 4-(4-{[(3-methanesulfonyl-methyl-amino)-pyrazin-2-ylmethyl]-amino}-5-(trifluoromethyl)-pyrimidin-2-ylamino)-N-methyl-benzamide hydrochloride salt (15A)

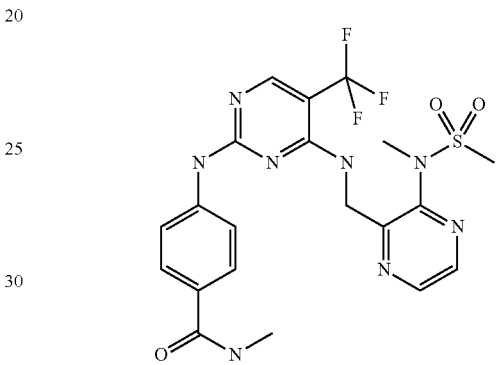

Step 1. A suspension of B20 (26.3 mmol), B2 (28.9 mmol) and diisopropylethyl amine (105 mmol) was mixed in 1:1 DCE:tBuOH (80 mL) and heated to 88° C. in a sealed flask for 1.5 hour. The mixture turned green and a solid precipitated. The suspension was diluted with Et2O/EtOH (10:1) and filtered to obtain 10.1 g of a white solid (75%). 8 g of this product was slurried in 400 mL of MeOH and to the mixture was added 18 mL 4.0M HCl in dioxane. This was stirred at room temperature for 1 hour, then it was filtered to obtain 15A as an off-white solid HCl salt (quant yield). 1H NMR (400 MHz, DMSO-$d_6$) δ ppm 2.75 (d, J=3.74 Hz, 3H), 3.18 (m, 6H), 5.01 (d, J=4.98 Hz, 2H), 7.52 (d, 2H), 7.67 (d, J=8.72 Hz, 2H), 7.98 (br. s., 1H), 8.29 (d, J=4.15 Hz, 1H), 8.42 (s, 1H), 8.59 (d, 1H), 8.68 (d, 1H), 10.38 (s, 1H). ESI-MS: 511.1 ($MH^+$), 509.2 $(M-H)^-$. FAK $IC_{50}$: 0.00179 μM (Table 1, Example 318)

Examples 16-415

Compounds 16-415 in Examples 16-415 (see Table 1) were prepared by the methods described above in the Detailed Description of the Invention and as described in Examples 1-15A. The amines used in these reactions were obtained commercially and used as received, prepared as described above for compounds B1-B20 or in Examples 1-15A above, or prepared by common synthetic methods for amines known to those skilled in the art. Unless otherwise noted, compounds having chiral centers were prepared as racemic mixtures.

Table 1 also contains biological kinase inhibition (IC50 values) for compounds 16-415.

The present invention is not to be limited in scope by the specific embodiments described herein. Indeed, various modifications of the invention in addition to those described

TABLE 1

IC50 values against FAK kinase.

| Ex. | Structure | Compound Name | FAK IC50, μM |
|---|---|---|---|
| 16 | 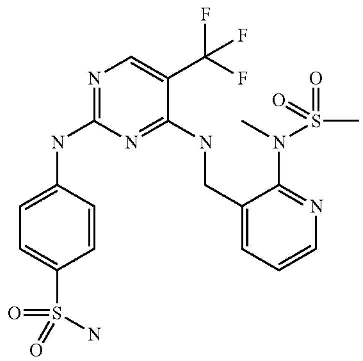 [SMILES: CN(c1ncccc1CNc1nc(Nc2ccc(S(N)(=O)=O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzenesulfon-amide (16) | 0.00409 |
| 17 | 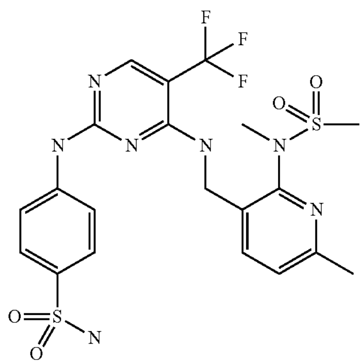 [SMILES: Cc1ccc(CNc2nc(Nc3ccc(S(N)(=O)=O)cc3)ncc2C(F)(F)F)c(N(C)S(C)(=O)=O)n1] | 4-({4-[({6-methyl-2-[methyl(methylsulfonyl)amino]pyridin-3-yl}methyl)amino]-5-(trifluoromethyl)pyrimidin-2-yl}amino)benzene-sulfonamide (17) | 0.00126 |
| 18 | 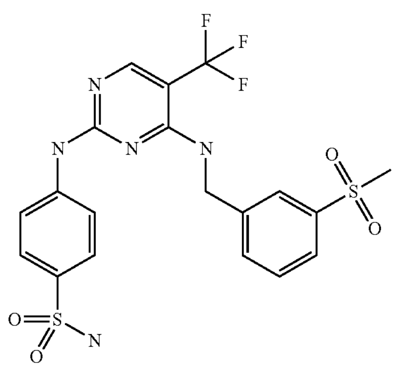 [SMILES: CS(=O)(=O)c1cccc(CNc2nc(Nc3ccc(S(N)(=O)=O)cc3)ncc2C(F)(F)F)c1] | 4-{[4-{[3-(methylsulfonyl)benzyl]amino}-5-(trifluoromethyl)pyrimidin-2-yl]amino}benzene-sulfonamide (18) | 0.0132 |
| 19 | 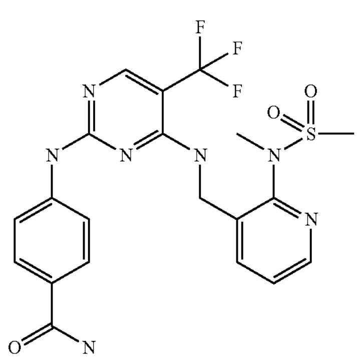 [SMILES: CN(c1ncccc1CNc1nc(Nc2ccc(C(N)=O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzamide (19) | 0.0034 |

TABLE 1-continued

IC50 values against FAK kinase.

| Ex. | Structure | Compound Name | FAK IC50, µM |
|---|---|---|---|
| 20 | 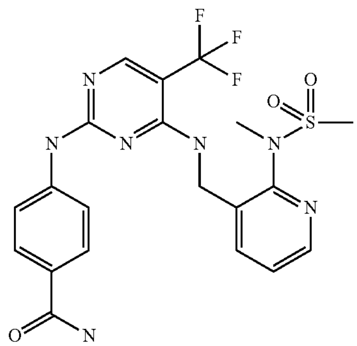 [SMILES: CN(c1ncccc1CNc1nc(Nc2ccc(C(N)=O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzamide (20), hydrochloride salt | 0.0006 |
| 21 | 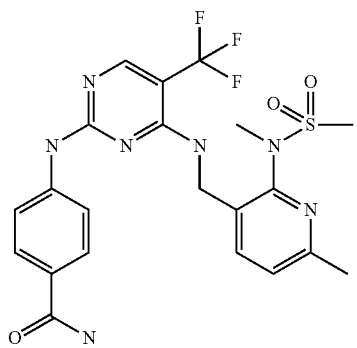 [SMILES: Cc1ccc(CNc2nc(Nc3ccc(C(N)=O)cc3)ncc2C(F)(F)F)c(N(C)S(C)(=O)=O)n1] | 4-({4-[({6-methyl-2-[methyl(methylsulfonyl)amino]pyridin-3-yl}methyl)amino]-5-(trifluoromethyl)pyrimidin-2-yl}amino)benzamide (21) | 0.001 |
| 22 | 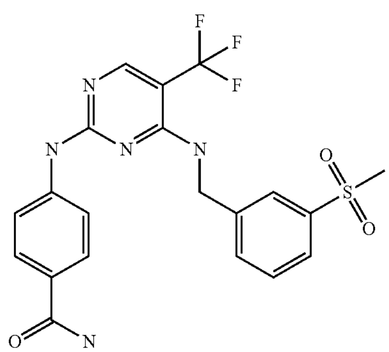 [SMILES: CS(=O)(=O)c1cccc(CNc2nc(Nc3ccc(C(N)=O)cc3)ncc2C(F)(F)F)c1] | 4-{[4-{[3-(methylsulfonyl)benzyl]amino}-5-(trifluoromethyl)pyrimidin-2-yl]amino}benzamide (22) | 0.00356 |
| 23 | 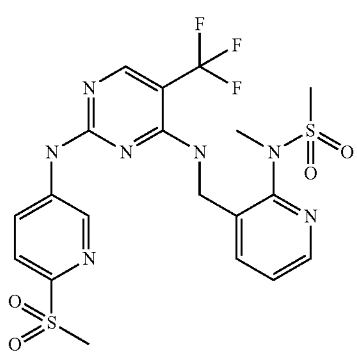 [SMILES: CN(c1ncccc1CNc1nc(Nc2ccc(S(C)(=O)=O)nc2)ncc1C(F)(F)F)S(C)(=O)=O] | N-methyl-N-[3-({[2-{[6-(methylsulfonyl)pyridin-3-yl]amino}-5-(trifluoromethyl)pyrimidin-4-yl]amino}methyl)pyridin-2-yl]methanesulfonamide (23) | 0.0686 |

TABLE 1-continued

IC50 values against FAK kinase.

| Ex. | Structure | Compound Name | FAK IC50, μM |
|---|---|---|---|
| 24 | 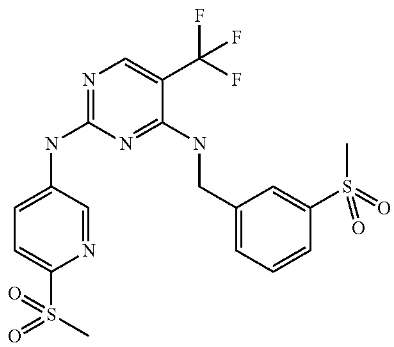 [SMILES: CS(=O)(=O)c1cccc(CNc2nc(Nc3ccc(S(C)(=O)=O)nc3)ncc2C(F)(F)F)c1] | N-4-[3-(methylsulfonyl)benzyl]-N-2-[6-(methylsulfonyl)pyridin-3-yl]-5-(trifluoromethyl)-pyrimidine-2,4-diamine (24) | 0.337 |
| 25 | 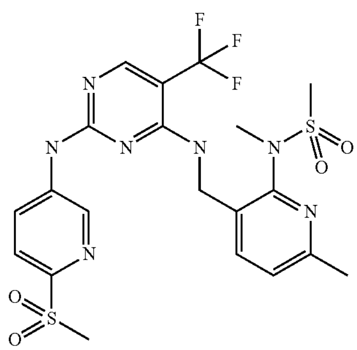 [SMILES: Cc1ccc(CNc2nc(Nc3ccc(S(C)(=O)=O)nc3)ncc2C(F)(F)F)c(N(C)S(C)(=O)=O)n1] | N-methyl-N-[6-methyl-3-({[2-{[6-(methylsulfonyl)pyridin-3-yl]amino}-5-(trifluoromethyl)pyrimidin-4-yl]amino}methyl)pyridin-2-yl]methanesulfonamide (25) | 0.0129 |
| 26 | 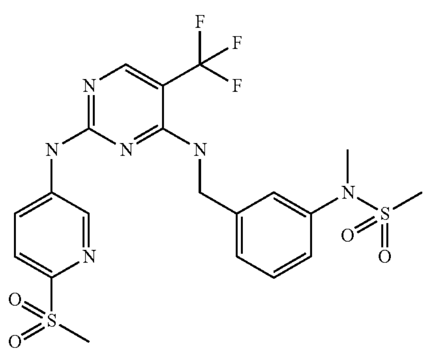 [SMILES: CN(c1cccc(CNc2nc(Nc3ccc(S(C)(=O)=O)nc3)ncc2C(F)(F)F)c1)S(C)(=O)=O] | N-methyl-N-[3-({[2-{[6-(methylsulfonyl)pyridin-3-yl]amino}-5-(trifluoromethyl)pyrimidin-4-yl]amino}methyl)phenyl]methanesulfonamide (26) | 0.154 |
| 27 | 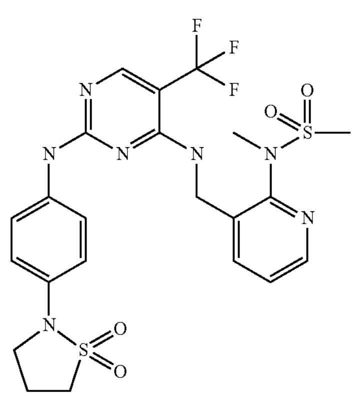 [SMILES: CN(c1ncccc1CNc1nc(Nc2ccc(N3CCCS3(=O)=O)cc2)ncc1C(F)(F)F)S(C)(=O)=O] | N-[3-({[2-{[4-(1,1-dioxidoisothiazolidin-2-yl)phenyl]amino}-5-(trifluoromethyl)pyrimidin-4-yl]amino}methyl)pyridin-2-yl]-N-methylmethane-sulfonamide (27) | 0.00138 |

TABLE 1-continued

IC50 values against FAK kinase.

| Ex. | Structure | Compound Name | FAK IC50, μM |
|---|---|---|---|
| 28 | 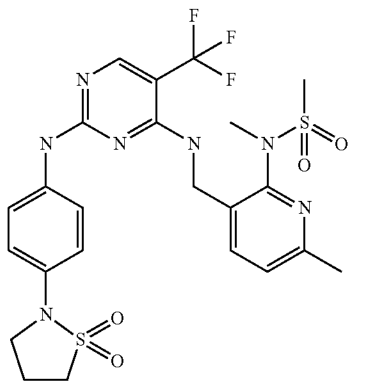 [SMILES: Cc1ccc(CNc2nc(Nc3ccc(N4CCCS4(=O)=O)cc3)ncc2C(F)(F)F)c(N(C)S(C)(=O)=O)n1] | N-[3-({[2-{[4-(1,1-dioxidoisothiazolidin-2-yl)phenyl]amino}-5-(trifluoromethyl)pyrimidin-4-yl]amino}methyl)-6-methylpyridin-2-yl]-N-methylmethanesulfonamide (28) | 0.00201 |
| 29 | 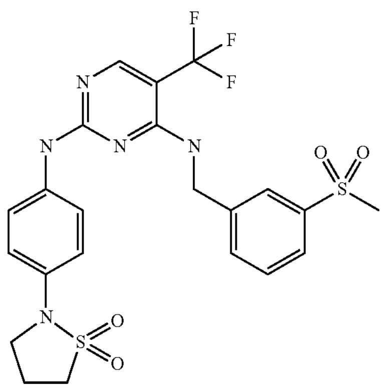 [SMILES: CS(=O)(=O)c1cccc(CNc2nc(Nc3ccc(N4CCCS4(=O)=O)cc3)ncc2C(F)(F)F)c1] | N~2~-[4-(1,1-dioxidoisothiazolidin-2-yl)phenyl]-N~4~-[3-(methylsulfonyl)benzyl]-5-(trifluoromethyl)pyrimidine-2,4-diamine (29) | 0.00209 |
| 30 | 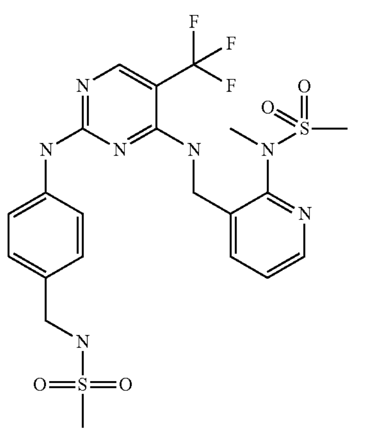 [SMILES: CN(c1ncccc1CNc1nc(Nc2ccc(CNS(C)(=O)=O)cc2)ncc1C(F)(F)F)S(C)(=O)=O] | N-methyl-N-{3-[({2-[(4-{[(methylsulfonyl)amino]methyl}phenyl)amino]-5-(trifluoromethyl)pyrimidin-4-yl}amino)methyl]pyridin-2-yl}methanesulfonamide (30) | 0.00072 |
| 31 | 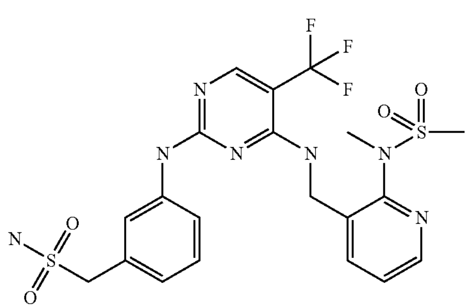 [SMILES: CN(c1ncccc1CNc1nc(Nc2cccc(CS(N)(=O)=O)c2)ncc1C(F)(F)F)S(C)(=O)=O] | N-[3-({[2-({3-[(aminosulfonyl)methyl]phenyl}amino)-5-(trifluoromethyl)pyrimidin-4-yl]amino}methyl)pyridin-2-yl]-N-methylmethane-sulfonamide (31) | 0.00222 |

TABLE 1-continued

IC50 values against FAK kinase.

| Ex. | Structure | Compound Name | FAK IC50, μM |
|---|---|---|---|
| 32 | 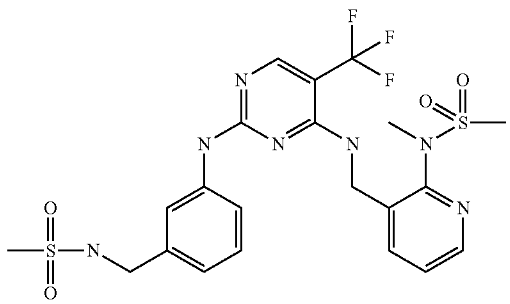 | N-methyl-N-{3-[({2-[(3-{[(methylsulfonyl)amino]methyl}phenyl)amino]-5-(trifluoromethyl)pyrimidin-4-yl}amino)methyl]pyridin-2-yl}methanesulfonamide (32) | |
| 33 | 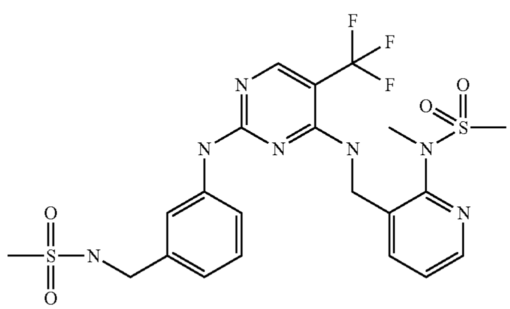 | N-methyl-N-{3-[({2-[(3-{[(methylsulfonyl)amino]methyl}phenyl)amino]-5-(trifluoromethyl)pyrimidin-4-yl}amino)methyl]pyridin-2-yl}methanesulfonamide (33), hydrochloride salt | 0.00133 |
| 34 | 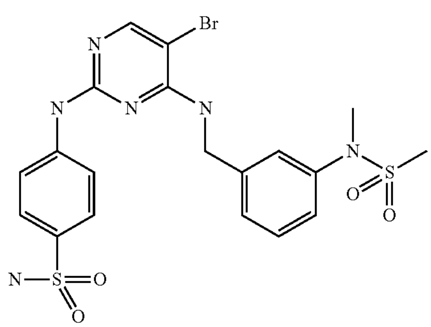 [SMILES: CN(c1cccc(CNc2nc(Nc3ccc(S(N)(=O)=O)cc3)ncc2Br)c1)S(C)(=O)=O] | 4-{[5-bromo-4-({3-[methyl(methylsulfonyl)amino]benzyl}amino)pyrimidin-2-yl]amino}benzenesulfonamide (34) | 0.0156 |
| 35 | 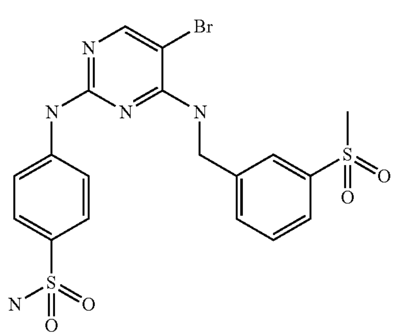 [SMILES: CS(=O)(=O)c1cccc(CNc2nc(Nc3ccc(S(N)(=O)=O)cc3)ncc2Br)c1] | 4-[(5-bromo-4-{[3-(methylsulfonyl)benzyl]amino}pyrimidin-2-yl)amino]benzene-sulfonamide (35) | 0.0176 |

TABLE 1-continued

IC50 values against FAK kinase.

| Ex. | Structure | Compound Name | FAK IC50, μM |
|---|---|---|---|
| 36 | 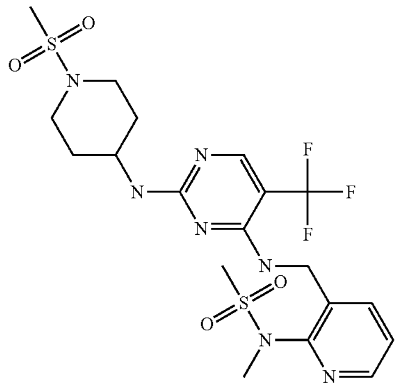 [SMILES: CN(c1ncccc1CNc1nc(NC2CCN(S(C)(=O)=O)CC2)ncc1C(F)(F)F)S(C)(=O)=O] | N-methyl-N-[3-({[2-{[1-(methylsulfonyl)piperidin-4-yl]amino}-5-(trifluoromethyl)pyrimidin-4-yl]amino}methyl)pyridin-2-yl]methanesulfonamide (36) | 0.188 |
| 37 | 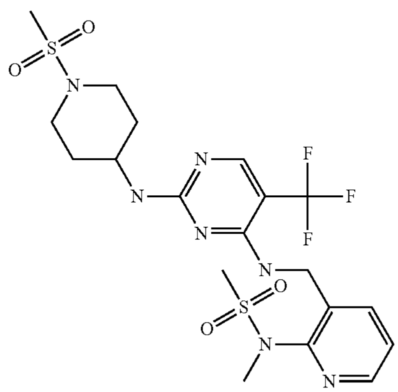 [SMILES: CN(c1ncccc1CNc1nc(NC2CCN(S(C)(=O)=O)CC2)ncc1C(F)(F)F)S(C)(=O)=O] | N-methyl-N-[3-({[2-{[1-(methylsulfonyl)piperidin-4-yl]amino}-5-(trifluoromethyl)pyrimidin-4-yl]amino}methyl)pyridin-2-yl]methanesulfonarnide (37), trifluoroacetic acid salt | |
| 38 | 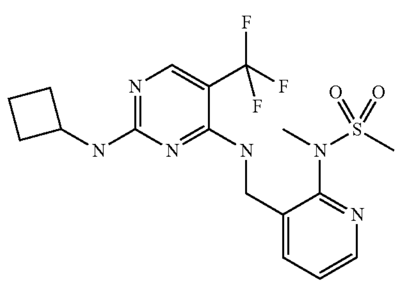 [SMILES: CN(c1ncccc1CNc1nc(NC2CCC2)ncc1C(F)(F)F)S(C)(=O)=O] | N-[3-({[2-(cyclobutylamino)-5-(trifluoromethyl)pyrimidin-4-yl]amino}methyl)pyridin-2-yl]-N-methylmethane-sulfonamide (38) | 0.497 |
| 39 | ABS | N-[3-({[2-{[(3R)-1-acetylpyrrolidin-3-yl]amino}-5-(trifluoromethyl)pyrimidin-4-yl]amino}methyl)pyridin-2-yl]-N-methylmethane-sulfonamide (39) | 1 |

TABLE 1-continued

IC50 values against FAK kinase.

| Ex. | Structure | Compound Name | FAK IC50, µM |
|---|---|---|---|
| 40 | 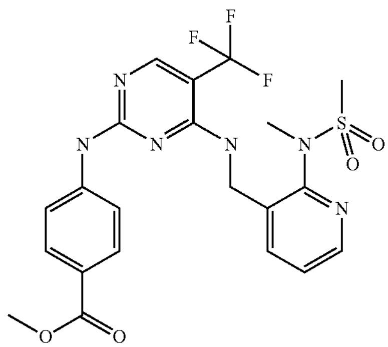 [SMILES: COC(=O)c1ccc(Nc2ncc(C(F)(F)F)c(NCc3cccnc3N(C)S(C)(=O)=O)n2)cc1] | methyl 4-({4-[({2-[methyl(methylsulfonyl)amino]pyridin-3-yl}methyl)amino]-5-(trifluoromethyl)pyrimidin-2-yl}amino)benzoate (40) | 0.00059 |
| 41 | 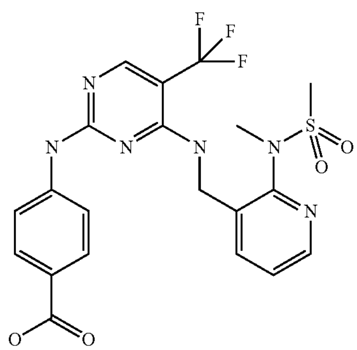 [SMILES: CN(c1ncccc1CNc1nc(Nc2ccc(C(=O)O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzoic acid (41) | |
| 42 | 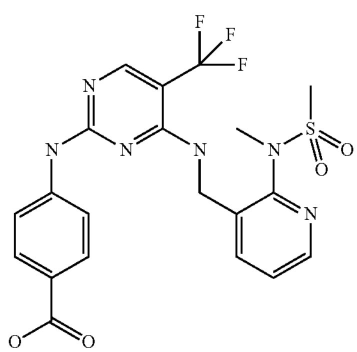 [SMILES: CN(c1ncccc1CNc1nc(Nc2ccc(C(=O)O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzoic acid (42), sodium salt | 0.188 |
| 43 | 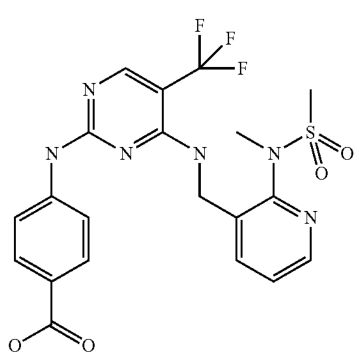 [SMILES: CN(c1ncccc1CNc1nc(Nc2ccc(C(=O)O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)benzoic acid (43), trifluoroacetic acid salt | 0.0006 |

TABLE 1-continued

IC50 values against FAK kinase.

| Ex. | Structure | Compound Name | FAK IC50, μM |
|---|---|---|---|
| 44 | 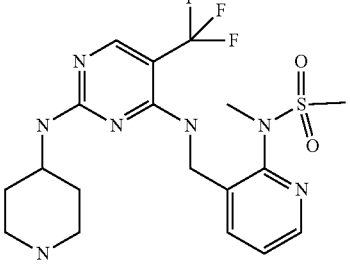 | N-methyl-N-[3-({[2-(piperidin-4-ylamino)-5-(trifluoromethyl)pyrimidin-4-yl]amino}methyl)pyridin-2-yl]methanesulfonamide (44) | 0.188 |
| 45 | 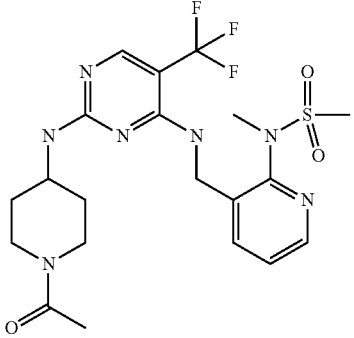 [SMILES: CC(=O)N1CCC(Nc2ncc(C(F)(F)F)c(NCc3cccnc3N(C)S(C)(=O)=O)n2)CC1] | N-{3-[({2-[(1-acetylpiperidin-4-yl)amino]-5-(trifluoromethyl)pyrimidin-4-yl}amino)methyl]pyridin-2-yl}-N-methylmethane-sulfonamide (45) | 0.188 |
| 46 | 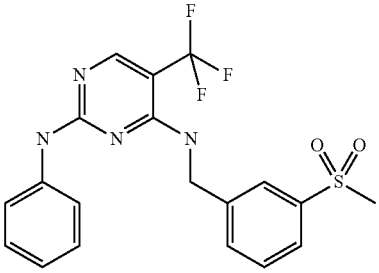 [SMILES: CS(=O)(=O)c1cccc(CNc2nc(Nc3ccccc3)ncc2C(F)(F)F)c1] | N-4-[3-(methylsulfonyl)benzyl]-N-2-phenyl-5-(trifluoromethyl)pyrimidine-2,4-diamine (46) | 0.00102 |
| 47 | 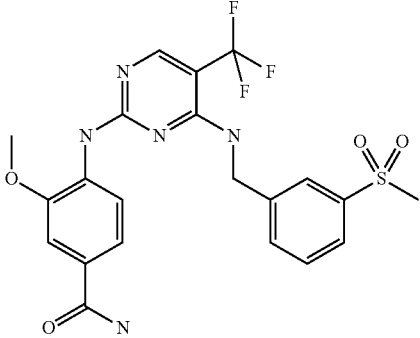 [SMILES: COc1cc(C(N)=O)ccc1Nc1ncc(C(F)(F)F)c(NCc2cccc(S(C)(=O)=O)c2)n1] | 3-methoxy-4-{[4-{[3-(methylsulfonyl)benzyl]amino}-5-(trifluoromethyl)pyrimidin-2-yl]amino}benzamide (47) | 0.00059 |

TABLE 1-continued

IC50 values against FAK kinase.

| Ex. | Structure | Compound Name | FAK IC50, μM |
|---|---|---|---|
| 48 | 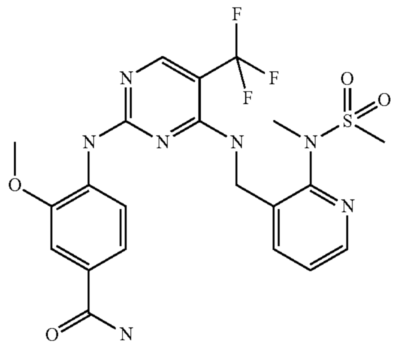 [SMILES: COc1cc(C(N)=O)ccc1Nc1ncc(C(F)(F)F)c(NCc2cccnc2N(C)S(C)(=O)=O)n1] | 3-methoxy-4-({4-[({2-[methyl(methylsulfonyl)amino]pyridin-3-yl}methyl)amino]-5-(trifluoromethyl)pyrimidin-2-yl}amino)benzamide (48) | 0.00059 |
| 49 | 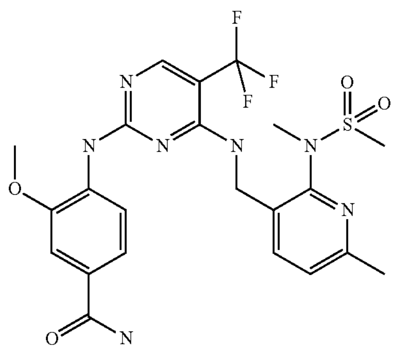 [SMILES: COc1cc(C(N)=O)ccc1Nc1ncc(C(F)(F)F)c(NCc2ccc(C)nc2N(C)S(C)(=O)=O)n1] | 3-methoxy-4-({4-[({6-methyl-2-[methyl(methylsulfonyl)-amino]pyridin-3-yl}methyl)amino]-5-(trifluoromethyl)pyrimidin-2-yl}amino)benzamide (49) | 0.00059 |
| 50 | 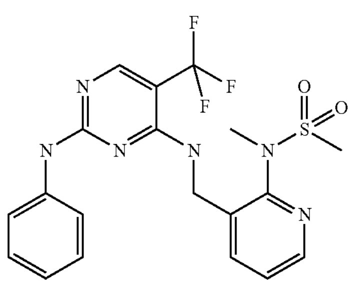 [SMILES: CN(c1ncccc1CNc1nc(Nc2ccccc2)ncc1C(F)(F)F)S(C)(=O)=O] | N-[3-({[2-anilino-5-(trifluoromethyl)pyrimidin-4-yl]amino}methyl)pyridin-2-yl]-N-methylmethane-sulfonamide (50) | 0.00059 |
| 51 | 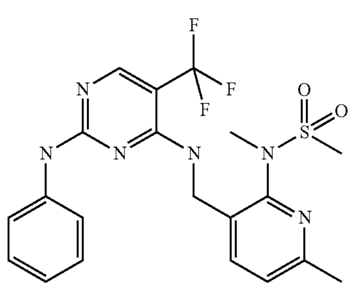 [SMILES: Cc1ccc(CNc2nc(Nc3ccccc3)ncc2C(F)(F)F)c(N(C)S(C)(=O)=O)n1] | N-[3-({[2-anilino-5-(trifluoromethyl)pyrimidin-4-yl]amino}methyl)-6-methylpyridin-2-yl]-N-methylmethanesulfonamide (51) | 0.00059 |

TABLE 1-continued

IC50 values against FAK kinase.

| Ex. | Structure | Compound Name | FAK IC50, μM |
|---|---|---|---|
| 52 | 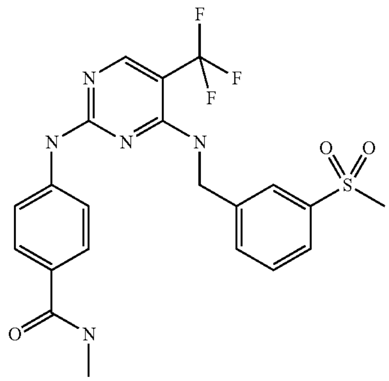 [SMILES: CNC(=O)c1ccc(Nc2ncc(C(F)(F)F)c(NCc3cccc(S(C)(=O)=O)c3)n2)cc1] | N-methyl-4-{[4-{[3-(methylsulfonyl)benzyl]amino}-5-(trifluoromethyl)pyrimidin-2-yl]amino}benzamide (52) | 0.00195 |
| 53 | 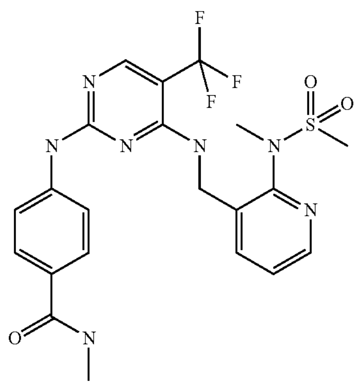 [SMILES: CNC(=O)c1ccc(Nc2ncc(C(F)(F)F)c(NCc3cccnc3N(C)S(C)(=O)=O)n2)cc1] | N-methyl-4-({4-[({2-[methyl(methylsulfonyl)amino]pyridin-3-yl}methyl)amino]-5-(trifluoromethyl)pyrimidin-2-yl}amino)benzamide (53) | 0.00059 |
| 54 | 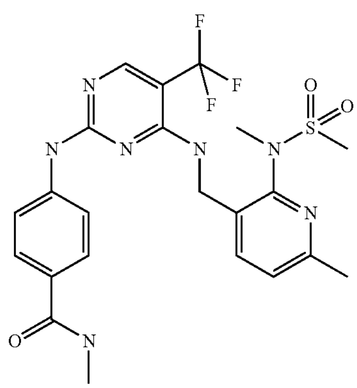 [SMILES: CNC(=O)c1ccc(Nc2ncc(C(F)(F)F)c(NCc3ccc(C)nc3N(C)S(C)(=O)=O)n2)cc1] | N-methyl-4-({4-[({6-methyl-2-[methyl(methylsulfonyl)amino]pyridin-3-yl}methyl)amino]-5-(trifluoromethyl)pyrimidin-2-yl}amino)benzamide (54) | 0.00059 |
| 55 | 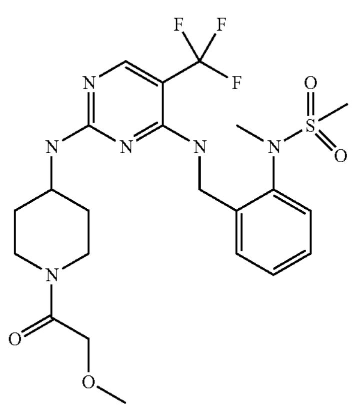 [SMILES: COCC(=O)N1CCC(Nc2ncc(C(F)(F)F)c(NCc3ccccc3N(C)S(C)(=O)=O)n2)CC1] | N-[3-({[2-{[1-(methoxyacetyl)piperidin-4-yl]amino}-5-(trifluoromethyl)pyrimidin-4-yl]amino}methyl)pyridin-2-yl]-N-methylmethane-sulfonamide (55) | 0.188 |

TABLE 1-continued

IC50 values against FAK kinase.

| Ex. | Structure | Compound Name | FAK IC50, μM |
|---|---|---|---|
| 56 | 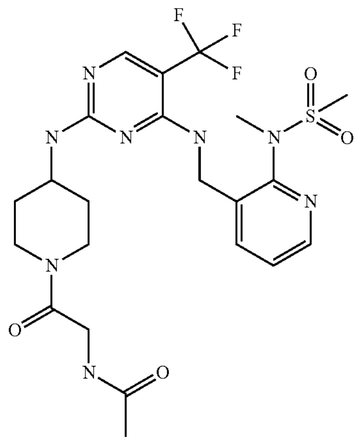 [SMILES: CC(=O)NCC(=O)N1CCC(Nc2ncc(C(F)(F)F)c(NCc3cccnc3N(C)S(C)(=O)=O)n2)CC1] | N-{2-[4-({4-[({2-[methyl(methylsulfonyl)amino]pyridin-3-yl}methyl)amino]-5-(trifluoromethyl)pyrimidin-2-yl}amino)piperidin-1-yl]-2-oxoethyl}acetamide (56) | 0.188 |
| 57 | 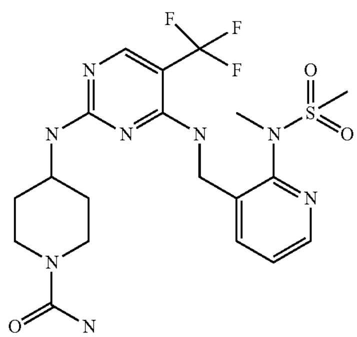 [SMILES: CN(c1ncccc1CNc1nc(NC2CCN(C(N)=O)CC2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)piperidine-1-carboxamide (57) | 0.188 |
| 58 | 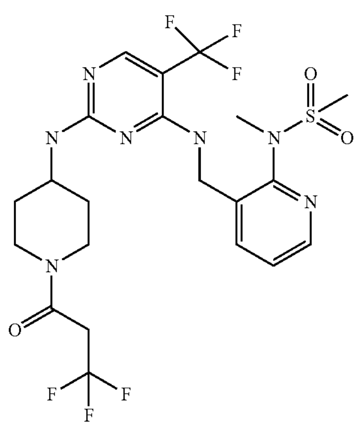 [SMILES: CN(c1ncccc1CNc1nc(NC2CCN(C(=O)CC(F)(F)F)CC2)ncc1C(F)(F)F)S(C)(=O)=O] | N-methyl-N-[3-({[5-(trifluoromethyl)-2-{[1-(3,3,3-trifluoropropanoyl)piperidin-4-yl]amino}pyrimidin-4-yl]amino}methyl)pyridin-2-yl]methanesulfonamide (58) | 0.165 |
| 59 | 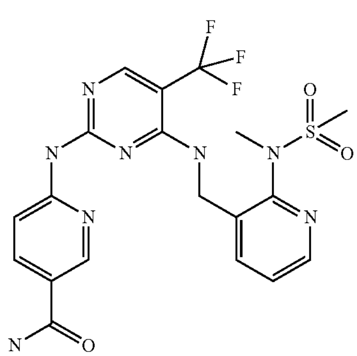 [SMILES: CN(c1ncccc1CNc1nc(Nc2ccc(C(N)=O)cn2)ncc1C(F)(F)F)S(C)(=O)=O] | 6-({4-[({2-[methyl(methylsulfonyl)amino]pyridin-3-yl}methyl)amino]-5-(trifluoromethyl)pyrimidin-2-yl}amino)nicotinamide (59) | 0.00893 |

TABLE 1-continued

IC50 values against FAK kinase.

| Ex. | Structure | Compound Name | FAK IC50, μM |
|---|---|---|---|
| 60 | 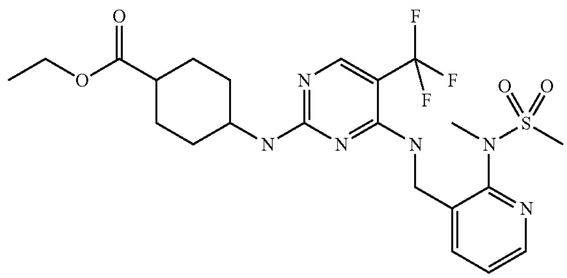 [SMILES: CCOC(=O)C1CCC(Nc2ncc(C(F)(F)F)c(NCc3cccnc3N(C)S(C)(=O)=O)n2)CC1] | ethyl cis-4-({4-[({2-[methyl(methylsulfonyl)amino]pyridin-3-yl}methyl)amino]-5-(trifluoromethyl)pyrimidin-2-yl}amino)cyclohexanecarboxylate (60) | 0.188 |
| 61 | 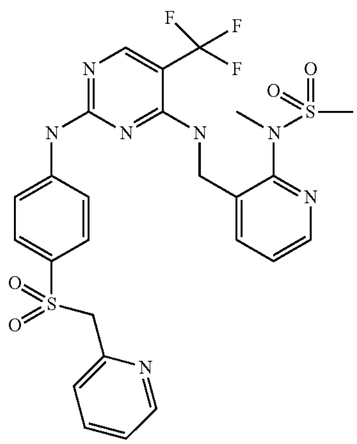 [SMILES: CN(c1ncccc1CNc1nc(Nc2ccc(S(=O)(=O)Cc3ccccn3)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)-N-pyridin-2-ylbenzenesulfonamide (61) | 0.00102 |
| 62 | 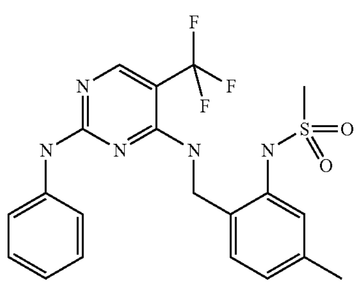 | N-[2-({[2-anilino-5-(trifluoromethyl)pyrimidin-4-yl]amino}methyl)-5-methylphenyl]methanesulfonamide (62) | 0.0103 |
| 63 | 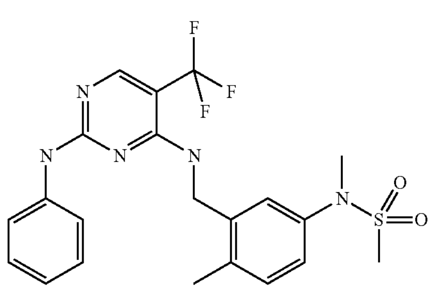 [SMILES: Cc1ccc(N(C)S(C)(=O)=O)cc1CNc1nc(Nc2ccccc2)ncc1C(F)(F)F] | N-[3-({[2-anilino-5-(trifluoromethyl)pyrimidin-4-yl]amino}methyl)-4-methylphenyl]-N-methylmethanesulfonamide (63) | 0.0006 |

TABLE 1-continued

IC50 values against FAK kinase.

| Ex. | Structure | Compound Name | FAK IC50, μM |
|---|---|---|---|
| 64 | 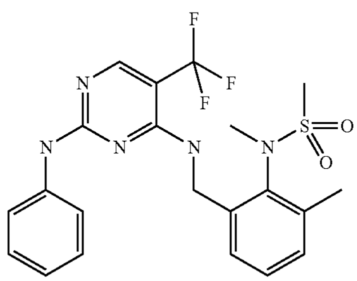 [SMILES: Cc1cccc(CNc2nc(Nc3ccccc3)ncc2C(F)(F)F)c1N(C)S(C)(=O)=O] | N-[2-({[2-anilino-5-(trifluoromethyl)pyrimidin-4-yl]amino}methyl)-6-methylphenyl]-N-methylmethanesulfonamide (64) | 0.0006 |
| 65 | 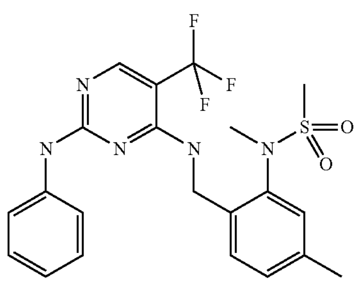 [SMILES: Cc1ccc(CNc2nc(Nc3ccccc3)ncc2C(F)(F)F)c(N(C)S(C)(=O)=O)c1] | N-[2-({[2-anilino-5-(trifluoromethyl)pyrimidin-4-yl]amino}methyl)-5-methylphenyl]-N-methylmethanesulfonamide (65) | 0.0006 |
| 66 | 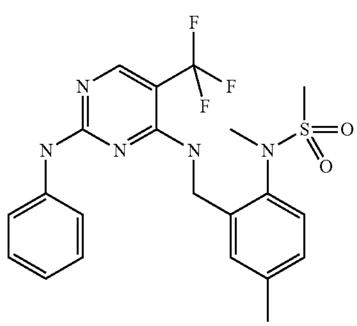 [SMILES: Cc1ccc(N(C)S(C)(=O)=O)c(CNc2nc(Nc3ccccc3)ncc2C(F)(F)F)c1] | N-[2-({[2-anilino-5-(trifluoromethyl)pyrimidin-4-yl]amino}methyl)-4-methylphenyl]-N-methylmethanesulfonamide (66) | 0.0006 |
| 67 | 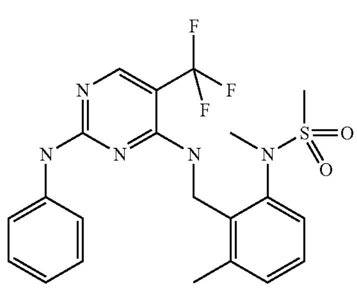 [SMILES: Cc1cccc(N(C)S(C)(=O)=O)c1CNc1nc(Nc2ccccc2)ncc1C(F)(F)F] | N-[2-({[2-anilino-5-(trifluoromethyl)pyrimidin-4-yl]amino}methyl)-3-methylphenyl]-N-methylmethanesulfonamide (67) | 0.0006 |
| 68 | 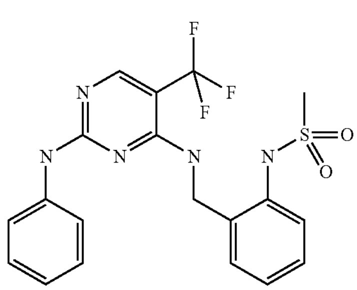 [SMILES: CS(=O)(=O)Nc1ccccc1CNc1nc(Nc2ccccc2)ncc1C(F)(F)F] | N-[2-({[2-anilino-5-(trifluoromethyl)pyrimidin-4-yl]amino}methyl)phenyl]methanesulfonamide (68) | 0.00059 |

TABLE 1-continued

IC50 values against FAK kinase.

| Ex. | Structure | Compound Name | FAK IC50, μM |
|---|---|---|---|
| 69 | 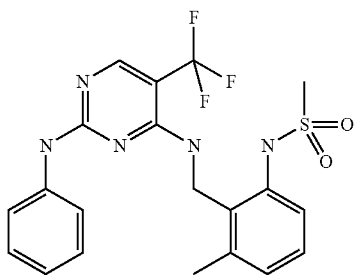 [SMILES: Cc1cccc(NS(C)(=O)=O)c1CNc1nc(Nc2ccccc2)ncc1C(F)(F)F] | N-[2-({[2-anilino-5-(trifluoromethyl)pyrimidin-4-yl]amino}methyl)-3-methylphenyl]methanesulfonamide (69) | 0.0006 |
| 70 | 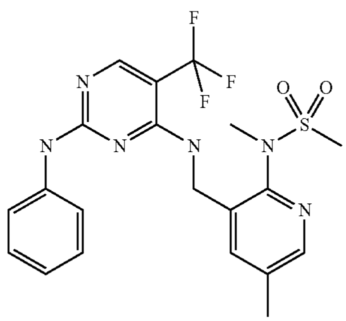 [SMILES: Cc1cnc(N(C)S(C)(=O)=O)c(CNc2nc(Nc3ccccc3)ncc2C(F)(F)F)c1] | N-[3-({[2-anilino-5-(trifluoromethyl)pyrimidin-4-yl]amino}methyl)-5-methylpyridin-2-yl]-N-methylmethanesulfonamide (70) | 0.0006 |
| 71 | 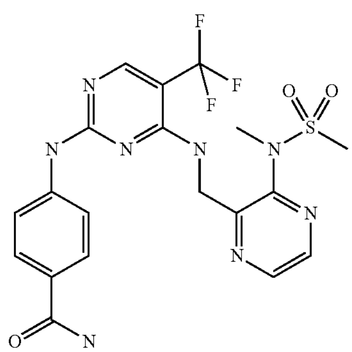 [SMILES: CN(c1nccnc1CNc1nc(Nc2ccc(C(N)=O)cc2)ncc1C(F)(F)F)S(C)(=O)=O] | 4-({4-[({3-[methyl(methylsulfonyl)amino]pyrazin-2-yl}methyl)amino]-5-(trifluoromethyl)pyrimidin-2-yl}amino)benzamide (71) | 0.0006 |
| 72 | 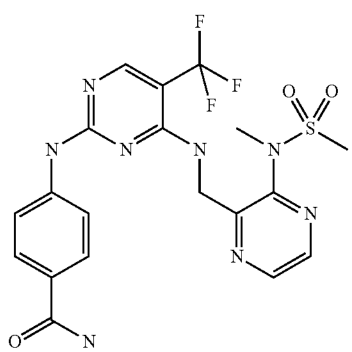 [SMILES: CN(c1nccnc1CNc1nc(Nc2ccc(C(N)=O)cc2)ncc1C(F)(F)F)S(C)(=O)=O] | 4-({4-[({3-[methyl(methylsulfonyl)amino]pyrazin-2-yl}methyl)amino]-5-(trifluoromethyl)pyrimidin-2-yl}amino)benzamide (72), hydrochloride salt | |

TABLE 1-continued

IC50 values against FAK kinase.

| Ex. | Structure | Compound Name | FAK IC50, μM |
|---|---|---|---|
| 73 | 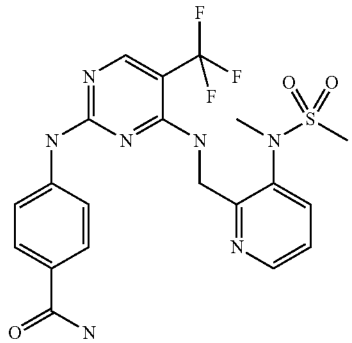 | 4-({4-[({3-[methyl(methylsulfonyl)amino]pyridin-2-yl}methyl)amino]-5-(trifluoromethyl)pyrimidin-2-yl}amino)benzamide (73) | 0.0006 |
| 74 | 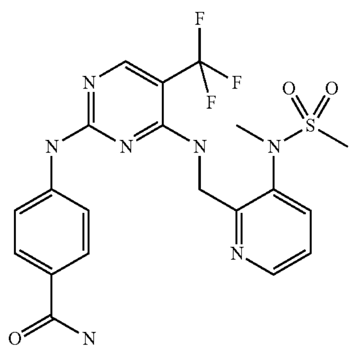 [SMILES: CN(c1cccnc1CNc1nc(Nc2ccc(C(N)=O)cc2)ncc1C(F)(F)F)S(C)(=O)=O] | 4-({4-[({3-[methyl(methylsulfonyl)amino]pyridin-2-yl}methyl)amino]-5-(trifluoromethyl)pyrimidin-2-yl}amino)benzamide (74), hydrochloride salt | |
| 75 | 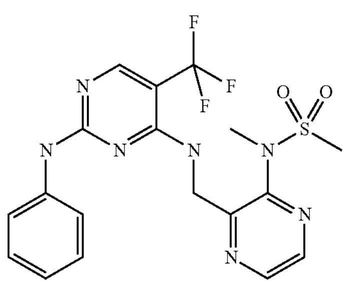 [SMILES: CN(c1nccnc1CNc1nc(Nc2ccccc2)ncc1C(F)(F)F)S(C)(=O)=O] | N-[3-({[2-anilino-5-(trifluoromethyl)pyrimidin-4-yl]amino}methyl)pyrazin-2-yl]-N-methylmethanesulfonamide (75) | 0.0006 |
| 76 | 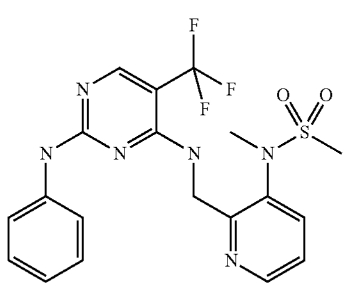 [SMILES: CN(c1cccnc1CNc1nc(Nc2ccccc2)ncc1C(F)(F)F)S(C)(=O)=O] | N-[2-({[2-anilino-5-(trifluoromethyl)pyrimidin-4-yl]amino}methyl)pyridin-3-yl]-N-methylmethanesulfonamide (76) | 0.093 |

TABLE 1-continued

IC50 values against FAK kinase.

| Ex. | Structure | Compound Name | FAK IC50, μM |
|---|---|---|---|
| 77 | 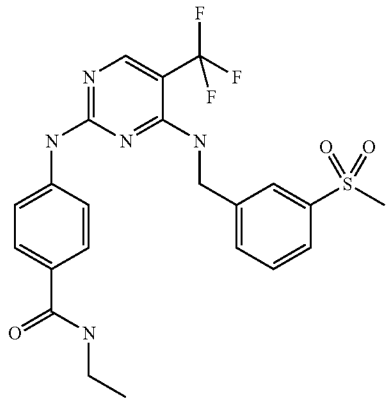 [SMILES: CCNC(=O)c1ccc(Nc2ncc(C(F)(F)F)c(NCc3cccc(S(C)(=O)=O)c3)n2)cc1] | N-ethyl-4-{[4-{[3-(methylsulfonyl)benzyl]amino}-5-(trifluoromethyl)pyrimidin-2-yl]amino}benzamide (77) | 0.0006 |
| 78 | 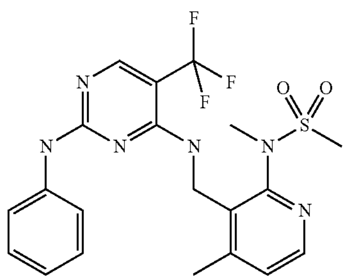 [SMILES: Cc1ccnc(N(C)S(C)(=O)=O)c1CNc1nc(Nc2ccccc2)ncc1C(F)(F)F] | N-[3-({[2-anilino-5-(trifluoromethyl)pyrimidin-4-yl]amino}methyl)-4-methylpyridin-2-yl]-N-methylmethanesulfonamide (78) | 0.0006 |
| 79 | 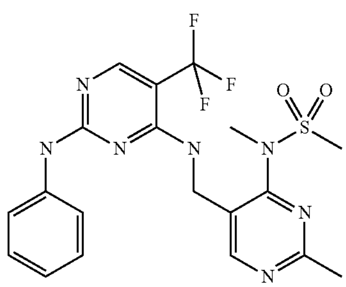 [SMILES: Cc1ncc(CNc2nc(Nc3ccccc3)ncc2C(F)(F)F)c(N(C)S(C)(=O)=O)n1] | N-[5-({[2-anilino-5-(trifluoromethyl)pyrimidin-4-yl]amino}methyl)-2-methylpyrimidin-4-yl]-N-methylmethanesulfonamide (79) | 0.00262 |
| 80 | 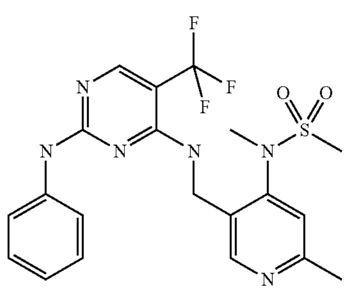 [SMILES: Cc1cc(N(C)S(C)(=O)=O)c(CNc2nc(Nc3ccccc3)ncc2C(F)(F)F)cn1] | N-[5-({[2-anilino-5-(trifluoromethyl)pyrimidin-4-yl]amino}methyl)-2-methylpyridin-4-yl]-N-methylmethanesulfonamide (80) | 0.00059 |
| 81 | 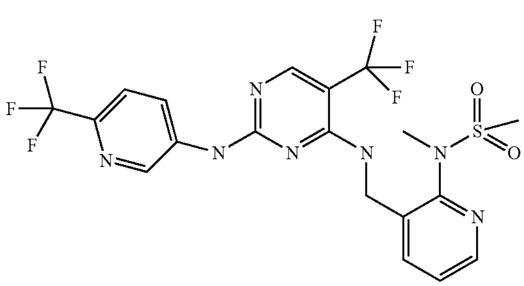 [SMILES: CN(c1ncccc1CNc1nc(Nc2ccc(C(F)(F)F)nc2)ncc1C(F)(F)F)S(C)(=O)=O] | N-methyl-N-[3-({[5-(trifluoromethyl)-2-{[6-(trifluoromethyl)pyridin-3-yl]amino}pyrimidin-4-yl]amino}methyl)pyridin-2-yl]methanesulfonamide (81) | 0.0158 |

TABLE 1-continued

IC50 values against FAK kinase.

| Ex. | Structure | Compound Name | FAK IC50, μM |
|---|---|---|---|
| 82 | 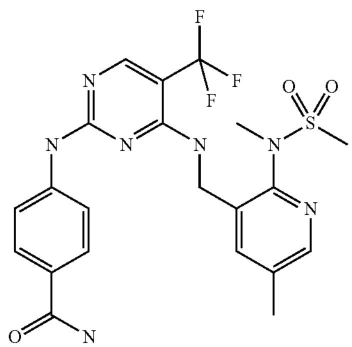 [SMILES: Cc1cnc(N(C)S(C)(=O)=O)c(CNc2nc(Nc3ccc(C(N)=O)cc3)ncc2C(F)(F)F)c1] | 4-({4-[({5-methyl-2-[methyl(methylsulfonyl)amino]pyridin-3-yl}methyl)amino]-5-(trifluoromethyl)pyrimidin-2-yl}amino)benzamide (82) | 0.0006 |
| 83 | 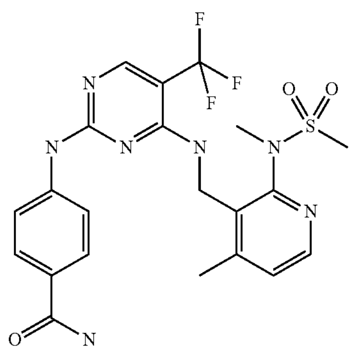 [SMILES: Cc1ccnc(N(C)S(C)(=O)=O)c1CNc1nc(Nc2ccc(C(N)=O)cc2)ncc1C(F)(F)F] | 4-({4-[({4-methyl-2-[methyl(methylsulfonyl)amino]pyridin-3-yl}methyl)amino]-5-(trifluoromethyl)pyrimidin-2-yl}amino)benzamide (83) | 0.0006 |
| 84 | 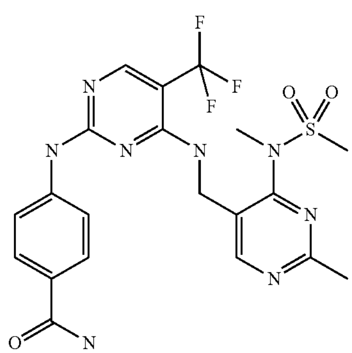 [SMILES: Cc1ncc(CNc2nc(Nc3ccc(C(N)=O)cc3)ncc2C(F)(F)F)c(N(C)S(C)(=O)=O)n1] | 4-({4-[({2-methyl-4-[methyl(methylsulfonyl)amino]pyrimidin-5-yl}methyl)amino]-5-(trifluoromethyl)pyrimidin-2-yl}amino)benzamide (84) | 0.00171 |
| 85 | 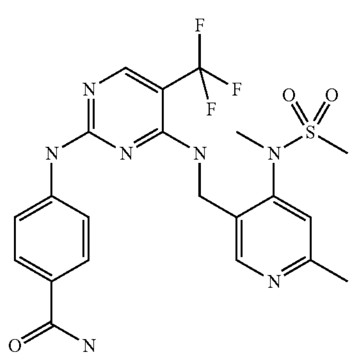 [SMILES: Cc1cc(N(C)S(C)(=O)=O)c(CNc2nc(Nc3ccc(C(N)=O)cc3)ncc2C(F)(F)F)cn1] | 4-({4-[({6-methyl-4-[methyl(methylsulfonyl)amino]pyridin-3-yl}methyl)amino]-5-(trifluoromethyl)pyrimidin-2-yl}amino)benzamide (85) | 0.00084 |

TABLE 1-continued

IC50 values against FAK kinase.

| Ex. | Structure | Compound Name | FAK IC50, µM |
|---|---|---|---|
| 86 | 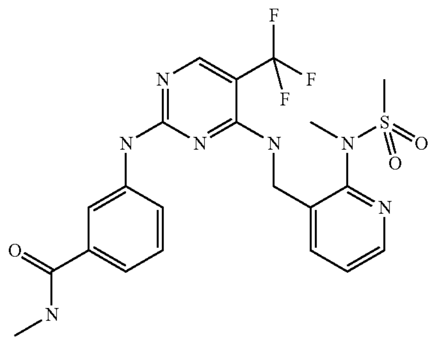 [SMILES: CNC(=O)c1cccc(Nc2ncc(C(F)(F)F)c(NCc3cccnc3N(C)S(C)(=O)=O)n2)c1] | N-methyl-3-({4-[({2-[methyl(methylsulfonyl)amino]pyridin-3-yl}methyl)amino]-5-(trifluoromethyl)pyrimidin-2-yl}amino)benzamide (86) | 0.00161 |
| 87 | 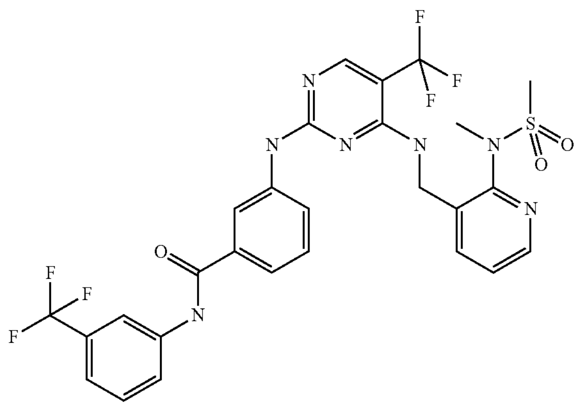 [SMILES: CN(c1ncccc1CNc1nc(Nc2cccc(C(=O)Nc3cccc(C(F)(F)F)c3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[3-(trifluoromethyl)phenyl]benzamide (87) | |
| 88 | 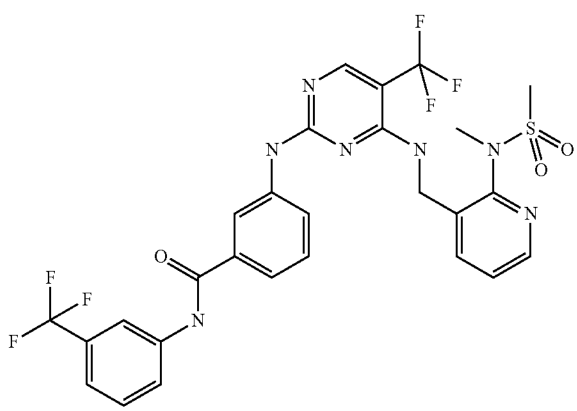 [SMILES: CN(c1ncccc1CNc1nc(Nc2cccc(C(=O)Nc3cccc(C(F)(F)F)c3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[3-(trifluoromethyl)phenyl]benzamide (88), hydrochloride salt | 0.0215 |
| 89 | 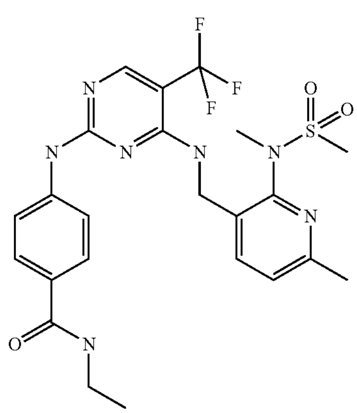 [SMILES: CCNC(=O)c1ccc(Nc2ncc(C(F)(F)F)c(NCc3ccc(C)nc3N(C)S(C)(=O)=O)n2)cc1] | N-ethyl-4-({4-[({6-methyl-2-[methyl(methylsulfonyl)amino]pyridin-3-yl}methyl)amino]-5-(trifluoromethyl)pyrimidin-2-yl}amino)benzamide (89) | 0.0006 |

TABLE 1-continued

IC50 values against FAK kinase.

| Ex. | Structure | Compound Name | FAK IC50, μM |
|---|---|---|---|
| 90 | 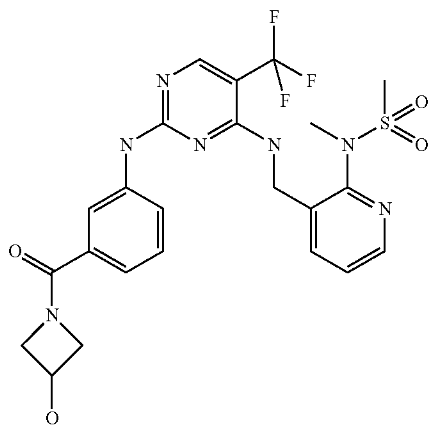 [SMILES: CN(c1ncccc1CNc1nc(Nc2cccc(C(=O)N3CC(O)C3)c2)ncc1C(F)(F)F)S(C)(=O)=O] | N-[3-({[2-({3-[(3-hydroxyazetidin-1-yl)carbonyl]phenyl}amino)-5-(trifluoromethyl)pyrimidin-4-yl]amino}methyl)pyridin-2-yl]-N-methylmethane-sulfonamide (90) | 0.00072 |
| 91 | 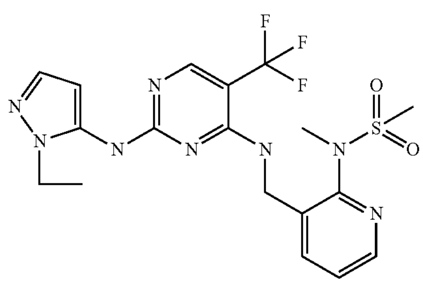 [SMILES: CCn1nccc1Nc1ncc(C(F)(F)F)c(NCc2cccnc2N(C)S(C)(=O)=O)n1] | N-{3-[({2-[(1-ethyl-1H-pyrazol-5-yl)amino]-5-(trifluoromethyl)pyrimidin-4-yl}amino)methyl]pyridin-2-yl}-N-methylmethane-sulfonamide (91) | 0.188 |
| 92 | 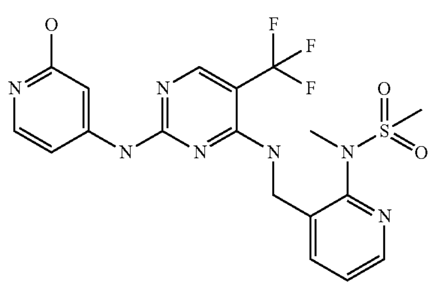 [SMILES: CN(c1ncccc1CNc1nc(Nc2ccnc(O)c2)ncc1C(F)(F)F)S(C)(=O)=O] | N-{3-[({2-[(2-chloropyridin-4-yl)amino]-5-(trifluoromethyl)pyrimidin-4-yl}amino)methyl]pyridin-2-yl}-N-methylmethane-sulfonamide (92) | 0.00192 |
| 93 | 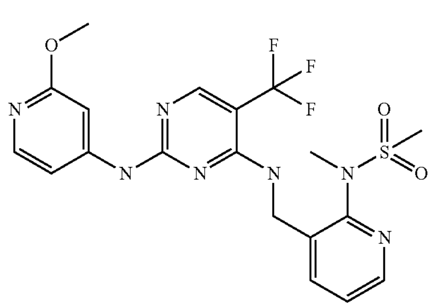 [SMILES: COc1cc(Nc2ncc(C(F)(F)F)c(NCc3cccnc3N(C)S(C)(=O)=O)n2)ccn1] | N-{3-[({2-[(2-methoxypyridin-4-yl)amino]-5-(trifluoromethyl)pyrimidin-4-yl}amino)methyl]pyridin-2-yl}-N-methylmethane-sulfonamide (93) | 0.0006 |

TABLE 1-continued

IC50 values against FAK kinase.

| Ex. | Structure | Compound Name | FAK IC50, µM |
|---|---|---|---|
| 94 | 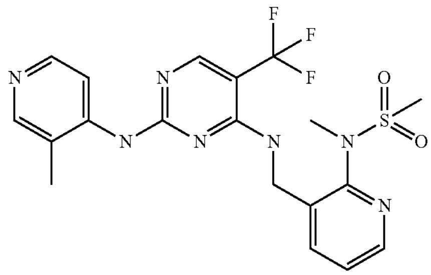 [SMILES: Cc1cnccc1Nc1ncc(C(F)(F)F)c(NCc2cccnc2N(C)S(C)(=O)=O)n1] | N-methyl-N-{3-[({2-[(3-methylpyridin-4-yl)amino]-5-(trifluoromethyl)pyrimidin-4-yl}amino)methyl]pyridin-2-yl}methanesulfonamide (94) | 0.00801 |
| 95 | 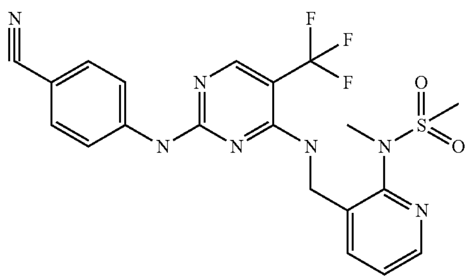 [SMILES: CN(c1ncccc1CNc1nc(Nc2ccc(C#N)cc2)ncc1C(F)(F)F)S(C)(=O)=O] | N-{3-[({2-[(4-cyanophenyl)amino]-5-(trifluoromethyl)pyrimidin-4-yl}amino)methyl]pyridin-2-yl}-N-methylmethanesulfonamide (95) | 0.0006 |
| 96 | 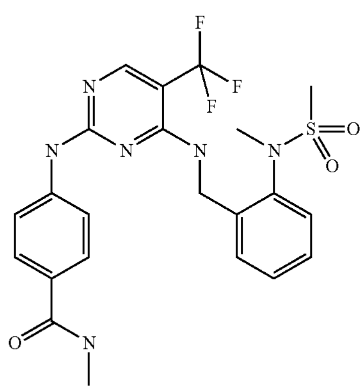 [SMILES: CNC(=O)c1ccc(Nc2ncc(C(F)(F)F)c(NCc3ccccc3N(C)S(C)(=O)=O)n2)cc1] | N-methyl-4-{[4-({2-[methyl(methylsulfonyl)amino]benzyl}amino)-5-(trifluoromethyl)pyrimidin-2-yl]amino}benzamide (96) | 0.00059 |
| 97 | 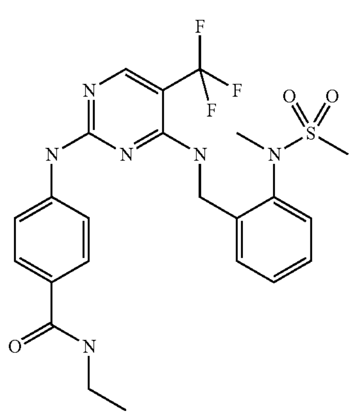 [SMILES: CCNC(=O)c1ccc(Nc2ncc(C(F)(F)F)c(NCc3ccccc3N(C)S(C)(=O)=O)n2)cc1] | N-ethyl-4-({4-[({3-[methyl(methylsulfonyl)amino]pyridin-2-yl}methyl)amino]-5-(trifluoromethyl)pyrimidin-2-yl}amino)benzamide (97) | 0.00059 |

TABLE 1-continued

IC50 values against FAK kinase.

| Ex. | Structure | Compound Name | FAK IC50, μM |
|---|---|---|---|
| 98 | 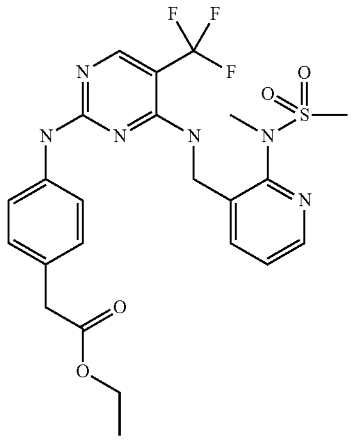 [SMILES: CCOC(=O)Cc1ccc(Nc2ncc(C(F)(F)F)c(NCc3cccnc3N(C)S(C)(=O)=O)n2)cc1] | ethyl [4-({4-[({2-[methyl(methylsulfonyl)amino]pyridin-3-yl}methyl)amino]-5-(trifluoromethyl)pyrimidin-2-yl}amino)phenyl]acetate (98) | 0.00059 |
| 99 | 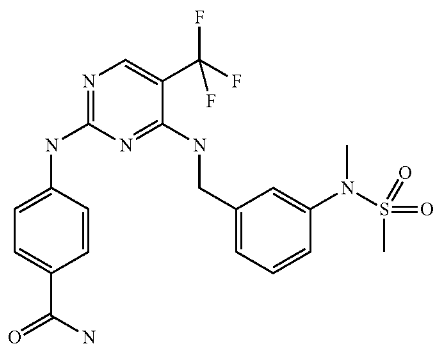 [SMILES: CN(c1cccc(CNc2nc(Nc3ccc(C(N)=O)cc3)ncc2C(F)(F)F)c1)S(C)(=O)=O] | 4-{[4-({3-[methyl(methylsulfonyl)amino]benzyl}amino)-5-(trifluoromethyl)pyrimidin-2-yl]amino}benzamide (99) | 0.00038 |
| 100 | 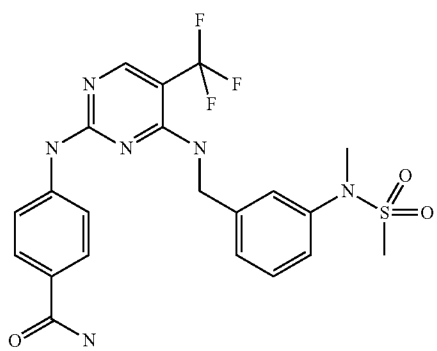 [SMILES: CN(c1cccc(CNc2nc(Nc3ccc(C(N)=O)cc3)ncc2C(F)(F)F)c1)S(C)(=O)=O] | 4-{[4-({3-[methyl(methylsulfonyl)amino]benzyl}amino)-5-(trifluoromethyl)pyrimidin-2-yl]amino}benzamide (100), hydrochloride salt | |
| 101 | 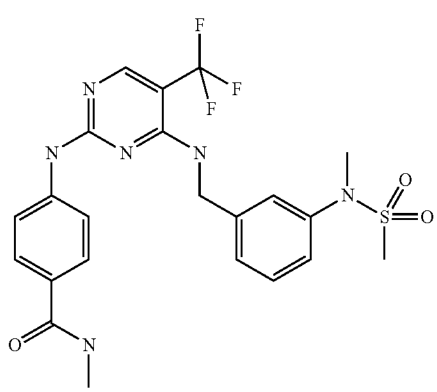 [SMILES: CNC(=O)c1ccc(Nc2ncc(C(F)(F)F)c(NCc3cccc(N(C)S(C)(=O)=O)c3)n2)cc1] | N-methyl-4-{[4-({3-[methyl(methylsulfonyl)amino]benzyl}amino)-5-(trifluoromethyl)pyrimidin-2-yl]amino}benzamide (101) | 0.00059 |

TABLE 1-continued

IC50 values against FAK kinase.

| Ex. | Structure | Compound Name | FAK IC50, μM |
|---|---|---|---|
| 102 | 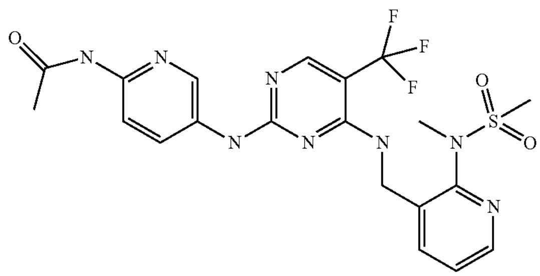 [SMILES: CC(=O)Nc1ccc(Nc2ncc(C(F)(F)F)c(NCc3cccnc3N(C)S(C)(=O)=O)n2)cn1] | N-[5-({4-[({2-[methyl(methylsulfonyl)amino]pyridin-3-yl}methyl)amino]-5-(trifluoromethyl)pyrimidin-2-yl}amino)pyridin-2-yl]acetamide (102) | 0.00233 |
| 103 | 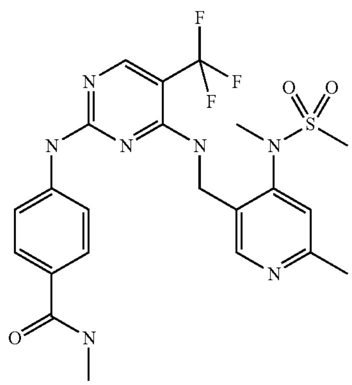 [SMILES: CNC(=O)c1ccc(Nc2ncc(C(F)(F)F)c(NCc3cnc(C)cc3N(C)S(C)(=O)=O)n2)cc1] | N-methyl-4-({4-[({6-methyl-4-[methyl(methylsulfonyl)amino]pyridin-3-yl}methyl)amino]-5-(trifluoromethyl)pyrimidin-2-yl}amino)benzamide (103) | 0.00059 |
| 104 | 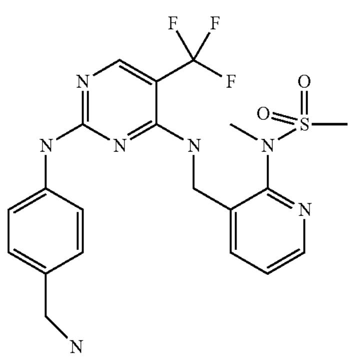 [SMILES: CN(c1ncccc1CNc1nc(Nc2ccc(CN)cc2)ncc1C(F)(F)F)S(C)(=O)=O] | N-[3-({[2-{[4-(aminomethyl)phenyl]amino}-5-(trifluoromethyl)pyrimidin-4-yl]amino}methyl)pyridin-2-yl]-N-methylmethanesulfonamide (104) | 0.00059 |
| 105 | 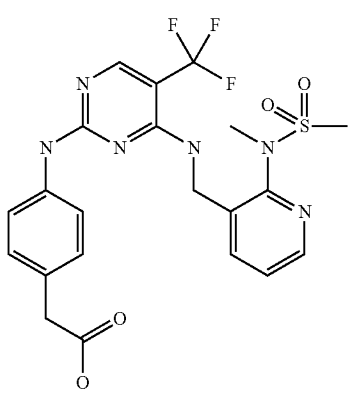 [SMILES: CN(c1ncccc1CNc1nc(Nc2ccc(CC(=O)O)cc2)ncc1C(F)(F)F)S(C)(=O)=O] | [4-({4-[({2-[methyl(methylsulfonyl)amino]pyridin-3-yl}methyl)amino]-5-(trifluoromethyl)pyrimidin-2-yl}amino)phenyl]acetic acid (105) | 0.00094 |

TABLE 1-continued

IC50 values against FAK kinase.

| Ex. | Structure | Compound Name | FAK IC50, μM |
|---|---|---|---|
| 106 | 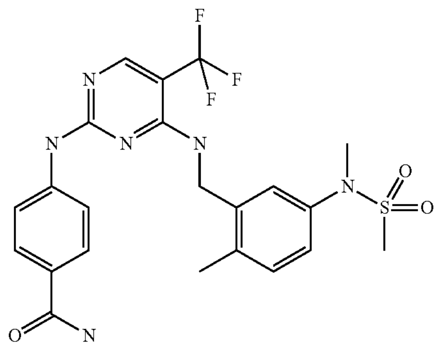 [SMILES: Cc1ccc(N(C)S(C)(=O)=O)cc1CNc1nc(Nc2ccc(C(N)=O)cc2)ncc1C(F)(F)F] | 4-{[4-({2-methyl-5-[methyl(methylsulfonyl)amino]benzyl}amino)-5-(trifluoromethyl)pyrimidin-2-yl]amino}benzamide (106) | 0.00096 |
| 107 | 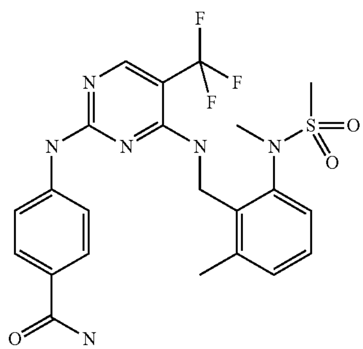 [SMILES: Cc1cccc(N(C)S(C)(=O)=O)c1CNc1nc(Nc2ccc(C(N)=O)cc2)ncc1C(F)(F)F] | 4-{[4-({2-methyl-6-[methyl(methylsulfonyl)amino]benzyl}amino)-5-(trifluoromethyl)pyrimidin-2-yl]amino}benzamide (107) | 0.00059 |
| 108 | 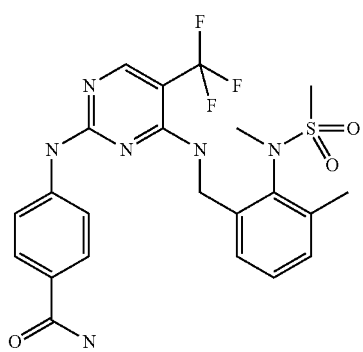 [SMILES: Cc1cccc(CNc2nc(Nc3ccc(C(N)=O)cc3)ncc2C(F)(F)F)c1N(C)S(C)(=O)=O] | 4-{[4-({3-methyl-2-[methyl(methylsulfonyl)amino]benzyl}amino)-5-(trifluoromethyl)pyrimidin-2-yl]amino}benzamide (108) | 0.0006 |
| 109 | 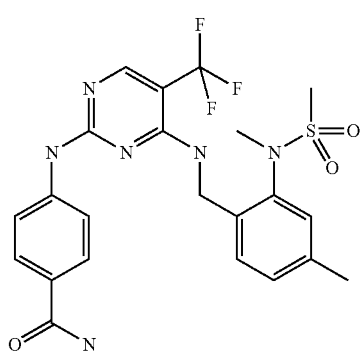 [SMILES: Cc1ccc(CNc2nc(Nc3ccc(C(N)=O)cc3)ncc2C(F)(F)F)c(N(C)S(C)(=O)=O)c1] | 4-{[4-({4-methyl-2-[methyl(methylsulfonyl)amino]benzyl}amino)-5-(trifluoromethyl)pyrimidin-2-yl]amino}benzamide (109) | 0.0006 |

TABLE 1-continued

IC50 values against FAK kinase.

| Ex. | Structure | Compound Name | FAK IC50, µM |
|---|---|---|---|
| 110 | 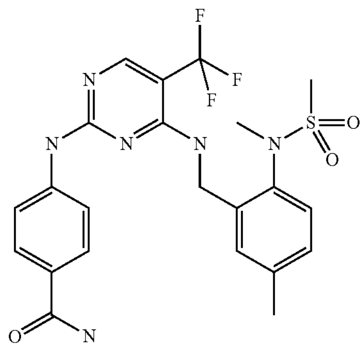 [SMILES: Cc1ccc(N(C)S(C)(=O)=O)c(CNc2nc(Nc3ccc(C(N)=O)cc3)ncc2C(F)(F)F)c1] | 4-{[4-({5-methyl-2-[methyl(methylsulfonyl)amino]benzyl}amino)-5-(trifluoromethyl)pyrimidin-2-yl]amino}benzamide (110) | 0.0006 |
| 111 | 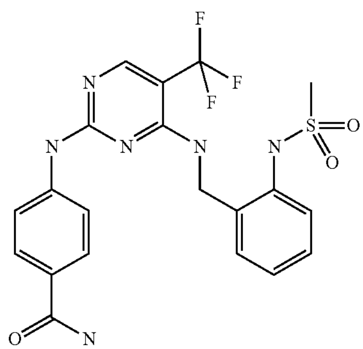 [SMILES: CS(=O)(=O)Nc1ccccc1CNc1nc(Nc2ccc(C(N)=O)cc2)ncc1C(F)(F)F] | 4-{[4-({2-[(methylsulfonyl)amino]benzyl}amino)-5-(trifluoromethyl)pyrimidin-2-yl]amino}benzamide (111) | 0.0006 |
| 112 | 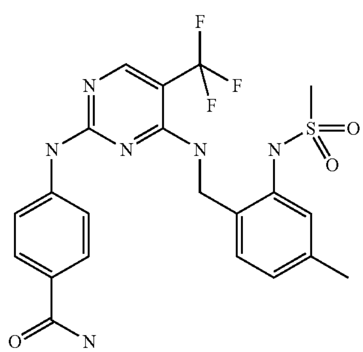 [SMILES: Cc1ccc(CNc2nc(Nc3ccc(C(N)=O)cc3)ncc2C(F)(F)F)c(NS(C)(=O)=O)c1] | 4-{[4-({4-methyl-2-[(methylsulfonyl)amino]benzyl}amino)-5-(trifluoromethyl)pyrimidin-2-yl]amino}benzamide (112) | 0.0006 |
| 113 | 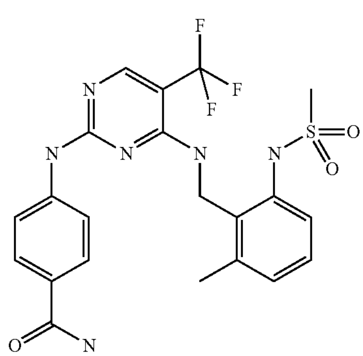 [SMILES: Cc1cccc(NS(C)(=O)=O)c1CNc1nc(Nc2ccc(C(N)=O)cc2)ncc1C(F)(F)F] | 4-{[4-({2-methyl-6-[(methylsulfonyl)amino]benzyl}amino)-5-(trifluoromethyl)pyrimidin-2-yl]amino}benzamide (113) | 0.0006 |

TABLE 1-continued

IC50 values against FAK kinase.

| Ex. | Structure | Compound Name | FAK IC50, µM |
|---|---|---|---|
| 114 | 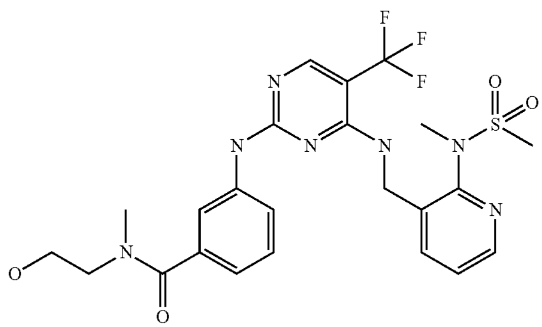 [SMILES: CN(CCO)C(=O)c1cccc(Nc2ncc(C(F)(F)F)c(NCc3cccnc3N(C)S(C)(=O)=O)n2)c1] | N-(2-hydroxyethyl)-N-methyl-3-({4-[({2-[methyl(methylsulfonyl)amino]pyridin-3-yl}methyl)amino]-5-(trifluoromethyl)pyrimidin-2-yl}amino)benzamide (114) | |
| 115 | 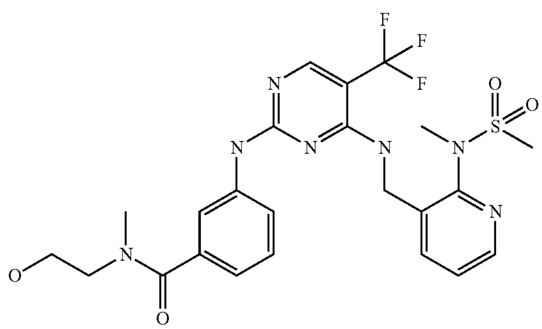 [SMILES: CN(CCO)C(=O)c1cccc(Nc2ncc(C(F)(F)F)c(NCc3cccnc3N(C)S(C)(=O)=O)n2)c1] | N-(2-hydroxyethyl)-N-methyl-3-({4-[({2-[methyl(methylsulfonyl)amino]pyridin-3-yl}methyl)amino]-5-(trifluoromethyl)pyrimidin-2-yl}amino)benzamide (115), trifluoroacetic acid salt | 0.00088 |
| 116 | 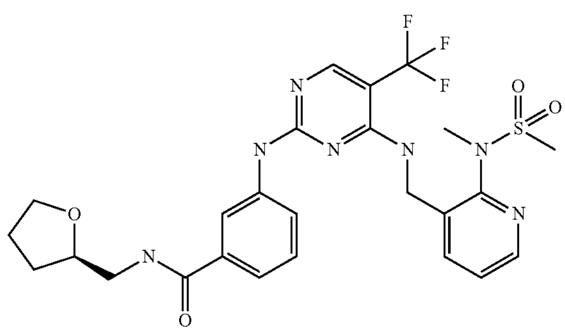 [SMILES: CN(c1ncccc1CNc1nc(Nc2cccc(C(=O)NC[C@H]3CCCO3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[(2R)-tetrahydrofuran-2-ylmethyl]benzamide (116) | |
| 117 | 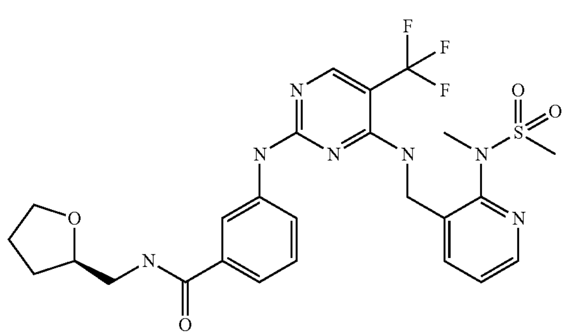 [SMILES: CN(c1ncccc1CNc1nc(Nc2cccc(C(=O)NC[C@H]3CCCO3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[(2R)-tetrahydrofuran-2-ylmethyl]benzamide (117), trifluoroacetic acid salt | 0.00147 |

TABLE 1-continued

IC50 values against FAK kinase.

| Ex. | Structure | Compound Name | FAK IC50, μM |
|---|---|---|---|
| 118 | 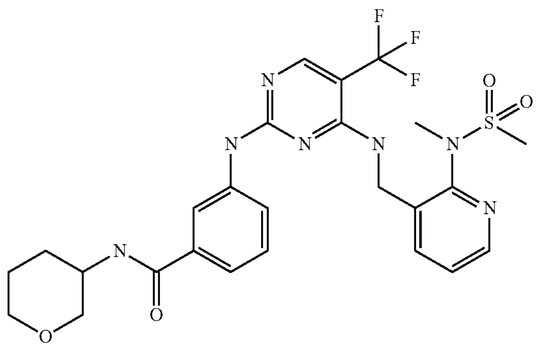 [SMILES: CN(c1ncccc1CNc1nc(Nc2cccc(C(=O)NC3CCCOC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(tetrahydro-2H-pyran-3-yl)benzamide (118) | |
| 119 | 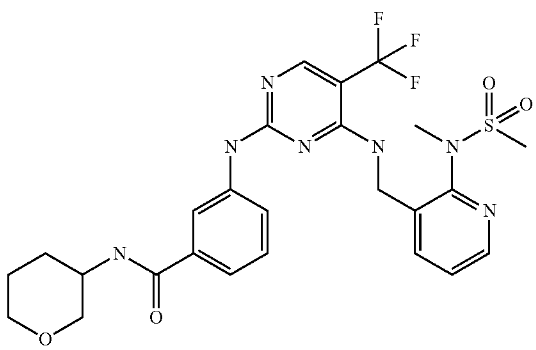 [SMILES: CN(c1ncccc1CNc1nc(Nc2cccc(C(=O)NC3CCCOC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(tetrahydro-2H-pyran-3-yl)benzamide (119), trifluoroacetic acid salt | 0.00114 |
| 120 | 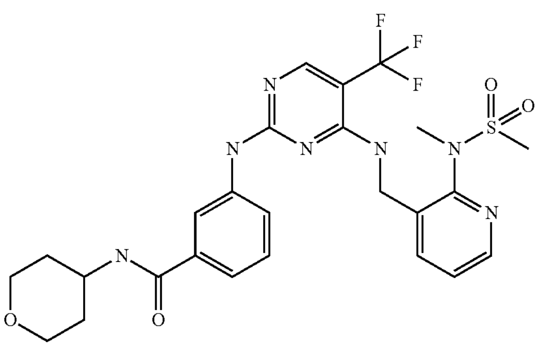 [SMILES: CN(c1ncccc1CNc1nc(Nc2cccc(C(=O)NC3CCOCC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(tetrahydro-2H-pyran-4-yl)benzamide (120) | |
| 121 | 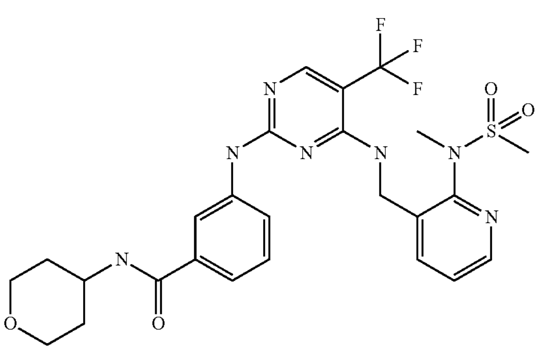 [SMILES: CN(c1ncccc1CNc1nc(Nc2cccc(C(=O)NC3CCOCC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(tetrahydro-2H-pyran-4-yl)benzamide (121), trifluoroacetic acid salt | 0.00094 |

TABLE 1-continued

IC50 values against FAK kinase.

| Ex. | Structure | Compound Name | FAK IC50, μM |
|---|---|---|---|
| 122 | 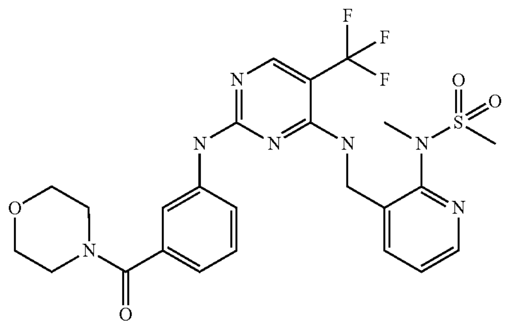 [SMILES: CN(c1ncccc1CNc1nc(Nc2cccc(C(=O)N3CCOCC3)c2)ncc1C(F)(F)F)S(C)(=O)=O] | N-methyl-N-[3-({[2-{[3-(morpholin-4-ylcarbonyl)phenyl]amino}-5-(trifluoromethyl)pyrimidin-4-yl]amino}methyl)pyridin-2-yl]methanesulfonamide (122) | |
| 123 | 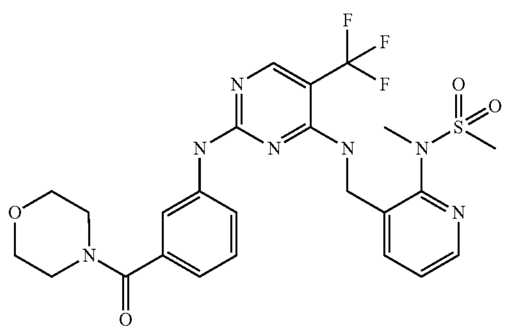 [SMILES: CN(c1ncccc1CNc1nc(Nc2cccc(C(=O)N3CCOCC3)c2)ncc1C(F)(F)F)S(C)(=O)=O] | N-methyl-N-[3-({[2-{[3-(morpholin-4-ylcarbonyl)phenyl]amino}-5-(trifluoromethyl)pyrimidin-4-yl]amino}methyl)pyridin-2-yl]methanesulfonamide (123), trifluoroacetic acid salt | 0.00215 |
| 124 | 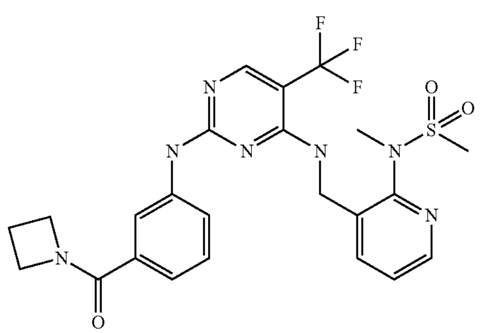 [SMILES: CN(c1ncccc1CNc1nc(Nc2cccc(C(=O)N3CCC3)c2)ncc1C(F)(F)F)S(C)(=O)=O] | N-[3-({[2-{[3-(azetidin-1-ylcarbonyl)phenyl]amino}-5-(trifluoromethyl)pyrimidin-4-yl]amino}methyl)pyridin-2-yl]-N-methylmethane-sulfonamide (124) | |
| 125 | 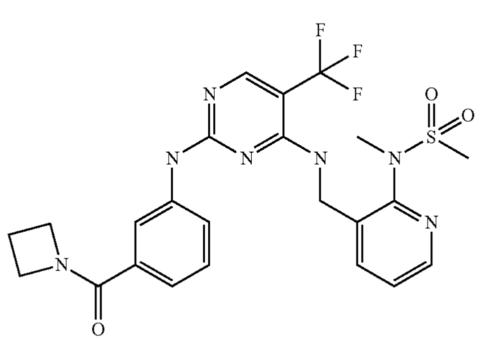 [SMILES: CN(c1ncccc1CNc1nc(Nc2cccc(C(=O)N3CCC3)c2)ncc1C(F)(F)F)S(C)(=O)=O] | N-[3-({[2-{[3-(azetidin-1-ylcarbonyl)phenyl]amino}-5-(trifluoromethyl)pyrimidin-4-yl]amino}methyl)pyridin-2-yl]-N-methylmethanesulfonamide (125), trifluoroacetic acid salt | 0.00127 |

TABLE 1-continued

IC50 values against FAK kinase.

| Ex. | Structure | Compound Name | FAK IC50, μM |
|---|---|---|---|
| 126 | 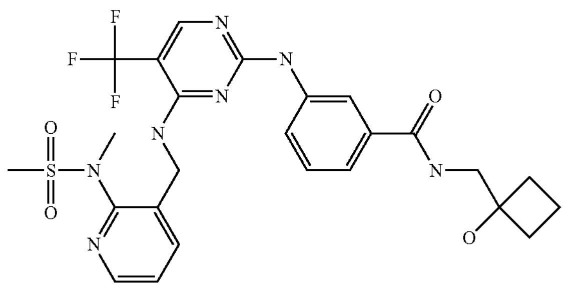 [SMILES: CN(c1ncccc1CNc1nc(Nc2cccc(C(=O)NCC3(O)CCC3)c2)ncc1C(F)(F)F)S(C)(=O)=O] | N-[(1-hydroxycyclobutyl)methyl]-3-({4-[({2-[methyl(methylsulfonyl)amino]pyridin-3-yl}methyl)amino]-5-(trifluoromethyl)pyrimidin-2-yl}amino)benzamide (126) | |
| 127 | 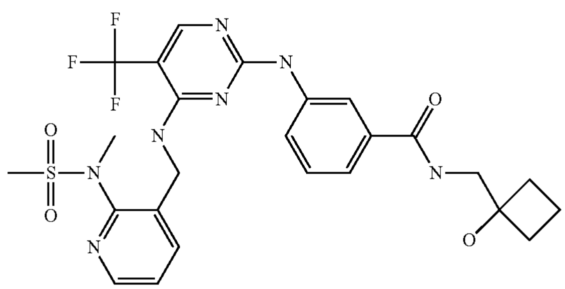 [SMILES: CN(c1ncccc1CNc1nc(Nc2cccc(C(=O)NCC3(O)CCC3)c2)ncc1C(F)(F)F)S(C)(=O)=O] | N-[(1-hydroxycyclobutyl)methyl]-3-({4-[({2-[methyl(methylsulfonyl)amino]pyridin-3-yl}methyl)amino]-5-(trifluoromethyl)pyrimidin-2-yl}amino)benzamide (127), trifluoroacetic acid salt | 0.00211 |
| 128 | 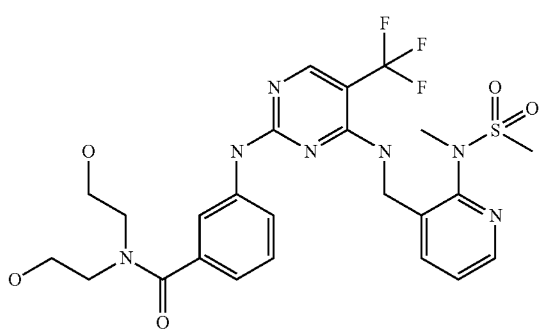 [SMILES: CN(c1ncccc1CNc1nc(Nc2cccc(C(=O)N(CCO)CCO)c2)ncc1C(F)(F)F)S(C)(=O)=O] | N,N-bis(2-hydroxyethyl)-3-({4-[({2-[methyl(methylsulfonyl)amino]pyridin-3-yl}methyl)amino]-5-(trifluoromethyl)pyrimidin-2-yl}amino)benzamide (128) | |
| 129 | 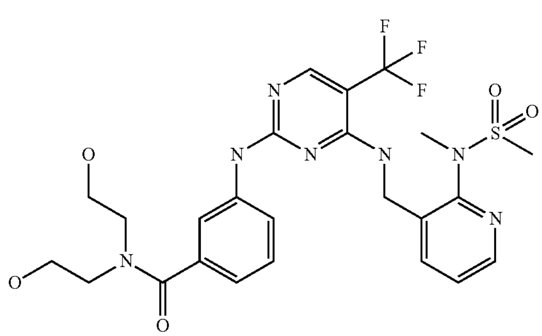 [SMILES: CN(c1ncccc1CNc1nc(Nc2cccc(C(=O)N(CCO)CCO)c2)ncc1C(F)(F)F)S(C)(=O)=O] | N,N-bis(2-hydroxyethyl)-3-({4-[({2-[methyl(methylsulfonyl)amino]pyridin-3-yl}methyl)amino]-5-(trifluoromethyl)pyrimidin-2-yl}amino)benzamide (129), trifluoroacetic acid salt | 0.00076 |

TABLE 1-continued

IC50 values against FAK kinase.

| Ex. | Structure | Compound Name | FAK IC50, μM |
|---|---|---|---|
| 130 | 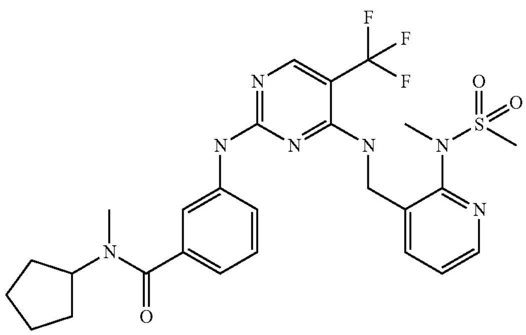 | N-cyclopentyl-N-methyl-3-({4-[({2-[methyl(methylsulfonyl)amino]pyridin-3-yl}methyl)amino]-5-(trifluoromethyl)pyrimidin-2-yl}amino)benzamide (130) | |
| 131 | 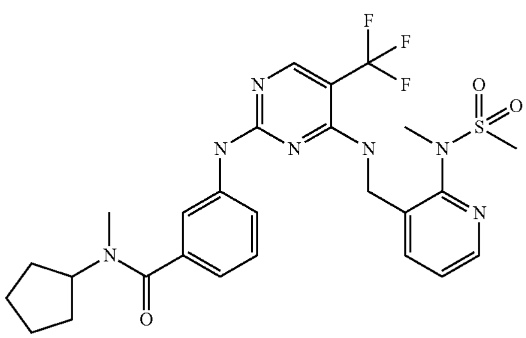 [SMILES: CN(C(=O)c1cccc(Nc2ncc(C(F)(F)F)c(NCc3cccnc3N(C)S(C)(=O)=O)n2)c1)C1CCCC1] | N-cyclopentyl-N-methyl-3-({4-[({2-[methyl(methylsulfonyl)amino]pyridin-3-yl}methyl)amino]-5-(trifluoromethyl)pyrimidin-2-yl}amino)benzamide (131), trifluoroacetic acid salt | 0.0108 |
| 132 | 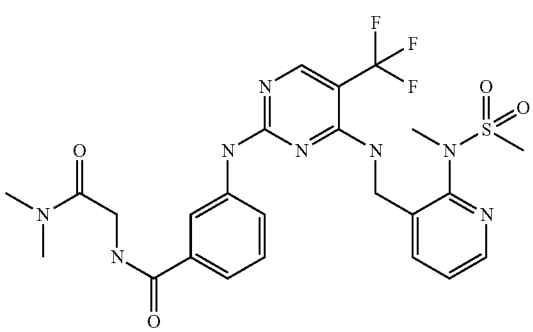 | N-[2-(dimethylamino)-2-oxoethyl]-3-({4-[({2-[methyl(methylsulfonyl)amino]pyridin-3-yl}methyl)amino]-5-(trifluoromethyl)pyrimidin-2-yl}amino)benzamide (132) | |
| 133 | 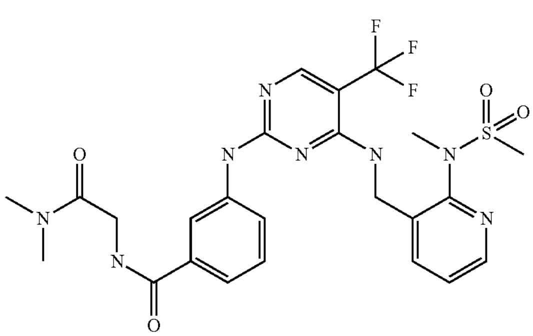 | N-[2-(dimethylamino)-2-oxoethyl]-3-({4-[({2-[methyl(methylsulfonyl)amino]pyridin-3-yl}methyl)amino]-5-(trifluoromethyl)pyrimidin-2-yl}amino)benzamide (133), trifluoroacetic acid salt | 0.00195 |

TABLE 1-continued

IC50 values against FAK kinase.

| Ex. | Structure | Compound Name | FAK IC50, μM |
|---|---|---|---|
| 134 | 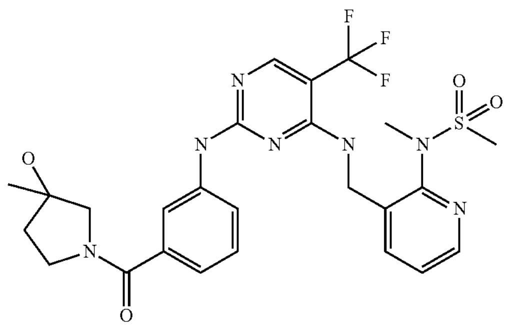 | N-[3-({[2-({3-[(3-hydroxy-3-methylpyrrolidin-1-yl)carbonyl]phenyl}amino)-5-(trifluoromethyl)pyrimidin-4-yl]amino}methyl)pyridin-2-yl]-N-methylmethane-sulfonamide (134) | |
| 135 | 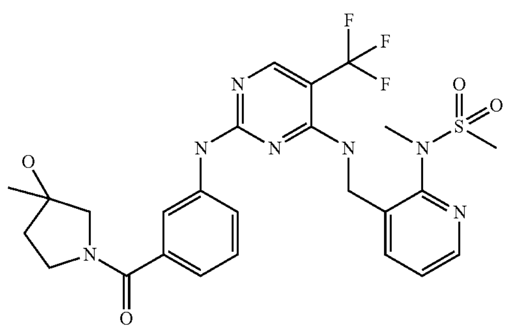 | N-[3-({[2-({3-[(3-hydroxy-3-methylpyrrolidin-1-yl)carbonyl]phenyl}amino)-5-(trifluoromethyl)pyrimidin-4-yl]amino}methyl)pyridin-2-yl]-N-methylmethane-sulfonamide (135), trifluoroacetic acid salt | 0.00333 |
| 136 | 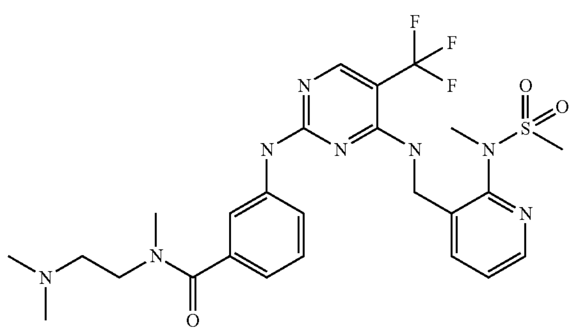 | N-[2-(dimethylamino)ethyl]-N-methyl-3-({4-[({2-[methyl(methylsulfonyl)amino]pyridin-3-yl}methyl)amino]-5-(trifluoromethyl)pyrimidin-2-yl}amino)benzamide (136) | |
| 137 | 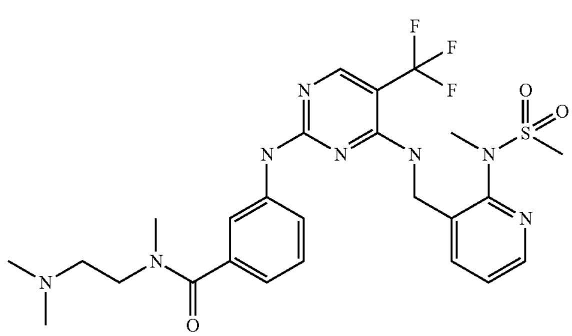 | N-[2-(dimethylamino)ethyl]-N-methyl-3-({4-[({2-[methyl(methylsulfonyl)amino]pyridin-3-yl}methyl)amino]-5-(trifluoromethyl)pyrimidin-2-yl}amino)benzamide (137), trifluoroacetic acid salt | 0.00433 |

TABLE 1-continued

IC50 values against FAK kinase.

| Ex. | Structure | Compound Name | FAK IC50, μM |
|---|---|---|---|
| 138 | 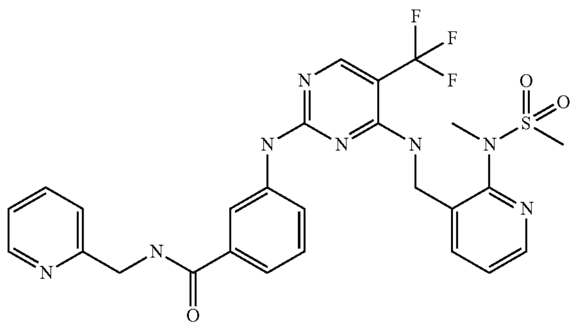 [SMILES: CN(c1ncccc1CNc1nc(Nc2cccc(C(=O)NCc3ccccn3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(pyridin-2-ylmethyl)benzamide (138) | |
| 139 | 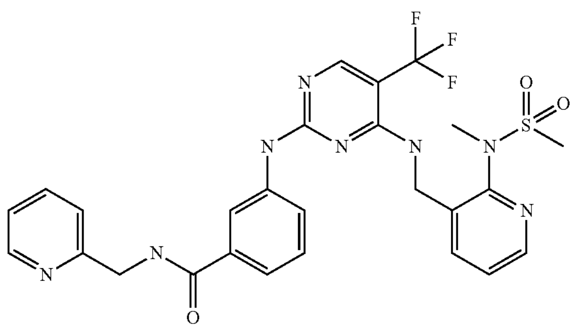 [SMILES: CN(c1ncccc1CNc1nc(Nc2cccc(C(=O)NCc3ccccn3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-(pyridin-2-ylmethyl)benzamide (139), trifluoroacetic acid salt | 0.00191 |
| 140 | 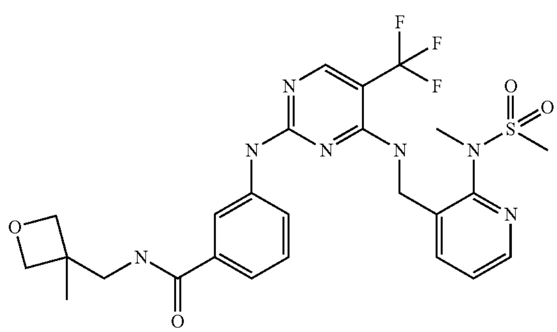 [SMILES: CN(c1ncccc1CNc1nc(Nc2cccc(C(=O)NCC3(C)COC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[(3-methyloxetan-3-yl)methyl]benzamide (140) | |
| 141 | 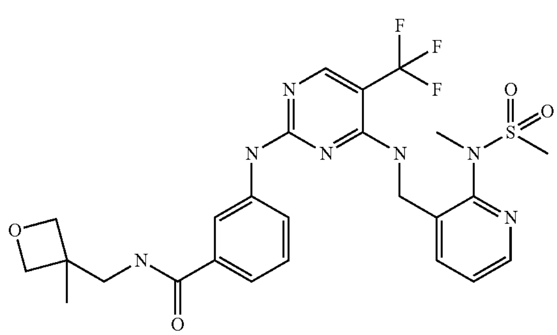 [SMILES: CN(c1ncccc1CNc1nc(Nc2cccc(C(=O)NCC3(C)COC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-[(3-methyloxetan-3-yl)methyl]benzamide (141), trifluoroacetic acid salt | 0.00084 |

TABLE 1-continued

IC50 values against FAK kinase.

| Ex. | Structure | Compound Name | FAK IC50, μM |
|---|---|---|---|
| 142 | ABS | N-methyl-N-{3-[({2-[(3-{[(3S)-3-methylmorpholin-4-yl]carbonyl}phenyl)amino]-5-(trifluoromethyl)pyrimidin-4-yl}amino)methyl]pyridin-2-yl}methanesulfonamide (142) | |
| 143 | ABS | N-methyl-N-{3-[({2-[(3-{[(3S)-3-methylmorpholin-4-yl]carbonyl}phenyl)amino]-5-(trifluoromethyl)pyrimidin-4-yl}amino)methyl]pyridin-2-yl}methanesulfonamide (143), trifluoroacetic acid salt | 0.0024 |
| 144 | 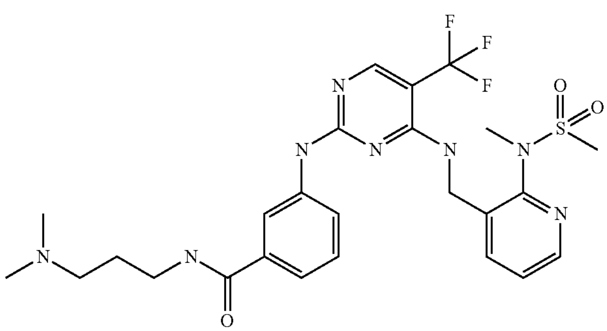 | N-[3-(dimethylamino)propyl]-3-({4-[({2-[methyl(methylsulfonyl)amino]pyridin-3-yl}methyl)amino]-5-(trifluoromethyl)pyrimidin-2-yl}amino)benzamide (144) | |
| 145 | 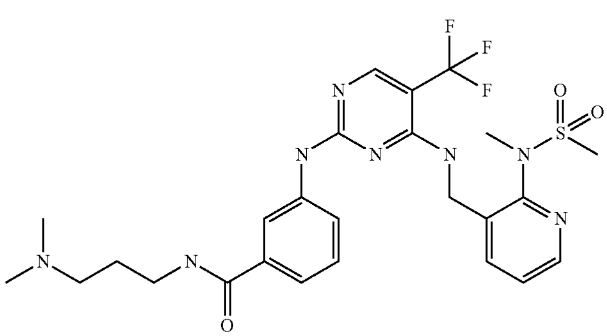 | N-[3-(dimethylamino)propyl]-3-({4-[({2-[methyl(methylsulfonyl)amino]pyridin-3-yl}methyl)amino]-5-(trifluoromethyl)pyrimidin-2-yl}amino)benzamide (145), trifluoroacetic acid salt | 0.00254 |

TABLE 1-continued

IC50 values against FAK kinase.

| Ex. | Structure | Compound Name | FAK IC50, µM |
|---|---|---|---|
| 146 | 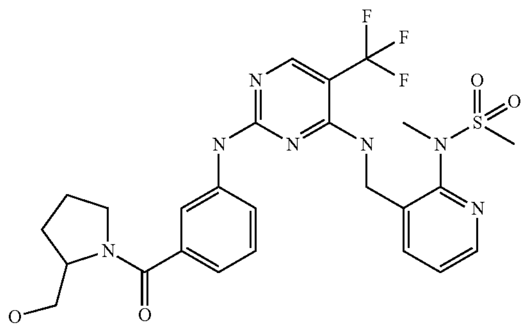 [SMILES: CN(c1ncccc1CNc1nc(Nc2cccc(C(=O)N3CCCC3CO)c2)ncc1C(F)(F)F)S(C)(=O)=O] | N-{3-[({2-[(3-{[2-(hydroxymethyl)pyrrolidin-1-yl]carbonyl}phenyl)amino]-5-(trifluoromethyl)pyrimidin-4-yl}amino)methyl]pyridin-2-yl}-N-methylmethane-sulfonamide (146) | |
| 147 | 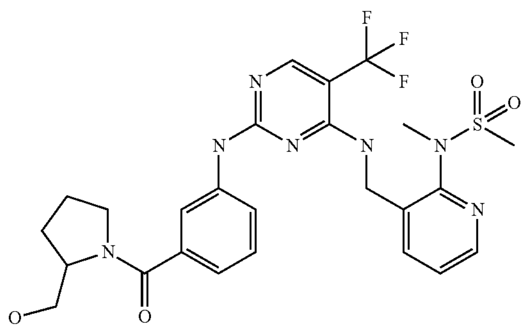 [SMILES: CN(c1ncccc1CNc1nc(Nc2cccc(C(=O)N3CCCC3CO)c2)ncc1C(F)(F)F)S(C)(=O)=O] | N-{3-[({2-[(3-{[2-(hydroxymethyl)pyrrolidin-1-yl]carbonyl}phenyl)amino]-5-(trifluoromethyl)pyrimidin-4-yl}amino)methyl]pyridin-2-yl}-N-methylmethane-sulfonamide (147), trifluoroacetic acid salt | 0.00474 |
| 148 | 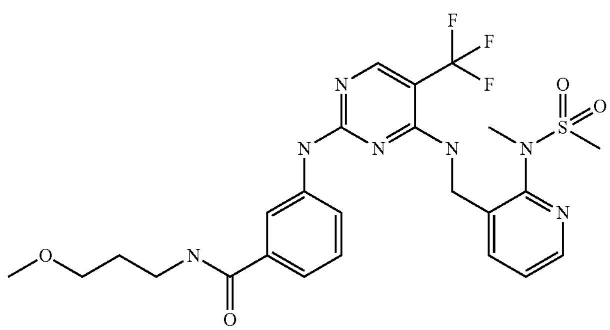 | N-(3-methoxypropyl)-3-({4-[({2-[methyl(methylsulfonyl)-amino]pyridin-3-yl}methyl)amino]-5-(trifluoromethyl)pyrimidin-2-yl}amino)benzamide (148) | |
| 149 | 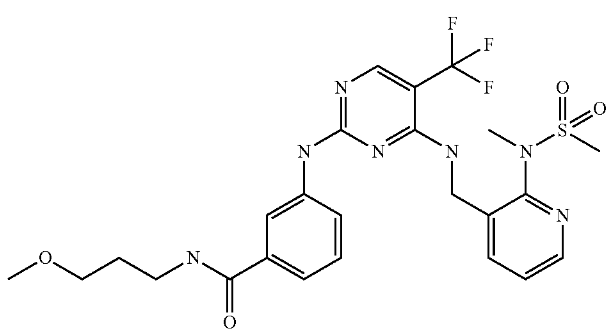 | N-(3-methoxypropyl)-3-({4-[({2-[methyl(methylsulfonyl)amino]pyridin-3-yl}methyl)amino]-5-(trifluoromethyl)pyrimidin-2-yl}amino)benzamide (149), trifluoroacetic acid salt | 0.00151 |

TABLE 1-continued

IC50 values against FAK kinase.

| Ex. | Structure | Compound Name | FAK IC50, μM |
|---|---|---|---|
| 150 | 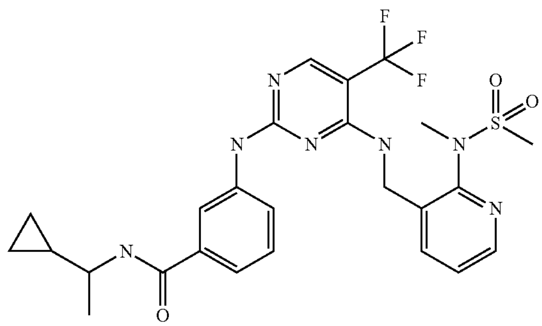 [SMILES: CC(NC(=O)c1cccc(Nc2ncc(C(F)(F)F)c(NCc3cccnc3N(C)S(C)(=O)=O)n2)c1)C1CC1] | N-(1-cyclopropylethyl)-3-({4-[({2-[methyl(methylsulfonyl)-amino]pyridin-3-yl}methyl)amino]-5-(trifluoromethyl)pyrimidin-2-yl}amino)benzamide (150) | |
| 151 | 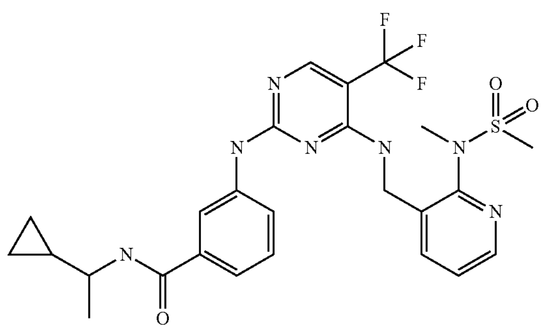 [SMILES: CC(NC(=O)c1cccc(Nc2ncc(C(F)(F)F)c(NCc3cccnc3N(C)S(C)(=O)=O)n2)c1)C1CC1] | N-(1-cyclopropylethyl)-3-({4-[({2-[methyl(methylsulfonyl)-amino]pyridin-3-yl}methyl)amino]-5-(trifluoromethyl)pyrimidin-2-yl}amino)benzamide (151), trifluoroacetic acid salt | 0.00524 |
| 152 | ABS | N-{3-[({2-[(3-{[(3R,4R)-3,4-difluoropyrrolidin-1-yl]carbonyl}phenyl)amino]-5-(trifluoromethyl)pyrimidin-4-yl}amino)methyl]pyridin-2-yl}-N-methylmethane-sulfonamide (152) | |
| 153 | ABS | N-{3-[({2-[(3-{[(3R,4R)-3,4-difluoropyrrolidin-1-yl]carbonyl}phenyl)amino]-5-(trifluoromethyl)pyrimidin-4-yl}amino)methyl]pyridin-2-yl}-N-methylmethane-sulfonamide (153), trifluoroacetic acid salt | 0.00335 |

TABLE 1-continued

IC50 values against FAK kinase.

| Ex. | Structure | Compound Name | FAK IC50, μM |
|---|---|---|---|
| 154 | 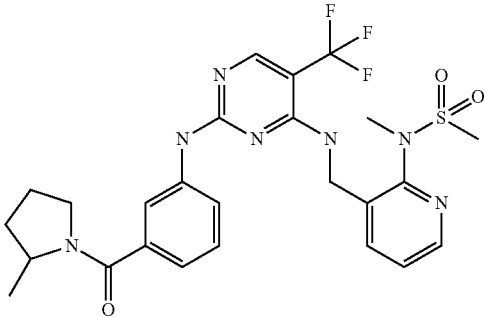 [SMILES: CC1CCCN1C(=O)c1cccc(Nc2ncc(C(F)(F)F)c(NCc3cccnc3N(C)S(C)(=O)=O)n2)c1] | N-methyl-N-[3-({[2-({3-[(2-methylpyrrolidin-1-yl)carbonyl]phenyl}amino)-5-(trifluoromethyl)pyrimidin-4-yl]amino}methyl)pyridin-2-yl]methanesulfonamide (154) | |
| 155 | 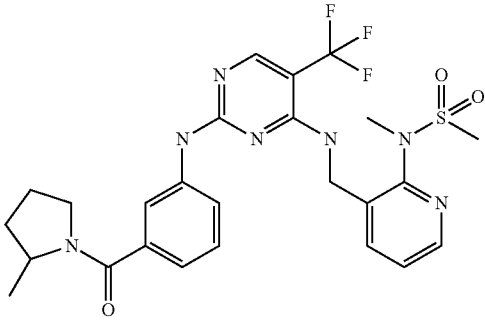 [SMILES: CC1CCCN1C(=O)c1cccc(Nc2ncc(C(F)(F)F)c(NCc3cccnc3N(C)S(C)(=O)=O)n2)c1] | N-methyl-N-[3-({[2-({3-[(2-methylpyrrolidin-1-yl)carbonyl]phenyl}amino)-5-(trifluoromethyl)pyrimidin-4-yl]amino}methyl)pyridin-2-yl]methanesulfonamide (155), trifluoroacetic acid salt | 0.00975 |
| 156 | ABS 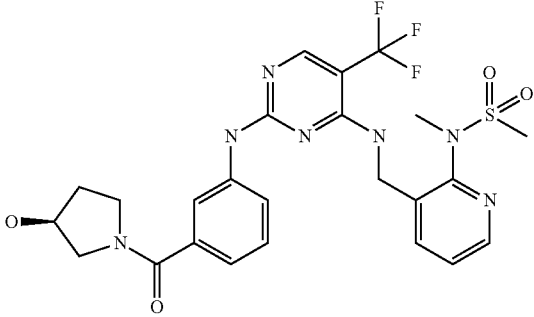 | N-{3-[({2-[(3-{[(3S)-3-hydroxypyrrolidin-1-yl]carbonyl}phenyl)amino]-5-(trifluoromethyl)pyrimidin-4-yl}amino)methyl]pyridin-2-yl}-N-methylmethane-sulfonamide (156) | |
| 157 | ABS 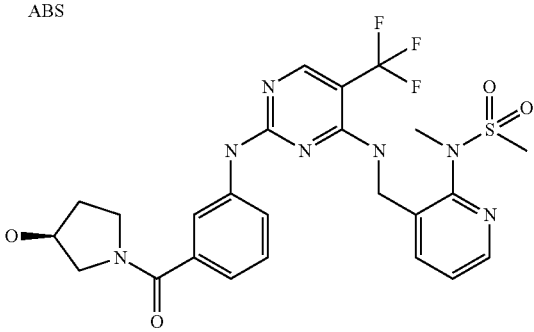 [SMILES: "ABS" ; CN(c1ncccc1CNc1nc(Nc2cccc(C(=O)N3CC[C@H](O)C3)c2)ncc1C(F)(F)F)S(C)(=O)=O] | N-{3-[({2-[(3-{[(3S)-3-hydroxypyrrolidin-1-yl]carbonyl}phenyl)amino]-5-(trifluoromethyl)pyrimidin-4-yl}amino)methyl]pyridin-2-yl}-N-methylmethane-sulfonamide (157), trifluoroacetic acid salt | 0.00424 |

TABLE 1-continued

IC50 values against FAK kinase.

| Ex. | Structure | Compound Name | FAK IC50, μM |
|---|---|---|---|
| 158 | ABS | N-{3-[({2-[(3-{[(3S)-3-hydroxypiperidin-1-yl]carbonyl}phenyl)amino]-5-(trifluoromethyl)pyrimidin-4-yl}amino)methyl]pyridin-2-yl}-N-methylmethane-sulfonamide (158) | |
| 159 | ABS | N-{3-[({2-[(3-{[(3S)-3-hydroxypiperidin-1-yl]carbonyl}phenyl)amino]-5-(trifluoromethyl)pyrimidin-4-yl}amino)methyl]pyridin-2-yl}-N-methylmethane-sulfonamide (159), trifluoroacetic acid salt | 0.00614 |
| 160 | ABS | N-[(1R)-1-(hydroxymethyl)-2-methylpropyl]-3-({4-[({2-[methyl(methylsulfonyl)amino]pyridin-3-yl}methyl)amino]-5-(trifluoromethyl)pyrimidin-2-yl}amino)benzamide (160) | |
| 161 | ABS | N-[(1R)-1-(hydroxymethyl)-2-methylpropyl]-3-({4-[({2-[methyl(methylsulfonyl)amino]pyridin-3-yl}methyl)amino]-5-(trifluoromethyl)pyrimidin-2-yl}amino)benzamide (161), trifluoroacetic acid salt | 0.00374 |

TABLE 1-continued

IC50 values against FAK kinase.

| Ex. | Structure | Compound Name | FAK IC50, μM |
|---|---|---|---|
| 162 | 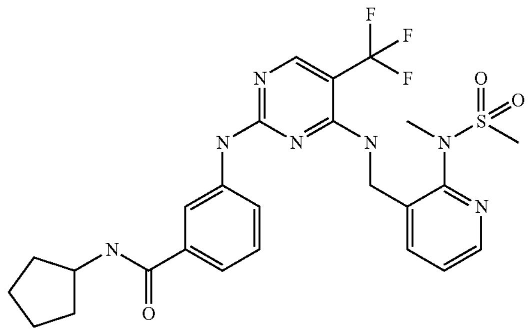 [SMILES: CN(c1ncccc1CNc1nc(Nc2cccc(C(=O)NC3CCCC3)c2)ncc1C(F)(F)F)S(C)(=O)=O] | N-cyclopentyl-3-({4-[({2-[methyl(methylsulfonyl)amino]pyridin-3-yl}methyl)amino]-5-(trifluoromethyl)pyrimidin-2-yl}amino)benzamide (162) | |
| 163 | 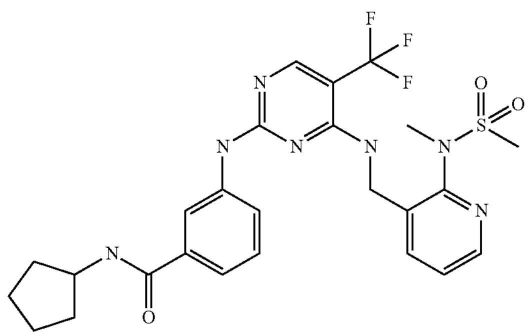 | N-cyclopentyl-3-({4[({2-[methyl(methylsulfonyl)amino]pyridin-3-yl}methyl)amino]-5-(trifluoromethyl)pyrimidin-2-yl}amino)benzamide (163), trifluoroacetic acid salt | 0.0051 |
| 164 | 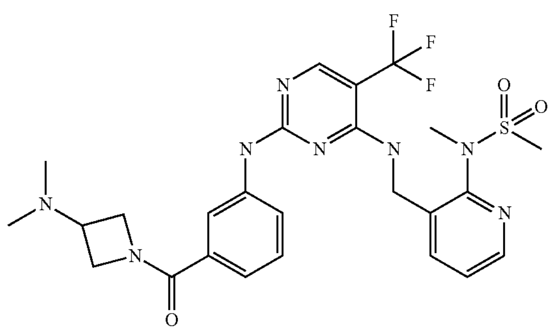 [SMILES: CN(C)C1CN(C(=O)c2cccc(Nc3ncc(C(F)(F)F)c(NCc4cccnc4N(C)S(C)(=O)=O)n3)c2)C1] | N-{3-[({2-[(3-{[3-(dimethylamino)azetidin-1-yl]carbonyl}phenyl)amino]-5-(trifluoromethyl)pyrimidin-4-yl}amino)methyl]pyridin-2-yl}-N-methylmethane-sulfonamide (164) | |
| 165 | 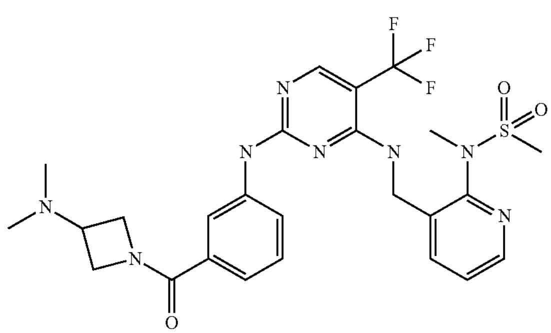 [SMILES: CN(C)C1CN(C(=O)c2cccc(Nc3ncc(C(F)(F)F)c(NCc4cccnc4N(C)S(C)(=O)=O)n3)c2)C1] | N-{3-[({2-[(3-{[3-(dimethylamino)azetidin-1-yl]carbonyl}phenyl)amino]-5-(trifluoromethyl)pyrimidin-4-yl}amino)methyl]pyridin-2-yl}-N-methylmethane-sulfonamide (165), trifluoroacetic acid salt | 0.00493 |

TABLE 1-continued

IC50 values against FAK kinase.

| Ex. | Structure | Compound Name | FAK IC50, μM |
|-----|-----------|---------------|--------------|
| 166 | 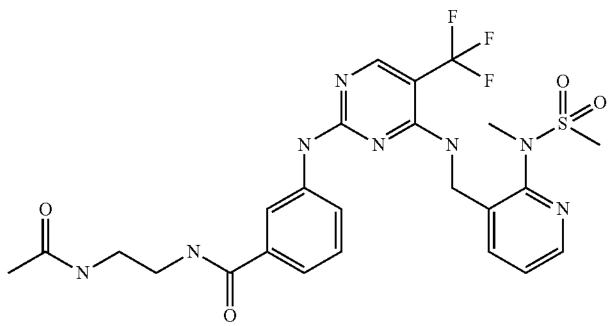 | N-[2-(acetylamino)ethyl]-3-({4-[({2-[methyl(methylsulfonyl)amino]pyridin-3-yl}methyl)amino]-5-(trifluoromethyl)pyrimidin-2-yl}amino)benzamide (166) | |
| 167 | 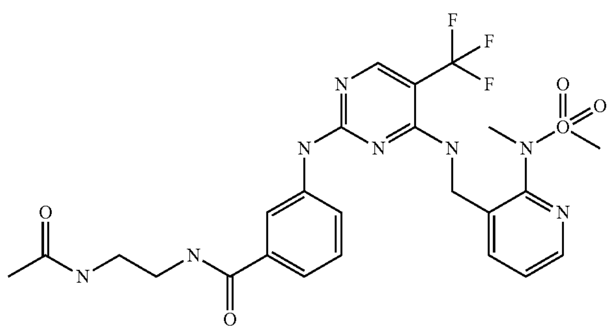 | N-[2-(acetylamino)ethyl]-3-({4-[({2-[methyl(methylsulfonyl)amino]pyridin-3-yl}methyl)amino]-5-(trifluoromethyl)pyrimidin-2-yl}amino)benzamide (167), trifluoroacetic acid salt | 0.00344 |
| 168 | ABS | N-[(1R)-1-(hydroxymethyl)propyl]-3-({4-[({2-[methyl(methylsulfonyl)amino]pyridin-3-yl}methyl)amino]-5-(trifluoromethyl)pyrimidin-2-yl}amino)benzamide (168) | |
| 169 | ABS | N-[(1R)-1-(hydroxymethyl)propyl]-3-({4-[({2-[methyl(methylsulfonyl)amino]pyridin-3-yl}methyl)amino]-5-(trifluoromethyl)pyrimidin-2-yl}amino)benzamide (169), trifluoroacetic acid salt | 0.00247 |

TABLE 1-continued

IC50 values against FAK kinase.

| Ex. | Structure | Compound Name | FAK IC50, μM |
|---|---|---|---|
| 170 | 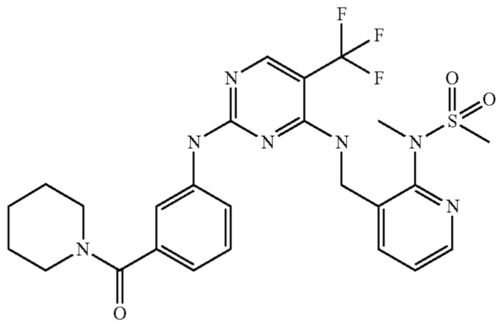 | N-methyl-N-[3-({[2-{[3-(piperidin-1-ylcarbonyl)phenyl]amino}-5-(trifluoromethyl)pyrimidin-4-yl]amino}methyl)pyridin-2-yl]methanesulfonamide (170) | |
| 171 | 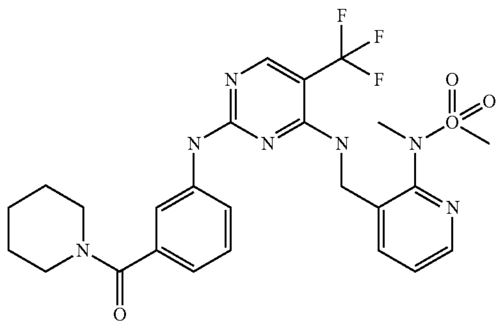 | N-methyl-N-[3-({[2-{[3-(piperidin-1-ylcarbonyl)phenyl]amino}-5-(trifluoromethyl)pyrimidin-4-yl]amino}methyl)pyridin-2-yl]methanesulfonamide (171), trifluoroacetic acid salt | 0.00791 |
| 172 | 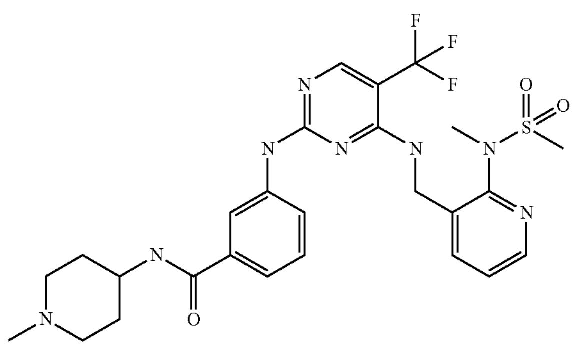 [SMILES: CN1CCC(NC(=O)c2cccc(Nc3ncc(C(F)(F)F)c(NCc4cccnc4N(C)S(C)(=O)=O)n3)c2)CC1] | 3-({4-[({2-[methyl(methylsulfonyl)amino]pyridin-3-yl}methyl)amino]-5-(trifluoromethyl)pyrimidin-2-yl}amino)-N-(1-methylpiperidin-4-yl)benzamide (172) | |
| 173 | 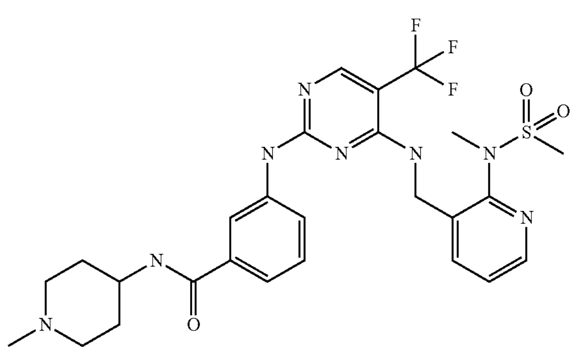 [SMILES: CN1CCC(NC(=O)c2cccc(Nc3ncc(C(F)(F)F)c(NCc4cccnc4N(C)S(C)(=O)=O)n3)c2)CC1] | 3-({4-[({2-[methyl(methylsulfonyl)amino]pyridin-3-yl}methyl)amino]-5-(trifluoromethyl)pyrimidin-2-yl}amino)-N-(1-methylpiperidin-4-yl)benzamide (173), trifluoroacetic acid salt | 0.00096 |

TABLE 1-continued

IC50 values against FAK kinase.

| Ex. | Structure | Compound Name | FAK IC50, μM |
|---|---|---|---|
| 174 | ABS | N-{3-[({2-[(3-{[(3R)-3-hydroxypyrrolidin-1-yl]carbonyl}phenyl)amino]-5-(trifluoromethyl) pyrimidin-4-yl}amino)methyl] pyridin-2-yl}-N-methylmethane-sulfonamide (174) | |
| 175 | ABS | N-{3-[({2-[(3-{[(3R)-3-hydroxypyrrolidin-1-yl]carbonyl}phenyl)amino]-5-(trifluoromethyl) pyrimidin-4-yl}amino)methyl]pyridin-2-yl}-N-methyl-methanesulfonamide (175), trifluoroacetic acid salt | 0.00408 |
| 176 | 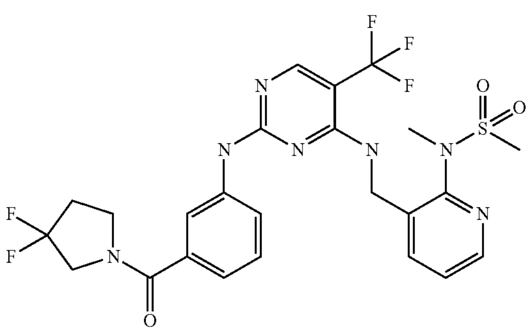 | N-[3-({[2-({3-[(3,3-difluoropyrrolidin-1-yl)carbonyl]phenyl}amino)-5-(trifluoromethyl)pyrimidin-4-yl]amino}methyl)pyridin-2-yl]-N-methylmethane-sulfonamide (176) | |
| 177 | 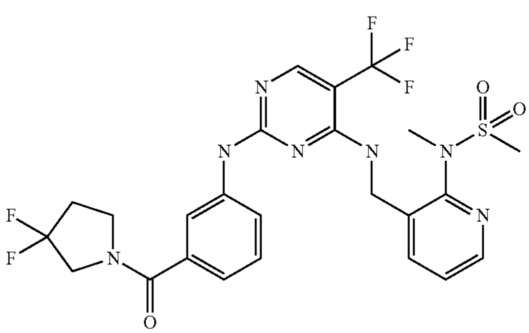 | N-[3-({[2-({3-[(3,3-difluoropyrrolidin-1-yl)carbonyl]phenyl}amino)-5-(trifluoromethyl) pyrimidin-4-yl]amino} methyl)pyridin-2-yl]-N-methylmethane-sulfonamide (177), trifluoroacetic acid salt | 0.00593 |

TABLE 1-continued

IC50 values against FAK kinase.

| Ex. | Structure | Compound Name | FAK IC50, μM |
|---|---|---|---|
| 178 | ABS 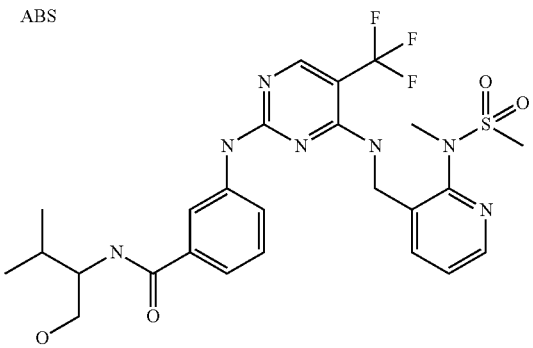 | N-[(1S)-1-(hydroxymethyl)-2-methylpropyl]-3-({4-[({2-[methyl(methylsulfonyl)amino]pyridin-3-yl}methyl)amino]-5-(trifluoromethyl)pyrimidin-2-yl}amino)benzamide (178) | |
| 179 | ABS 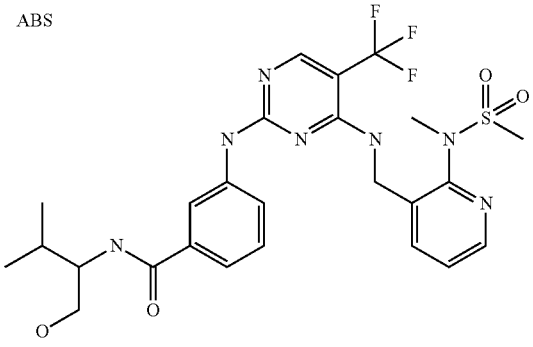 | N-[(1S)-1-(hydroxymethyl)-2-methylpropyl]-3-({4-[({2-[methyl(methylsulfonyl)amino]pyridin-3-yl}methyl)amino]-5-(trifluoromethyl)pyrimidin-2-yl}amino)benzamide (179), trifluoroacetic acid salt | 0.00109 |
| 180 | 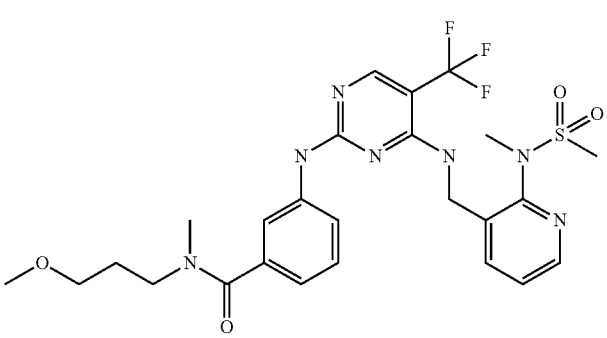 | N-(3-methoxypropyl)-N-methyl-3-({4-[({2-[methyl(methylsulfonyl)amino]pyridin-3-yl}methyl)amino]-5-(trifluoromethyl)pyrimidin-2-yl}amino)benzamide (180) | |
| 181 | 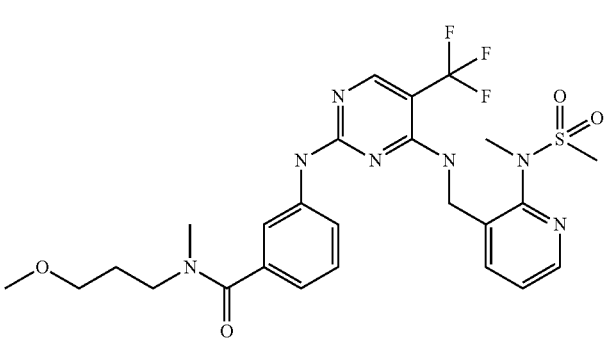 | N-(3-methoxypropyl)-N-methyl-3-({4-[({2-[methyl(methylsulfonyl)amino]pyridin-3-yl}methyl)amino]-5-(trifluoromethyl)pyrimidin-2-yl}amino)benzamide (181), trifluoroacetic acid salt | 0.00918 |

TABLE 1-continued

IC50 values against FAK kinase.

| Ex. | Structure | Compound Name | FAK IC50, μM |
|---|---|---|---|
| 182 | ABS | N-[(1S)-1-(hydroxymethyl)propyl]-3-({4-[({2-[methyl(methylsulfonyl)amino]pyridin-3-yl}methyl)amino]-5-(trifluoromethyl)pyrimidin-2-yl}amino)benzamide (182) | |
| 183 | ABS | N-[(1S)-1-(hydroxymethyl)propyl]-3-({4-[({2-[methyl(methylsulfonyl)amino]pyridin-3-yl}methyl)amino]-5-(trifluoromethyl)pyrimidin-2-yl}amino)benzamide (183), trifluoroacetic acid salt | 0.00196 |
| 184 | 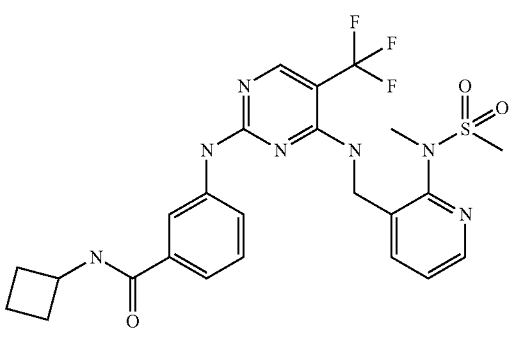 | N-cyclobutyl-3-({4-[({2-[methyl(methylsulfonyl)amino]pyridin-3-yl}methyl)amino]-5-(trifluoromethyl)pyrimidin-2-yl}amino)benzamide (184) | |
| 185 | 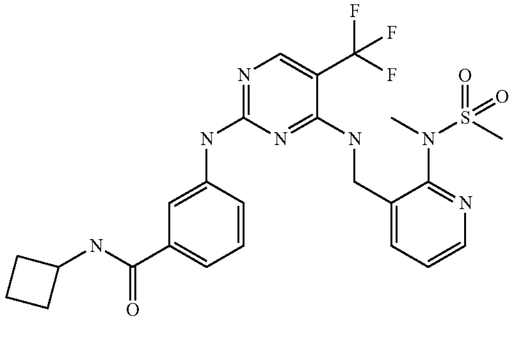 | N-cyclobutyl-3-({4-[({2-[methyl(methylsulfonyl)amino]pyridin-3-yl}methyl)amino]-5-(trifluoromethyl)pyrimidin-2-yl}amino)benzamide (185), trifluoroacetic acid salt | 0.00217 |

TABLE 1-continued

IC50 values against FAK kinase.

| Ex. | Structure | Compound Name | FAK IC50, μM |
|---|---|---|---|
| 186 | 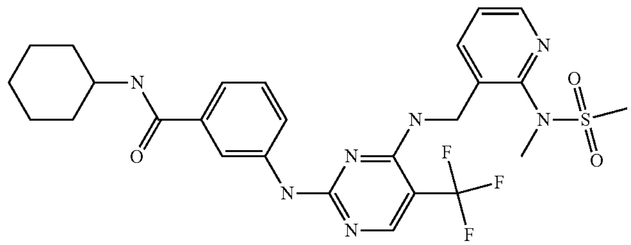 [SMILES: CN(c1ncccc1CNc1nc(Nc2cccc(C(=O)NC3CCCCC3)c2)ncc1C(F)(F)F)S(C)(=O)=O] | N-cyclohexyl-3-({4-[({2-[methyl(methylsulfonyl)amino]pyridin-3-yl}methyl)amino]-5-(trifluoromethyl)pyrimidin-2-yl}amino)benzamide (186) | |
| 187 | 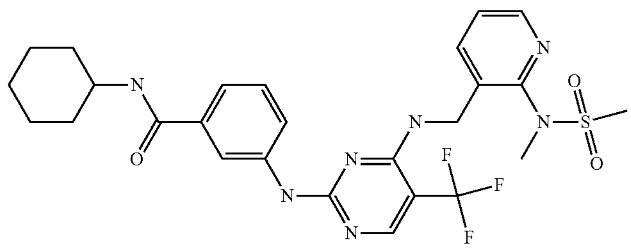 [SMILES: CN(c1ncccc1CNc1nc(Nc2cccc(C(=O)NC3CCCCC3)c2)ncc1C(F)(F)F)S(C)(=O)=O] | N-cyclohexyl-3-({4-[({2-[methyl(methylsulfonyl)amino]pyridin-3-yl}methyl)amino]-5-(trifluoromethyl)pyrimidin-2-yl}amino)benzamide (187), trifluoroacetic acid salt | 0.00584 |
| 188 | 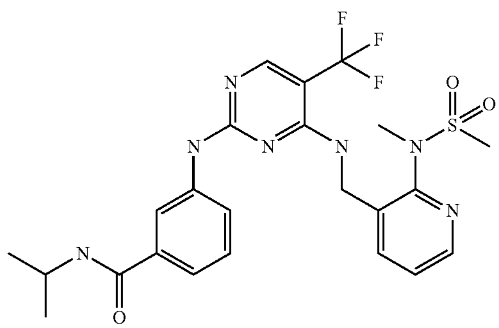 [SMILES: CC(C)NC(=O)c1cccc(Nc2ncc(C(F)(F)F)c(NCc3cccnc3N(C)S(C)(=O)=O)n2)c1] | N-isopropyl-3-({4-[({2-[methyl(methylsulfonyl)amino]pyridin-3-yl}methyl)amino]-5-(trifluoromethyl)pyrimidin-2-yl}amino)benzamide (188) | |
| 189 | 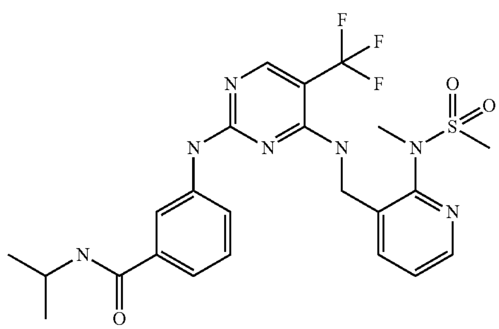 [SMILES: CC(C)NC(=O)c1cccc(Nc2ncc(C(F)(F)F)c(NCc3cccnc3N(C)S(C)(=O)=O)n2)c1] | N-isopropyl-3-({4-[({2-[methyl(methylsulfonyl)amino]pyridin-3-yl}methyl)amino]-5-(trifluoromethyl)pyrimidin-2-yl}amino)benzamide (189), trifluoroacetic acid salt | 0.0043 |
| 190 | 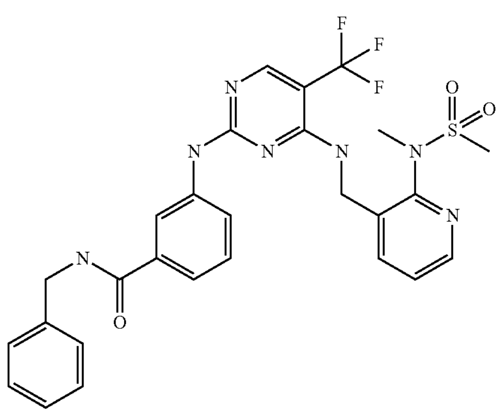 [SMILES: CN(c1ncccc1CNc1nc(Nc2cccc(C(=O)NCc3ccccc3)c2)ncc1C(F)(F)F)S(C)(=O)=O] | N-benzyl-3-({4-[({2-[methyl(methylsulfonyl)amino]pyridin-3-yl}methyl)amino]-5-(trifluoromethyl)pyrimidin-2-yl}amino)benzamide (190) | |

TABLE 1-continued

IC50 values against FAK kinase.

| Ex. | Structure | Compound Name | FAK IC50, μM |
|---|---|---|---|
| 191 | 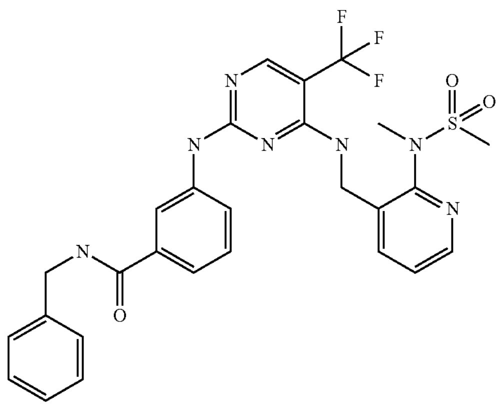 [SMILES: CN(c1ncccc1CNc1nc(Nc2cccc(C(=O)NCc3ccccc3)c2)ncc1C(F)(F)F)S(C)(=O)=O] | N-benzyl-3-({4-[({2-[methyl(methylsulfonyl)amino]pyridin-3-yl}methyl)amino]-5-(trifluoromethyl)pyrimidin-2-yl}amino)benzamide (191), trifluoroacetic acid salt | 0.0055 |
| 192 | 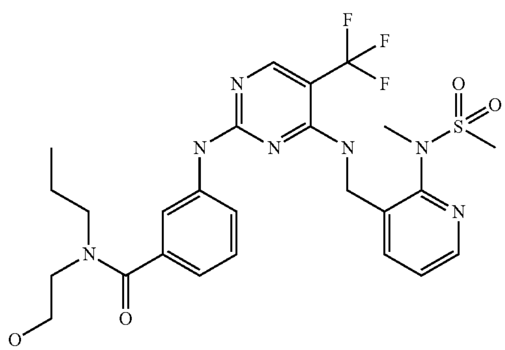 [SMILES: CCCN(CCO)C(=O)c1cccc(Nc2ncc(C(F)(F)F)c(NCc3cccnc3N(C)S(C)(=O)=O)n2)c1] | N-(2-hydroxyethyl)-3-({4-[({2-[methyl(methylsulfonyl)amino]pyridin-3-yl}methyl)amino]-5-(trifluoromethyl)pyrimidin-2-yl}amino)-N-propylbenzamide (192) | |
| 193 | 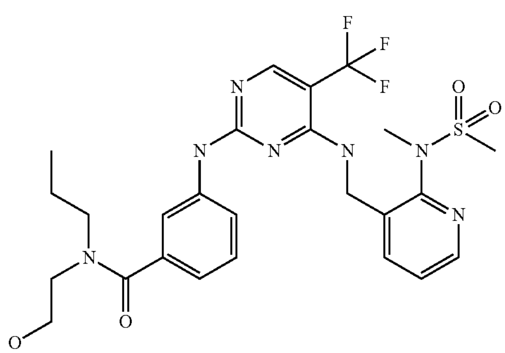 [SMILES: CCCN(CCO)C(=O)c1cccc(Nc2ncc(C(F)(F)F)c(NCc3cccnc3N(C)S(C)(=O)=O)n2)c1] | N-(2-hydroxyethyl)-3-({4-[({2-[methyl(methylsulfonyl)amino]pyridin-3-yl}methyl)amino]-5-(trifluoromethyl)pyrimidin-2-yl}amino)-N-propylbenzamide (193), trifluoroacetic acid salt | 0.0011 |
| 194 | 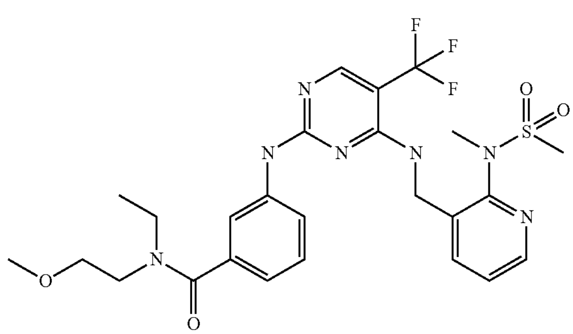 [SMILES: CCN(CCOC)C(=O)c1cccc(Nc2ncc(C(F)(F)F)c(NCc3cccnc3N(C)S(C)(=O)=O)n2)c1] | N-ethyl-N-(2-methoxyethyl)-3-({4-[({2-[methyl(methylsulfonyl)amino]pyridin-3-yl}methyl)amino]-5-(trifluoromethyl)pyrimidin-2-yl}amino)benzamide (194) | |

TABLE 1-continued

IC50 values against FAK kinase.

| Ex. | Structure | Compound Name | FAK IC50, μM |
|---|---|---|---|
| 195 | 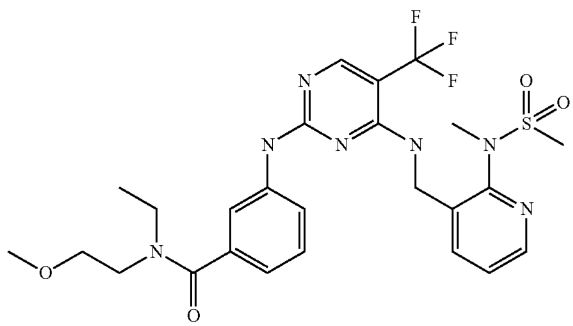 [SMILES: CCN(CCOC)C(=O)c1cccc(Nc2ncc(C(F)(F)F)c(NCc3cccnc3N(C)S(C)(=O)=O)n2)c1] | N-ethyl-N-(2-methoxyethyl)-3-({4-[({2-[methyl(methylsulfonyl)amino]pyridin-3-yl}methyl)amino]-5-(trifluoromethyl)pyrimidin-2-yl}amino)benzamide (195), trifluoroacetic acid salt | 0.00681 |
| 196 | 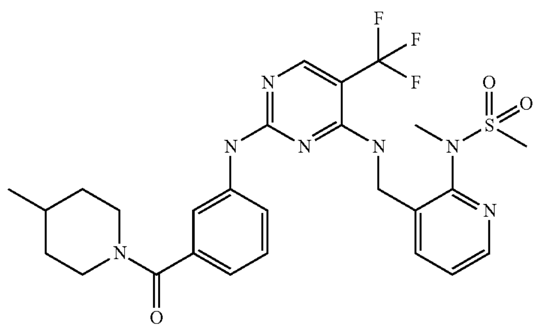 [SMILES: CC1CCN(C(=O)c2cccc(Nc3ncc(C(F)(F)F)c(NCc4cccnc4N(C)S(C)(=O)=O)n3)c2)CC1] | N-methyl-N-[3-({[2-({3-[(4-methylpiperidin-1-yl)carbonyl]phenyl}amino)-5-(trifluoromethyl)pyrimidin-4-yl]amino}methyl)pyridin-2-yl]methanesulfonamide (196) | |
| 197 | 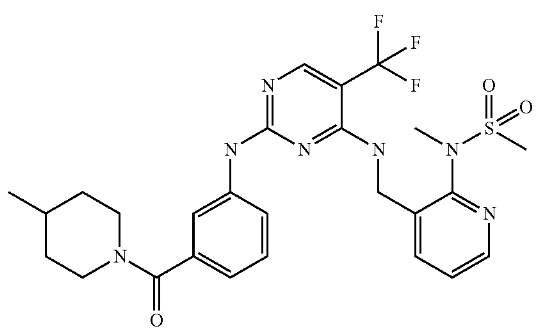 [SMILES: CC1CCN(C(=O)c2cccc(Nc3ncc(C(F)(F)F)c(NCc4cccnc4N(C)S(C)(=O)=O)n3)c2)CC1] | N-methyl-N-[3-({[2-({3-[(4-methylpiperidin-1-yl)carbonyl]phenyl}amino)-5-(trifluoromethyl)pyrimidin-4-yl]amino}methyl)pyridin-2-yl]methanesulfonamide (197), trifluoroacetic acid salt | 0.00447 |
| 198 | 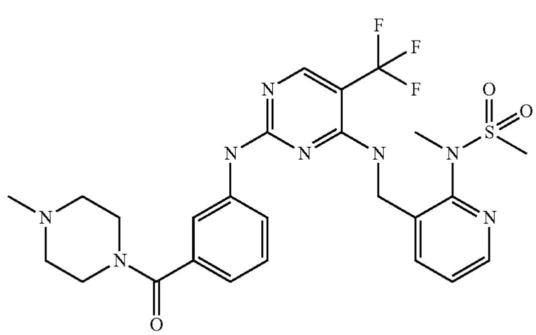 [SMILES: CN1CCN(C(=O)c2cccc(Nc3ncc(C(F)(F)F)c(NCc4cccnc4N(C)S(C)(=O)=O)n3)c2)CC1] | N-methyl-N-[3-({[2-({3-[(4-methylpiperazin-1-yl)carbonyl]phenyl}amino)-5-(trifluoromethyl)pyrimidin-4-yl]amino}methyl)pyridin-2-yl]methanesulfonamide (198) | |

TABLE 1-continued

IC50 values against FAK kinase.

| Ex. | Structure | Compound Name | FAK IC50, μM |
|---|---|---|---|
| 199 | 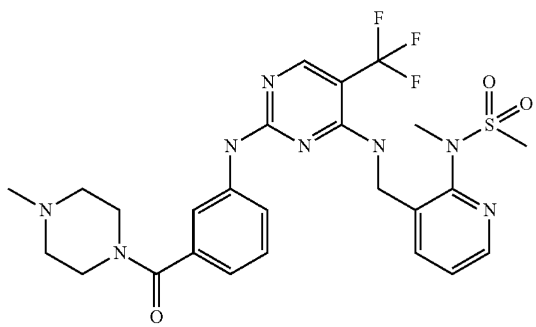 [SMILES: CN1CCN(C(=O)c2cccc(Nc3ncc(C(F)(F)F)c(NCc4cccnc4N(C)S(C)(=O)=O)n3)c2)CC1] | N-methyl-N-[3-({[2-({3-[(4-methylpiperazin-1-yl)carbonyl]phenyl}amino)-5-(trifluoromethyl)pyrimidin-4-yl]amino}methyl)pyridin-2-yl]methanesulfonamide (199), trifluoroacetic acid salt | 0.00256 |
| 200 | 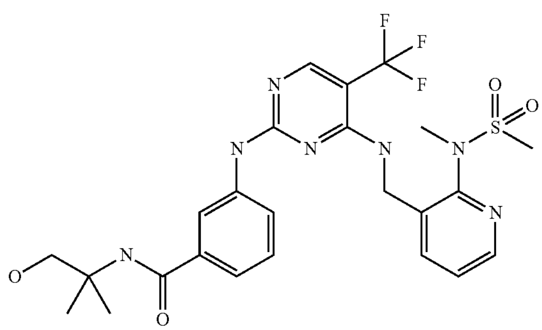 [SMILES: CN(c1ncccc1CNc1nc(Nc2cccc(C(=O)NC(C)(C)CO)c2)ncc1C(F)(F)F)S(C)(=O)=O] | N-(2-hydroxy-1,1-dimethylethyl)-3-({4-[({2-[methyl(methylsulfonyl)amino]pyridin-3-yl}methyl)amino]-5-(trifluoromethyl)pyrimidin-2-yl}amino)benzamide (200) | |
| 201 | 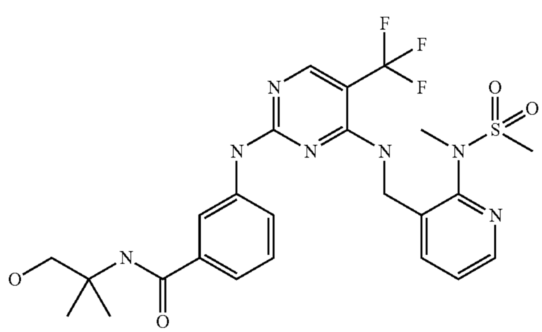 [SMILES: CN(c1ncccc1CNc1nc(Nc2cccc(C(=O)NC(C)(C)CO)c2)ncc1C(F)(F)F)S(C)(=O)=O] | N-(2-hydroxy-1,1-dimethylethyl)-3-({4-[({2-[methyl(methylsulfonyl)amino]pyridin-3-yl}methyl)amino]-5-(trifluoromethyl)pyrimidin-2-yl}amino)benzamide (201), trifluoroacetic acid salt | 0.00164 |
| 202 | 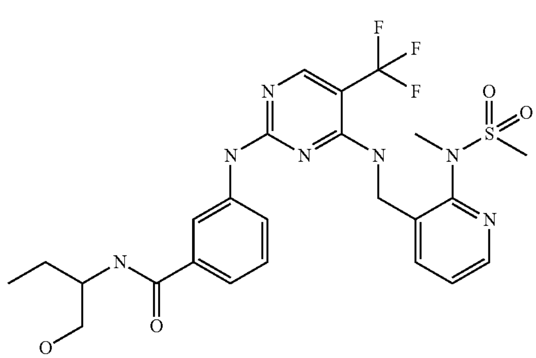 [SMILES: CCC(CO)NC(=O)c1cccc(Nc2ncc(C(F)(F)F)c(NCc3cccnc3N(C)S(C)(=O)=O)n2)c1] | N-[1-(hydroxymethyl)propyl]-3-({4-[({2-[methyl(methylsulfonyl)amino]pyridin-3-yl}methyl)amino]-5-(trifluoromethyl)pyrimidin-2-yl}amino)benzamide (202) | |

TABLE 1-continued

IC50 values against FAK kinase.

| Ex. | Structure | Compound Name | FAK IC50, μM |
|---|---|---|---|
| 203 | 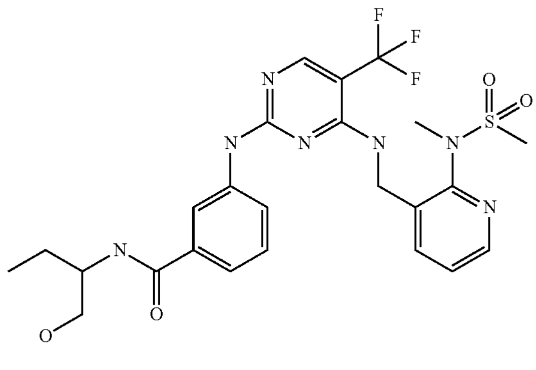 [SMILES: CCC(CO)NC(=O)c1cccc(Nc2ncc(C(F)(F)F)c(NCc3cccnc3N(C)S(C)(=O)=O)n2)c1] | N-[1-(hydroxymethyl) propyl]-3-({4-[({2-[methyl(methylsulfonyl) amino]pyridin-3-yl}methyl)amino]-5-(trifluoromethyl)pyrimidin-2-yl}amino)benzamide (203), trifluoroacetic acid salt | 0.00113 |
| 204 | 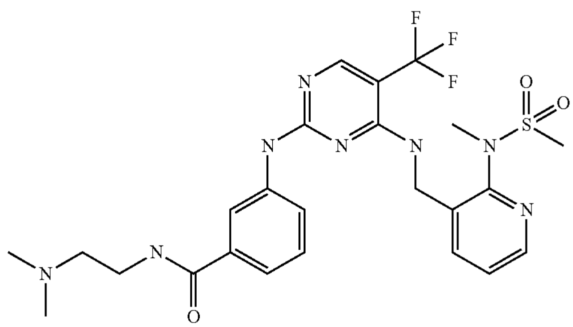 [SMILES: CN(C)CCNC(=O)c1cccc(Nc2ncc(C(F)(F)F)c(NCc3cccnc3N(C)S(C)(=O)=O)n2)c1] | N-[2-(dimethylamino) ethyl]-3-({4-[({2-[methyl(methylsulfonyl) amino]pyridin-3-yl}methyl)amino]-5-(trifluoromethyl)pyrimidin-2-yl}amino)benzamide (204) | |
| 205 | 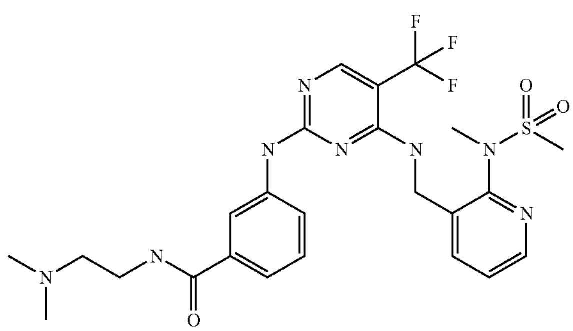 [SMILES: CN(C)CCNC(=O)c1cccc(Nc2ncc(C(F)(F)F)c(NCc3cccnc3N(C)S(C)(=O)=O)n2)c1] | N-[2-(dimethylamino) ethyl]-3-({4-[({2-[methyl(methylsulfonyl) amino]pyridin-3-yl}methyl)amino]-5-(trifluoromethyl)pyrimidin-2-yl}amino)benzamide (205), trifluoroacetic acid salt | 0.0032 |
| 206 | 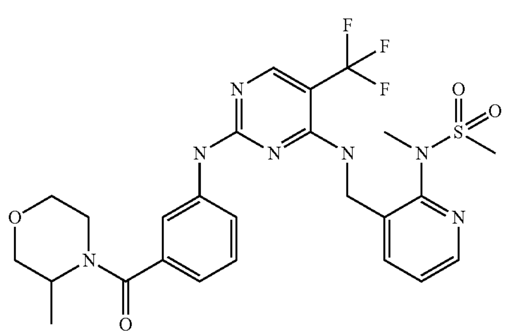 [SMILES: CC1COCCN1C(=O)c1cccc(Nc2ncc(C(F)(F)F)c(NCc3cccnc3N(C)S(C)(=O)=O)n2)c1] | N-methyl-N-{3-[({2-[(3-{[(3R)-3-methylmorpholin-4-yl]carbonyl}phenyl)amino]-5-(trifluoromethyl)pyrimidin-4-yl}amino)methyl]pyridin-2-yl}methanesulfonamide (206) | |

TABLE 1-continued

IC50 values against FAK kinase.

| Ex. | Structure | Compound Name | FAK IC50, μM |
|---|---|---|---|
| 207 | 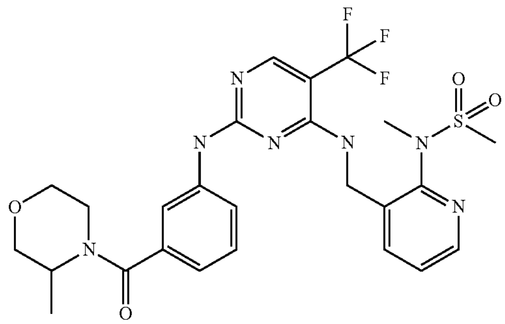 [SMILES: CC1COCCN1C(=O)c1cccc(Nc2ncc(C(F)(F)F)c(NCc3cccnc3N(C)S(C)(=O)=O)n2)c1] | N-methyl-N-{3-[({2-[(3-{[(3R)-3-methylmorpholin-4-yl]carbonyl}phenyl)amino]-5-(trifluoromethyl)pyrimidin-4-yl}amino)methyl]pyridin-2-yl}methanesulfonamide (207), trifluoroacetic acid salt | 0.00278 |
| 208 | 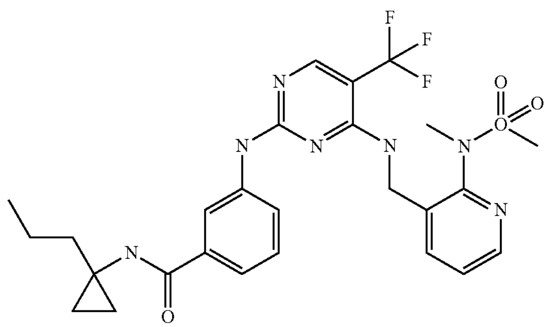 | 3-({4-[({2-[methyl(methylsulfonyl)amino]pyridin-3-yl}methyl)amino]-5-(trifluoromethyl)pyrimidin-2-yl}amino)-N-(1-propylcyclopropyl)benzamide (208) | |
| 209 | 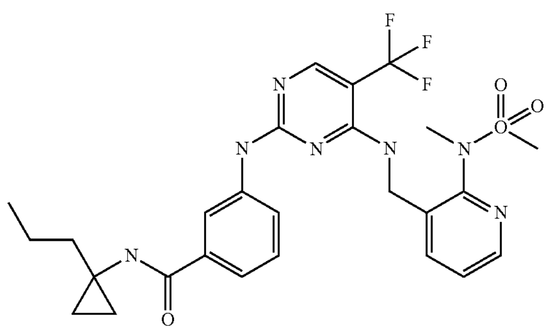 | 3-({4-[({2-[methyl(methylsulfonyl)amino]pyridin-3-yl}methyl)amino]-5-(trifluoromethyl)pyrimidin-2-yl}amino)-N-(1-propylcyclopropyl)benzamide (209), trifluoroacetic acid salt | 0.00368 |
| 210 | 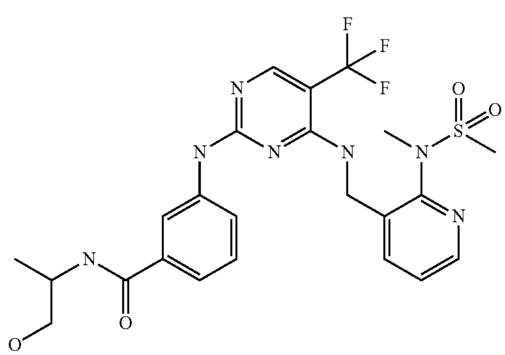 [SMILES: CC(CO)NC(=O)c1cccc(Nc2ncc(C(F)(F)F)c(NCc3cccnc3N(C)S(C)(=O)=O)n2)c1] | N-[(1S)-2-hydroxy-1-methylethyl]-3-({4-[({2-[methyl(methylsulfonyl)amino]pyridin-3-yl}methyl)amino]-5-(trifluoromethyl)pyrimidin-2-yl}amino)benzamide (210) | |

TABLE 1-continued

IC50 values against FAK kinase.

| Ex. | Structure | Compound Name | FAK IC50, μM |
|---|---|---|---|
| 211 | 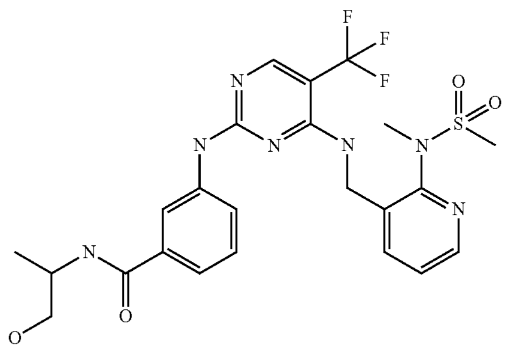 [SMILES: CC(CO)NC(=O)c1cccc(Nc2ncc(C(F)(F)F)c(NCc3cccnc3N(C)S(C)(=O)=O)n2)c1] | N-[(1S)-2-hydroxy-1-methylethyl]-3-({4-[({2-[methyl(methylsulfonyl)amino]pyridin-3-yl}methyl)amino]-5-(trifluoromethyl)pyrimidin-2-yl}amino)benzamide (211), trifluoroacetic acid salt | 0.00106 |
| 212 | 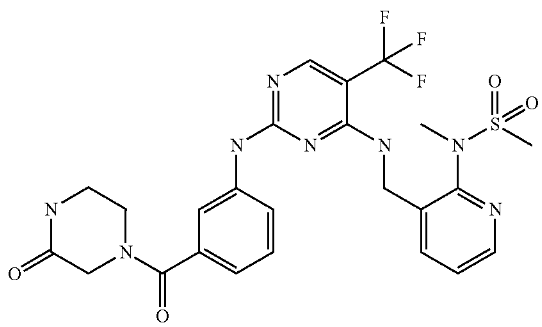 [SMILES: CN(c1ncccc1CNc1nc(Nc2cccc(C(=O)N3CCNC(=O)C3)c2)ncc1C(F)(F)F)S(C)(=O)=O] | N-methyl-N-[3-({[2-({3-[(3-oxopiperazin-1-yl)carbonyl]phenyl}amino)-5-(trifluoromethyl)pyrimidin-4-yl]amino}methyl)pyridin-2-yl]methanesulfonamide (212) | |
| 213 | 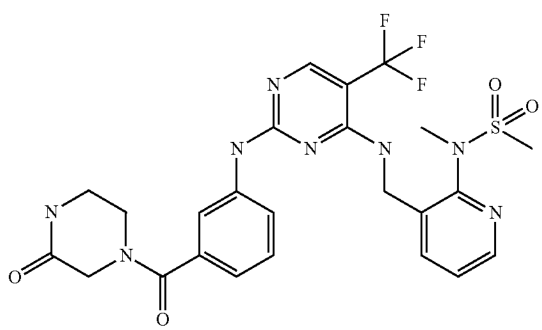 [SMILES: CN(c1ncccc1CNc1nc(Nc2cccc(C(=O)N3CCNC(=O)C3)c2)ncc1C(F)(F)F)S(C)(=O)=O] | N-methyl-N-[3-({[2-({3-[(3-oxopiperazin-1-yl)carbonyl]phenyl}amino)-5-(trifluoromethyl)pyrimidin-4-yl]amino}methyl)pyridin-2-yl]methanesulfonamide (213), trifluoroacetic acid salt | 0.00288 |
| 214 | 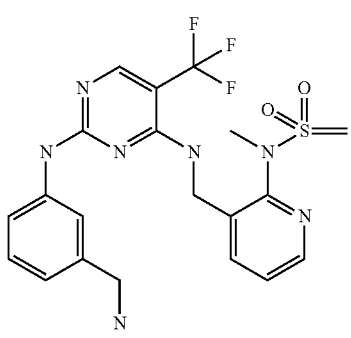 | N-[3-({[2-{[3-(aminomethyl)phenyl]amino}-5-(trifluoromethyl)pyrimidin-4-yl]amino}methyl)pyridin-2-yl]-N-methylmethanesulfonamide (214) | 0.0007 |

TABLE 1-continued

IC50 values against FAK kinase.

| Ex. | Structure | Compound Name | FAK IC50, μM |
|---|---|---|---|
| 215 | 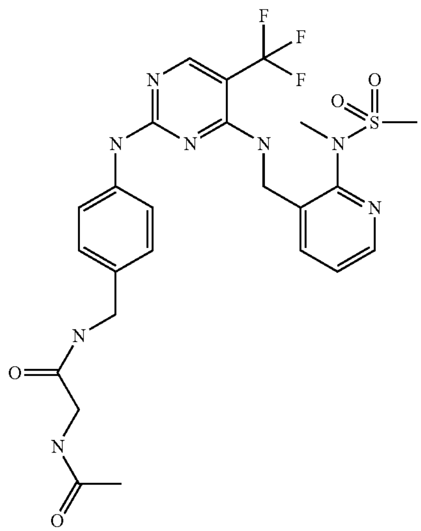 [SMILES: CC(=O)NCC(=O)NCc1ccc(Nc2ncc(C(F)(F)F)c(NCc3cccnc3N(C)S(C)(=O)=O)n2)cc1] | N~2~-acetyl-N-[4-({4-[({2-[methyl(methylsulfonyl)amino]pyridin-3-yl}methyl)amino]-5-(trifluoromethyl)pyrimidin-2-yl}amino)benzyl]glycinamide (215) | 0.0006 |
| 216 | 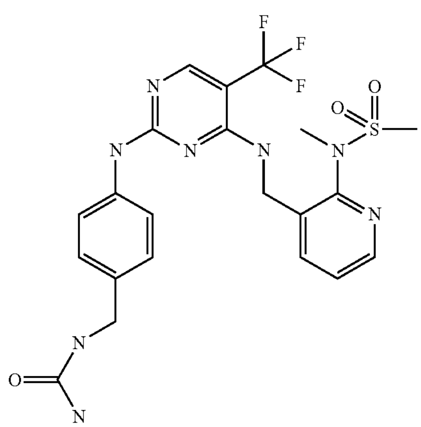 [SMILES: CN(c1ncccc1CNc1nc(Nc2ccc(CNC(N)=O)cc2)ncc1C(F)(F)F)S(C)(=O)=O] | N-{3-[({2-[(4-{[(aminocarbonyl)amino]methyl}phenyl)amino]-5-(trifluoromethyl)pyrimidin-4-yl}amino)methyl]pyridin-2-yl}-N-methylmethane-sulfonamide (216) | 0.0006 |
| 217 | 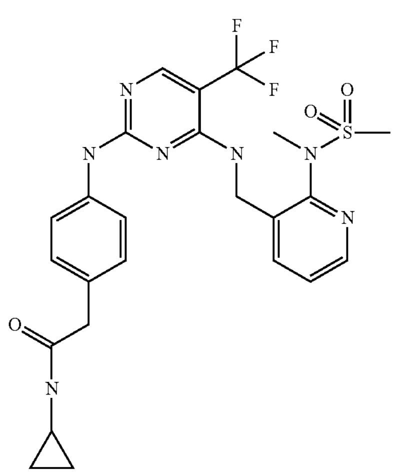 [SMILES: CN(c1ncccc1CNc1nc(Nc2ccc(CC(=O)NC3CC3)cc2)ncc1C(F)(F)F)S(C)(=O)=O] | N-cyclopropyl-2-[4-({4-[({2-[methyl(methylsulfonyl)amino]pyridin-3-yl}methyl)amino]-5-(trifluoromethyl)pyrimidin-2-yl}amino)phenyl]acetamide (217) | 0.0006 |

TABLE 1-continued

IC50 values against FAK kinase.

| Ex. | Structure | Compound Name | FAK IC50, μM |
|---|---|---|---|
| 218 | 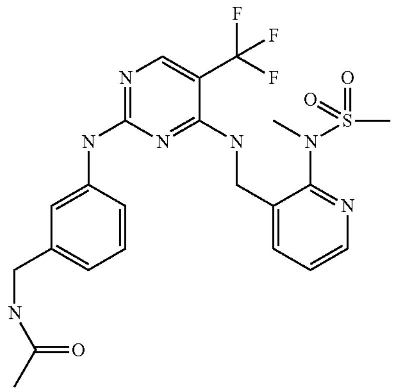 [SMILES: CC(=O)NCc1cccc(Nc2ncc(C(F)(F)F)c(NCc3cccnc3N(C)S(C)(=O)=O)n2)c1] | N-[3-({4-[({2-[methyl(methylsulfonyl)amino]pyridin-3-yl}methyl)amino]-5-(trifluoromethyl)pyrimidin-2-yl}amino)benzyl]acetamide (218) | 0.0006 |
| 219 | 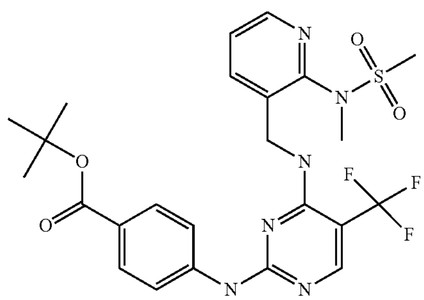 [SMILES: CN(c1ncccc1CNc1nc(Nc2ccc(C(=O)OC(C)(C)C)cc2)ncc1C(F)(F)F)S(C)(=O)=O] | tert-butyl 4-({4-[({2-[methyl(methylsulfonyl)amino]pyridin-3-yl}methyl)amino]-5-(trifluoromethyl)pyrimidin-2-yl}amino)benzoate (219) | 0.0006 |
| 220 | 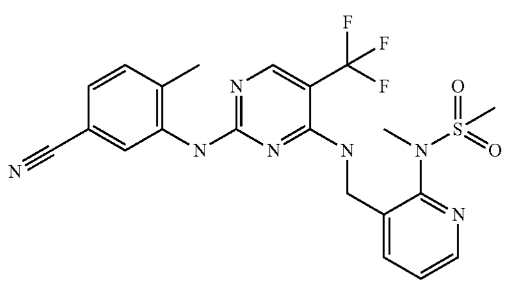 [SMILES: Cc1ccc(C#N)cc1Nc1ncc(C(F)(F)F)c(NCc2cccnc2N(C)S(C)(=O)=O)n1] | N-{3-[({2-[(5-cyano-2-methylphenyl)amino]-5-(trifluoromethyl)pyrimidin-4-yl}amino)methyl]pyridin-2-yl}-N-methylmethanesulfonamide (220) | 0.0006 |
| 221 | 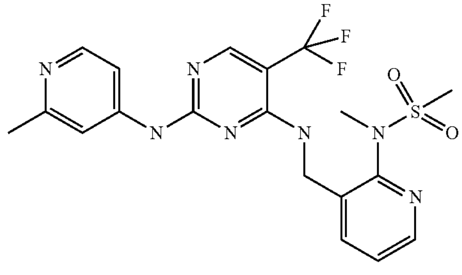 [SMILES: Cc1cc(Nc2ncc(C(F)(F)F)c(NCc3cccnc3N(C)S(C)(=O)=O)n2)ccn1] | N-methyl-N-{3-[({2-[(2-methylpyridin-4-yl)amino]-5-(trifluoromethyl)pyrimidin-4-yl}amino)methyl]pyridin-2-yl}methanesulfonamide (221) | 0.188 |

TABLE 1-continued

IC50 values against FAK kinase.

| Ex. | Structure | Compound Name | FAK IC50, μM |
|---|---|---|---|
| 222 | 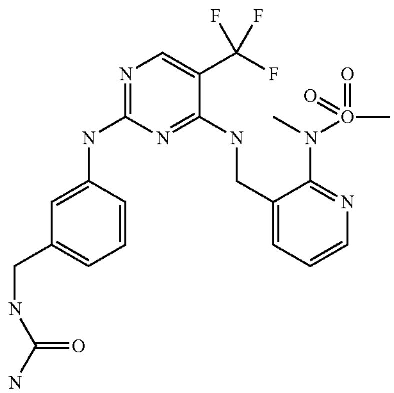 | N-{3-[({2-[(3-{[(aminocarbonyl)amino]-methyl}phenyl)amino]-5-(trifluoromethyl)pyrimidin-4-yl}amino)methyl]pyridin-2-yl}-N-methylmethanesulfonamide (222) | 0.0006 |
| 223 | 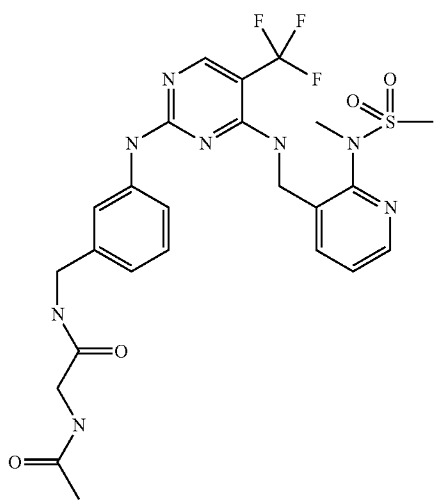 [SMILES: CC(=O)NCC(=O)NCc1cccc(Nc2ncc(C(F)(F)F)c(NCc3cccnc3N(C)S(C)(=O)=O)n2)c1] | N-2-acetyl-N-[3-({4-[({2-[methyl(methylsulfonyl)amino]pyridin-3-yl}methyl)amino]-5-(trifluoromethyl)pyrimidin-2-yl}amino)benzyl]glycinamide (223) | 0.0006 |
| 224 | 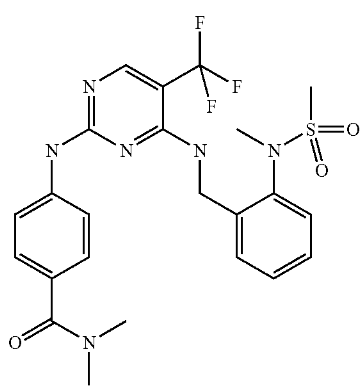 [SMILES: CN(C)C(=O)c1ccc(Nc2ncc(C(F)(F)F)c(NCc3ccccc3N(C)S(C)(=O)=O)n2)cc1] | N,N-dimethyl-4-{[4-({2-[methyl(methylsulfonyl)amino]benzyl}amino)-5-(trifluoromethyl)pyrimidin-2-yl]amino}benzamide (224) | 0.0006 |

TABLE 1-continued

IC50 values against FAK kinase.

| Ex. | Structure | Compound Name | FAK IC50, μM |
|---|---|---|---|
| 225 | 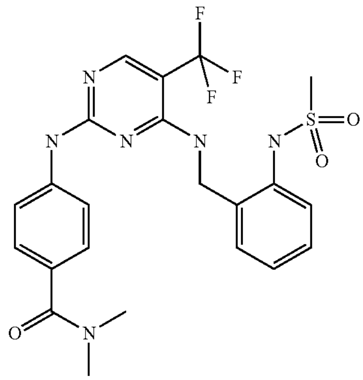 [SMILES: CN(C)C(=O)c1ccc(Nc2ncc(C(F)(F)F)c(NCc3ccccc3NS(C)(=O)=O)n2)cc1] | N,N-dimethyl-4-{[4-({2-[(methylsulfonyl)amino]benzyl}amino)-5-(trifluoromethyl)pyrimidin-2-yl]amino}benzamide (225) | 0.00098 |
| 226 | 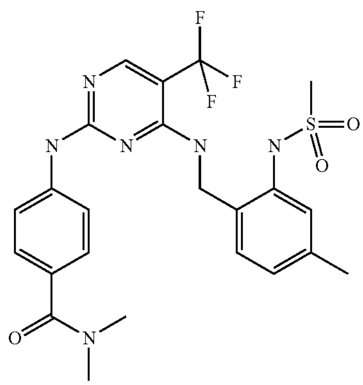 [SMILES: Cc1ccc(CNc2nc(Nc3ccc(C(=O)N(C)C)cc3)ncc2C(F)(F)F)c(NS(C)(=O)=O)c1] | N,N-dimethyl-4-{[4-({4-methyl-2-[(rnethylsulfonyl)amino]benzyl}amino)-5-(trifluoromethyl)pyrimidin-2-yl]amino}benzamide (226) | 0.00292 |
| 227 | 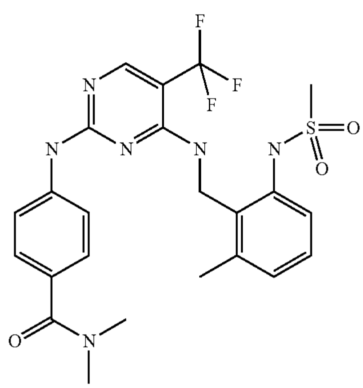 [SMILES: Cc1cccc(NS(C)(=O)=O)c1CNc1nc(Nc2ccc(C(=O)N(C)C)cc2)ncc1C(F)(F)F] | N,N-dimethyl-4-{[4-({2-methyl-6-[(methylsulfonyl)amino]benzyl}amino)-5-(trifluoromethyl)pyrimidin-2-yl]amino}benzamide (227) | 0.00343 |
| 228 | 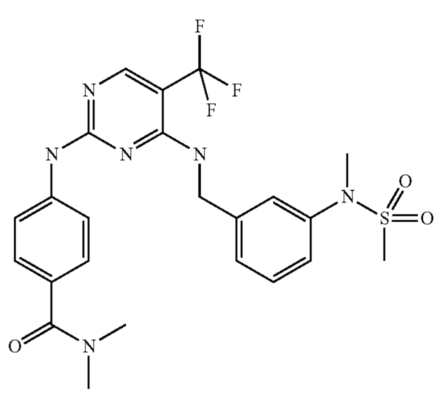 | N,N-dimethyl-4-{[4-({3-[methyl(methylsulfonyl)amino]benzyl}amino)-5-(trifluoromethyl)pyrimidin-2-yl]amino}benzamide (228) | 0.00219 |

TABLE 1-continued

IC50 values against FAK kinase.

| Ex. | Structure | Compound Name | FAK IC50, μM |
|---|---|---|---|
| 229 | 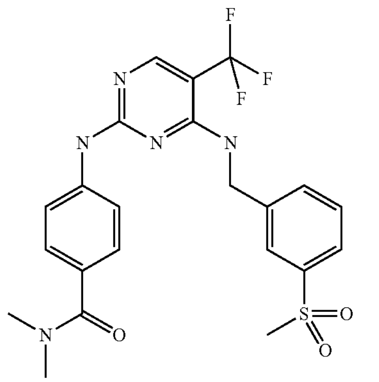 [SMILES: CN(C)C(=O)c1ccc(Nc2ncc(C(F)(F)F)c(NCc3cccc(S(C)(=O)=O)c3)n2)cc1] | N,N-dimethyl-4-{[4-{[3-(methylsulfonyl)benzyl]amino}-5-(trifluoromethyl)pyrimidin-2-yl]amino}benzamide (229) | 0.00493 |
| 230 | 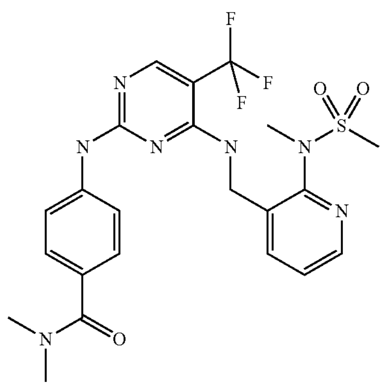 | N,N-dimethyl-4-({4-[({2-[methyl(methylsulfonyl)amino]pyridin-3-yl}methyl)amino]-5-(trifluoromethyl)pyrimidin-2-yl}amino)benzamide (230) | 0.00238 |
| 231 | 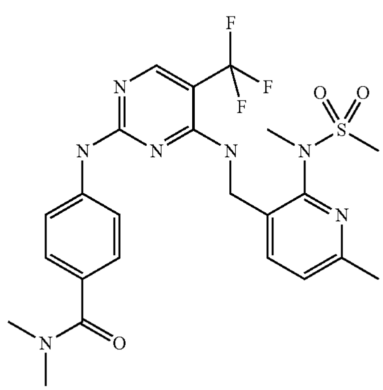 | N,N-dimethyl-4-({4-[({6-methyl-2-[methyl(methylsulfonyl)amino]pyridin-3-yl}methyl)amino]-5-(trifluoromethyl)pyrimidin-2-yl}amino)benzamide (231) | 0.0006 |

TABLE 1-continued

IC50 values against FAK kinase.

| Ex. | Structure | Compound Name | FAK IC50, μM |
|---|---|---|---|
| 232 | ABS 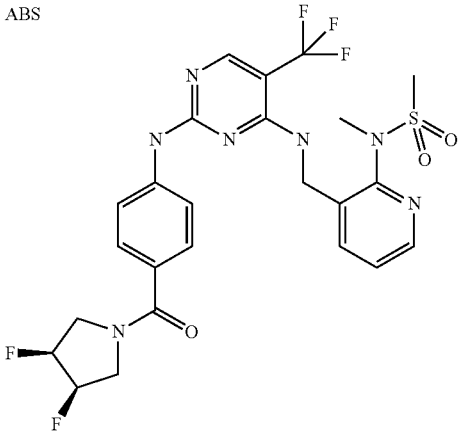 | N-{3-[({2-[(4-{[(3R,4R)-3,4-difluoropyrrolidin-1-yl]carbonyl}phenyl)amino]-5-(trifluoromethyl)pyrimidin-4-yl}amino)methyl]pyridin-2-yl}-N-methylmethane-sulfonamide (232) | 0.00262 |
| 233 | 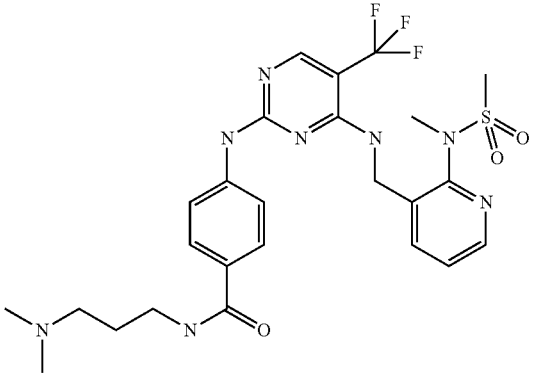 | N-[3-(dimethylamino)propyl]-4-({4-[({2-[methyl(methylsulfonyl)amino]pyridin-3-yl}methyl)amino]-5-(trifluoromethyl)pyrimidin-2-yl}amino)benzamide (233) | 0.00133 |
| 234 | 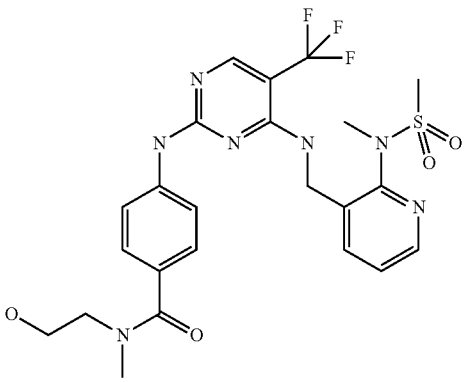 | N-(2-hydroxyethyl)-N-methyl-4-({4-[({2-[methyl(methylsulfonyl)amino]pyridin-3-yl}methyl)amino]-5-(trifluoromethyl)pyrimidin-2-yl}amino)benzamide (234) | 0.00232 |

TABLE 1-continued

IC50 values against FAK kinase.

| Ex. | Structure | Compound Name | FAK IC50, μM |
|---|---|---|---|
| 235 | 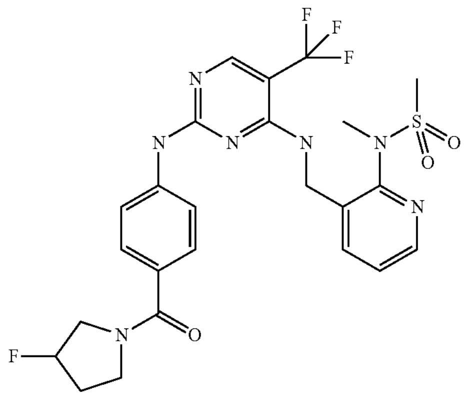 [SMILES: CN(c1ncccc1CNc1nc(Nc2ccc(C(=O)N3CCC(F)C3)cc2)ncc1C(F)(F)F)S(C)(=O)=O] | N-[3-({[2-({4-[(3-fluoropyrrolidin-1-yl)carbonyl]phenyl}amino)-5-(trifluoromethyl)pyrimidin-4-yl]amino}methyl)pyridin-2-yl]-N-methylmethane-sulfonamide (235) | 0.0006 |
| 236 ABS | | N-{3-[({2-[(4-{[(3S)-3-fluoropyrrolidin-1-yl]carbonyl}phenyl)amino]-5-(trifluoromethyl)pyrimidin-4-yl}amino)methyl]pyridin-2-yl}-N-methylmethane-sulfonamide (236) | 0.00141 |
| 237 | 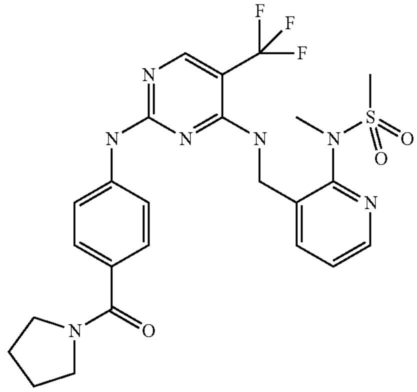 [SMILES: CN(c1ncccc1CNc1nc(Nc2ccc(C(=O)N3CCCC3)cc2)ncc1C(F)(F)F)S(C)(=O)=O] | N-methyl-N-[3-({[2-{[4-(pyrrolidin-1-ylcarbonyl)phenyl]amino}-5-(trifluoromethyl)pyrimidin-4-yl]amino}methyl)pyridin-2-yl]methanesulfonamide (237) | 0.00205 |

TABLE 1-continued

IC50 values against FAK kinase.

| Ex. | Structure | Compound Name | FAK IC50, μM |
|---|---|---|---|
| 238 | ABS | 4-({4-[({2-[methyl(methylsulfonyl)amino]pyridin-3-yl}methyl)amino]-5-(trifluoromethyl)pyrimidin-2-yl}amino)-N-[(2R)-tetrahydrofuran-2-ylmethyl]benzamide (238) | 0.00125 |
| 239 | 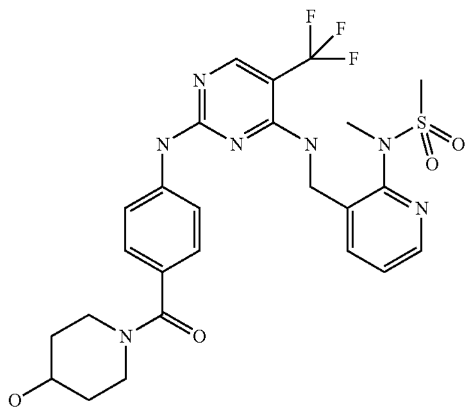 | N-[3-({[2-({4-[(4-hydroxypiperidin-1-yl)carbonyl]phenyl}amino)-5-(trifluoromethyl)pyrimidin-4-yl]amino}methyl)pyridin-2-yl]-N-methylmethane-sulfonamide (239) | 0.0006 |
| 240 | 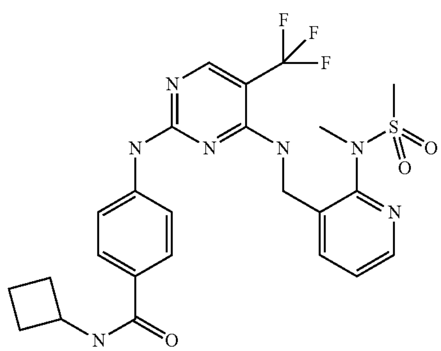 | N-cyclobutyl-4-({4-[({2-[methyl(methylsulfonyl)amino]pyridin-3-yl}methyl)amino]-5-(trifluoromethyl)pyrimidin-2-yl}amino)benzamide (240) | 0.00069 |
| 241 | 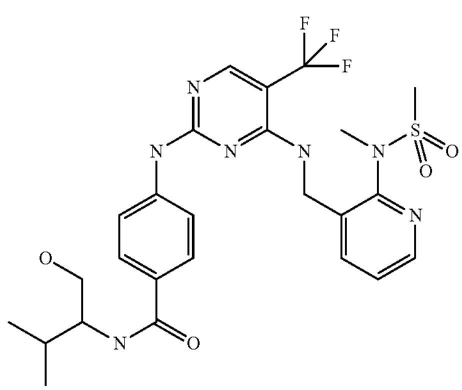 | N-[1-(hydroxymethyl)-2-methylpropyl]-4-({4-[({2-[methyl(methylsulfonyl)amino]pyridin-3-yl}methyl)amino]-5-(trifluoromethyl)pyrimidin-2-yl}amino)benzamide (241) | 0.0006 |

TABLE 1-continued

IC50 values against FAK kinase.

| Ex. | Structure | Compound Name | FAK IC50, μM |
|---|---|---|---|
| 242 | 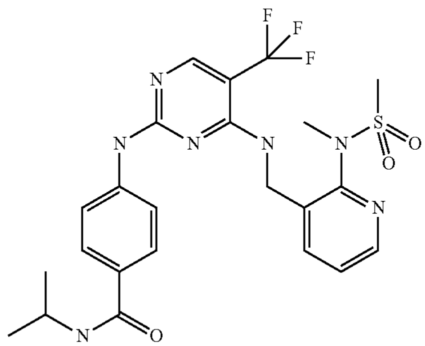 [SMILES: CC(C)NC(=O)c1ccc(Nc2ncc(C(F)(F)F)c(NCc3cccnc3N(C)S(C)(=O)=O)n2)cc1] | N-isopropyl-4-({4-[({2-[methyl(methylsulfonyl)amino]pyridin-3-yl}methyl)amino]-5-(trifluoromethyl)pyrimidin-2-yl}amino)benzamide (242) | 0.001 |
| 243 | 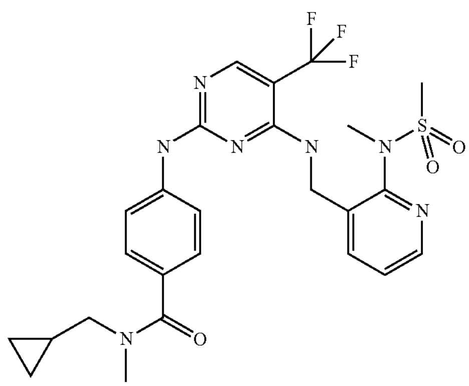 [SMILES: CN(CC1CC1)C(=O)c1ccc(Nc2ncc(C(F)(F)F)c(NCc3cccnc3N(C)S(C)(=O)=O)n2)cc1] | N-(cyclopropylmethyl)-N-methyl-4-({4-[({2-[methyl(methylsulfonyl)amino]pyridin-3-yl}methyl)amino]-5-(trifluoromethyl)pyrimidin-2-yl}amino)benzamide (243) | 0.0021 |
| 244 | 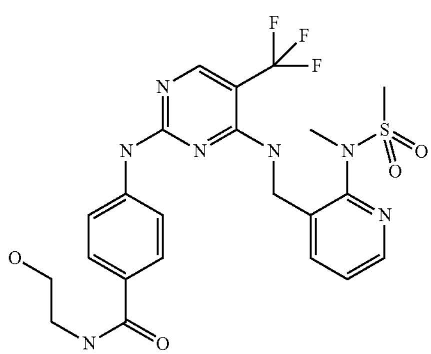 [SMILES: CN(c1ncccc1CNc1nc(Nc2ccc(C(=O)NCCO)cc2)ncc1C(F)(F)F)S(C)(=O)=O] | N-(2-hydroxyethyl)-4-({4-[({2-[methyl(methylsulfonyl)amino]pyridin-3-yl}methyl)amino]-5-(trifluoromethyl)pyrimidin-2-yl}amino)benzamide (244) | 0.00111 |
| 245 | 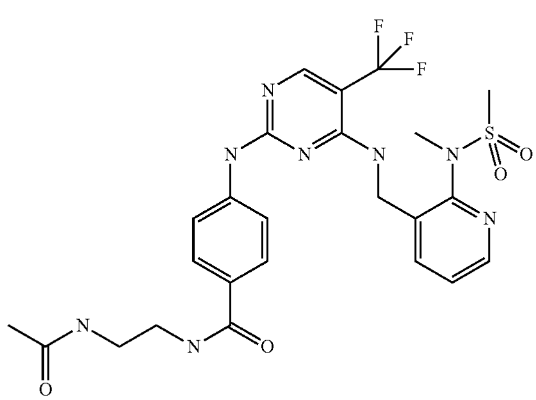 [SMILES: CC(=O)NCCNC(=O)c1ccc(Nc2ncc(C(F)(F)F)c(NCc3cccnc3N(C)S(C)(=O)=O)n2)cc1] | N-[2-(acetylamino)ethyl]-4-({4-[({2-[methyl(methylsulfonyl)amino]pyridin-3-yl}methyl)amino]-5-(trifluoromethyl)pyrimidin-2-yl}amino)benzamide (245) | 0.00262 |

TABLE 1-continued

IC50 values against FAK kinase.

| Ex. | Structure | Compound Name | FAK IC50, µM |
|---|---|---|---|
| 246 | 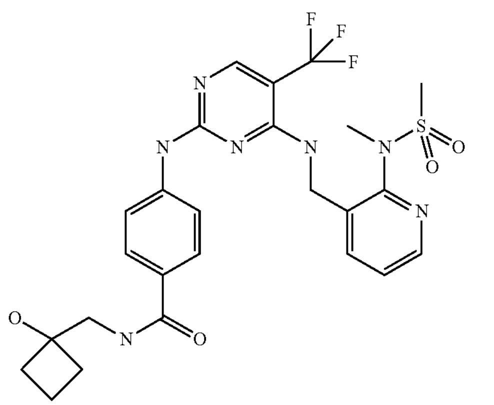 [SMILES: CN(c1ncccc1CNc1nc(Nc2ccc(C(=O)NCC3(O)CCC3)cc2)ncc1C(F)(F)F)S(C)(=O)=O] | N-[(1-hydroxycyclobutyl)methyl]-4-({4-[({2-[methyl(methylsulfonyl)amino]pyridin-3-yl}methyl)amino]-5-(trifluoromethyl)pyrimidin-2-yl}amino)benzamide (246) | 0.0006 |
| 247 | 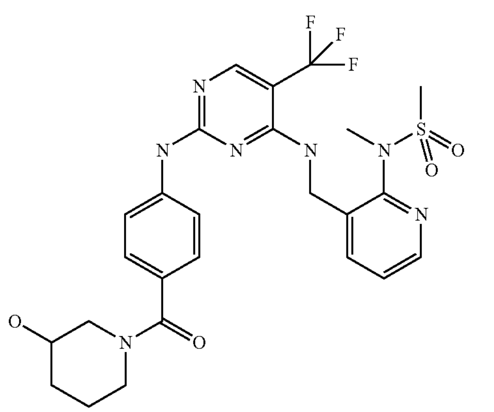 [SMILES: CN(c1ncccc1CNc1nc(Nc2ccc(C(=O)N3CCCC(O)C3)cc2)ncc1C(F)(F)F)S(C)(=O)=O] | N-[3-({[2-({4-[(3-hydroxypiperidin-1-yl)carbonyl]phenyl}amino)-5-(trifluoromethyl)pyrimidin-4-yl]amino}methyl)pyridin-2-yl]-N-methylmethanesulfonamide (247) | 0.00063 |
| 248 | 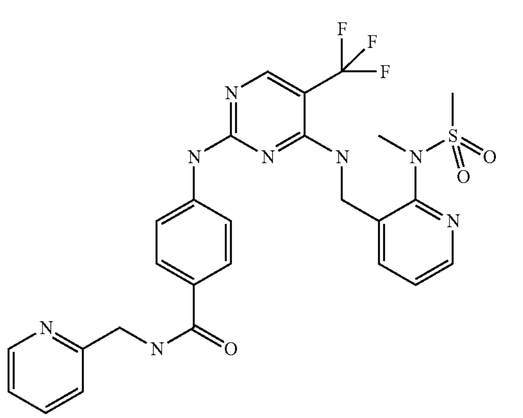 [SMILES: CN(c1ncccc1CNc1nc(Nc2ccc(C(=O)NCc3ccccn3)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)-N-(pyridin-2-ylmethyl)benzamide (248) | 0.00935 |

TABLE 1-continued

IC50 values against FAK kinase.

| Ex. | Structure | Compound Name | FAK IC50, μM |
|---|---|---|---|
| 249 | ABS | N-{3-[({2-[(4-{[(3R)-3-hydroxypyrrolidin-1-yl]carbonyl}phenyl)amino]-5-(trifluoromethyl)pyrimidin-4-yl}amino)methyl]pyridin-2-yl}-N-methylmethane-sulfonamide (249) | 0.00191 |
| 250 | 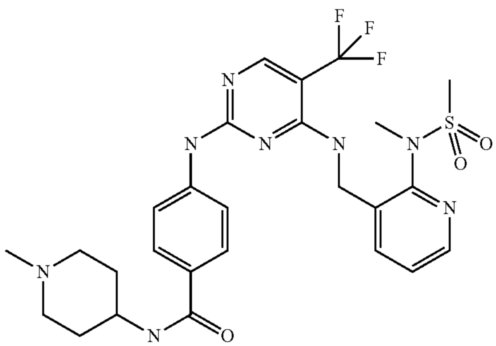 | 4-({4-[({2-[methyl(methylsulfonyl)amino]pyridin-3-yl}methyl)amino]-5-(trifluoromethyl)pyrimidin-2-yl}amino)-N-(1-methylpiperidin-4-yl)benzamide (250) | 0.00069 |
| 251 | 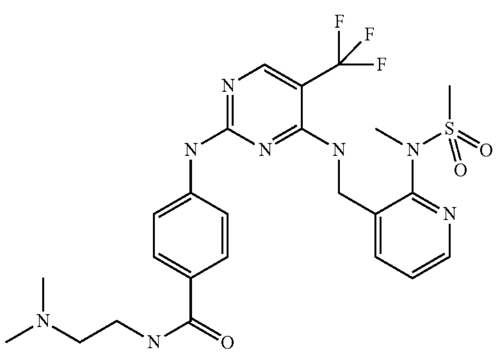 | N-[2-(dimethylamino)ethyl]-4-({4-[({2-[methyl(methylsulfonyl)amino]pyridin-3-yl}methyl)amino]-5-(trifluoromethyl)pyrimidin-2-yl}amino)benzamide (251) | 0.00121 |
| 252 | 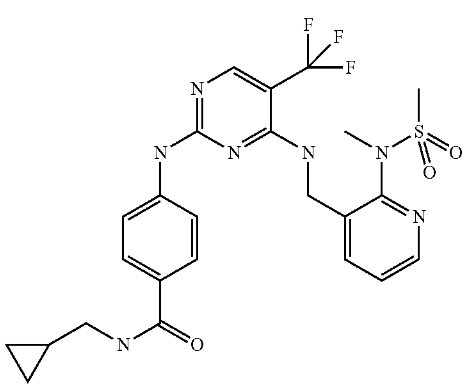 | N-(cyclopropylmethyl)-4-({4-[({2-[methyl(methylsulfonyl)amino]pyridin-3-yl}methyl)amino]-5-(trifluoromethyl)pyrimidin-2-yl}amino)benzamide (252) | 0.00148 |

TABLE 1-continued

IC50 values against FAK kinase.

| Ex. | Structure | Compound Name | FAK IC50, µM |
|---|---|---|---|
| 253 | 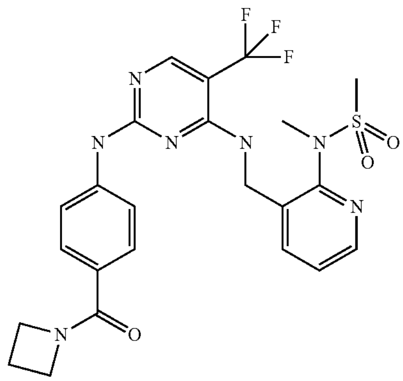 [SMILES: CN(c1ncccc1CNc1nc(Nc2ccc(C(=O)N3CCC3)cc2)ncc1C(F)(F)F)S(C)(=O)=O] | N-[3-({[2-{[4-(azetidin-1-ylcarbonyl)phenyl]amino}-5-(trifluoromethyl)pyrimidin-4-yl]amino}methyl)pyridin-2-yl]-N-methylmethane-sulfonamide (253) | 0.0006 |
| 254 | 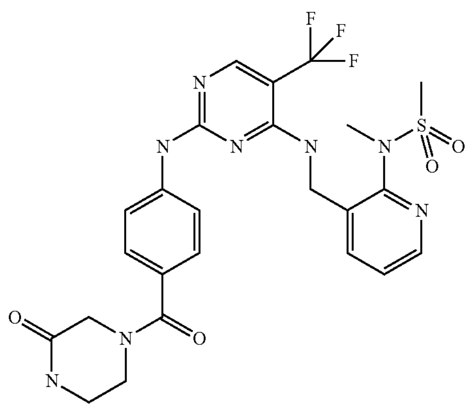 [SMILES: CN(c1ncccc1CNc1nc(Nc2ccc(C(=O)N3CCNC(=O)C3)cc2)ncc1C(F)(F)F)S(C)(=O)=O] | N-methyl-N-[3-({[2-({4-[(3-oxopiperazin-1-yl)carbonyl]phenyl}amino)-5-(trifluoromethyl)pyrimidin-4-yl]amino}methyl)pyridin-2-yl]methanesulfonamide (254) | 0.00133 |
| 255 | 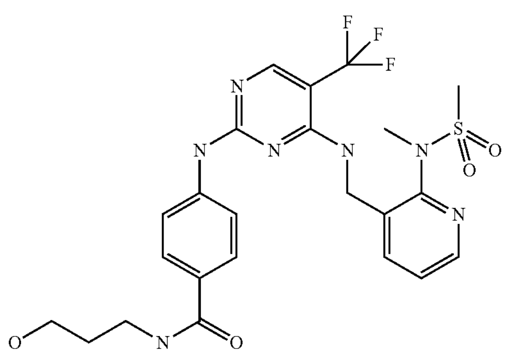 [SMILES: CN(c1ncccc1CNc1nc(Nc2ccc(C(=O)NCCCO)cc2)ncc1C(F)(F)F)S(C)(=O)=O] | N-(3-hydroxypropyl)-4-({4-[({2-[methyl(methylsulfonyl)amino]pyridin-3-yl}methyl)amino]-5-(trifluoromethyl)pyrimidin-2-yl}amino)benzamide (255) | 0.00082 |
| 256 | 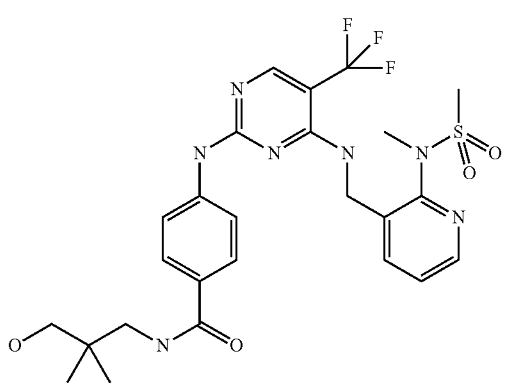 [SMILES: CN(c1ncccc1CNc1nc(Nc2ccc(C(=O)NCC(C)(C)CO)cc2)ncc1C(F)(F)F)S(C)(=O)=O] | N-(3-hydroxy-2,2-dimethylpropyl)-4-({4-[({2-[methyl(methylsulfonyl)amino]pyridin-3-yl}methyl)amino]-5-(trifluoromethyl)pyrimidin-2-yl}amino)benzamide (256) | 0.00157 |

TABLE 1-continued

IC50 values against FAK kinase.

| Ex. | Structure | Compound Name | FAK IC50, µM |
|---|---|---|---|
| 257 | ABS | N-[(1R)-1-(hydroxymethyl)butyl]-4-({4-[({2-[methyl(methylsulfonyl)amino]pyridin-3-yl}methyl)amino]-5-(trifluoromethyl)pyrimidin-2-yl}amino)benzamide (257) | 0.0058 |
| 258 | 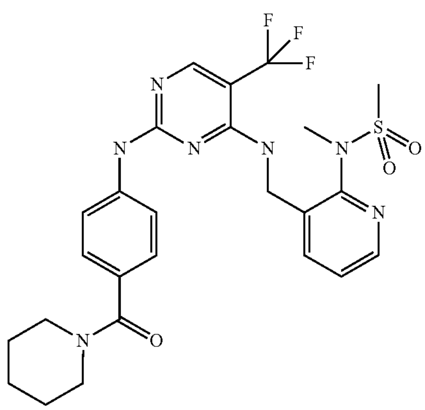 | N-methyl-N-[3-({[2-{[4-(piperidin-1-ylcarbonyl)phenyl]amino}-5-(trifluoromethyl)pyrimidin-4-yl]amino}methyl)pyridin-2-yl]methanesulfonamide (258) | 0.00179 |
| 259 | 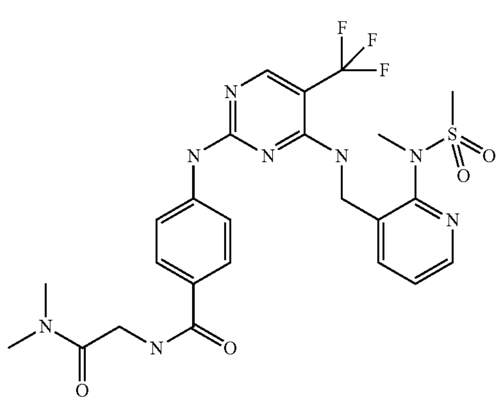 | N-[2-(dimethylamino)-2-oxoethyl]-4-({4-[({2-[methyl(methylsulfonyl)amino]pyridin-3-yl}methyl)amino]-5-(trifluoromethyl)pyrimidin-2-yl}amino)benzamide (259) | 0.00157 |

| Ex. | Structure | Compound Name | FAK IC50, μM |
|---|---|---|---|
| 260 | ABS | N-{3-[({2-[(4-{[(3S)-3-hydroxypiperidin-1-yl]carbonyl}phenyl)amino]-5-(trifluoromethyl)pyrimidin-4-yl}amino)methyl]pyridin-2-yl}-N-methylmethanesulfonamide (260) | 0.0023 |
| 261 | ABS | N-methyl-N-{3-[({2-[(4-{[(3S)-3-methylmorpholin-4-yl]carbonyl}phenyl)amino]-5-(trifluoromethyl)pyrimidin-4-yl}amino)methyl]pyridin-2-yl}methanesulfonamide (261) | 0.00113 |
| 262 | 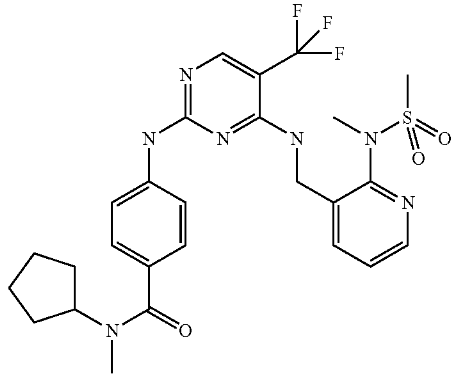 | N-cyclopentyl-N-methyl-4-({4-[({2-[methyl(methylsulfonyl)amino]pyridin-3-yl}methyl)amino]-5-(trifluoromethyl)pyrimidin-2-yl}amino)benzamide (262) | 0.0058 |

TABLE 1-continued

IC50 values against FAK kinase.

| Ex. | Structure | Compound Name | FAK IC50, μM |
|-----|-----------|---------------|--------------|
| 263 | 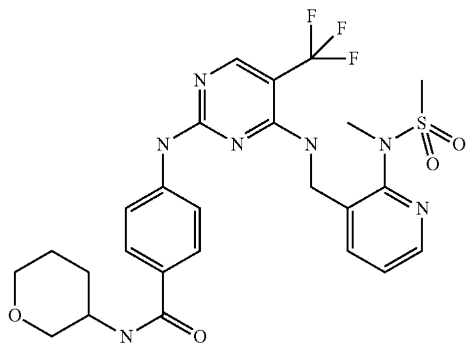 [SMILES: CN(c1ncccc1CNc1nc(Nc2ccc(C(=O)NC3CCCOC3)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}amino)-N-(tetrahydro-2H-pyran-3-yl)benzamide (263) | 0.00081 |
| 264 | 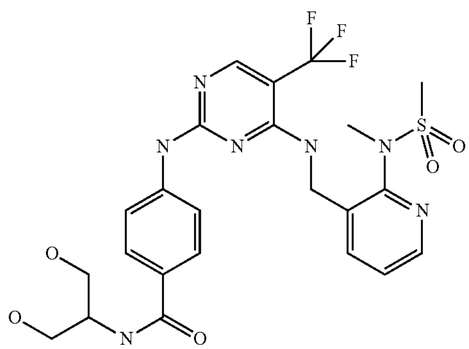 [SMILES: CN(c1ncccc1CNc1nc(Nc2ccc(C(=O)NC(CO)CO)cc2)ncc1C(F)(F)F)S(C)(=O)=O] | N-[2-hydroxy-1-(hydroxymethyl)ethyl]-4-({4-[({2-[methyl(methylsulfonyl)amino]pyridin-3-yl}methyl)amino]-5-(trifluoromethyl)pyrimidin-2-yl}amino)benzamide (264) | 0.0046 |
| 265 | 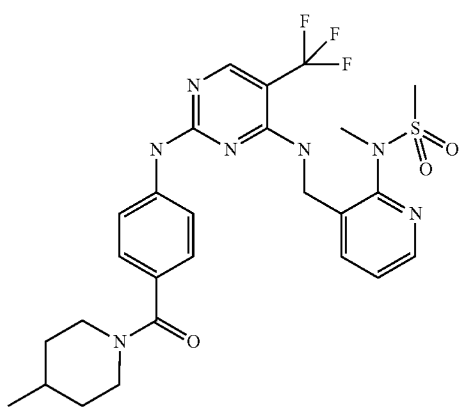 [SMILES: CC1CCN(C(=O)c2ccc(Nc3ncc(C(F)(F)F)c(NCc4cccnc4N(C)S(C)(=O)=O)n3)cc2)CC1] | N-methyl-N-[3-({[2-({4-[(4-methylpiperidin-1-yl)carbonyl]phenyl}amino)-5-(trifluoromethyl)pyrimidin-4-yl]amino}methyl)pyridin-2-yl]methanesulfonamide (265) | 0.0006 |
| 266 | 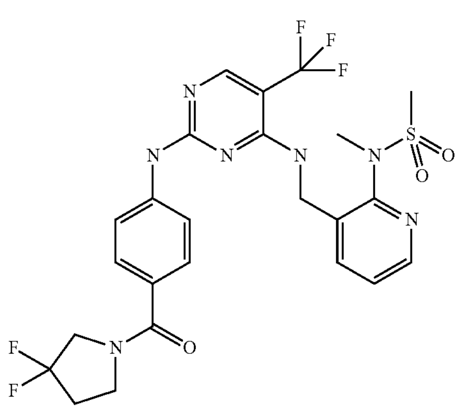 | N-[3-({[2-({4-[(3,3-difluoropyrrolidin-1-yl)carbonyl]phenyl}amino)-5-(trifluoromethyl)pyrimidin-4-yl]amino}methyl)pyridin-2-yl]-N-methylmethane-sulfonamide (266) | 0.0006 |

TABLE 1-continued

IC50 values against FAK kinase.

| Ex. | Structure | Compound Name | FAK IC50, µM |
|---|---|---|---|
| 267 | ABS | N-{3-[({2-[(4-{[(3S)-3-hydroxypyrrolidin-1-yl]carbonyl}phenyl)amino]-5-(trifluoromethyl)pyrimidin-4-yl}amino)methyl]pyridin-2-yl}-N-methylmethane-sulfonamide (267) | 0.00115 |
| 268 | 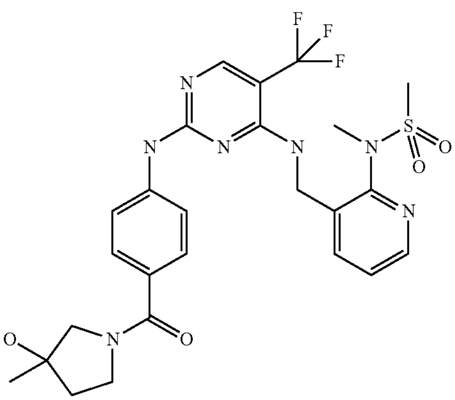 | N-[3-({[2-({4-[(3-hydroxy-3-methylpyrrolidin-1-yl)carbonyl]phenyl}amino)-5-(trifluoromethyl)pyrimidin-4-yl]amino}methyl)pyridin-2-yl]-N-methylmethane-sulfonamide (268) | 0.00262 |
| 269 | 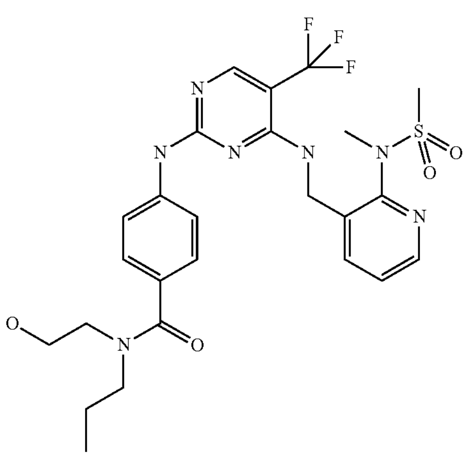 | N-(2-hydroxyethyl)-4-({4-[({2-[methyl(methylsulfonyl)amino]pyridin-3-yl}methyl)amino]-5-(trifluoromethyl)pyrimidin-2-yl}amino)-N-propylbenzamide (269) | 0.00869 |

TABLE 1-continued

IC50 values against FAK kinase.

| Ex. | Structure | Compound Name | FAK IC50, μM |
|---|---|---|---|
| 270 | 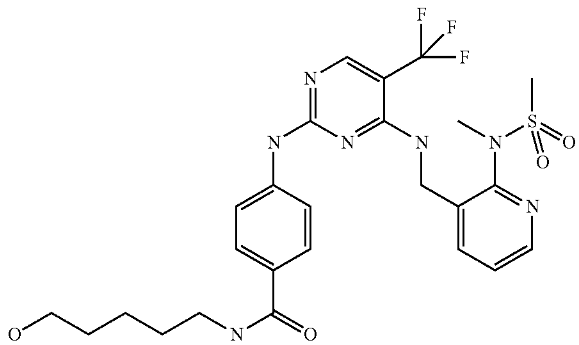 [SMILES: CN(c1ncccc1CNc1nc(Nc2ccc(C(=O)NCCCCCO)cc2)ncc1C(F)(F)F)S(C)(=O)=O] | N-(5-hydroxypentyl)-4-({4-[({2-[methyl(methylsulfonyl)amino]pyridin-3-yl}methyl)amino]-5-(trifluoromethyl)pyrimidin-2-yl}amino)benzamide (270) | 0.00099 |
| 271 | 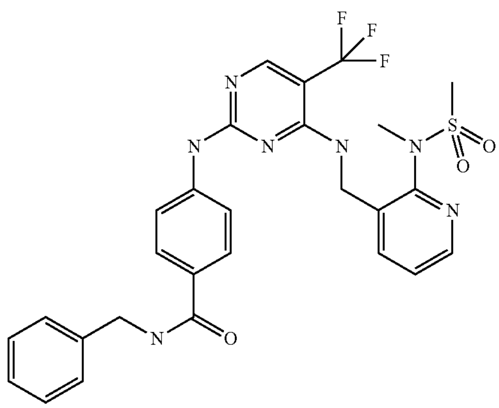 [SMILES: CN(c1ncccc1CNc1nc(Nc2ccc(C(=O)NCc3ccccc3)cc2)ncc1C(F)(F)F)S(C)(=O)=O] | N-benzyl-4-({4-[({2-[methyl(methylsulfonyl)amino]pyridin-3-yl}methyl)amino]-5-(trifluoromethyl)pyrimidin-2-yl}amino)benzamide (271) | 0.00114 |
| 272 | 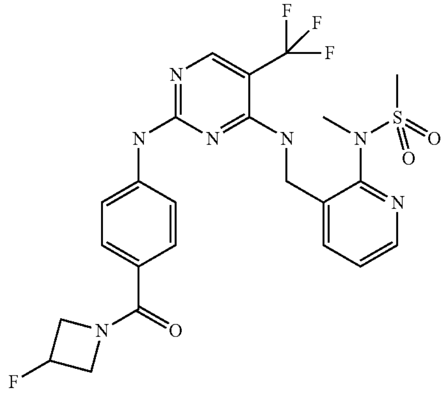 [SMILES: CN(c1ncccc1CNc1nc(Nc2ccc(C(=O)N3CC(F)C3)cc2)ncc1C(F)(F)F)S(C)(=O)=O] | N-[3-({[2-({4-[(3-fluoroazetidin-1-yl)carbonyl]phenyl}amino)-5-(trifluoromethyl)pyrimidin-4-yl]amino}methyl)pyridin-2-yl]-N-methylmethane-sulfonamide (272) | 0.00264 |

TABLE 1-continued

IC50 values against FAK kinase.

| Ex. | Structure | Compound Name | FAK IC50, μM |
|---|---|---|---|
| 273 | ABS | N-{[(1R,2R)-2-(hydroxymethyl)cyclopropyl]methyl}-4-({4-[({2-[methyl(methylsulfonyl)amino]pyridin-3-yl}methyl)amino]-5-(trifluoromethyl)pyrimidin-2-yl}amino)benzamide (273) | 0.00269 |
| 274 | 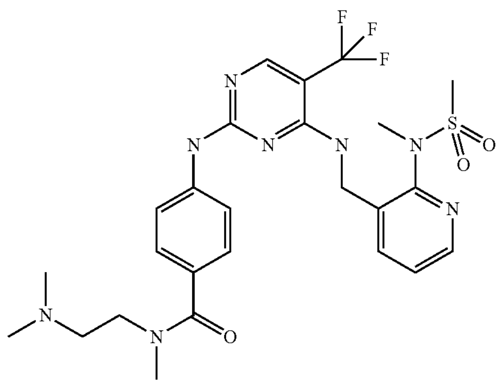 | N-[2-(dimethylamino)ethyl]-N-methyl-4-({4-[({2-[methyl(methylsulfonyl)amino]pyridin-3-yl}methyl)amino]-5-(trifluoromethyl)pyrimidin-2-yl}amino)benzamide (274) | 0.00466 |
| 275 | ABS | N-{3-[({2-[(4-{[(3R)-3-hydroxypiperidin-1-yl]carbonyl}phenyl)amino]-5-(trifluoromethyl)pyrimidin-4-yl}amino)methyl]pyridin-2-yl}-N-methylmethanesulfonamide (275) | 0.00236 |
| 276 | 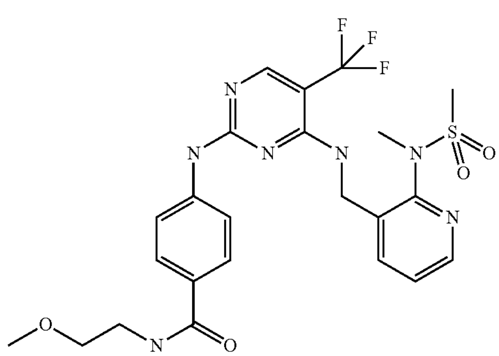 | N-(2-methoxyethyl)-4-({4-[({2-[methyl(methylsulfonyl)amino]pyridin-3-yl}methyl)amino]-5-(trifluoromethyl)pyrimidin-2-yl}amino)benzamide (276) | 0.0006 |

TABLE 1-continued

IC50 values against FAK kinase.

| Ex. | Structure | Compound Name | FAK IC50, µM |
|---|---|---|---|
| 277 | 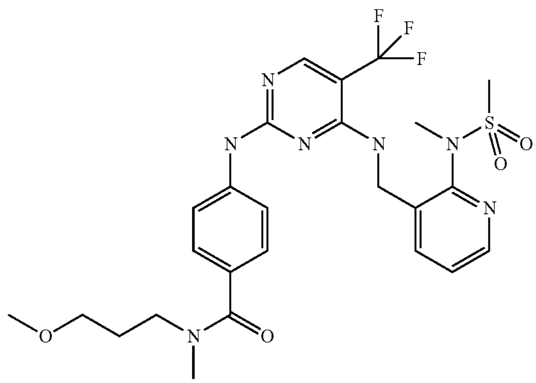 [SMILES: COCCCN(C)C(=O)c1ccc(Nc2ncc(C(F)(F)F)c(NCc3cccnc3N(C)S(C)(=O)=O)n2)cc1] | N-(3-methoxypropyl)-N-methyl-4-({4-[({2-[methyl(methylsulfonyl)amino]pyridin-3-yl}methyl)amino]-5-(trifluoromethyl)pyrimidin-2-yl}amino)benzamide (277) | 0.00236 |
| 278 | ABS | N-methyl-N-{3-[({2-[(4-{[(3R)-3-methylmorpholin-4-yl]carbonyl}phenyl)amino]-5-(trifluoromethyl)pyrimidin-4-yl}amino)methyl]pyridin-2-yl}methanesulfonamide (278) | 0.00664 |
| 279 | 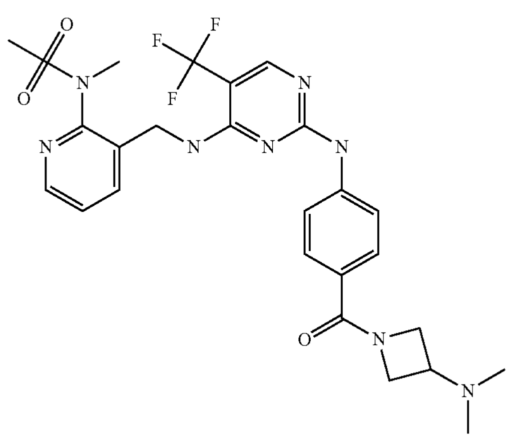 | N-{3-[({2-[(4-{[3-(dimethylamino)azetidin-1-yl]carbonyl}phenyl)amino]-5-(trifluoromethyl)pyrimidin-4-yl}amino)methyl]pyridin-2-yl}-N-methylmethanesulfonamide (279) | 0.00397 |

TABLE 1-continued

IC50 values against FAK kinase.

| Ex. | Structure | Compound Name | FAK IC50, μM |
|---|---|---|---|
| 280 | 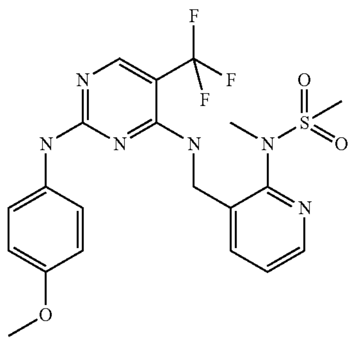 [SMILES: COc1ccc(Nc2ncc(C(F)(F)F)c(NCc3cccnc3N(C)S(C)(=O)=O)n2)cc1] | N-{3-[({2-[(4-methoxyphenyl)amino]-5-(trifluoromethyl)pyrimidin-4-yl}amino)methyl]pyridin-2-yl}-N-methylmethane-sulfonamide (280) | 0.0006 |
| 281 | 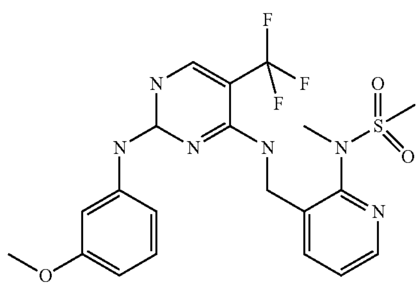 | N-{3-[({2-[(3-methoxyphenyl)amino]-5-(trifluoromethyl)pyrimidin-4-yl}amino)methyl]pyridin-2-yl}-N-methylmethane-sulfonamide (281) | 0.0006 |
| 282 | 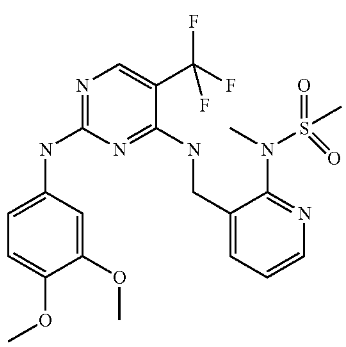 [SMILES: COc1ccc(Nc2ncc(C(F)(F)F)c(NCc3cccnc3N(C)S(C)(=O)=O)n2)cc1OC] | N-{3-[({2-[(3,4-dimethoxyphenyl)amino]-5-(trifluoromethyl)pyrimidin-4-yl}amino)methyl]pyridin-2-yl}-N-methylmethane-sulfonamide (282) | 0.0006 |
| 283 | 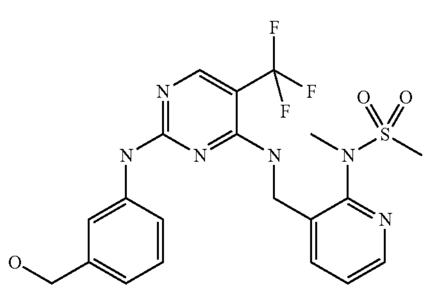 [SMILES: CN(c1ncccc1CNc1nc(Nc2cccc(CO)c2)ncc1C(F)(F)F)S(C)(=O)=O] | N-[3-({[2-{[3-(hydroxymethyl)phenyl]amino}-5-(trifluoromethyl)pyrimidin-4-yl]amino}methyl)pyridin-2-yl]-N-methylmethane-sulfonamide (283) | 0.0006 |

TABLE 1-continued

IC50 values against FAK kinase.

| Ex. | Structure | Compound Name | FAK IC50, μM |
|---|---|---|---|
| 284 | 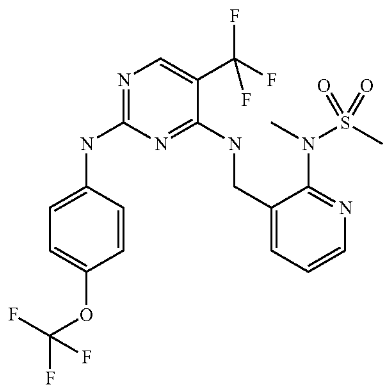 [SMILES: CN(c1ncccc1CNc1nc(Nc2ccc(OC(F)(F)F)cc2)ncc1C(F)(F)F)S(C)(=O)=O] | N-methyl-N-[3-({[2-{[4-(trifluoromethoxy)phenyl]amino}-5-(trifluoromethyl)pyrimidin-4-yl]amino}methyl)pyridin-2-yl]methanesulfonamide (284) | 0.00183 |
| 285 | 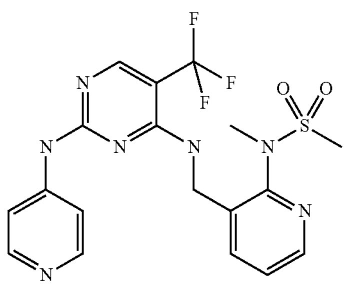 [SMILES: CN(c1ncccc1CNc1nc(Nc2ccncc2)ncc1C(F)(F)F)S(C)(=O)=O] | N-methyl-N-[3-({[2-(pyridin-4-ylamino)-5-(trifluoromethyl)pyrimidin-4-yl]amino}methyl)pyridin-2-yl]methanesulfonamide (285) | 0.00127 |
| 286 | 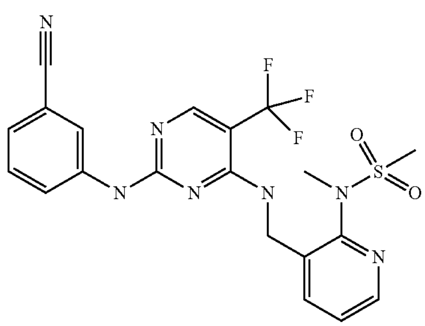 [SMILES: CN(c1ncccc1CNc1nc(Nc2cccc(C#N)c2)ncc1C(F)(F)F)S(C)(=O)=O] | N-{3-[({2-[(3-cyanophenyl)amino]-5-(trifluoromethyl)pyrimidin-4-yl}amino)methyl]pyridin-2-yl}-N-methylmethanesulfonamide (286) | 0.00164 |
| 287 | 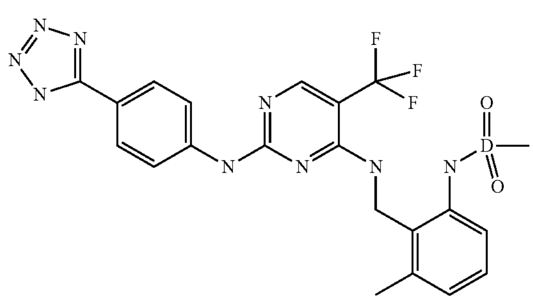 | N-[3-methyl-2-({[2-{[4-(1H-tetrazol-5-yl)phenyl]amino}-5-(trifluoromethyl)pyrimidin-4-yl]amino}methyl)phenyl]methanesulfonamide (287) | 0.00195 |

TABLE 1-continued

IC50 values against FAK kinase.

| Ex. | Structure | Compound Name | FAK IC50, μM |
|---|---|---|---|
| 288 | 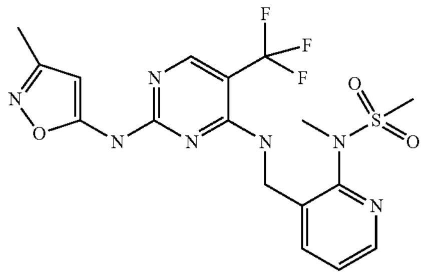 [SMILES: Cc1cc(Nc2ncc(C(F)(F)F)c(NCc3cccnc3N(C)S(C)(=O)=O)n2)on1] | N-methyl-N-{3-[({2-[(3-methylisoxazol-5-yl)amino]-5-(trifluoromethyl)pyrimidin-4-yl}amino)methyl]pyridin-2-yl}methanesulfonamide (288) | |
| 289 | 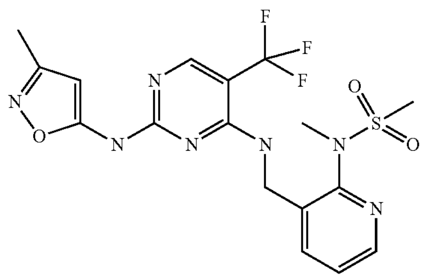 [SMILES: Cc1cc(Nc2ncc(C(F)(F)F)c(NCc3cccnc3N(C)S(C)(=O)=O)n2)on1] | N-methyl-N-{3-[({2-[(3-methylisoxazol-5-yl)amino]-5-(trifluoromethyl)pyrimidin-4-yl}amino)methyl]pyridin-2-yl}methanesulfonamide (289), formic acid salt | 0.0182 |
| 290 | 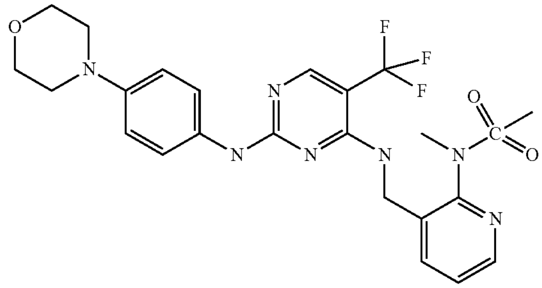 | N-methyl-N-{3-[({2-[(4-morpholin-4-ylphenyl)amino]-5-(trifluoromethyl)pyrimidin-4-yl}amino)methyl]pyridin-2-yl}methanesulfonamide (290) | |
| 291 | 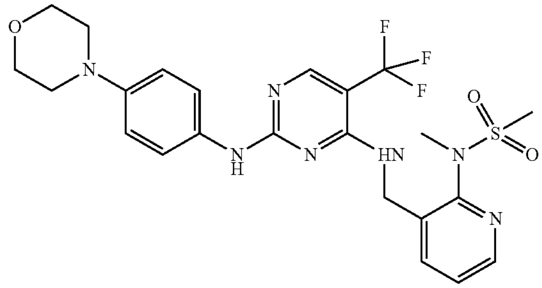 [SMILES: CN(c1ncccc1CNc1nc(Nc2ccc(N3CCOCC3)cc2)ncc1C(F)(F)F)S(C)(=O)=O] | N-methyl-N-{3-[({2-[(4-morpholin-4-ylphenyl)amino]-5-(trifluoromethyl)pyrimidin-4-yl}amino)methyl]pyridin-2-yl}methanesulfonamide (291), hydrochloride salt | <0.000595 |
| 292 | 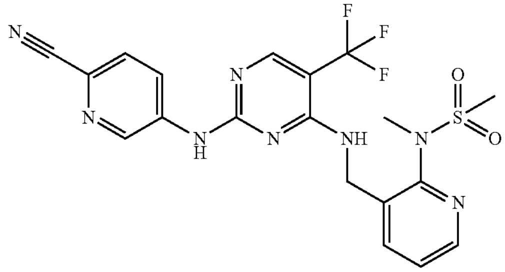 [SMILES: CN(c1ncccc1CNc1nc(Nc2ccc(C#N)nc2)ncc1C(F)(F)F)S(C)(=O)=O] | N-{3-[({2-[(6-cyanopyridin-3-yl)amino]-5-(trifluoromethyl)pyrimidin-4-yl}amino)methyl]pyridin-2-yl}-N-methylmethanesulfonamide (292), trifluoroacetic acid salt | 0.0233 |

TABLE 1-continued

IC50 values against FAK kinase.

| Ex. | Structure | Compound Name | FAK IC50, μM |
|---|---|---|---|
| 293 | 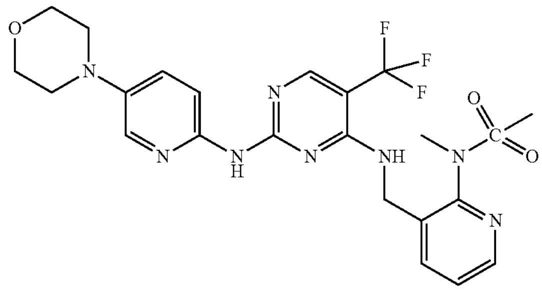 | N-methyl-N-{3-[({2-[(5-morpholin-4-ylpyridin-2-yl)amino]-5-(trifluoromethyl)pyrimidin-4-yl}amino)methyl]pyridin-2-yl}methanesulfonamide (293), trifluoroacetic acid salt | <0.000595 (n = 2) |
| 294 | 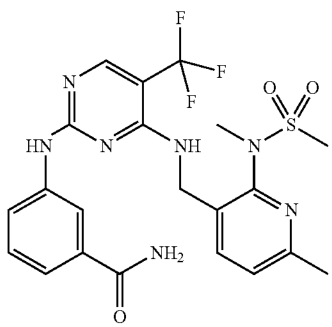 [SMILES: Cc1ccc(CNc2nc(Nc3cccc(C(N)=O)c3)ncc2C(F)(F)F)c(N(C)S(C)(=O)=O)n1] | 3-({4-[({6-methyl-2-[methyl(methylsulfonyl)amino]pyridin-3-yl}methyl)amino]-5-(trifluoromethyl)pyrimidin-2-yl}amino)benzamide (294) | <0.000595 |
| 295 | 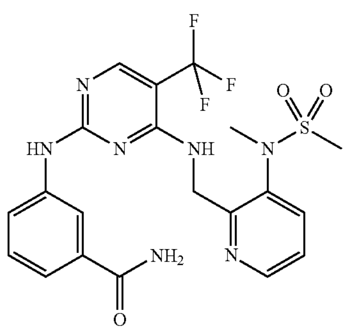 [SMILES: CN(c1cccnc1CNc1nc(Nc2cccc(C(N)=O)c2)ncc1C(F)(F)F)S(C)(=O)=O] | 3-({4-[({3-[methyl(methylsulfonyl)amino]pyridin-2-yl}methyl)amino]-5-(trifluoromethyl)pyrimidin-2-yl}amino)benzamide (295) | 0.00133 |
| 296 | 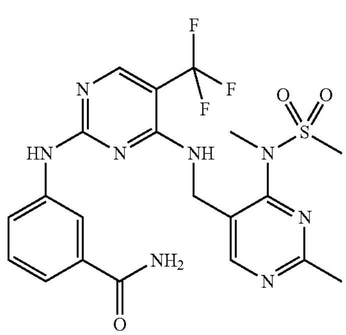 [SMILES: Cc1ncc(CNc2nc(Nc3cccc(C(N)=O)c3)ncc2C(F)(F)F)c(N(C)S(C)(=O)=O)n1] | 3-({4-[({2-methyl-4-[methyl(methylsulfonyl)amino]pyrimidin-5-yl}methyl)amino]-5-(trifluoromethyl)pyrimidin-2-yl}amino)benzamide (296) | 0.00389 |

TABLE 1-continued

IC50 values against FAK kinase.

| Ex. | Structure | Compound Name | FAK IC50, μM |
|---|---|---|---|
| 297 | 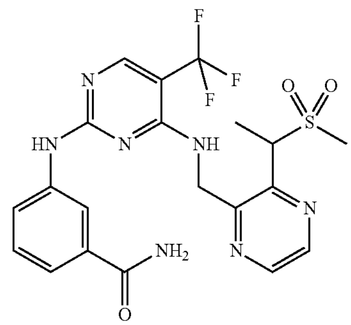 [SMILES: CC(c1nccnc1CNc1nc(Nc2cccc(C(N)=O)c2)ncc1C(F)(F)F)S(C)(=O)=O] | 3-({4-[({3-[methyl(methylsulfonyl)amino]pyrazin-2-yl}methyl)amino]-5-(trifluoromethyl)pyrimidin-2-yl}amino)benzamide (297) | 0.00226 |
| 298 | 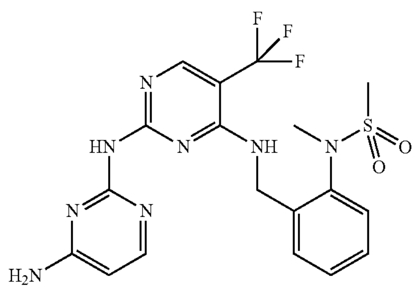 [SMILES: CN(c1ccccc1CNc1nc(Nc2nccc(N)n2)ncc1C(F)(F)F)S(C)(=O)=O] | N-{3-[({2-[(4-aminopyrimidin-2-yl)amino]-5-(trifluoromethyl)pyrimidin-4-yl}amino)methyl]pyridin-2-yl}-N-methylmethanesulfonamide (298) | 0.0328 |
| 299 | 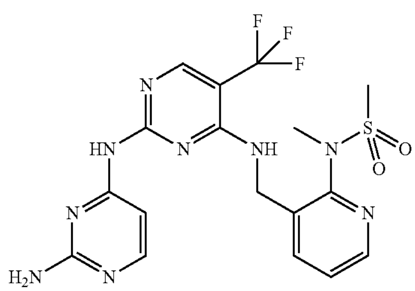 [SMILES: CN(c1ncccc1CNc1nc(Nc2ccnc(N)n2)ncc1C(F)(F)F)S(C)(=O)=O] | N-{3-[({2-[(2-aminopyrimidin-4-yl)amino]-5-(trifluoromethyl)pyrimidin-4-yl}amino)methyl]pyridin-2-yl}-N-methylmethanesulfonamide (299) | >0.188 |
| 300 | ABS | 4-{[(7R)-8-cyclopentyl-7-ethyl-5-methyl-6-oxo-5,6,7,8-tetrahydropteridin-2-yl]amino}-3-methoxy-N-(1-methylpiperidin-4-yl)benzamide (300) | 0.121 |

TABLE 1-continued

IC50 values against FAK kinase.

| Ex. | Structure | Compound Name | FAK IC50, μM |
|---|---|---|---|
| 301 | 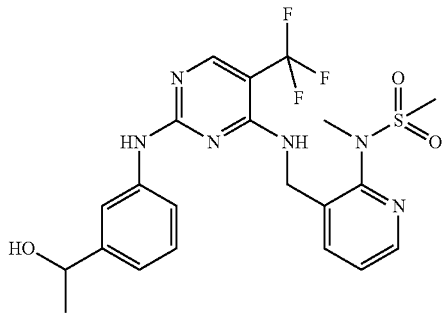 [SMILES: CC(O)c1cccc(Nc2ncc(C(F)(F)F)c(NCc3cccnc3N(C)S(C)(=O)=O)n2)c1] | N-[3-({[2-{[3-(1-hydroxyethyl)phenyl]amino}-5-(trifluoromethyl)pyrimidin-4-yl]amino}methyl)pyridin-2-yl]-N-methylmethane-sulfonamide (301) | <0.000595 |
| 302 | 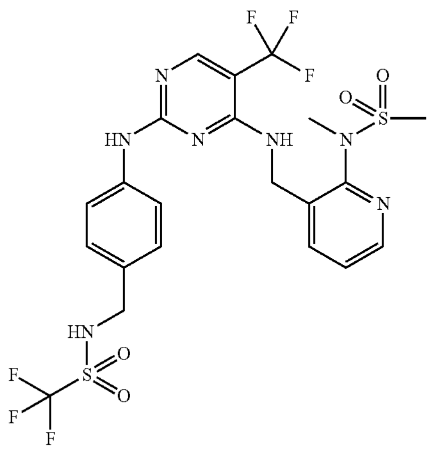 [SMILES: CN(c1ncccc1CNc1nc(Nc2ccc(CNS(=O)(=O)C(F)(F)F)cc2)ncc1C(F)(F)F)S(C)(=O)=O] | 1,1,1-trifluoro-N-[4-({4-[({2-[methyl(methylsulfonyl)amino]pyridin-3-yl}methyl)amino]-5-(trifluoromethyl)pyrimidin-2-yl}amino)benzyl]methanesulfonamide (302) | 0.00100 |
| 303 | 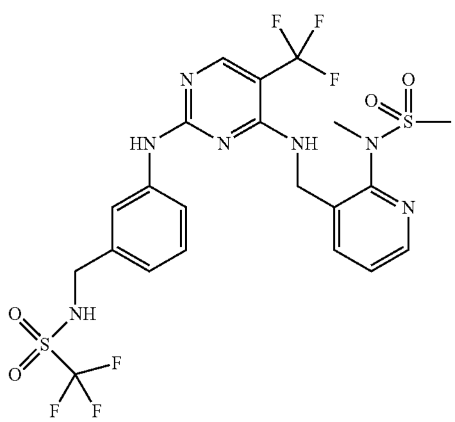 [SMILES: CN(c1ncccc1CNc1nc(Nc2cccc(CNS(=O)(=O)C(F)(F)F)c2)ncc1C(F)(F)F)S(C)(=O)=O] | 1,1,1-trifluoro-N-[3-({4-[({2-[methyl(methylsulfonyl)amino]pyridin-3-yl}methyl)amino]-5-(trifluoromethyl)pyrimidin-2-yl}amino)benzyl]methanesulfonamide (303) | 0.000727 |
| 304 | 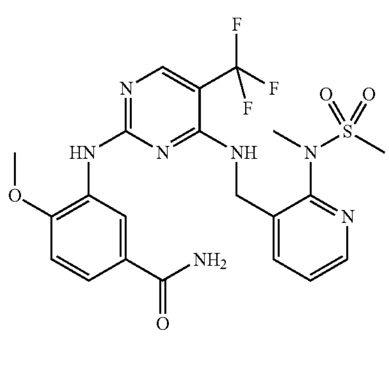 [SMILES: COc1ccc(C(N)=O)cc1Nc1ncc(C(F)(F)F)c(NCc2cccnc2N(C)S(C)(=O)=O)n1] | 4-methoxy-3-({4-[({2-[methyl(methylsulfonyl)amino]pyridin-3-yl}methyl)amino]-5-(trifluoromethyl)pyrimidin-2-yl}amino)benzamide (304) | 0.000777 |

TABLE 1-continued

IC50 values against FAK kinase.

| Ex. | Structure | Compound Name | FAK IC50, μM |
|---|---|---|---|
| 305 | 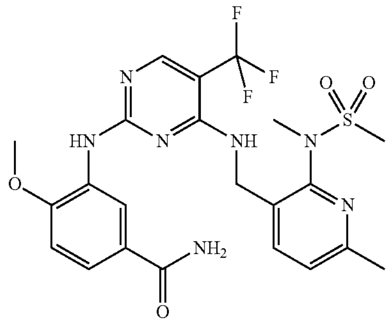 [SMILES: COc1ccc(C(N)=O)cc1Nc1ncc(C(F)(F)F)c(NCc2ccc(C)nc2N(C)S(C)(=O)=O)n1] | 4-methoxy-3-({4-[({6-methyl-2-[methyl(methylsulfonyl)-amino]pyridin-3-yl}methyl)amino]-5-(trifluoromethyl)pyrimidin-2-yl}amino)benzamide (305) | 0.000646 |
| 306 | 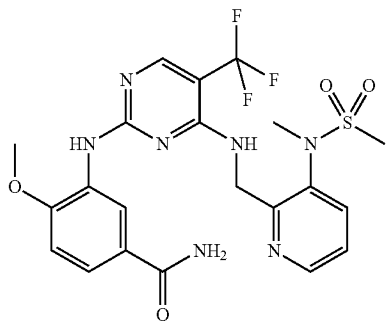 [SMILES: COc1ccc(C(N)=O)cc1Nc1ncc(C(F)(F)F)c(NCc2ncccc2N(C)S(C)(=O)=O)n1] | 4-methoxy-3-({4-[({3-[methyl(methylsulfonyl)amino]pyridin-2-yl}methyl)amino]-5-(trifluoromethyl)pyrimidin-2-yl}amino)benzamide (306) | 0.000696 |
| 307 | 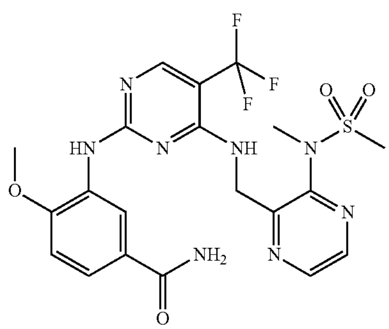 [SMILES: COc1ccc(C(N)=O)cc1Nc1ncc(C(F)(F)F)c(NCc2nccnc2N(C)S(C)(=O)=O)n1] | 4-methoxy-3-({4-[({3-[methyl(methylsulfonyl)amino]pyrazin-2-yl}methyl)amino]-5-(trifluoromethyl)pyrimidin-2-yl}amino)benzamide (307) | 0.00111 |
| 308 | 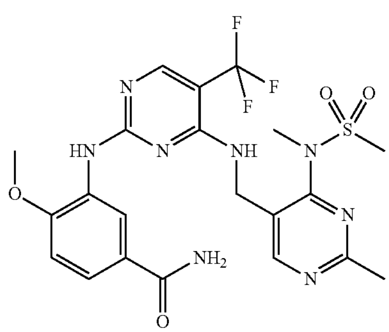 [SMILES: COc1ccc(C(N)=O)cc1Nc1ncc(C(F)(F)F)c(NCc2cnc(C)nc2N(C)S(C)(=O)=O)n1] | 4-methoxy-3-({4-[({2-methyl-4-[methyl(methylsulfonyl)-amino]pyrimidin-5-yl}methyl)amino]-5-(trifluoromethyl)pyrimidin-2-yl}amino)benzamide (308) | 0.00350 |

TABLE 1-continued

IC50 values against FAK kinase.

| Ex. | Structure | Compound Name | FAK IC50, μM |
|---|---|---|---|
| 309 | 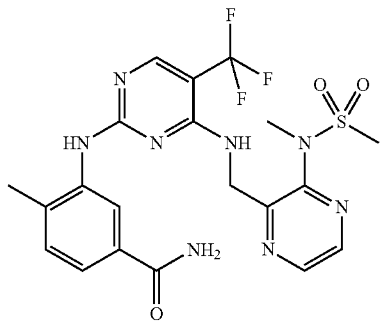 | 4-methyl-3-({4-[({3-[methyl(methylsulfonyl)amino]pyrazin-2-yl}methyl)amino]-5-(trifluoromethyl)pyrimidin-2-yl}amino)benzamide (309) | 0.00351 |
| 310 | 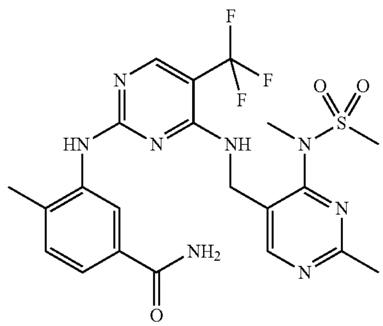 | 4-methyl-3-({4-[({2-methyl-4-[methyl(methylsulfonyl)amino]pyrimidin-5-yl}methyl)amino]-5-(trifluoromethyl)pyrimidin-2-yl}amino)benzamide (310) | 0.00504 |
| 311 | 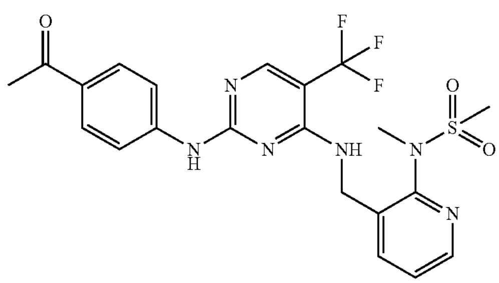 [SMILES: CC(=O)c1ccc(Nc2ncc(C(F)(F)F)c(NCc3cccnc3N(C)S(C)(=O)=O)n2)cc1] | N-{3-[({2-[(4-acetylphenyl)amino]-5-(trifluoromethyl)pyrimidin-4-yl}amino)methyl]pyridin-2-yl}-N-methylmethanesulfonamide (311) | 0.00100 |
| 312 | 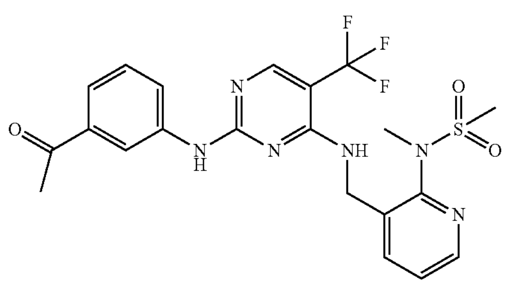 [SMILES: CC(=O)c1cccc(Nc2ncc(C(F)(F)F)c(NCc3cccnc3N(C)S(C)(=O)=O)n2)c1] | N-{3-[({2-[(3-acetylphenyl)amino]-5-(trifluoromethyl)pyrimidin-4-yl}amino)methyl]pyridin-2-yl}-N-methylmethanesulfonamide (312) | 0.00126 |
| 313 | 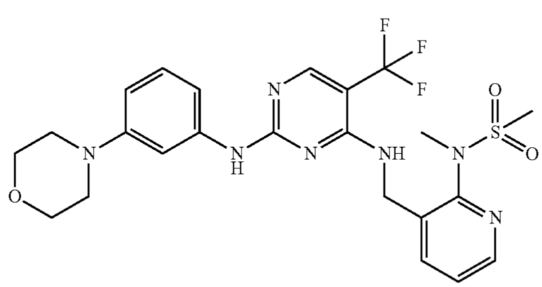 [SMILES: CN(c1ncccc1CNc1nc(Nc2cccc(N3CCOCC3)c2)ncc1C(F)(F)F)S(C)(=O)=O] | N-methyl-N-{3-[({2-[(3-morpholin-4-ylphenyl)amino]-5-(trifluoromethyl)pyrimidin-4-yl}amino)methyl]pyridin-2-yl}methanesulfonamide (313) | 0.00202 |

TABLE 1-continued

IC50 values against FAK kinase.

| Ex. | Structure | Compound Name | FAK IC50, μM |
|---|---|---|---|
| 314 | 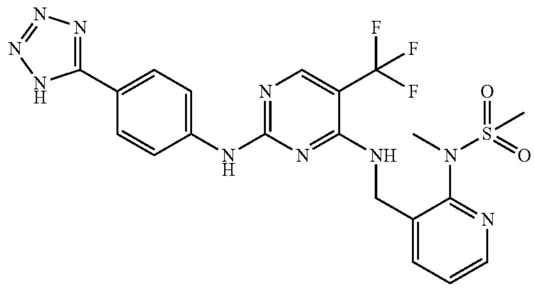 [SMILES: CN(c1ncccc1CNc1nc(Nc2ccc(-c3nnn[nH]3)cc2)ncc1C(F)(F)F)S(C)(=O)=O] | N-methyl-N-[3-({[2-{[4-(1H-tetrazol-5-yl)phenyl]amino}-5-(trifluoromethyl)pyrimidin-4-yl]amino}methyl)pyridin-2-yl]methanesulfonamide (314) | <0.000595 |
| 315 | 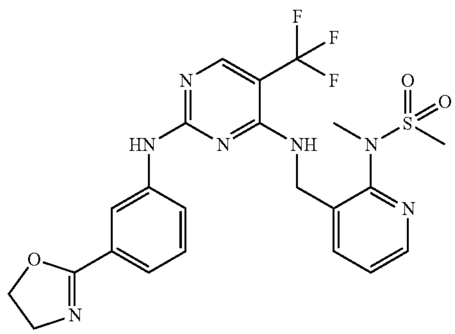 [SMILES: CN(c1ncccc1CNc1nc(Nc2cccc(C3=NCCO3)c2)ncc1C(F)(F)F)S(C)(=O)=O] | N-[3-({[2-{[3-(4,5-dihydro-1,3-oxazol-2-yl)phenyl]amino}-5-(trifluoromethyl)pyrimidin-4-yl]amino}methyl)pyridin-2-yl]-N-methylmethanesulfonamide (315) | 0.000914 |
| 316 | 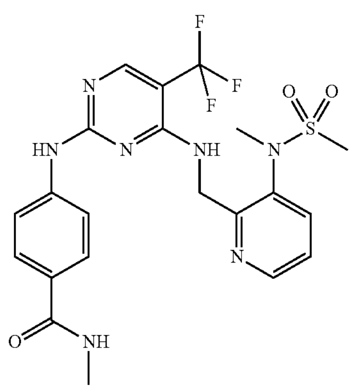 [SMILES: CNC(=O)c1ccc(Nc2ncc(C(F)(F)F)c(NCc3ncccc3N(C)S(C)(=O)=O)n2)cc1] | N-methyl-4-({4-[({3-[methyl(methylsulfonyl)amino]pyridin-2-yl}methyl)amino]-5-(trifluoromethyl)pyrimidin-2-yl}amino)benzamide (316) | 0.000965 |
| 317 | 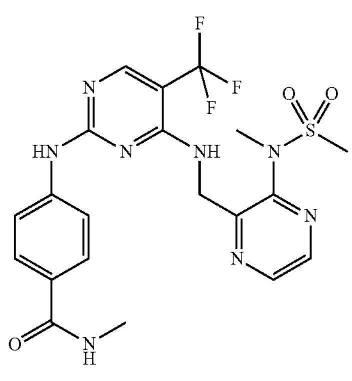 [SMILES: CNC(=O)c1ccc(Nc2ncc(C(F)(F)F)c(NCc3nccnc3N(C)S(C)(=O)=O)n2)cc1] | N-methyl-4-({4-[({3-[methyl(methylsulfonyl)amino]pyrazin-2-yl}methyl)amino]-5-(trifluoromethyl)pyrimidin-2-yl}amino)benzamide (317) | <0.000595 |

TABLE 1-continued

IC50 values against FAK kinase.

| Ex. | Structure | Compound Name | FAK IC50, μM |
|---|---|---|---|
| 318 | 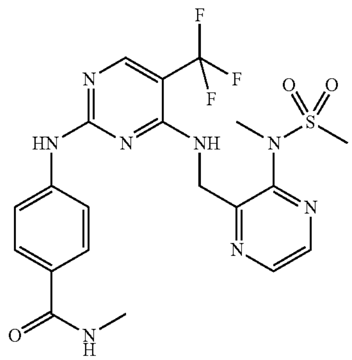 [SMILES: CNC(=O)c1ccc(Nc2ncc(C(F)(F)F)c(NCc3nccnc3N(C)S(C)(=O)=O)n2)cc1] | N-methyl-4-({4-[({3-[methyl(methylsulfonyl)amino]pyrazin-2-yl}methyl)amino]-5-(trifluoromethyl)pyrimidin-2-yl}amino)benzamide (318), hydrochloride salt | 0.00179 |
| 319 | 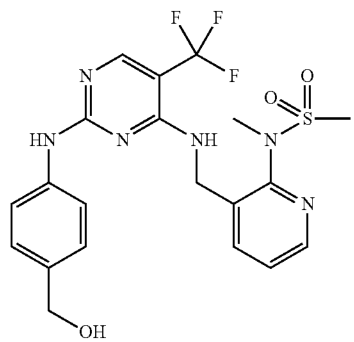 [SMILES: CN(c1ncccc1CNc1nc(Nc2ccc(CO)cc2)ncc1C(F)(F)F)S(C)(=O)=O] | N-[3-({[2-{[4-(hydroxymethyl)phenyl]amino}-5-(trifluoromethyl)pyrimidin-4-yl]amino}methyl)pyridin-2-yl]-N-methylmethane-sulfonamide (319) | <0.000595 |
| 320 | 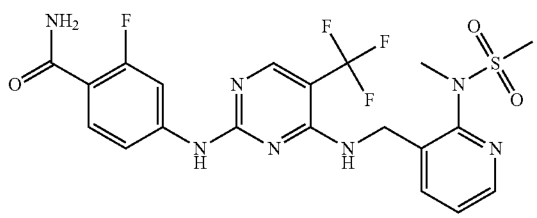 [SMILES: CN(c1ncccc1CNc1nc(Nc2ccc(C(N)=O)c(F)c2)ncc1C(F)(F)F)S(C)(=O)=O] | 2-fluoro-4-({4-[({2-[methyl(methylsulfonyl)amino]pyridin-3-yl}methyl)amino]-5-(trifluoromethyl)pyrimidin-2-yl}amino)benzamide (320), formic acid salt | <0.000595 |
| 321 | 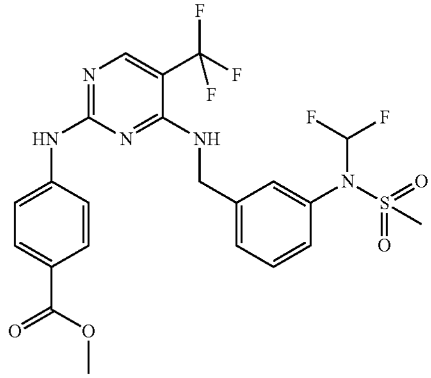 [SMILES: COC(=O)c1ccc(Nc2ncc(C(F)(F)F)c(NCc3cccc(N(C(F)F)S(C)(=O)=O)c3)n2)cc1] | 4-{[4-({3-[(difluoromethyl)(methyl-sulfonyl)amino]benzyl}amino)-5-(trifluoromethyl)pyrimidin-2-yl]amino}benzoate (321) | 0.119 (0.0159-0.883 n = 2) |

TABLE 1-continued

IC50 values against FAK kinase.

| Ex. | Structure | Compound Name | FAK IC50, µM |
|---|---|---|---|
| 322 | 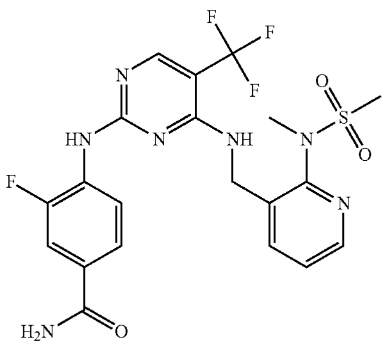 [SMILES: CN(c1ncccc1CNc1nc(Nc2ccc(C(N)=O)cc2F)ncc1C(F)(F)F)S(C)(=O)=O] | 3-fluoro-4-({4-[({2-[methyl(methylsulfonyl)amino]pyridin-3-yl}methyl)amino]-5-(trifluoromethyl)pyrimidin-2-yl}amino)benzamide (322), formic acid salt | <0.000595 |
| 323 | 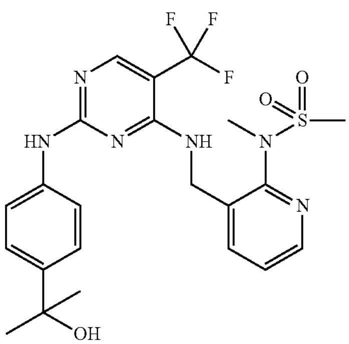 [SMILES: CN(c1ncccc1CNc1nc(Nc2ccc(C(C)(C)O)cc2)ncc1C(F)(F)F)S(C)(=O)=O] | N-[3-({[2-{[4-(1-hydroxy-1-methylethyl)phenyl]amino}-5-(trifluoromethyl)pyrimidin-4-yl]amino}methyl)pyridin-2-yl]-N-methylmethane-sulfonamide (323) | 0.00150 |
| 324 | 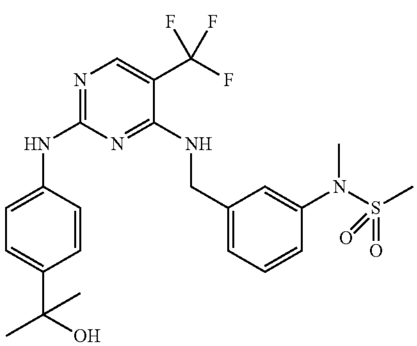 [SMILES: CN(c1cccc(CNc2nc(Nc3ccc(C(C)(C)O)cc3)ncc2C(F)(F)F)c1)S(C)(=O)=O] | N-[3-({[2-{[4-(1-hydroxy-1-methylethyl)phenyl]amino}-5-(trifluoromethyl)pyrimidin-4-yl]amino}methyl)phenyl]-N-methylmethanesulfonamide (324) | 0.00187 |
| 325 | 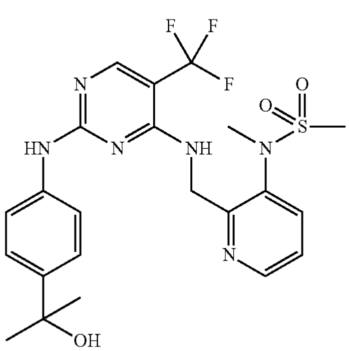 | N-[2-({[2-{[4-(1-hydroxy-1-methylethyl)phenyl]amino}-5-(trifluoromethyl)pyrimidin-4-yl]amino}methyl)pyridin-3-yl]-N-methylmethane-sulfonamide (325) | 0.00266 |

TABLE 1-continued

IC50 values against FAK kinase.

| Ex. | Structure | Compound Name | FAK IC50, μM |
|---|---|---|---|
| 326 | 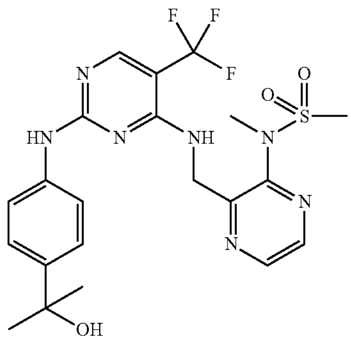 | N-[3-({[2-{[4-(1-hydroxy-1-methylethyl)phenyl]amino}-5-(trifluoromethyl)pyrimidin-4-yl]amino}methyl)pyrazin-2-yl]-N-methylmethane-sulfonamide (326) | 0.00162 |
| 327 | 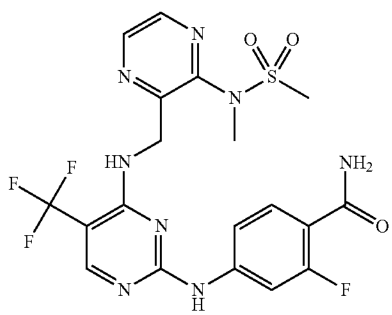 [SMILES: CN(c1nccnc1CNc1nc(Nc2ccc(C(N)=O)c(F)c2)ncc1C(F)(F)F)S(C)(=O)=O] | 2-fluoro-4-({4-[({3-[methyl(methylsulfonyl)amino]pyrazin-2-yl}methyl)amino]-5-(trifluoromethyl)pyrimidin-2-yl}amino)benzamide (327), formic acid salt | 0.00169 |
| 328 | 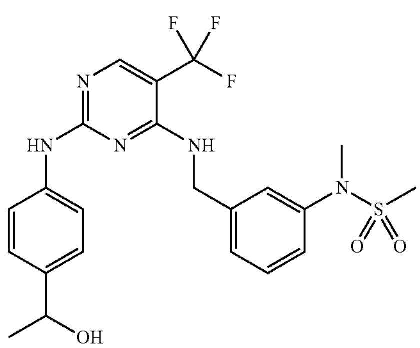 [SMILES: CC(O)c1ccc(Nc2ncc(C(F)(F)F)c(NCc3cccc(N(C)S(C)(=O)=O)c3)n2)cc1] | N-[3-({[2-{[4-(1-hydroxyethyl)phenyl]amino}-5-(trifluoromethyl)pyrimidin-4-yl]amino}methyl)phenyl]-N-methylmethanesulfonamide (328) | 0.000619 |
| 329 | 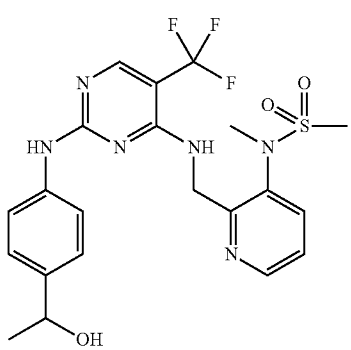 [SMILES: CC(O)c1ccc(Nc2ncc(C(F)(F)F)c(NCc3ncccc3N(C)S(C)(=O)=O)n2)cc1] | N-[2-({[2-{[4-(1-hydroxyethyl)phenyl]amino}-5-(trifluoromethyl)pyrimidin-4-yl]amino}methyl)pyridin-3-yl]-N-methylmethane-sulfonamide (329) | 0.000914 |

TABLE 1-continued

IC50 values against FAK kinase.

| Ex. | Structure | Compound Name | FAK IC50, μM |
|---|---|---|---|
| 330 | 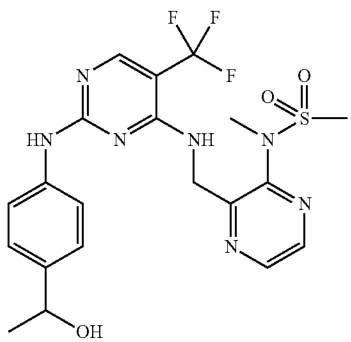 [SMILES: CC(O)c1ccc(Nc2ncc(C(F)(F)F)c(NCc3nccnc3N(C)S(C)(=O)=O)n2)cc1] | N-[3-({[2-{[4-(1-hydroxyethyl)phenyl]amino}-5-(trifluoromethyl)pyrimidin-4-yl]amino}methyl)pyrazin-2-yl]-N-methylmethane-sulfonamide (330) | 0.000750 |
| 331 | 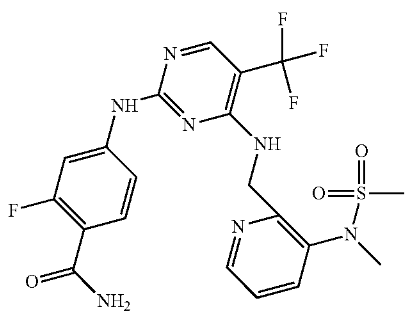 [SMILES: CN(c1cccnc1CNc1nc(Nc2ccc(C(N)=O)c(F)c2)ncc1C(F)(F)F)S(C)(=O)=O] | 2-fluoro-4-({4-[({3-[methyl(methylsulfonyl)amino]pyridin-2-yl}methyl)amino]-5-(trifluoromethyl)pyrimidin-2-yl}amino)benzamide (331), hydrochloride salt | 0.00177 |
| 332 | 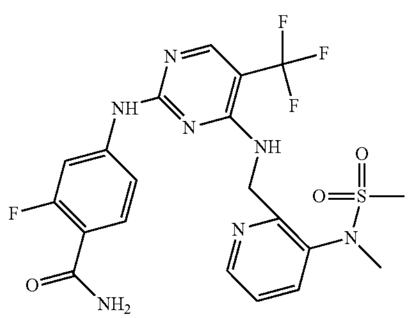 [SMILES: CN(c1cccnc1CNc1nc(Nc2ccc(C(N)=O)c(F)c2)ncc1C(F)(F)F)S(C)(=O)=O] | 2-fluoro-4-({4-[({3-[methyl(methylsulfonyl)amino]ypyridin-2-l}methyl)amino]-5-(trifluoromethyl)pyrimidin-2-yl}amino)benzamide (332), formic acid salt | 0.000863 |
| 333 | 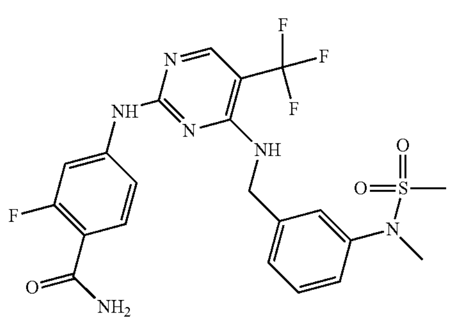 [SMILES: CN(c1cccc(CNc2nc(Nc3ccc(C(N)=O)c(F)c3)ncc2C(F)(F)F)c1)S(C)(=O)=O] | 2-fluoro-4-{[4-({3-[methyl(methylsulfonyl)amino]benzyl}amino)-5-(trifluoromethyl)pyrimidin-2-yl]amino}benzamide (333) | 0.00214 |

TABLE 1-continued

IC50 values against FAK kinase.

| Ex. | Structure | Compound Name | FAK IC50, μM |
|---|---|---|---|
| 334 | 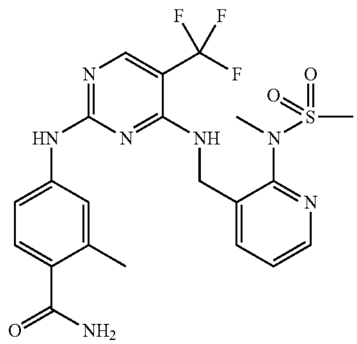 | 2-methyl-4-({4-[({2-[methyl(methylsulfonyl)amino]pyridin-3-yl}methyl)amino]-5-(trifluoromethyl)pyrimidin-2-yl}amino)benzamide (334) | <0.000595 (n = 2) |
| 335 | 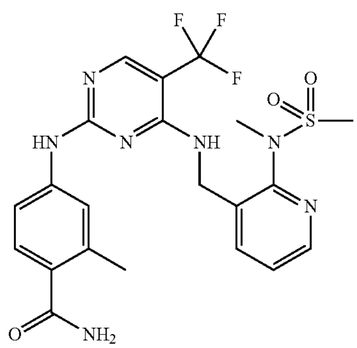 | 2-methyl-4-({4-[({2-[methyl(methylsulfonyl)amino]pyridin-3-yl}methyl)amino]-5-(trifluoromethyl)pyrimidin-2-yl}amino)benzamide (335), hydrochloride salt | <0.000595 (n = 2) |
| 336 | 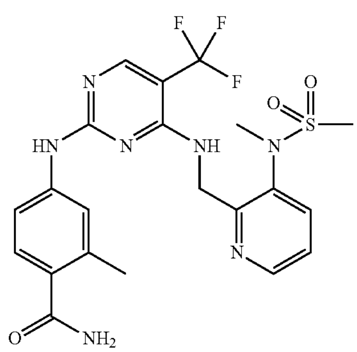 | 2-methyl-4-({4-[({3-[methyl(methylsulfonyl)amino]pyridin-2-yl}methyl)amino]-5-(trifluoromethyl)pyrimidin-2-yl}amino)benzamide (336) | <0.000595 |
| 337 | 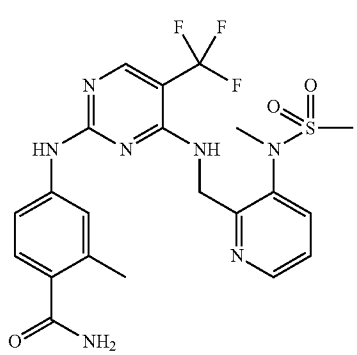 [SMILES: Cc1cc(Nc2ncc(C(F)(F)F)c(NCc3ncccc3N(C)S(C)(=O)=O)n2)ccc1C(N)=O] | 2-methyl-4-({4-[({3-[methyl(methylsulfonyl)amino]pyridin-2-yl}methyl)amino]-5-(trifluoromethyl)pyrimidin-2-yl}amino)benzamide (337), hydrochloride salt | <0.000595 |

TABLE 1-continued

IC50 values against FAK kinase.

| Ex. | Structure | Compound Name | FAK IC50, μM |
|---|---|---|---|
| 338 | 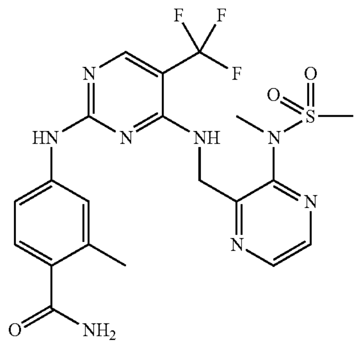 [SMILES: Cc1cc(Nc2ncc(C(F)(F)F)c(NCc3nccnc3N(C)S(C)(=O)=O)n2)ccc1C(N)=O] | 2-methyl-4-({4-[({3-[methyl(methylsulfonyl)amino]pyrazin-2-yl}methyl)amino]-5-(trifluoromethyl)pyrimidin-2-yl}amino)benzamide (338) | <0.000595 |
| 339 | 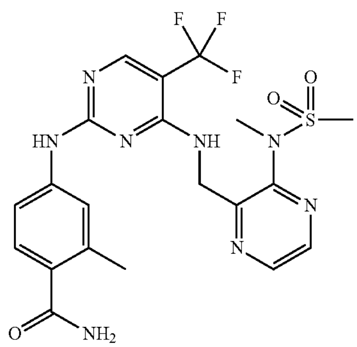 | 2-methyl-4-({4-[({3-[methyl(methylsulfonyl)amino]pyrazin-2-yl}methyl)amino]-5-(trifluoromethyl)pyrimidin-2-yl}amino)benzamide (339), hydrochloride salt | <0.000595 |
| 340 | 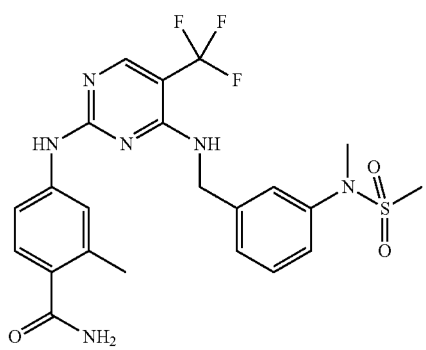 [SMILES: Cc1cc(Nc2ncc(C(F)(F)F)c(NCc3cccc(N(C)S(C)(=O)=O)c3)n2)ccc1C(N)=O] | 2-methyl-4-{[4-({3-[methyl(methylsulfonyl)amino]benzyl}amino)-5-(trifluoromethyl)pyrimidin-2-yl]amino}benzamide (340) | <0.000595 |
| 341 | 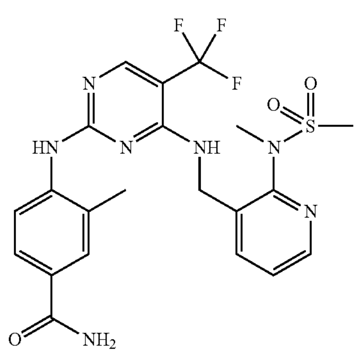 [SMILES: Cc1cc(C(N)=O)ccc1Nc1ncc(C(F)(F)F)c(NCc2cccnc2N(C)S(C)(=O)=O)n1] | 3-methyl-4-({4-[({2-[methyl(methylsulfonyl)amino]pyridin-3-yl}methyl)amino]-5-(trifluoromethyl)pyrimidin-2-yl}amino)benzamide (341) | <0.000595 |

TABLE 1-continued

IC50 values against FAK kinase.

| Ex. | Structure | Compound Name | FAK IC50, μM |
|---|---|---|---|
| 342 | 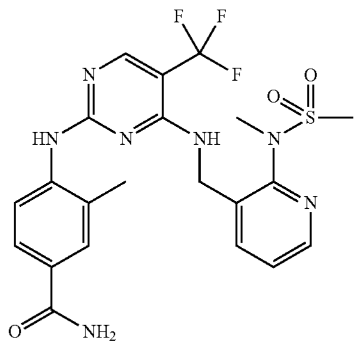 [SMILES: Cc1cc(C(N)=O)ccc1Nc1ncc(C(F)(F)F)c(NCc2cccnc2N(C)S(C)(=O)=O)n1] | 3-methyl-4-({4-[({2-[methyl(methylsulfonyl)amino]pyridin-3-yl}methyl)amino]-5-(trifluoromethyl)pyrimidin-2-yl}amino)benzamide (342), hydrochloride salt | 0.00103 |
| 343 | 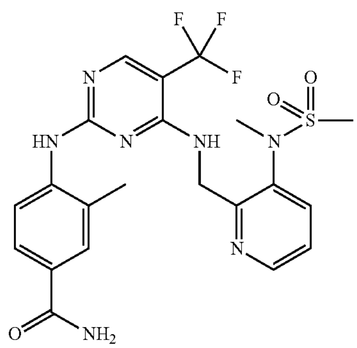 [SMILES: Cc1cc(C(N)=O)ccc1Nc1ncc(C(F)(F)F)c(NCc2ncccc2N(C)S(C)(=O)=O)n1] | 3-methyl-4-({4-[({3-[methyl(methylsulfonyl)amino]pyridin-2-yl}methyl)amino]-5-(trifluoromethyl)pyrimidin-2-yl}amino)benzamide (343) | 0.000993 |
| 344 | 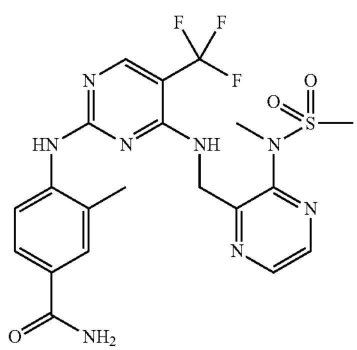 [SMILES: Cc1cc(C(N)=O)ccc1Nc1ncc(C(F)(F)F)c(NCc2nccnc2N(C)S(C)(=O)=O)n1] | 3-methyl-4-({4-[({3-[methyl(methylsulfonyl)amino]pyrazin-2-yl}methyl)amino]-5-(trifluoromethyl)pyrimidin-2-yl}amino)benzamide (344) | 0.000900 |
| 345 | 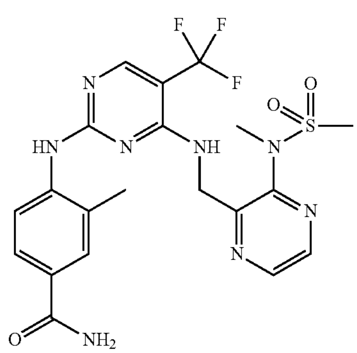 [SMILES: Cc1cc(C(N)=O)ccc1Nc1ncc(C(F)(F)F)c(NCc2nccnc2N(C)S(C)(=O)=O)n1] | 3-methyl-4-({4-[({3-[methyl(methylsulfonyl)amino]pyrazin-2-yl}methyl)amino]-5-(trifluoromethyl)pyrimidin-2-yl}amino)benzamide (345), hydrochloride salt | 0.000981 |

TABLE 1-continued

IC50 values against FAK kinase.

| Ex. | Structure | Compound Name | FAK IC50, μM |
|---|---|---|---|
| 346 | 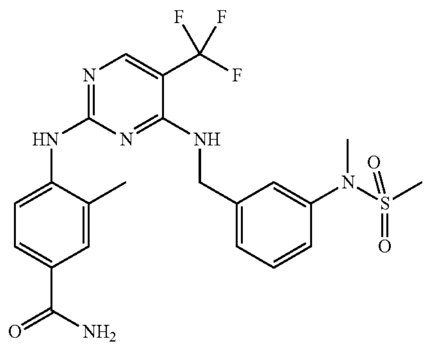 [SMILES: Cc1cc(C(N)=O)ccc1Nc1ncc(C(F)(F)F)c(NCc2cccc(N(C)S(C)(=O)=O)c2)n1] | 3-methyl-4-{[4-({3-[methyl(methylsulfonyl)amino]benzyl}amino)-5-(trifluoromethyl)pyrimidin-2-yl]amino}benzamide (346) | 0.000886 |
| 347 | 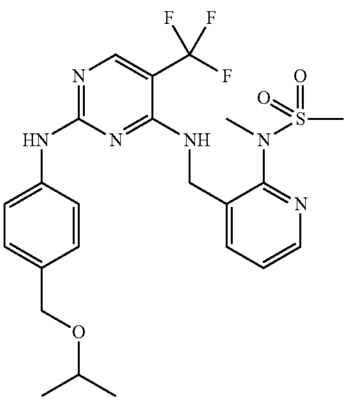 [SMILES: CC(C)OCc1ccc(Nc2ncc(C(F)(F)F)c(NCc3cccnc3N(C)S(C)(=O)=O)n2)cc1] | N-[3-({[2-{[4-(isopropoxymethyl)phenyl]amino}-5-(trifluoromethyl)pyrimidin-4-yl]amino}methyl)pyridin-2-yl]-N-methylmethane-sulfonamide (347) | 0.00215 |
| 348 | 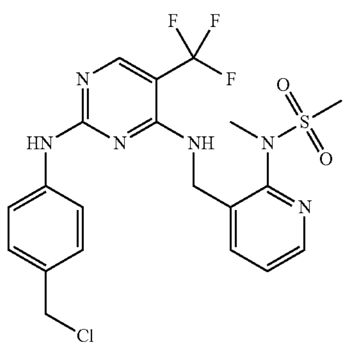 [SMILES: CN(c1ncccc1CNc1nc(Nc2ccc(CCl)cc2)ncc1C(F)(F)F)S(C)(=O)=O] | N-[3-({[2-{[4-(chloromethyl)phenyl]amino}-5-(trifluoromethyl)pyrimidin-4-yl]amino}methyl)pyridin-2-yl]-N-methylmethane-sulfonamide (348) | 0.00155 |
| 349 | 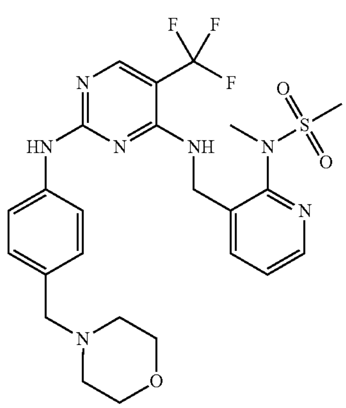 [SMILES: CN(c1ncccc1CNc1nc(Nc2ccc(CN3CCOCC3)cc2)ncc1C(F)(F)F)S(C)(=O)=O] | N-methyl-N-[3-({[2-{[4-(morpholin-4-ylmethyl)phenyl]amino}-5-(trifluoromethyl)pyrimidin-4-yl]amino}methyl)pyridin-2-yl]methanesulfonamide (349) | <0.000595 |

TABLE 1-continued

IC50 values against FAK kinase.

| Ex. | Structure | Compound Name | FAK IC50, μM |
|---|---|---|---|
| 350 | 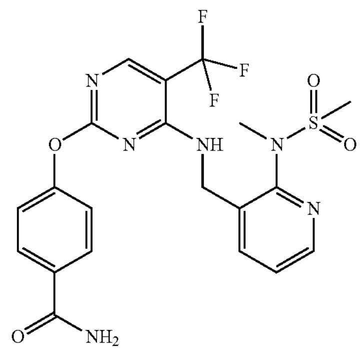 [SMILES: CN(c1ncccc1CNc1nc(Oc2ccc(C(N)=O)cc2)ncc1C(F)(F)F)S(C)(=O)=O] | 4-({4-[({2-[methyl(methylsulfonyl)amino]pyridin-3-yl}methyl)amino]-5-(trifluoromethyl)pyrimidin-2-yl}oxy)benzamide (350) | 0.0637 |
| 351 | ABS | N-[3-({[2-({4-[(1R)-1-aminoethyl]phenyl}amino)-5-(trifluoromethyl)pyrimidin-4-yl]amino}methyl)pyrazin-2-yl]-N-methylmethane-sulfonamide (351), hydrochloride salt | 0.000616 |
| 352 | ABS | N-[2-({[2-({4-[(1R)-1-aminoethyl]phenyl}amino)-5-(trifluoromethyl)pyrimidin-4-yl]amino}methyl)pyridin-3-yl]-N-methylmethane-sulfonamide (352), hydrochloride salt | <0.000595 |
| 353 | ABS | N-[3-({[2-({4-[(1R)-1-aminoethyl]phenyl}amino)-5-(trifluoromethyl)pyrimidin-4-yl]amino}methyl)phenyl]-N-methylmethanesulfonamide (353), hydrochloride salt | <0.000595 |

TABLE 1-continued

IC50 values against FAK kinase.

| Ex. | Structure | Compound Name | FAK IC50, μM |
|---|---|---|---|
| 354 | ABS | N-[3-({[2-({4-[(1R)-1-aminoethyl]phenyl}amino)-5-(trifluoromethyl)pyrimidin-4-yl]amino}methyl)pyridin-2-yl]-N-methylmethane-sulfonamide (354), hydrochloride salt | <0.000595 |
| 355 | ABS | N-[3-({[2-({4-[(1S)-1-aminoethyl]phenyl}amino)-5-(trifluoromethyl)pyrimidin-4-yl]amino}methyl)pyrazin-2-yl]-N-methylmethane-sulfonamide (355), hydrochloride salt | <0.000595 |
| 356 | ABS | N-[2-({[2-({4-[(1S)-1-aminoethyl]phenyl}amino)-5-(trifluoromethyl)pyrimidin-4-yl]amino}methyl)pyridin-3-yl]-N-methylmethane-sulfonamide (356), hydrochloride salt | 0.000593 |
| 357 | 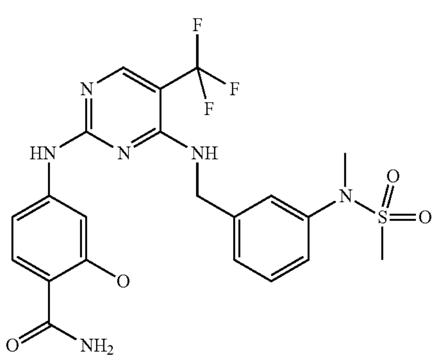 | 2-chloro-4-{[4-({3-[methyl(methylsulfonyl)amino]abenzyl}mino)-5-(trifluoromethyl)pyrimidin-2-yl]amino}benzamide (357) | 0.00147 |

TABLE 1-continued

IC50 values against FAK kinase.

| Ex. | Structure | Compound Name | FAK IC50, μM |
|---|---|---|---|
| 358 | 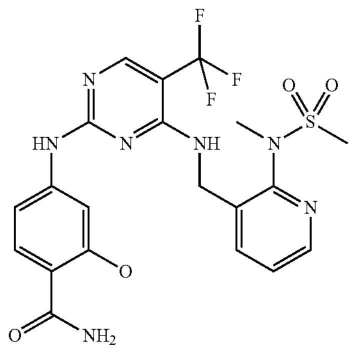 | 2-chloro-4-({4-[({2-[methyl(methylsulfonyl)amino]pyridin-3-yl}methyl)amino]-5-(trifluoromethyl)pyrimidin-2-yl}amino)benzamide (358) | <0.000595 |
| 359 | 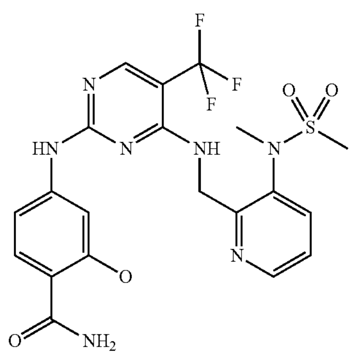 [SMILES: CN(c1cccnc1CNc1nc(Nc2ccc(C(N)=O)c(O)c2)ncc1C(F)(F)F)S(C)(=O)=O] | 2-chloro-4-({4-[({3-[methyl(methylsulfonyl)amino]pyridin-2-yl}methyl)amino]-5-(trifluoromethyl)pyrimidin-2-yl}amino)benzamide (359) | <0.000595 |
| 360 | 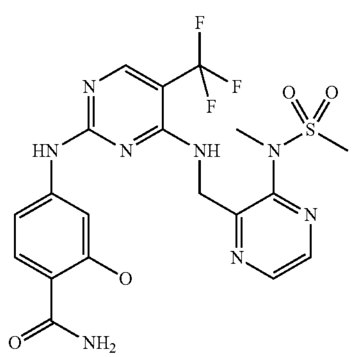 [SMILES: CN(c1nccnc1CNc1nc(Nc2ccc(C(N)=O)c(O)c2)ncc1C(F)(F)F)S(C)(=O)=O] | 2-chloro-4-({4-[({3-[methyl(methylsulfonyl)amino]pyrazin-2-yl}methyl)amino]-5-(trifluoromethyl)pyrimidin-2-yl}amino)benzamide (360) | <0.000595 |
| 361 | 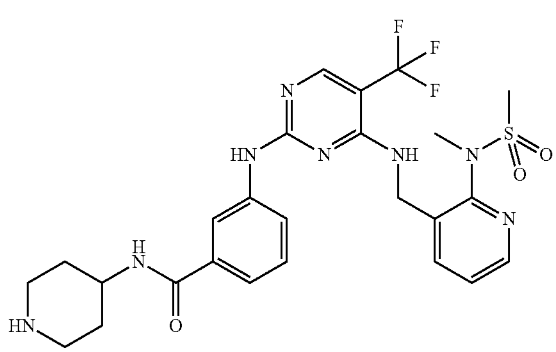 [SMILES: CN(c1ncccc1CNc1nc(Nc2cccc(C(=O)NC3CCNCC3)c2)ncc1C(F)(F)F)S(C)(=O)=O] | 3-({4-[({2-[methyl(methylsulfonyl)amino]pyridin-3-yl}methyl)amino]-5-(trifluoromethyl)pyrimidin-2-yl}amino)-N-piperidin-4-ylbenzamide (361), hydrochloride salt | 0.00870 |

TABLE 1-continued

IC50 values against FAK kinase.

| Ex. | Structure | Compound Name | FAK IC50, μM |
|---|---|---|---|
| 362 | 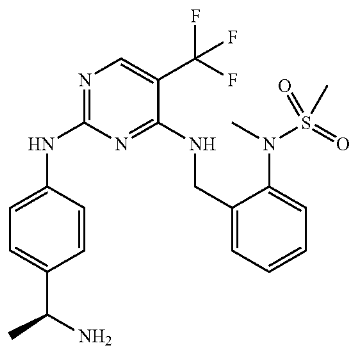 [SMILES: C[C@H](N)c1ccc(Nc2ncc(C(F)(F)F)c(NCc3ccccc3N(C)S(C)(=O)=O)n2)cc1] | N-[2-({[2-({4-[(1R)-1-aminoethyl]phenyl}amino)-5-(trifluoromethyl)pyrimidin-4-yl]amino}methyl)phenyl]-N-methylmethanesulfonamide (362), hydrochloride salt | <0.000595 |
| 363 | 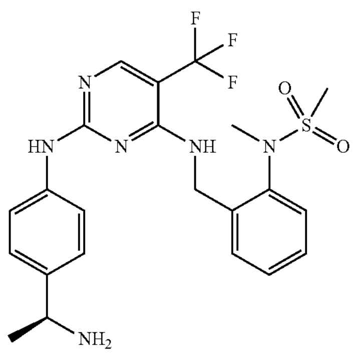 [SMILES: C[C@H](N)c1ccc(Nc2ncc(C(F)(F)F)c(NCc3ccccc3N(C)S(C)(=O)=O)n2)cc1] | N-[2-({[2-({4-[(1S)-1-aminoethyl]phenyl}amino)-5-(trifluoromethyl)pyrimidin-4-yl]amino}methyl)phenyl]-N-methylmethanesulfonamide (363), hydrochloride salt | <0.000595 |
| 364 | 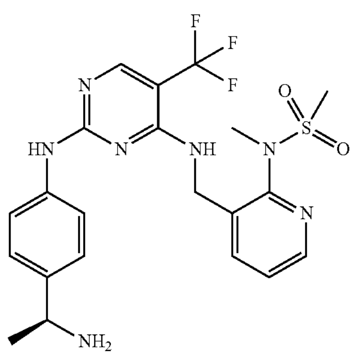 [SMILES: C[C@H](N)c1ccc(Nc2ncc(C(F)(F)F)c(NCc3cccnc3N(C)S(C)(=O)=O)n2)cc1] | N-[3-({[2-({4-[(1S)-1-aminoethyl]phenyl}amino)-5-(trifluoromethyl)pyrimidin-4-yl]amino}methyl)pyridin-2-yl]-N-methylmethane-sulfonamide (364), hydrochloride salt | 0.000644 |
| 365 | ABS | N-[3-({[2-({4-[(1S)-1-aminoethyl]phenyl}amino)-5-(trifluoromethyl)pyrimidin-4-yl]amino}methyl)phenyl]-N-methylmethanesulfonamide (365), hydrochloride salt | 0.000976 |

US 8,440,822 B2
281                                                                                          282

TABLE 1-continued

IC50 values against FAK kinase.

| Ex. | Structure | Compound Name | FAK IC50, μM |
|---|---|---|---|
| 366 | 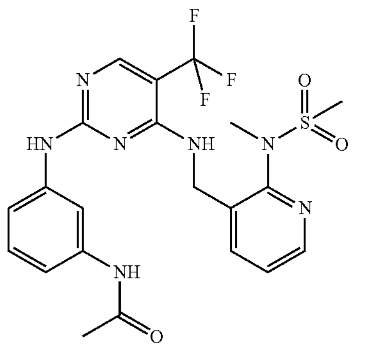 [SMILES: CC(=O)Nc1cccc(Nc2ncc(C(F)(F)F)c(NCc3cccnc3N(C)S(C)(=O)=O)n2)c1] | N-[3-({4-[({2-[methyl(methylsulfonyl)amino]pyridin-3-yl}methyl)amino]-5-(trifluoromethyl)pyrimidin-2-yl}amino)phenyl]acetamide (366) | <0.000595 |
| 367 | 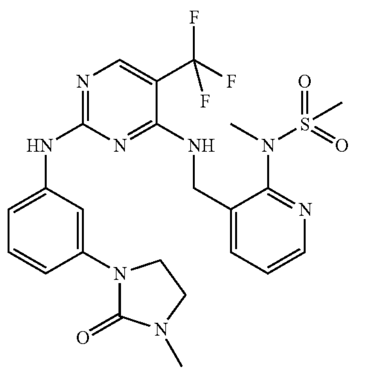 [SMILES: CN1CCN(c2cccc(Nc3ncc(C(F)(F)F)c(NCc4cccnc4N(C)S(C)(=O)=O)n3)c2)C1=O] | N-methyl-N-[3-({[2-{[3-(3-methyl-2-oxoimidazolidin-1-yl)phenyl]amino}-5-(trifluoromethyl)pyrimidin-4-yl]amino}methyl)pyridin-2-yl]methanesulfonamide (367) | 0.00164 |
| 368 | 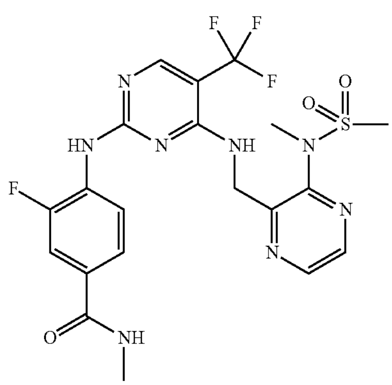 [SMILES: CNC(=O)c1ccc(Nc2ncc(C(F)(F)F)c(NCc3nccnc3N(C)S(C)(=O)=O)n2)c(F)c1] | 3-fluoro-N-methyl-4-({4-[({3-[methyl(methylsulfonyl)amino]pyrazin-2-yl}methyl)amino]-5-(trifluoromethyl)pyrimidin-2-yl}amino)benzamide (368) | <0.000595 |
| 369 | 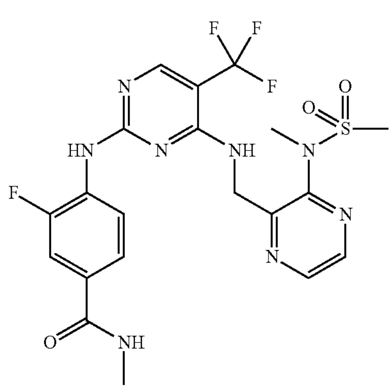 [SMILES: CNC(=O)c1ccc(Nc2ncc(C(F)(F)F)c(NCc3nccnc3N(C)S(C)(=O)=O)n2)c(F)c1] | 3-fluoro-N-methyl-4-({4-[({3-[methyl(methylsulfonyl)amino]pyrazin-2-yl}methyl)amino]-5-(trifluoromethyl)pyrimidin-2-yl}amino)benzamide (369), hydrochloride salt | 0.00149 |

TABLE 1-continued

IC50 values against FAK kinase.

| Ex. | Structure | Compound Name | FAK IC50, μM |
|---|---|---|---|
| 370 | 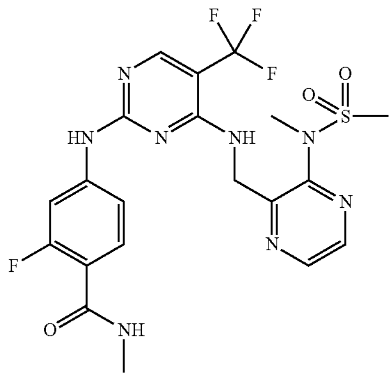 [SMILES: CNC(=O)c1ccc(Nc2ncc(C(F)(F)F)c(NCc3nccnc3N(C)S(C)(=O)=O)n2)cc1F] | 2-fluoro-N-methyl-4-({4-[({3-[methyl(methylsulfonyl)amino]pyrazin-2-yl}methyl)amino]-5-(trifluoromethyl)pyrimidin-2-yl}amino)benzamide (370) | 0.000600 |
| 371 | 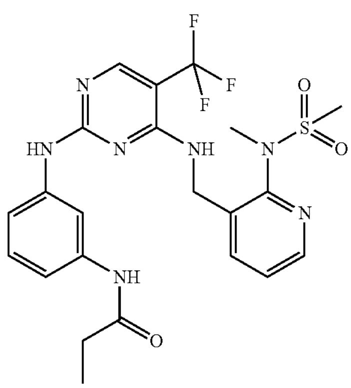 [SMILES: CCC(=O)Nc1cccc(Nc2ncc(C(F)(F)F)c(NCc3cccnc3N(C)S(C)(=O)=O)n2)c1] | N-[3-({4-[({2-[methyl(methylsulfonyl)amino]pyridin-3-yl}methyl)amino]-5-(trifluoromethyl)pyrimidin-2-yl}amino)phenyl]propanamide (371) | 0.00194 |
| 372 | 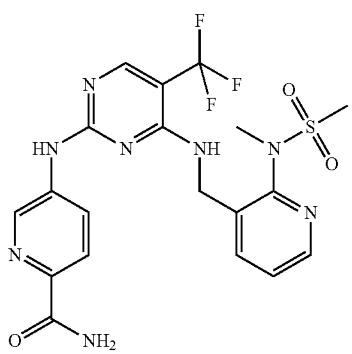 [SMILES: CN(c1ncccc1CNc1nc(Nc2ccc(C(N)=O)nc2)ncc1C(F)(F)F)S(C)(=O)=O] | 5-({4-[({2-[methyl(methylsulfonyl)amino]pyridin-3-yl}methyl)amino]-5-(trifluoromethyl)pyrimidin-2-yl}amino)pyridine-2-carboxamide (372), formic acid salt | 0.00400 |
| 373 | 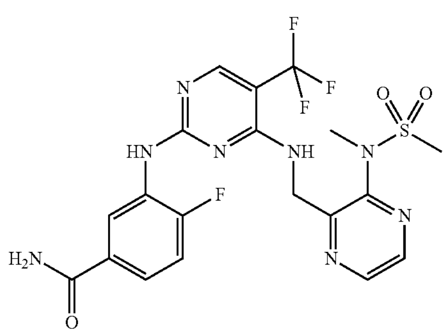 [SMILES: CN(c1nccnc1CNc1nc(Nc2cc(C(N)=O)ccc2F)ncc1C(F)(F)F)S(C)(=O)=O] | 4-fluoro-3-({4-[({3-[methyl(methylsulfonyl)amino]pyrazin-2-yl}methyl)amino]-5-(trifluoromethyl)pyrimidin-2-yl}amino)benzamide (373) | 0.00749 |

TABLE 1-continued

IC50 values against FAK kinase.

| Ex. | Structure | Compound Name | FAK IC50, µM |
|---|---|---|---|
| 374 | 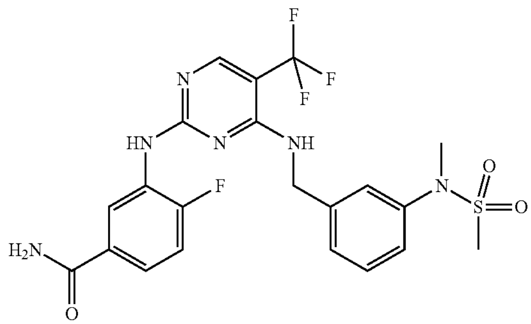 [SMILES: CN(c1cccc(CNc2nc(Nc3cc(C(N)=O)ccc3F)ncc2C(F)(F)F)c1)S(C)(=O)=O] | 4-fluoro-3-{[4-({3-[methyl(methylsulfonyl)amino] benzyl}amino)-5-(trifluoromethyl) pyrimidin-2-yl]amino} benzamide (374) | 0.0155 |
| 375 | 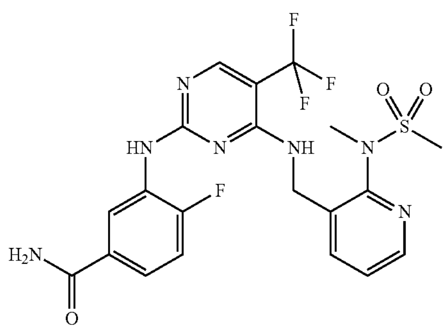 | 4-fluoro-3-({4-[({2-[methyl(methylsulfonyl)amino] pyridin-3-yl}methyl)amino]-5-(trifluoromethyl)pyrimidin-2-yl}amino)benzamide (375) | 0.00629 |
| 376 | 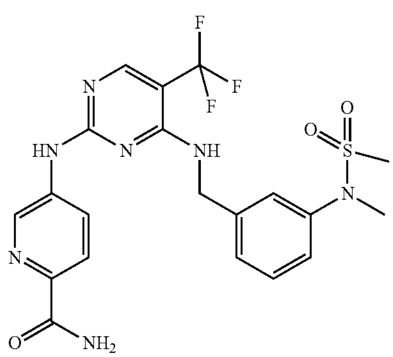 [SMILES: CN(c1cccc(CNc2nc(Nc3ccc(C(N)=O)nc3)ncc2C(F)(F)F)c1)S(C)(=O)=O] | 5-{[4-({3-[methyl(methylsulfonyl)amino] benzyl}amino)-5-(trifluoromethyl) pyrimidin-2-yl]amino}pyridine-2-carboxamide (376), formic acid salt | 0.00615 |
| 377 | 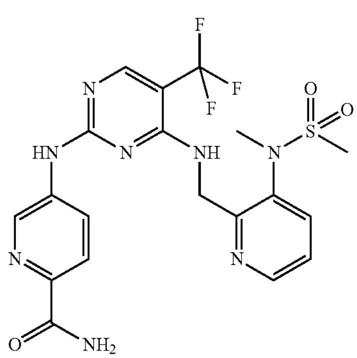 [SMILES: CN(c1cccnc1CNc1nc(Nc2ccc(C(N)=O)nc2)ncc1C(F)(F)F)S(C)(=O)=O] | 5-({4-[({3-[methyl(methylsulfonyl)amino] pyridin-2-yl}methyl)amino]-5-(trifluoromethyl)pyrimidin-2-yl}amino)pyridine-2-carboxamide (377), formic acid salt | 0.0153 |

TABLE 1-continued

IC50 values against FAK kinase.

| Ex. | Structure | Compound Name | FAK IC50, μM |
|---|---|---|---|
| 378 | 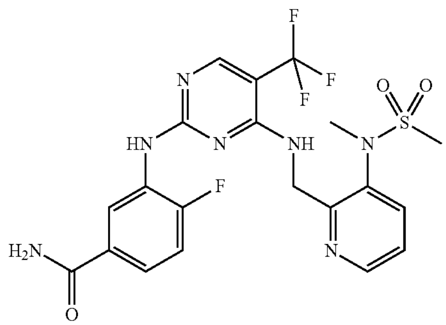 [SMILES: CN(c1cccnc1CNc1nc(Nc2cc(C(N)=O)ccc2F)ncc1C(F)(F)F)S(C)(=O)=O] | 4-fluoro-3-({4-[({3-[methyl(methylsulfonyl)amino]pyridin-2-yl}methyl)amino]-5-(trifluoromethyl)pyrimidin-2-yl}amino)benzamide (378) | 0.00194 |
| 379 | 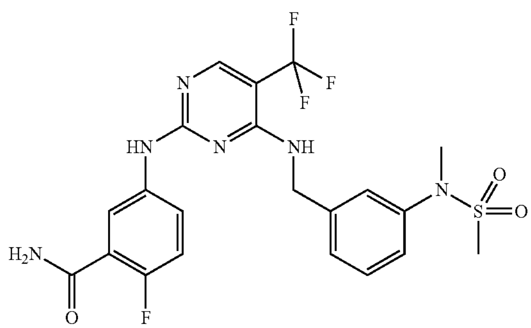 [SMILES: CN(c1cccc(CNc2nc(Nc3ccc(F)c(C(N)=O)c3)ncc2C(F)(F)F)c1)S(C)(=O)=O] | 2-fluoro-5-{[4-({3-[methyl(methylsulfonyl)amino]benzyl}amino)-5-(trifluoromethyl)pyrimidin-2-yl]amino}benzamide (379), hydrochloride salt | 0.00478 |
| 380 | 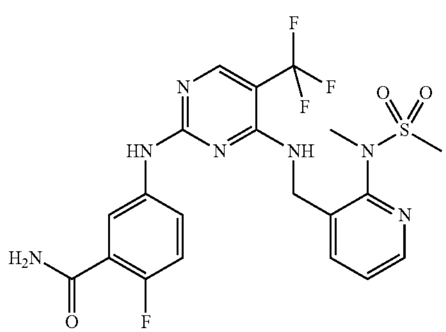 [SMILES: CN(c1ncccc1CNc1nc(Nc2ccc(F)c(C(N)=O)c2)ncc1C(F)(F)F)S(C)(=O)=O] | 2-fluoro-5-({4-[({2-[methyl(methylsulfonyl)amino]pyridin-3-yl}methyl)amino]-5-(trifluoromethyl)pyrimidin-2-yl}amino)benzamide (380), hydrochloride salt | 0.00160 |
| 381 | 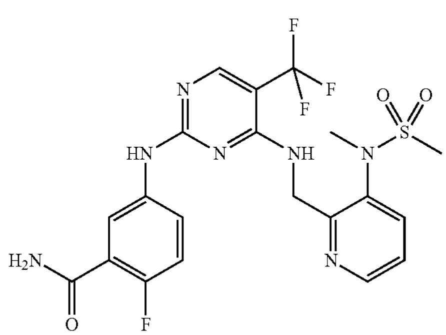 [SMILES: CN(c1cccnc1CNc1nc(Nc2ccc(F)c(C(N)=O)c2)ncc1C(F)(F)F)S(C)(=O)=O] | 2-fluoro-5-({4-[({3-[methyl(methylsulfonyl)amino]pyridin-2-yl}methyl)amino]-5-(trifluoromethyl)pyrimidin-2-yl}amino)benzamide (381), hydrochloride salt | 0.00455 |

TABLE 1-continued

IC50 values against FAK kinase.

| Ex. | Structure | Compound Name | FAK IC50, μM |
|---|---|---|---|
| 382 | 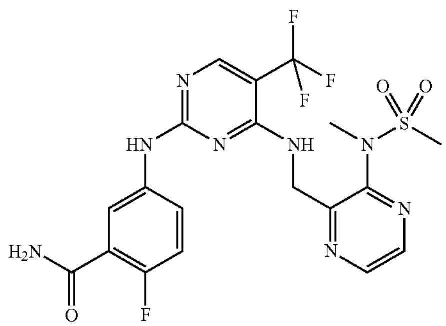 | 2-fluoro-5-({4-[({3-[methyl(methylsulfonyl)amino]pyrazin-2-yl}methyl)amino]-5-(trifluoromethyl)pyrimidin-2-yl}amino)benzamide (382), hydrochloride salt | 0.0107 |
| 383 | 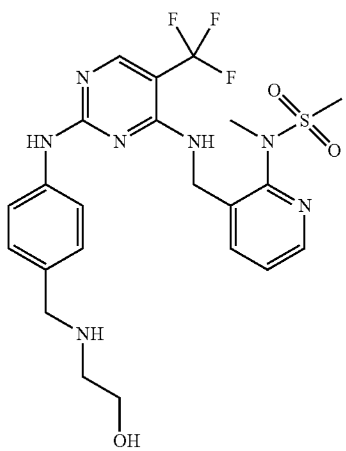 [SMILES: CN(c1ncccc1CNc1nc(Nc2ccc(CNCCO)cc2)ncc1C(F)(F)F)S(C)(=O)=O] | N-{3-[({2-[(4-{[(2-hydroxyethyl)amino]methyl}phenyl)amino]-5-(trifluoromethyl)pyrimidin-4-yl}amino)methyl]pyridin-2-yl}-N-methylmethane-sulfonamide (383) | <0.000595 |
| 384 | 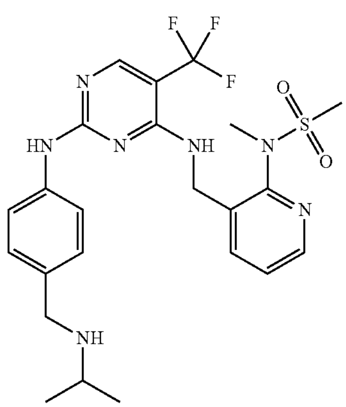 [SMILES: CC(C)NCc1ccc(Nc2ncc(C(F)(F)F)c(NCc3cccnc3N(C)S(C)(=O)=O)n2)cc1] | N-[3-({[2-({4-[(isopropylamino)methyl]phenyl}amino)-5-(trifluoromethyl)pyrimidin-4-yl]amino}methyl)pyridin-2-yl]-N-methylmethane-sulfonamide (384) | <0.000595 |
| 385 | 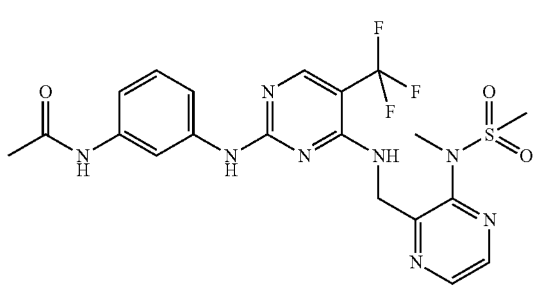 [SMILES: CC(=O)Nc1cccc(Nc2ncc(C(F)(F)F)c(NCc3nccnc3N(C)S(C)(=O)=O)n2)c1] | N-[3-({4-[({3-[methyl(methylsulfonyl)amino]pyrazin-2-yl}methyl)amino]-5-(trifluoromethyl)pyrimidin-2-yl}amino)phenyl]acetamide (385) | 0.00144 |

TABLE 1-continued

IC50 values against FAK kinase.

| Ex. | Structure | Compound Name | FAK IC50, µM |
|---|---|---|---|
| 386 | 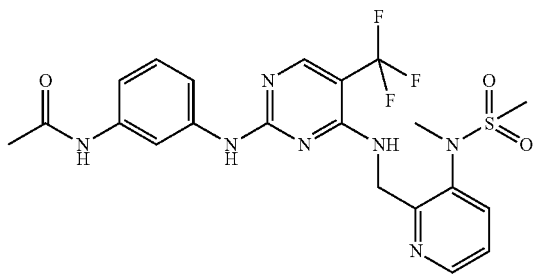 [SMILES: CC(=O)Nc1cccc(Nc2ncc(C(F)(F)F)c(NCc3ncccc3N(C)S(C)(=O)=O)n2)c1] | N-[3-({4-[({3-[methyl(methylsulfonyl)amino]pyridin-2-yl}methyl)amino]-5-(trifluoromethyl)pyrimidin-2-yl}amino)phenyl]acetamide (386) | 0.00165 |
| 387 | 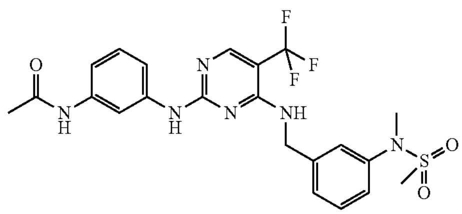 [SMILES: CC(=O)Nc1cccc(Nc2ncc(C(F)(F)F)c(NCc3cccc(N(C)S(C)(=O)=O)c3)n2)c1] | N-(3-{[4-({3-[methyl(methylsulfonyl)amino]benzyl}amino)-5-(trifluoromethyl)pyrimidin-2-yl]amino}phenyl)acetamide (387) | 0.00295 |
| 388 | 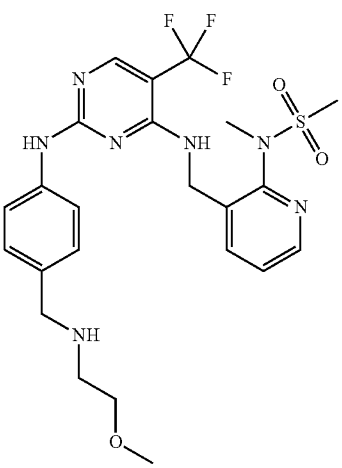 [SMILES: COCCNCc1ccc(Nc2ncc(C(F)(F)F)c(NCc3cccnc3N(C)S(C)(=O)=O)n2)cc1] | N-{3-[({2-[(4-{[(2-methoxyethyl)amino]methyl}phenyl)amino]-5-(trifluoromethyl)pyrimidin-4-yl}amino)methyl]pyridin-2-yl}-N-methylmethanesulfonamide (388) | <0.000595 |
| 389 | 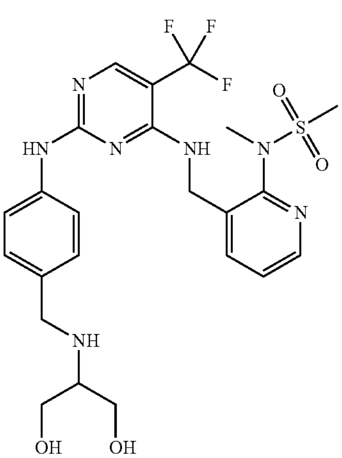 [SMILES: CN(c1ncccc1CNc1nc(Nc2ccc(CNC(CO)CO)cc2)ncc1C(F)(F)F)S(C)(=O)=O] | N-[3-({[2-{[4-({[2-hydroxy-1-(hydroxymethyl)ethyl]amino}methyl)phenyl]amino}-5-(trifluoromethyl)pyrimidin-4-yl]amino}methyl)pyridin-2-yl]-N-methylmethanesulfonamide (389) | <0.000595 |

TABLE 1-continued

IC50 values against FAK kinase.

| Ex. | Structure | Compound Name | FAK IC50, μM |
|---|---|---|---|
| 390 | 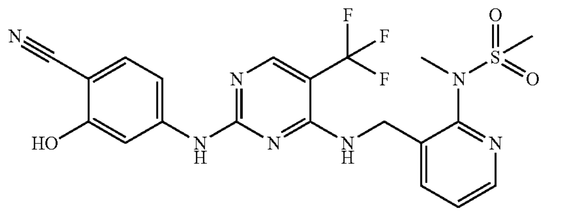 [SMILES: CN(c1ncccc1CNc1nc(Nc2ccc(C#N)c(O)c2)ncc1C(F)(F)F)S(C)(=O)=O] | N-{3-[({2-[(4-cyano-3-hydroxyphenyl)amino]-5-(trifluoromethyl)pyrimidin-4-yl}amino)methyl]pyridin-2-yl}-N-methylmethane-sulfonamide (390) | 0.000746 |
| 391 | 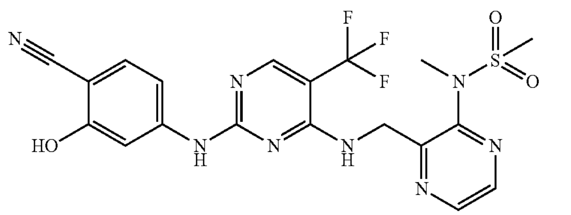 [SMILES: CN(c1nccnc1CNc1nc(Nc2ccc(C#N)c(O)c2)ncc1C(F)(F)F)S(C)(=O)=O] | N-{3-[({2-[(4-cyano-3-hydroxyphenyl)amino]-5-(trifluoromethyl)pyrimidin-4-yl}amino)methyl]pyrazin-2-yl}-N-methylmethane-sulfonamide (391), hydrochloride salt | 0.00124 |
| 392 | 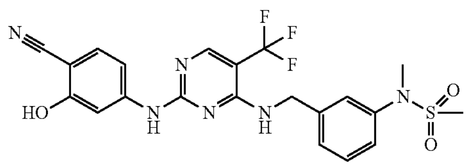 [SMILES: CN(c1cccc(CNc2nc(Nc3ccc(C#N)c(O)c3)ncc2C(F)(F)F)c1)S(C)(=O)=O] | N-{3-[({2-[(4-cyano-3-hydroxyphenyl)amino]-5-(trifluoromethyl)pyrimidin-4-yl}amino)methyl]phenyl}-N-methylmethanesulfonamide (392) | 0.00451 |
| 393 | 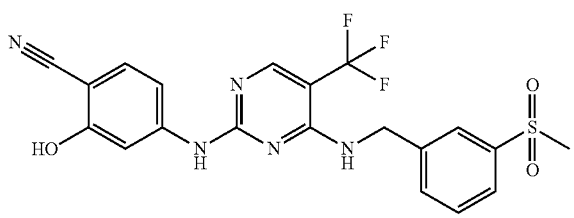 [SMILES: CS(=O)(=O)c1cccc(CNc2nc(Nc3ccc(C#N)c(O)c3)ncc2C(F)(F)F)c1] | 2-hydroxy-4-{[4-{[3-(methylsulfonyl)benzyl]amino}-5-(trifluoromethyl)pyrimidin-2-yl]amino}benzonitrile (393) | 0.00741 |
| 394 | 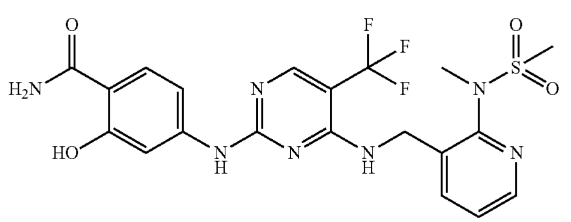 | 2-hydroxy-4-({4-[({2-[methyl(methylsulfonyl)amino]pyridin-3-yl}methyl)amino]-5-(trifluoromethyl)pyrimidin-2-yl}amino)benzamide (394), formic acid salt | <0.000595 |
| 395 | 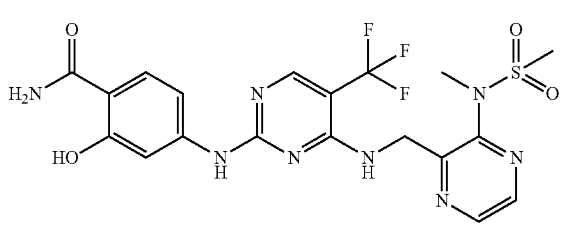 [SMILES: CN(c1ncccc1CNc1nc(Nc2ccc(C(N)=O)c(O)c2)ncc1C(F)(F)F)S(C)(=O)=O] | 2-hydroxy-4-({4-[({3-[methyl(methylsulfonyl)amino]pyrazin-2-yl}methyl)amino]-5-(trifluoromethyl)pyrimidin-2-yl}amino)benzamide (395), formic acid salt | 0.000849 |
| 396 | 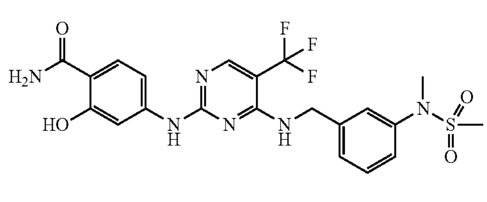 [SMILES: CN(c1cccc(CNc2nc(Nc3ccc(C(N)=O)c(O)c3)ncc2C(F)(F)F)c1)S(C)(=O)=O] | 2-hydroxy-4-{[4-({3-[methyl(methylsulfonyl)amino]benzyl}amino)-5-(trifluoromethyl)pyrimidin-2-yl]amino}benzamide (396), formic acid salt | 0.00313 |

TABLE 1-continued

IC50 values against FAK kinase.

| Ex. | Structure | Compound Name | FAK IC50, μM |
|---|---|---|---|
| 397 | 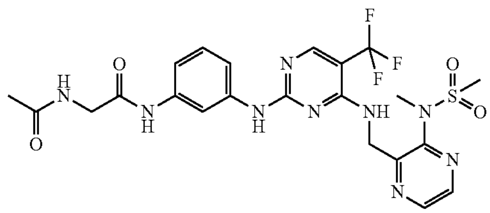 [SMILES: CC(=O)NCC(=O)Nc1cccc(Nc2ncc(C(F)(F)F)c(NCc3nccnc3N(C)S(C)(=O)=O)n2)c1] | N-2-acetyl-N-[3-({4-[({3-[methyl(methylsulfonyl)amino]pyrazin-2-yl}methyl)amino]-5-(trifluoromethyl)pyrimidin-2-yl}amino)phenyl]glycinamide (397) | 0.00151 |
| 398 | 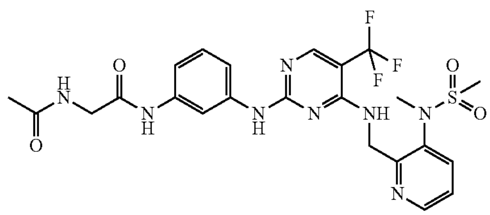 [SMILES: CC(=O)NCC(=O)Nc1cccc(Nc2ncc(C(F)(F)F)c(NCc3ncccc3N(C)S(C)(=O)=O)n2)c1] | N~2~-acetyl-N-[3-({4-[({3-[methyl(methylsulfonyl)amino]pyridin-2-yl}methyl)amino]-5-(trifluoromethyl)pyrimidin-2-yl}amino)phenyl]glycinamide (398) | 0.00218 |
| 399 | 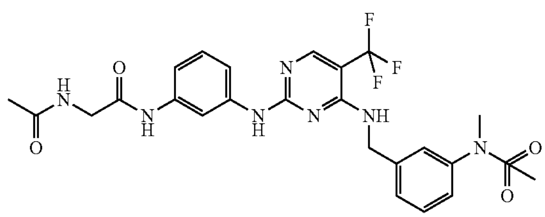 | N-2-acetyl-N-(3-{[4-({3-[methyl(methylsulfonyl)amino]benzyl}amino)-5-(trifluoromethyl)pyrimidin-2-yl]amino}phenyl)glycinamide (399) | 0.00557 |
| 400 | 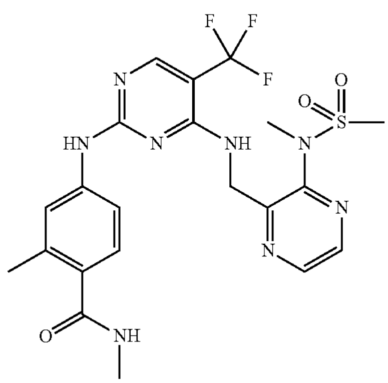 | N,2-dimethyl-4-({4-[({3-[methyl(methylsulfonyl)amino]pyrazin-2-yl}methyl)amino]-5-(trifluoromethyl)pyrimidin-2-yl}amino)benzamide (400), hydrochloride salt | 0.000660 |
| 401 | 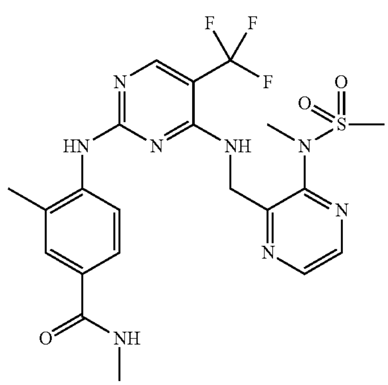 | N,3-dimethyl-4-({4-[({3-[methyl(methylsulfonyl)amino]pyrazin-2-yl}methyl)amino]-5-(trifluoromethyl)pyrimidin-2-yl}amino)benzamide (401), hydrochloride salt | 0.00117 |

TABLE 1-continued

IC50 values against FAK kinase.

| Ex. | Structure | Compound Name | FAK IC50, μM |
|---|---|---|---|
| 402 | 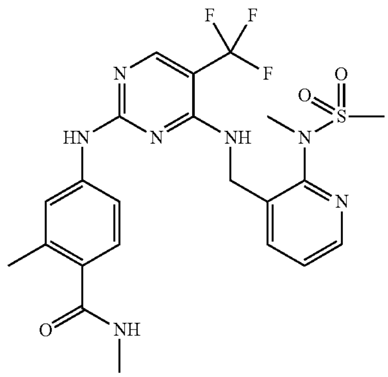 | N,2-dimethyl-4-({4-[({2-[methyl(methylsulfonyl)amino]pyridin-3-yl}methyl)amino]-5-(trifluoromethyl)pyrimidin-2-yl}amino)benzamide (402), hydrochloride salt | <0.000595 |
| 403 | 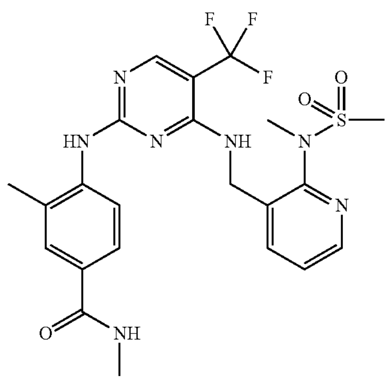 | N,3-dimethyl-4-({4-[({2-[methyl(methylsulfonyl)amino]pyridin-3-yl}methyl)amino]-5-(trifluoromethyl)pyrimidin-2-yl}amino)benzamide (403), hydrochloride salt | 0.00109 |
| 404 | 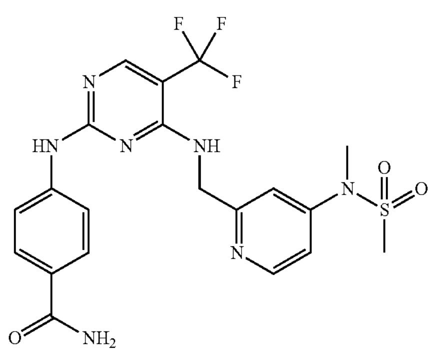 [SMILES: CN(c1ccnc(CNc2nc(Nc3ccc(C(N)=O)cc3)ncc2C(F)(F)F)c1)S(C)(=O)=O] | 4-({4-[({4-[methyl(methylsulfonyl)amino]pyridin-2-yl}methyl)amino]-5-(trifluoromethyl)pyrimidin-2-yl}amino)benzamide (404), formic acid salt | 0.00207 |
| 405 | 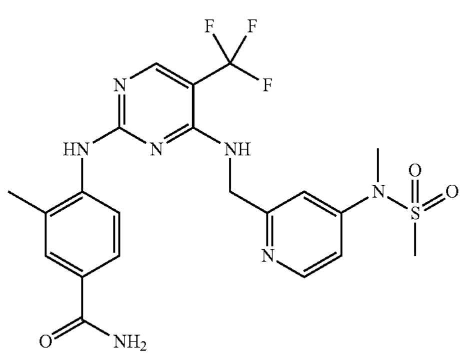 [SMILES: Cc1cc(C(N)=O)ccc1Nc1ncc(C(F)(F)F)c(NCc2cc(N(C)S(C)(=O)=O)ccn2)n1] | 3-methyl-4-({4-[({4-[methyl(methylsulfonyl)amino]pyridin-2-yl}methyl)amino]-5-(trifluoromethyl)pyrimidin-2-yl}amino)benzamide (405), formic acid salt | 0.0173 |

TABLE 1-continued

IC50 values against FAK kinase.

| Ex. | Structure | Compound Name | FAK IC50, μM |
|---|---|---|---|
| 406 | 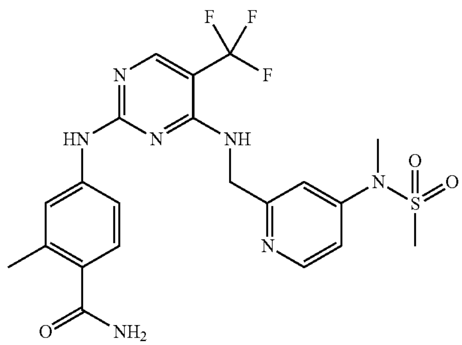 [SMILES: Cc1cc(Nc2ncc(C(F)(F)F)c(NCc3cc(N(C)S(C)(=O)=O)ccn3)n2)ccc1C(N)=O] | 2-methyl-4-({4-[({4-[methyl(methylsulfonyl)amino]pyridin-2-yl}methyl)amino]-5-(trifluoromethyl)pyrimidin-2-yl}amino)benzamide (406), formic acid salt | 0.000784 |
| 407 | 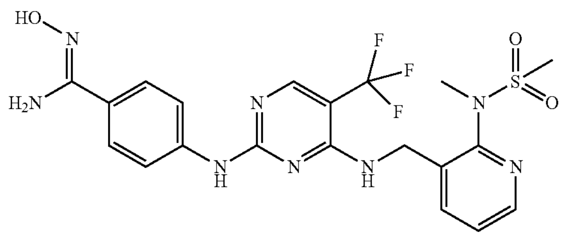 [SMILES: CN(c1ncccc1CNc1nc(Nc2ccc(/C(N)=N/O)cc2)ncc1C(F)(F)F)S(C)(=O)=O] | N'-hydroxy-4-({4-[({2-[methyl(methylsulfonyl)amino]pyridin-3-yl}methyl)amino]-5-(trifluoromethyl)pyrimidin-2-yl}amino)benzenecarboximidamide (407), formic acid salt | <0.000595 |
| 408 | 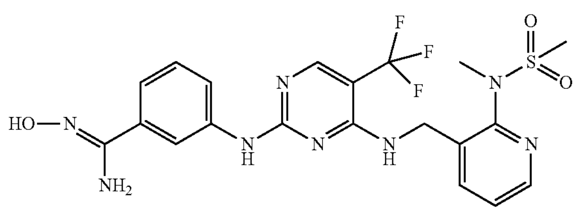 [SMILES: CN(c1ncccc1CNc1nc(Nc2cccc(/C(N)=N/O)c2)ncc1C(F)(F)F)S(C)(=O)=O] | N'-hydroxy-3-({4-[({2-[methyl(methylsulfonyl)amino]pyridin-3-yl}methyl)amino]-5-(trifluoromethyl)pyrimidin-2-yl}amino)benzenecarboximidamide (408), formic acid salt | 0.00229 |
| 409 | 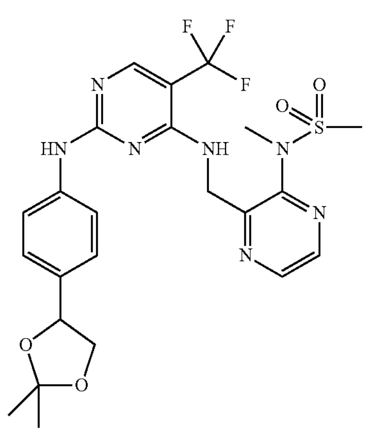 | N-[3-({[2-{[4-(2,2-dimethyl-1,3-dioxolan-4-yl)phenyl]amino}-5-(trifluoromethyl)pyrimidin-4-yl]amino}methyl)pyrazin-2-yl]-N-methylmethane-sulfonamide (409) | 0.00475 |

TABLE 1-continued

IC50 values against FAK kinase.

| Ex. | Structure | Compound Name | FAK IC50, μM |
|---|---|---|---|
| 410 | 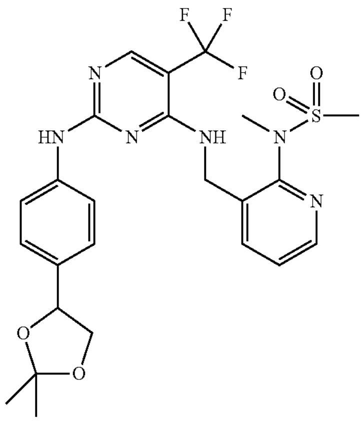 | N-[3-({[2-{[4-(2,2-dimethyl-1,3-dioxolan-4-yl)phenyl]amino}-5-(trifluoromethyl)pyrimidin-4-yl]amino}methyl)pyridin-2-yl]-N-methylmethane-sulfonamide (410) | 0.00119 |
| 411 | 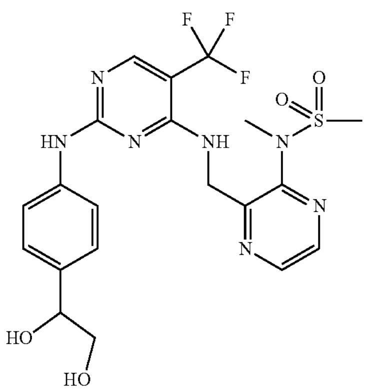 | N-[3-({[2-{[4-(1,2-dihydroxyethyl)phenyl]amino}-5-(trifluoromethyl)pyrimidin-4-yl]amino}methyl)pyrazin-2-yl]-N-methylmethane-sulfonamide (411), hydrochloride salt | 0.000941 |
| 412 | 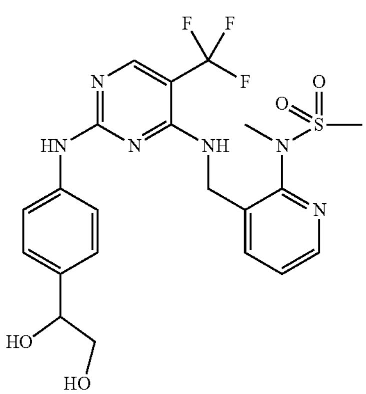 [SMILES: CN(c1ncccc1CNc1nc(Nc2ccc(C(O)CO)cc2)ncc1C(F)(F)F)S(C)(=O)=O] | N-[3-({[2-{[4-(1,2-dihydroxyethyl)phenyl]amino}-5-(trifluoromethyl)pyrimidin-4-yl]amino}methyl)pyridin-2-yl]-N-methylmethane-sulfonamide (412), hydrochloride salt | <0.000595 |

TABLE 1-continued

IC50 values against FAK kinase.

| Ex. | Structure | Compound Name | FAK IC50, μM |
|---|---|---|---|
| 413 | 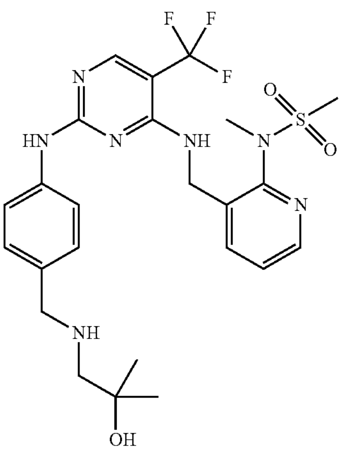 [SMILES: CN(c1ncccc1CNc1nc(Nc2ccc(CNCC(C)(C)O)cc2)ncc1C(F)(F)F)S(C)(=O)=O] | N-{3-[({2-[(4-{[(2-hydroxy-2-methylpropyl)amino]methyl}phenyl)amino]-5-(trifluoromethyl)pyrimidin-4-yl}amino)methyl]pyridin-2-yl}-N-methylmethanesulfonamide (413) | <0.000595 |
| 414 | 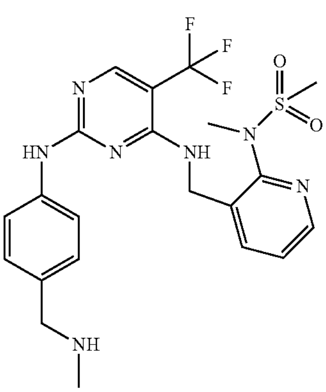 [SMILES: CNCc1ccc(Nc2ncc(C(F)(F)F)c(NCc3cccnc3N(C)S(C)(=O)=O)n2)cc1] | N-methyl-N-[3-({[2-({4-[(methylamino)methyl]phenyl}amino)-5-(trifluoromethyl)pyrimidin-4-yl]amino}methyl)pyridin-2-yl]methanesulfonamide (414), hydrochloride salt | <0.000595 |
| 415 | 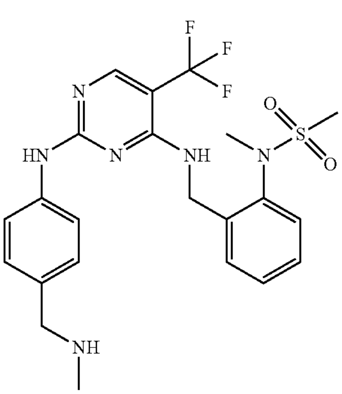 [SMILES: CNCc1ccc(Nc2ncc(C(F)(F)F)c(NCc3ccccc3N(C)S(C)(=O)=O)n2)cc1] | N-methyl-N-[2-({[2-({4-[(methylamino)methyl]phenyl}amino)-5-(trifluoromethyl)pyrimidin-4-yl]amino}methyl)phenyl]methanesulfonamide (415), hydrochloride salt | <0.000595 |

We claim:

1. A method of making a compound of Formula (I), the method comprising

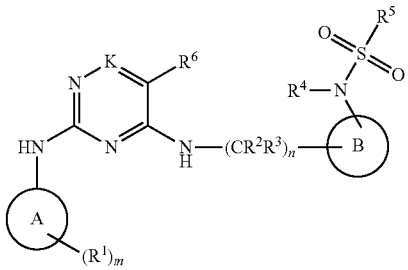
(I)

reacting a compound of Formula (II)

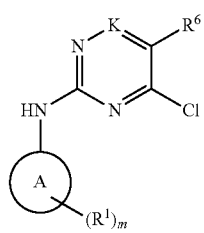
(II)

with a compound of Formula (III),

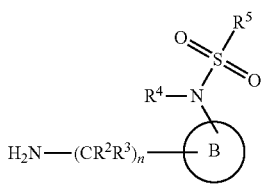
(III)

thereby providing the compound of Formula (I); wherein

A is phenyl;

B is phenyl or a 5- to 6-membered heteroaryl;

K is CH;

each $R^1$ is independently selected from the group consisting of —H, halo, —$CF_3$, —CN, —$NO_2$, —$NR^7R^8$, —$NR^7C(NR^7R^8)(=CR^9)$, —$CR^7(NR^7R^8)(=NR^7)$, —$NR^7C(NR^7R^8)(=NR^7)$, —$NR^7C(O)R^9$, —$C(O)NR^7R^8$, —$C(O)R^9$, —$C(O)C(O)R^9$, —$C(O)OR^{10}$, —$OC(O)R^9$, —$OR^{10}$, —$OC(O)OR^{10}$, —$S(O)_jR^{11}$, —$S(O)(=NR^7)R^8$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_1$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl, —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl moieties of said $R^1$ is optionally independently substituted by one to three $R^{12}$ groups;

$R^2$ and $R^3$ are each independently selected from the group consisting of —H, -halo, —$OR^{10}$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{10}$)aryl and —($C_1$-$C_9$)heteroaryl moieties of said $R^2$ and $R^3$ is optionally substituted by one to three $R^{12}$ groups;

$R^4$ and $R^5$ are each independently selected from the group consisting of —H, —$NR^7R^8$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, —($C_4$-$C_9$)heterocycloalkenyl, —($C_6$-$C_{10}$)aryl and —($C_1$-$C_9$)heteroaryl moieties of said $R^4$ and $R^5$ is optionally substituted by one to three $R^{12}$ groups;

$R^6$ is —$CF_3$;

$R^7$ and $R^8$ are each independently selected from the group consisting of —H, —$OR^{10}$, —$S(O)_jR^{11}$, —$NO_2$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl —($C_6$-$C_{10}$)aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{10}$)aryl and —($C_1$-$C_9$)heteroaryl moieties of said $R^7$ and $R^8$ is optionally substituted by one to three $R^{12}$ groups;

each $R^9$ is independently selected from the group consisting of —H, -halo, —$NR^{13}R^{14}$, —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl —($C_6$-$C_{10}$) aryl, and —($C_1$-$C_9$)heteroaryl; and wherein each of the foregoing —($C_1$-$C_6$)alkyl, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_2$-$C_9$)heterocycloalkyl, ($C_4$-$C_9$)heterocycloalkenyl, —($C_6$-$C_{10}$)aryl and —($C_1$-$C_9$)heteroaryl moieties of said $R^9$ is optionally substituted by one to three $R^{12}$ groups;

each $R^{10}$ is independently selected from the group consisting of —H, —($C_2$-$C_6$)alkenyl, —($C_2$-$C_6$)alkynyl, —($C_3$-$C_{10}$)cycloalkyl, —($C_5$-$C_{10}$)cycloalkenyl, —($C_6$-$C_{10}$)bicycloalkyl, —($C_6$-$C_{10}$)bicycloalkenyl, —($C_2$-$C_9$)heterocycloalkyl, —($C_4$-$C_9$)heterocycloalkenyl, —($C_6$-$C_9$)heterobicycloalkyl, —($C_6$-$C_9$)heterobicycloalkenyl —($C_6$-$C_{10}$)aryl, and —($C_1$-$C_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_6$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said R$^{10}$ is optionally substituted by one to three R$^{12}$ groups;

R$^{11}$ each is independently selected from the group consisting of —H, —NR$^{13}$R$^{14}$, —C(O)R$^{13}$, —CF$_3$, —(C$_1$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_2$-C$_9$)heterocycloalkyl, (C$_4$-C$_9$)heterocycloalkenyl, —(C$_6$-C$_{10}$)aryl and —(C$_1$-C$_9$)heteroaryl moieties of said is optionally substituted by one to three R$^{12}$ groups;

each R$^{12}$ is independently selected from the group consisting of —H, —OR$^{13}$, —C(O)R$^{13}$, —C(O)OR$^{13}$, —OC(O)R$^{13}$, —OC(O)OR$^{13}$, —C(O)NR$^{13}$R$^{14}$, —NR$^{13}$C(O)NR$^{13}$R$^{14}$, —NR$^{13}$R$^{14}$, —NR$^{13}$C(NR$^{13}$R$^{14}$)(=NR$^{13}$), —NR$^{13}$C(NR$^{13}$R$^{14}$)(=N—C(O)R$^{13}$), —NR$^{13}$C(O)R$^{14}$, —NR$^{13}$S(O)$_j$R$^{13}$, —S(O)$_j$R$^{13}$, —CF$_3$, —CN, —(C$_1$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{12}$ is optionally independently substituted by one to three groups selected from the group consisting of -halo, —CF$_3$, —CN, —NO$_2$, —OH, —O((C$_1$-C$_6$)alkyl), —C(O)R$^{15}$, —C(O)NR$^{15}$R$^{16}$, —S(O)$_j$R$^{15}$, and —S(O)$_j$NR$^{15}$R$^{16}$, —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

R$^{13}$ and R$^{14}$ are each independently selected from the group consisting of —H, —NR$^{15}$C(O)R$^{16}$, —CF$_3$, —CN, —S(O)$_j$R$^{15}$, —(C$_1$-C$_6$)alkyl, —(C$_2$-C$_6$)alkenyl, —(C$_2$-C$_6$)alkynyl, —C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{13}$ and R$^{14}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

R$^{15}$ and R$^{16}$ are each independently selected from the group consisting of —H, —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl; and wherein each of the foregoing —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl, —(C$_6$-C$_9$)heterobicycloalkenyl, —(C$_6$-C$_{10}$)aryl, and —(C$_1$-C$_9$)heteroaryl of said R$^{15}$ and R$^{16}$ is optionally independently substituted by one to three groups selected from the group consisting of -halo, —CF$_3$, —CN, —NO$_2$, —OH, —O((C$_1$-C$_6$)alkyl), —C(O)((C$_1$-C$_6$)alkyl), —(C$_3$-C$_{10}$)cycloalkyl, —(C$_2$-C$_9$)heterocycloalkyl, —SH, —S((C$_1$-C$_6$)alkyl), —NH$_2$, —NH((C$_1$-C$_6$)alkyl) and —N((C$_1$-C$_6$)alkyl)$_2$;

wherein one or two carbon ring atoms in each of the aforementioned —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkenyl in said R$^1$-R$^{14}$ groups may optionally and independently be replaced with —C(O)— or —C(S)—;

wherein two groups attached to the same tetravalent carbon atom in each of the aforementioned —(C$_1$-C$_6$)alkyl, —(C$_2$-C$_6$)alkenyl, —(C$_2$-C$_6$)alkynyl, —(C$_3$-C$_{10}$)cycloalkyl, —(C$_5$-C$_{10}$)cycloalkenyl, —(C$_6$-C$_{10}$)bicycloalkyl, —(C$_6$-C$_{10}$)bicycloalkenyl, —(C$_2$-C$_9$)heterocycloalkyl, —(C$_4$-C$_9$)heterocycloalkenyl, —(C$_6$-C$_9$)heterobicycloalkyl and —(C$_6$-C$_9$)heterobicycloalkeny of said R$^1$ to R$^{14}$ groups may optionally join to form a ring system selected from the group consisting of a —(C$_3$-C$_{10}$)cycloalkyl, —(C$_5$-C$_{10}$)cycloalkenyl, —(C$_2$-C$_9$)heterocycloalkyl, and —(C$_4$-C$_9$)heterocycloalkenyl; and wherein j is an integer from 0 to 2;

n is an integer from 1 to 3; and m is an integer from 0 to 3.

2. A method of making a compound of the Formula (IV), the method comprising

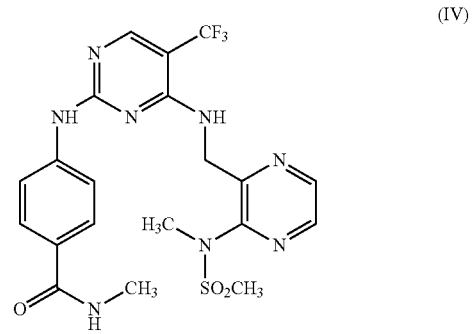 [SMILES: CNC(=O)c1ccc(Nc2ncc(C(F)(F)F)c(NCc3nccnc3N(C)S(C)(=O)=O)n2)cc1]

(IV)

reacting a compound of the Formula (V)

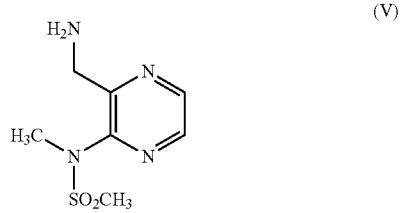

with a compound of the Formula (VI)

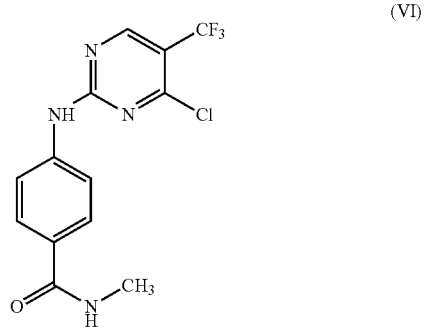 [SMILES: CNC(=O)c1ccc(Nc2ncc(C(F)(F)F)c(Cl)n2)cc1]

thereby providing a compound of the Formula (IV).

3. The method of claim 2, wherein the reaction of the compound of Formula (V) and the compound of Formula (VI) is performed in the presence of a solvent.

4. The method of claim 3, wherein the solvent comprises dichloroethane and tBuOH.

5. The method of claim 4, wherein the ratio of dichloroethane to tBuOH is 1:1.

6. The method of claim 2, wherein the reaction of the compound of Formula (V) and the compound of Formula (VI) is performed in the presence of a base.

7. The method of claim 6, wherein the base is Hunig's base.

8. The method of claim 2, wherein the reaction of the compound of Formula (V) and the compound of Formula (VI) is performed in a sealed container.

9. The method of claim 2, wherein the reaction of the compound of Formula (V) and the compound of Formula (VI) is performed at elevated temperature.

10. The method of claim 9, wherein the reaction of the compound of Formula (V) and the compound of Formula (VI) is performed at 88° C.

11. The method of claim 2, wherein the reaction of the compound of Formula (V) and the compound of Formula (VI) is performed for 1.5 hour.

12. The method of claim 2, further comprising isolating the compound of Formula (IV), wherein isolating the compound of Formula (IV) comprises precipitating the compound of Formula (IV) from the reaction mixture.

13. The method of claim 12, wherein isolating the compound of Formula (IV) comprises dilution of the reaction mixture with $Et_2O$/EtOH.

14. The method of claim 13, wherein the ratio of $Et_2O$/EtOH is 10:1.

15. The method of claim 12, wherein the isolation of the compound of Formula (IV) further comprises filtration.

16. The method of claim 2, wherein the compound of Formula (IV) is converted into a salt thereof.

17. The method of claim 16, wherein the salt is the HCl salt.

18. The method of claim 17, wherein the HCl salt is formed by a reaction with 4M HCl in dioxane.

19. The method of claim 18, wherein the reaction with 4M HCl is performed in a solvent.

20. The method of claim 19, wherein the solvent is methanol.

21. The method of claim 18, wherein the reaction with 4M HCl is performed at ambient temperature.

22. The method of claim 18, wherein the reaction with 4M HCl is performed for 1 hour.

23. The method of claim 18, wherein the isolation of the HCl salt of Formula (IV) comprises filtration.

24. The method of claim 2, wherein the compound of Formula (VI) is made by a method which comprises reacting a compound of Formula (VII)

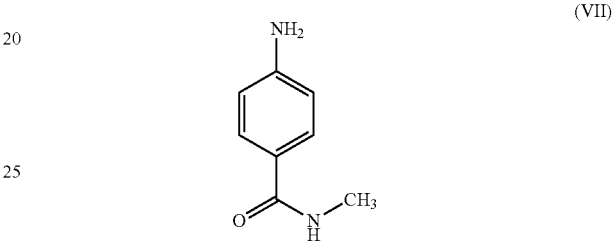

with a compound Formula (VIII)

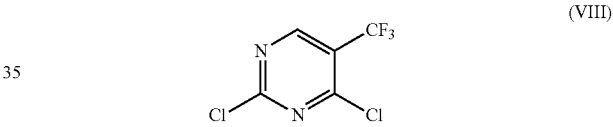

thereby providing a compound of the Formula (VI).

25. The method of claim 24, wherein the reaction of the compound of Formula (VII) and the compound of Formula (VIII) is performed in a solvent.

26. The method of claim 25, wherein the solvent comprises dichloroethane and tBuOH.

27. The method of claim 26, wherein the ratio of dichloroethane to tBuOH is 1:1.

28. The method of claim 24, wherein the reaction of the compound of Formula (VII) and the compound of Formula (VIII) is performed in the presence of a zinc salt.

29. The method of claim 28, wherein the zinc salt is $ZnBr_2$.

30. The method of claim 24, wherein the reaction of the compound of Formula (VII) and the compound of Formula (VIII) is performed in the presence of a base.

31. The method of claim 30, wherein the base is triethylamine.

32. The method of claim 24, wherein the compound of Formula (VII) and the compound of Formula (VIII) is added to a reaction vessel at decreased temperature.

33. The method of claim 32, wherein the temperature during addition of the compound of Formula (VII) and the compound of Formula (VIII) is 5° C.

34. The method of claim 24, wherein the reaction of the compound of Formula (VII) and the compound of Formula (VIII) is performed at 25° C.

35. The method of claim 24, wherein the reaction of the compound of Formula (VII) and the compound of Formula (VIII) is performed for 20 hours.

36. The method of claim 24, wherein the compound of Formula (VI) is purified using column chromatography.

37. The method of claim 36, wherein the compound of Formula (VI) is further purified by trituration with water.

38. The method of isolating the compound of Formula (VI) in claim 37 by filtration.

* * * * *